US010978195B2

(12) United States Patent
Blahnik et al.

(10) Patent No.: US 10,978,195 B2
(45) Date of Patent: Apr. 13, 2021

(54) PHYSICAL ACTIVITY AND WORKOUT MONITOR

(71) Applicant: Apple Inc., Cupertino, CA (US)

(72) Inventors: Jay Blahnik, San Francisco, CA (US); Gary Ian Butcher, San Jose, CA (US); Kevin Will Chen, Sunnyvale, CA (US); David Chance Graham, Campbell, CA (US); Daniel S. Keen, San Jose, CA (US); Justin Shane Rushing, San Francisco, CA (US); T. Allan Shortlidge, San Francisco, CA (US); Anton M. Davydov, Gilroy, CA (US); Alan C. Dye, San Francisco, CA (US); Jonathan P. Ive, San Francisco, CA (US); Zachery Kennedy, San Jose, CA (US); Zachury Minjack, San Francisco, CA (US); Dennis S. Park, San Francisco, CA (US); Brian Schmitt, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/925,652

(22) Filed: Mar. 19, 2018

(65) Prior Publication Data
US 2018/0206766 A1 Jul. 26, 2018

Related U.S. Application Data

(63) Continuation of application No. 14/839,922, filed on Aug. 29, 2015, now Pat. No. 9,918,664.
(Continued)

(51) Int. Cl.
G16H 20/30 (2018.01)
A61B 5/11 (2006.01)
(Continued)

(52) U.S. Cl.
CPC ............ *G16H 20/30* (2018.01); *A61B 5/1112* (2013.01); *A61B 5/1116* (2013.01);
(Continued)

(58) Field of Classification Search
CPC ... A61B 5/1118; A61B 5/1112; A61B 5/6801; A61B 5/1116; A61B 5/7435;
(Continued)

(56) References Cited

U.S. PATENT DOCUMENTS 4,205,628 A 6/1980 Null
4,842,266 A 6/1989 Sweeney et al.
(Continued)

FOREIGN PATENT DOCUMENTS

CA 2815518 A1 5/2012
CN 1337638 A 2/2002
(Continued)

OTHER PUBLICATIONS

Advisory Action received for U.S. Appl. No. 14/732,773, dated Nov. 9, 2018, 6 pages.
(Continued)

*Primary Examiner* — Rene T Towa
(74) *Attorney, Agent, or Firm* — Dentons US LLP

(57) ABSTRACT

The present disclosure relates to devices and processes for monitoring attributes of a user's physical activity (e.g., workout) or inactivity, and to user interfaces (e.g., an activity indicator) for displaying the same. In some examples, a device determines whether physical activity corresponds to a first type based on a first set of criteria, and whether physical activity corresponds to a second type based on a second set of criteria. In some examples, the device controls an inactivity timer that measures user's inactivity. In some examples, the device displays a first visual representation of an attribute or amount of a first type of physical activity, and
(Continued)

a second visual representation of an attribute or amount of a second type. In some examples, the device displays a third visual representation of an attribute or amount of a third type of activity. In some examples, the third visual representation corresponds to user's inactivity.

48 Claims, 111 Drawing Sheets

Related U.S. Application Data

(60) Provisional application No. 62/129,828, filed on Mar. 7, 2015, provisional application No. 62/044,990, filed on Sep. 2, 2014.

(51) Int. Cl.
 *G16H 20/40* (2018.01)
 *A61B 5/00* (2006.01)
 *G06F 3/048* (2013.01)

(52) U.S. Cl.
 CPC ........... *A61B 5/1118* (2013.01); *A61B 5/1123* (2013.01); *A61B 5/6801* (2013.01); *A61B 5/7435* (2013.01); *G16H 20/40* (2018.01); *A61B 2503/10* (2013.01); *G06F 3/048* (2013.01)

(58) Field of Classification Search
 CPC .. A61B 5/1123; A61B 2503/10; G16H 20/40; G16H 20/30; G06F 19/3481; G06F 3/048
 See application file for complete search history.

(56) References Cited

U.S. PATENT DOCUMENTS

| | | | |
|---|---|---|---|
| 5,423,863 A | 6/1995 | Felblinger et al. | |
| 5,788,655 A | 8/1998 | Yoshimura et al. | |
| 6,013,008 A | 1/2000 | Fukushima | |
| 6,095,949 A | 8/2000 | Arai | |
| 6,095,984 A | 8/2000 | Amano et al. | |
| 6,097,371 A | 8/2000 | Siddiqui et al. | |
| 6,244,988 B1 | 6/2001 | Delman | |
| 6,323,846 B1 | 11/2001 | Westerman et al. | |
| 6,416,471 B1 | 7/2002 | Kumar et al. | |
| 6,570,557 B1 | 5/2003 | Westerman et al. | |
| 6,603,477 B1 | 8/2003 | Tittle | |
| 6,639,584 B1 | 10/2003 | Li | |
| 6,662,023 B1 | 12/2003 | Helle | |
| 6,677,932 B1 | 1/2004 | Westerman | |
| 6,705,972 B1 | 3/2004 | Takano et al. | |
| 6,837,827 B1 | 1/2005 | Lee et al. | |
| 6,866,613 B1 | 3/2005 | Brown et al. | |
| 7,081,905 B1 | 7/2006 | Raghunath | |
| 7,128,693 B2 | 10/2006 | Brown et al. | |
| 7,130,664 B1 | 10/2006 | Williams | |
| 7,251,454 B2 | 7/2007 | White | |
| 7,614,008 B2 | 11/2009 | Ording | |
| 7,633,076 B2 | 12/2009 | Huppi et al. | |
| 7,653,883 B2 | 1/2010 | Hotelling et al. | |
| 7,657,849 B2 | 2/2010 | Chaudhri et al. | |
| 7,662,065 B1 | 2/2010 | Kahn et al. | |
| 7,663,607 B2 | 2/2010 | Hotelling et al. | |
| 7,739,148 B2 | 6/2010 | Suzuki et al. | |
| 7,844,914 B2 | 11/2010 | Andre et al. | |
| 7,957,762 B2 | 6/2011 | Herz et al. | |
| 8,006,002 B2 | 8/2011 | Kalayjian et al. | |
| 8,105,208 B2 | 1/2012 | Oleson et al. | |
| 8,239,784 B2 | 8/2012 | Hotelling et al. | |
| 8,279,180 B2 | 10/2012 | Hotelling et al. | |
| 8,321,006 B1 | 11/2012 | Snyder et al. | |
| 8,341,557 B2 | 12/2012 | Pisula et al. | |
| 8,381,135 B2 | 2/2013 | Hotelling et al. | |
| 8,475,339 B2 | 7/2013 | Hwang et al. | |
| 8,479,122 B2 | 7/2013 | Hotelling et al. | |
| 8,543,081 B2 | 9/2013 | Scott et al. | |
| 8,666,361 B2 | 3/2014 | Chu et al. | |
| 8,676,170 B2 | 3/2014 | Porrati et al. | |
| 8,784,115 B1 | 7/2014 | Chuang | |
| 8,825,445 B2 | 9/2014 | Hoffman et al. | |
| 8,910,299 B2 | 12/2014 | Michalske | |
| 8,934,963 B1 | 1/2015 | Farazi | |
| 8,990,006 B1 | 3/2015 | Wallace et al. | |
| 9,020,538 B1 | 4/2015 | White et al. | |
| 9,224,291 B2 | 12/2015 | Moll-carrillo et al. | |
| 9,557,881 B1 | 1/2017 | Jain et al. | |
| 9,589,445 B2 | 3/2017 | White et al. | |
| 9,712,629 B2 | 7/2017 | Molettiere et al. | |
| 9,813,642 B1 | 11/2017 | Chen et al. | |
| 9,817,481 B2 | 11/2017 | Pantelopoulos et al. | |
| 9,854,653 B1 | 12/2017 | Ackmann et al. | |
| 9,880,805 B1 | 1/2018 | Guralnick | |
| 9,940,682 B2 | 4/2018 | Hoffman et al. | |
| 10,300,334 B1 | 5/2019 | Chuang | |
| 10,304,347 B2 | 5/2019 | Wilson et al. | |
| 10,339,830 B2 | 7/2019 | Han et al. | |
| 10,398,381 B1 | 9/2019 | Heneghan et al. | |
| 10,777,314 B1 | 9/2020 | Williams et al. | |
| 2001/0049470 A1 | 12/2001 | Mault et al. | |
| 2002/0015024 A1 | 2/2002 | Westerman et al. | |
| 2002/0045960 A1 | 4/2002 | Phillips et al. | |
| 2002/0086774 A1 | 7/2002 | Warner | |
| 2002/0118121 A1 | 8/2002 | Lehrman et al. | |
| 2003/0023178 A1 | 1/2003 | Bischoff et al. | |
| 2003/0064860 A1 | 4/2003 | Yamashita et al. | |
| 2003/0182628 A1 | 9/2003 | Lira | |
| 2003/0216971 A1 | 11/2003 | Sick et al. | |
| 2003/0226695 A1 | 12/2003 | Mault | |
| 2004/0014567 A1 | 1/2004 | Mendel | |
| 2004/0077462 A1 | 4/2004 | Brown et al. | |
| 2004/0128286 A1 | 7/2004 | Yasushi et al. | |
| 2005/0075214 A1 | 4/2005 | Brown et al. | |
| 2005/0079905 A1 | 4/2005 | Martens | |
| 2005/0124324 A1 | 6/2005 | Thomas et al. | |
| 2005/0139852 A1 | 6/2005 | Chen et al. | |
| 2005/0172311 A1* | 8/2005 | Hjelt | A61B 5/6831 725/10 |
| 2005/0190059 A1 | 9/2005 | Wehrenberg | |
| 2005/0197063 A1 | 9/2005 | White | |
| 2005/0216867 A1 | 9/2005 | Marvit et al. | |
| 2005/0228735 A1 | 10/2005 | Duquette | |
| 2005/0272564 A1 | 12/2005 | Pyles et al. | |
| 2006/0017692 A1 | 1/2006 | Wehrenberg et al. | |
| 2006/0020174 A1 | 1/2006 | Matsumura et al. | |
| 2006/0026536 A1 | 2/2006 | Hotelling et al. | |
| 2006/0033724 A1 | 2/2006 | Chaudhri et al. | |
| 2006/0052727 A1 | 3/2006 | Palestrant | |
| 2006/0098109 A1 | 5/2006 | Ooki | |
| 2006/0106741 A1 | 5/2006 | Janarthanan | |
| 2006/0155578 A1 | 7/2006 | Eisenberger et al. | |
| 2006/0197753 A1 | 9/2006 | Hotelling | |
| 2006/0250524 A1 | 11/2006 | Roche | |
| 2007/0021269 A1 | 1/2007 | Shum | |
| 2007/0032733 A1 | 2/2007 | Burton | |
| 2007/0056727 A1 | 3/2007 | Newman | |
| 2007/0113726 A1 | 5/2007 | Oliver et al. | |
| 2007/0135043 A1 | 6/2007 | Hayes et al. | |
| 2007/0136093 A1 | 6/2007 | Rankin et al. | |
| 2007/0143433 A1 | 6/2007 | Daigle | |
| 2007/0249949 A1 | 10/2007 | Hadley | |
| 2007/0271065 A1 | 11/2007 | Gupta et al. | |
| 2008/0052945 A1 | 3/2008 | Matas et al. | |
| 2008/0058626 A1 | 3/2008 | Miyata et al. | |
| 2008/0076637 A1 | 3/2008 | Gilley et al. | |
| 2008/0086318 A1 | 4/2008 | Gilley et al. | |
| 2008/0096726 A1 | 4/2008 | Riley et al. | |
| 2008/0141135 A1 | 6/2008 | Mason et al. | |
| 2008/0150731 A1 | 6/2008 | Laukkanen et al. | |
| 2008/0161707 A1 | 7/2008 | Farringdon et al. | |
| 2008/0200312 A1 | 8/2008 | Tagliabue | |
| 2008/0300110 A1 | 12/2008 | Smith et al. | |
| 2008/0320391 A1 | 12/2008 | Lemay et al. | |
| 2009/0012988 A1 | 1/2009 | Brown | |

(56) References Cited

U.S. PATENT DOCUMENTS

| | | |
|---|---|---|
| 2009/0118100 A1 | 5/2009 | Oliver et al. |
| 2009/0164567 A1 | 6/2009 | Hara |
| 2009/0192823 A1 | 7/2009 | Hawkins et al. |
| 2009/0199130 A1 | 8/2009 | Tsern et al. |
| 2009/0205041 A1 | 8/2009 | Michalske |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0233771 A1 | 9/2009 | Quatrochi et al. |
| 2009/0262088 A1 | 10/2009 | Moll-carrillo et al. |
| 2009/0287103 A1 | 11/2009 | Pillai |
| 2009/0319243 A1 | 12/2009 | Suarez-Rivera et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1 | 3/2010 | Rottler et al. |
| 2010/0064255 A1 | 3/2010 | Rottler et al. |
| 2010/0076331 A1 | 3/2010 | Chan et al. |
| 2010/0079291 A1 | 4/2010 | Kroll et al. |
| 2010/0121700 A1 | 5/2010 | Wigder et al. |
| 2010/0145209 A1 | 6/2010 | Lee et al. |
| 2010/0179832 A1 | 7/2010 | Van deursen et al. |
| 2010/0194692 A1 | 8/2010 | Orr et al. |
| 2010/0198453 A1 | 8/2010 | Dorogusker et al. |
| 2010/0281374 A1 | 11/2010 | Schulz et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0088086 A1 | 4/2011 | Swink et al. |
| 2011/0098928 A1 | 4/2011 | Hoffman et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0167369 A1 | 7/2011 | Van Os |
| 2011/0201911 A1 | 8/2011 | Johnson et al. |
| 2011/0213276 A1* | 9/2011 | Sarussi ............... A61B 5/1118 |
| | | 600/595 |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1 | 1/2012 | Lee et al. |
| 2012/0015779 A1 | 1/2012 | Powch et al. |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0232414 A1 | 9/2012 | Mollicone et al. |
| 2012/0253485 A1* | 10/2012 | Weast ............... G06F 1/163 |
| | | 700/91 |
| 2012/0258684 A1 | 10/2012 | Franz et al. |
| 2012/0274508 A1 | 11/2012 | Brown et al. |
| 2012/0302840 A1 | 11/2012 | Kubo |
| 2012/0317167 A1 | 12/2012 | Rahman et al. |
| 2012/0326873 A1 | 12/2012 | Utter, II |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0141233 A1 | 6/2013 | Jacobs et al. |
| 2013/0143512 A1 | 6/2013 | Hernandez et al. |
| 2013/0151285 A1 | 6/2013 | Mclaren et al. |
| 2013/0184613 A1 | 7/2013 | Homsi et al. |
| 2013/0187923 A1 | 7/2013 | Yoshimoto et al. |
| 2013/0188322 A1* | 7/2013 | Lowe ............... G08C 19/16 |
| | | 361/749 |
| 2013/0197679 A1 | 8/2013 | Balakrishnan et al. |
| 2013/0198672 A1 | 8/2013 | Yoon et al. |
| 2013/0203475 A1 | 8/2013 | Kil et al. |
| 2013/0217979 A1 | 8/2013 | Blackadar et al. |
| 2013/0225118 A1 | 8/2013 | Jang et al. |
| 2013/0231575 A1* | 9/2013 | Erkkila ............... A61B 5/14551 |
| | | 600/483 |
| 2013/0231711 A1 | 9/2013 | Kaib |
| 2013/0233097 A1 | 9/2013 | Hayner et al. |
| 2013/0262155 A1 | 10/2013 | Hinkamp |
| 2013/0290013 A1 | 10/2013 | Forrester |
| 2013/0295872 A1 | 11/2013 | Guday et al. |
| 2013/0325394 A1 | 12/2013 | Yuen et al. |
| 2013/0325396 A1 | 12/2013 | Yuen et al. |
| 2013/0332286 A1 | 12/2013 | Medelius et al. |
| 2013/0345978 A1 | 12/2013 | Lush et al. |
| 2014/0038781 A1 | 2/2014 | Foley et al. |
| 2014/0067096 A1 | 3/2014 | Aibara |
| 2014/0081666 A1 | 3/2014 | Teller et al. |
| 2014/0139637 A1 | 5/2014 | Mistry et al. |
| 2014/0176346 A1 | 6/2014 | Brumback et al. |
| 2014/0176475 A1 | 6/2014 | Myers et al. |
| 2014/0189584 A1 | 7/2014 | Weng et al. |
| 2014/0199966 A1 | 7/2014 | Schushan |
| 2014/0200691 A1 | 7/2014 | Lee et al. |
| 2014/0218369 A1 | 8/2014 | Yuen et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0282153 A1 | 9/2014 | Christiansen et al. |
| 2014/0288680 A1 | 9/2014 | Hoffman et al. |
| 2014/0336796 A1 | 11/2014 | Agnew |
| 2014/0337450 A1 | 11/2014 | Choudhary et al. |
| 2014/0337451 A1 | 11/2014 | Choudhary et al. |
| 2014/0344723 A1 | 11/2014 | Malik et al. |
| 2014/0344951 A1 | 11/2014 | Brewer |
| 2014/0371887 A1 | 12/2014 | Hoffman et al. |
| 2015/0018632 A1 | 1/2015 | Khair |
| 2015/0052618 A1 | 2/2015 | Michalske |
| 2015/0057943 A1 | 2/2015 | Self et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0118657 A1 | 4/2015 | Shrake et al. |
| 2015/0130830 A1 | 5/2015 | Nagasaki et al. |
| 2015/0142689 A1 | 5/2015 | Squires |
| 2015/0153943 A1 | 6/2015 | Wang |
| 2015/0181314 A1 | 6/2015 | Swanson |
| 2015/0185967 A1 | 7/2015 | Ly et al. |

(56) References Cited

U.S. PATENT DOCUMENTS

| | | |
|---|---|---|
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220883 A1 | 8/2015 | B'far et al. |
| 2015/0269848 A1 | 9/2015 | Yuen et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0347711 A1 | 12/2015 | Soli et al. |
| 2015/0350861 A1 | 12/2015 | Soli et al. |
| 2015/0374310 A1 | 12/2015 | Lee |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0048298 A1 | 2/2016 | Choi et al. |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0065505 A1 | 3/2016 | Iskander |
| 2016/0085937 A1 | 3/2016 | Dettinger et al. |
| 2016/0089569 A1 | 3/2016 | Blahnik |
| 2016/0140828 A1 | 5/2016 | Deforest |
| 2016/0156584 A1 | 6/2016 | Hum et al. |
| 2016/0196635 A1 | 7/2016 | Cho et al. |
| 2016/0220225 A1 | 8/2016 | Wang et al. |
| 2016/0235374 A1 | 8/2016 | Miller et al. |
| 2016/0250517 A1 | 9/2016 | Tilvis et al. |
| 2016/0256741 A1* | 9/2016 | Holma .................. A61B 5/02 |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0301794 A1 | 10/2016 | Schlakman et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0053542 A1 | 2/2017 | Wilson et al. |
| 2017/0095695 A1 | 4/2017 | Mangusson et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0319941 A1 | 11/2017 | Smith et al. |
| 2017/0330297 A1 | 11/2017 | Cronin et al. |
| 2017/0333752 A1 | 11/2017 | Korkala et al. |
| 2017/0348562 A1 | 12/2017 | Jung et al. |
| 2017/0354845 A1 | 12/2017 | Williams et al. |
| 2017/0357520 A1 | 12/2017 | De vries et al. |
| 2018/0000426 A1 | 1/2018 | Li |
| 2018/0001184 A1 | 1/2018 | Tran et al. |
| 2018/0053200 A1 | 2/2018 | Cronin et al. |
| 2018/0056132 A1 | 3/2018 | Foley et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0126248 A1 | 5/2018 | Dion et al. |
| 2018/0150709 A1 | 5/2018 | Ha |
| 2018/0189077 A1 | 7/2018 | Gupta et al. |
| 2018/0272190 A1 | 9/2018 | Miura et al. |
| 2018/0329584 A1 | 11/2018 | Williams et al. |
| 2018/0345078 A1 | 12/2018 | Blahnik et al. |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0104951 A1 | 4/2019 | Valys et al. |
| 2019/0209777 A1 | 7/2019 | O'connell et al. |
| 2019/0232110 A1 | 8/2019 | Williams et al. |
| 2019/0232111 A1 | 8/2019 | Williams et al. |
| 2019/0274565 A1 | 9/2019 | Soli et al. |
| 2019/0279520 A1 | 9/2019 | Wilson et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0387982 A1 | 12/2019 | Buller |
| 2020/0014967 A1 | 1/2020 | Putnam |
| 2020/0101365 A1 | 4/2020 | Wilson et al. |
| 2020/0297249 A1 | 9/2020 | Williams et al. |
| 2020/0357522 A1 | 11/2020 | Pahwa et al. |
| 2020/0381100 A1 | 12/2020 | Williams et al. |
| 2020/0382613 A1 | 12/2020 | Sundstrom et al. |
| 2021/0007632 A1 | 1/2021 | Blahnik et al. |
| 2021/0007633 A1 | 1/2021 | Blahnik et al. |

FOREIGN PATENT DOCUMENTS

| | | |
|---|---|---|
| CN | 1397904 A | 2/2003 |
| CN | 1585943 A | 2/2005 |
| CN | 101150810 A | 3/2008 |
| CN | 101541387 A | 9/2009 |
| CN | 101651870 A | 2/2010 |
| CN | 101836894 A | 9/2010 |
| CN | 102339201 A | 2/2012 |
| CN | 102448555 A | 5/2012 |
| CN | 102804238 A | 11/2012 |
| CN | 102989159 A | 3/2013 |
| CN | 103212197 A | 7/2013 |
| CN | 103370924 A | 10/2013 |
| CN | 103403627 A | 11/2013 |
| CN | 104288983 A | 1/2015 |
| CN | 104501043 A | 4/2015 |
| CN | 106537397 A | 3/2017 |
| CN | 106709235 A | 5/2017 |
| CN | 106878550 A | 6/2017 |
| EP | 1935339 A1 | 6/2008 |
| EP | 2025368 A2 | 2/2009 |
| JP | 6-187118 A | 7/1994 |
| JP | 2001-76078 A | 3/2001 |
| JP | 2002-190007 A | 7/2002 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-230679 A | 9/2006 |
| JP | 2007-260288 A | 10/2007 |
| JP | 2008-104758 A | 5/2008 |
| JP | 2008-183339 A | 8/2008 |
| JP | 2010-12335 A | 1/2010 |
| JP | 2010-122901 A | 6/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-259253 A | 12/2011 |
| JP | 2012-59264 A | 3/2012 |
| JP | 2012-524640 A | 10/2012 |
| JP | 2012-230503 A | 11/2012 |
| JP | 2013-103020 A | 5/2013 |

(56) References Cited

FOREIGN PATENT DOCUMENTS

| | | |
|---|---|---|
| JP | 2013-117690 A | 6/2013 |
| JP | 2013-544140 A | 12/2013 |
| JP | 2016-502875 A | 2/2016 |
| JP | 2016-177151 A | 10/2016 |
| JP | 2017-134689 A | 8/2017 |
| JP | 2017-532069 A | 11/2017 |
| KR | 10-2011-0017076 A | 2/2011 |
| KR | 10-2012-0023657 A | 3/2012 |
| KR | 10-2013-0111569 A | 10/2013 |
| KR | 10-2013-0111570 A | 10/2013 |
| KR | 10-2013-0135282 A | 12/2013 |
| KR | 10-2017-0003608 A | 1/2017 |
| TW | 201210368 A1 | 3/2012 |
| TW | 201240499 A1 | 10/2012 |
| WO | 99/41682 A2 | 8/1999 |
| WO | 2002/27530 A2 | 4/2002 |
| WO | 2005/070289 A1 | 8/2005 |
| WO | 2009/129402 A1 | 10/2009 |
| WO | 2010/126825 A1 | 11/2010 |
| WO | 2012/021507 A2 | 2/2012 |
| WO | 2012/061440 A2 | 5/2012 |
| WO | 2012/078079 A2 | 6/2012 |
| WO | 2013/052789 A1 | 4/2013 |
| WO | 2013/109762 A1 | 7/2013 |
| WO | 2013/109777 A1 | 7/2013 |
| WO | 2013/109916 A1 | 7/2013 |
| WO | 2013/173838 A2 | 11/2013 |
| WO | 2014/207294 A1 | 12/2014 |
| WO | 2015/198488 A1 | 12/2015 |
| WO | 2016/036582 A2 | 3/2016 |
| WO | 2017/037242 A1 | 3/2017 |
| WO | 2012/061438 A2 | 2/2019 |
| WO | 2019/024603 A1 | 2/2019 |

OTHER PUBLICATIONS

International Search Report and Written Opinion received for PCT Patent Application No. PCT/US2018/031662, dated Sep. 27, 2018, 19 pages.
Invitation to Pay Addition Fees and Partial International Search Report received for PCT Patent Application No. PCT/US2018/031662, dated Jul. 16, 2018, 13 pages.
Non-Final Office Action received for U.S. Appl. No. 15/608,848, dated Nov. 2, 2018, 21 pages.
Office Action received for Australian Patent Application No. 2018200428, dated Nov. 15, 2018, 4 pages.
Office Action received for Japanese Patent Application No. 2016-557650, dated Nov. 9, 2018, 6 pages (3 pages of English Translation and 3 pages of Official Copy).
Office Action received for Korean Patent Application No. 10-2016-7014577, dated Oct. 31, 2018, 11 pages (5 pages of English Translation and 6 pages of Official Copy).
Cho, H. S., Satisfactory Innovative Smart-watch (fitbit force) . . . review after seven days of use, such as the amount of sleep and movement (improving sleep is the object of X-Blue), Online Available at: https://x-blueuv.blogspot.com/2013/12/fitbit-force.html, Dec. 3, 2013, 6 pages (Official Copy Only) (See Communication. under 37 CFR § 1.98(a) (3)).
Final Office Action received for U.S. Appl. No. 14/732,773, dated Jul. 13, 2018, 48 pages.
Certification of Examination received for Australian Patent Application No. 2018100158, dated Oct. 23, 2018, 2 pages.
Office Action received for Japanese Patent Application No. 2018-014096, dated Nov. 6, 2018, 15 pages (7 pages of English Translation and 8 pages of Official Copy).
Office Action received for Danish Patent Application No. PA201770191, dated Nov. 21, 2018, 4 pages.
"Graphs and Charts", available at: <https://www.teachervision.com/lesson-planning/graph-chart-teacher-resources>, retrieved on Dec. 12, 2018, 4 pages.

International Preliminary Report on Patentability received for PCT Patent Application No. PCT/US2017/035554, dated Dec. 20, 2018, 39 pages.
Non-Final Office Action received for U.S. Appl. No. 14/732,773, dated Feb. 8, 2019, 32 pages.
Office Action received for Japanese Patent Application No. 2018-068846, dated Jan. 8, 2019, 6 pages (3 pages of English Translation and 3 pages of Official copy).
Non-Final Office Action received for U.S. Appl. No. 15/183,663, dated Jul. 9, 2018, 13 pages.
Office Action received for Danish Patent Application No. PA201770423, dated Jun. 12, 2018, 7 pages.
CNET, "Google Fit's Automatic Activity Tracking is getting Smarter on Android", Available online at: https://www.youtube.conn/watch?v=lttzlCid_d8, May 18, 2016, 1 page.
Garmin, "Fenix 5x Owner's Manual", Online Available at:—https://web.archive.org/web/20180127170640/https://static.garmin.com/pumac/fenix5x_OM_EN.pdf, Jul. 2017, 42 pages.
Rainmaker, "Garmin Fenix3 New Auto Climb Functionality", Available online at: https://www.youtube.com/watch?v=iuavOSNpVRc, Feb. 19, 2015, 1 page.
Rizknows, "Tom Tom Multisport Cardio Review", Online available at:—https://www.youtube.com/watch?v=WoVCzLrSN9A, Sep. 4, 2015, 1 page.
Smith, Ian, "Garmin Fenix 5 Activity/Smart Watch Review", Online Available at:—https://www.youtube.com/watch?v=6PkQxXQxpoU, Sep. 2, 2017, 1 page.
Sportstechguides, "Garmin Fenix 5: How to Add Power Data Fields", Online Available at:—https://www.youtube.com/watch?v=ZkPptnnXEiQ, Apr. 29, 2017, 2 pages.
Sportstechguides, "Garmin Fenix 5: How to Set Up Run Alerts", Online Available at:—https://www.youtube.com/watch?v=gSMwv8vlhB4, May 13, 2017, 2 pages.
Suunto, "Suunto Spartan—Heart Rate Zones", Online Available at:—https://www.youtube.com/watch?v=aixfoCnS0OU, Mar. 19, 2018, 2 page.
"Suunto Spartan Trainer Wrist HR 1.12", Online Available at:—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Tomtom, "TomTom Runner & Multi-Sport Reference Guide", Online available at:—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Zlelik, "Garmin Fenix 5 Open Water Swimming Activity Demo", Online Available at:—https://www.youtube.com/watch?v=iSVhdvw2dcs, Jun. 9, 2017, 1 page.
Decision to Refuse received for European Patent Application No. 15771747.1, dated Aug. 10, 2018, 22 pages.
Minutes of Oral proceedings received for European Patent Application No. 15771747.1, dated Aug. 10, 2018, 11 pages.
Office Action received for Japanese Patent Application No. 2018-014096, dated Jun. 29, 2018, 20 pages (11 pages of English Translation and 9 pages of Official Copy).
Corrected Notice of Allowance received for U.S. Appl. No. 15/183,663, dated Feb. 25, 2019, 3 pages.
Extended European Search Report received for European Patent Application No. 16837432.0, dated Mar. 11, 2019, 10 pages.
Office Action received for Australian Patent Application No. 2018101855, dated Feb. 22, 2019, 4 pages.
Advisory Action received for U.S. Appl. No. 14/839,922, dated Mar. 24, 2017, 4 pages.
Final Office Action received for U.S. Appl. No. 14/599,425, dated May 19, 2017, 24 pages.
Final Office Action received for U.S. Appl. No. 14/599,425, dated Oct. 8, 2015, 20 pages.
Final Office Action received for U.S. Appl. No. 14/839,922, dated Dec. 14, 2016, 22 pages.
Intention to Grant received for Danish Patent Application No. PA201570668, dated Mar. 27, 2017, 2 pages.
International Preliminary Report on Patentability received for PCT Patent Application No. PCT/US2013/073195, dated Jun. 7, 2016, 9 pages.

(56) References Cited

OTHER PUBLICATIONS

International Preliminary Report on Patentability received for PCT Patent Application No. PCT/US2015/032474, dated Dec. 15, 2016, 7 pages.
International Preliminary Report on Patentability received for PCT Patent Application No. PCT/US2015/047282, dated Mar. 16, 2017, 26 pages.
International Search Report and Written Opinion received for PCT Patent Application No. PCT/US2015/032474, dated Aug. 19, 2015, 8 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Additional Fees received for PCT Patent Application No. PCT/US2015/047282, dated Dec. 22, 2015, 7 pages.
"Iphone User Guide for iOS 7.1 Software", Mar. 10, 2014, pp. 1-162.
Kamijo, Noboru, "Next Generation Mobile System—Watchpad1. 5", Available at <http://researcher.ibm.com/researcher/view_group_subpage.php?id=5617>, retrieved on Jul. 4, 2015, 2 pages.
Non-Final Office Action received for U.S. Appl. No. 14/503,372, dated Dec. 5, 2014, 11 pages.
Non-Final Office Action received for U.S. Appl. No. 14/599,425, dated Mar. 17, 2015, 16 pages.
Non-Final Office Action received for U.S. Appl. No. 14/599,425, dated Oct. 26, 2016, 22 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Notice of Allowance received for Chinese Patent Application No. 201520358505.5, dated Jan. 13, 2016, 3 pages (2 pages of English Translation and 1 page of Official copy).
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Korean Patent Application No. 10-2016-7033638, dated May 31, 2017, 5 pages (2 pages of English Translation and 3 pages of Official copy).
Notice of Allowance received for Taiwanese Patent Application No. 104117509, dated Mar. 31, 2017, 3 pages (Official copy only).
Notice of Allowance received for Taiwanese Patent Application No. 104128685, dated May 3, 2017, 3 pages (Official copy only).
Notice of Allowance received for U.S. Appl. No. 14/839,916, dated Aug. 31, 2016, 11 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Office Action received for Australian Patent Application No. 2015100734, dated Jul. 29, 2015, 5 pages.
Office Action received for Australian Patent Application No. 2015267240, dated Apr. 10, 2017, 5 pages.
Office Action received for Australian Patent Application No. 2015312215, dated Oct. 13, 2016, 3 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action received for Danish Patent Application No. PA201670656, dated Nov. 3, 2016, 8 pages.
Office Action received for European Patent Application No. 15730890.9, dated Aug. 3, 2017, 4 pages.
Office Action received for European Patent Application no. 15771747.1, dated Oct. 31, 2017, 7 pages.
Office Action received for Japanese Patent Application No. 2016-535045, dated May 12, 2017, 10 pages (5 pages of English Translation and 5 pages of Official copy).
Office Action received for Japanese Patent Application No. 2016-557650, dated Aug. 10, 2017, 10 pages (5 pages of English Translation and 5 pages of Official copy).
Office Action received for Korean Patent Application No. 10-2016-7033638, dated Jan. 31, 2017, 6 pages (2 pages of English Translation and 4 pages of Official copy).
Office Action received for Taiwanese Patent Application No. 104117509, dated Aug. 22, 2016, 6 pages (3 pages of English Translation and 3 pages of Official copy).
Office Action received for Taiwanese Patent Application No. 104128685, dated Jan. 4, 2017, 40 pages (15 pages of English Translation and 25 pages of Official Copy).
Search Report and Opinion received for Danish Patent Application No. PA201770191, dated Jun. 30, 2017, 9 pages.
Notice of Allowance received for U.S. Appl. No. 15/183,663, dated Jan. 17, 2019, 6 pages.
Notice of Allowance received for U.S. Appl. No. 15/616,480, dated Jan. 3, 2019, 8 pages.
Apple, "Iphone Users Guide", Available at: http://mesnotices.20minutes.fr/manuel-notice-mode-emploi/APPLE/IPHONE%2D%5FE#, Retrieved on Mar. 27, 2008, Jun. 2007, 137 pages.
Codrington, Simon, "Intuitive Scrolling Interfaces with Css Scroll Snap Points", Online Available at: https://www.sitepoint.com/intuitive-scrolling-interfaces-with-css-scroll-snap-points/, Dec. 8, 2015, 14 pages.
"Dwprogressbar V2: Stepping and Events", Aug. 31, 2008, 4 pages.
Extended European Search Report received for European Patent Application No. 18154145.9, dated Mar. 2, 2018, 8 pages.
Final Office Action received for U.S. Appl. No. 12/205,847, dated Apr. 25, 2012, 42 pages.
International Preliminary Report on Patentability received for PCT Application No. PCT/US2016/037686, dated Mar. 1, 2018, 12 pages.
International Search Report and Written Opinion received for PCT Patent Application No. PCT/US2017/035554, dated Sep. 22, 2017, 42 pages.
Invitation to Pay Additional Fees received for PCT Patent Application No. PCT/US2017/035554, dated Jul. 20, 2017, 2 pages.
Jenbsjourney, "Wondering About a Fitbit?", Available at: https://jenbsjourney.blogspot.kr/2013/08/wondering-about-fitbit.html, Aug. 6, 2013, 12 pages.
"Mugs", Online Available at: https://web.archive.org/web/20151029034349/http://le-mugs.com/, Published on Oct. 29, 2015.
"My Calstep", Online Available at: http://www.surprisesoftware.com/mycalstep/, retrieved from the Wayback Machine, Published on May 9, 2007, 2 pages.
Non-Final Office Action received for U.S. Appl. No. 12/205,847, dated Oct. 3, 2011, 59 pages.
Non-Final Office Action received for U.S. Appl. No. 14/732,773, dated Jan. 19, 2018, 45 pages.
Notice of Acceptance received for Australian Patent Application No. 2015312215, dated Oct. 9, 2017, 3 pages.

(56) References Cited

OTHER PUBLICATIONS

Notice of Allowance received for Japanese Patent Application No. 2016-535045, dated Mar. 2, 2018, 4 pages (1 page of English Translation and 3 pages of Official copy).
Notice of Allowance received for U.S. Appl. No. 12/205,847, dated Aug. 20, 2012, 13 pages.
Notice of Allowance received for U.S. Appl. No. 14/839,916, dated Jan. 10, 2018, 19 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018200428, dated Mar. 7, 2018, 4 pages.
Office Action received for Danish Patent Application No. PA201670656, dated May 30, 2018, 5 pages.
Office Action received for Danish Patent Application No. PA201770191, dated Jan. 25, 2018, 3 pages.
Office Action received for European Patent Application No. 13811085.3, dated Apr. 20, 2018, 15 pages.
Office Action received for European Patent Application No. 18154145.9, dated Apr. 3, 2018, 6 pages.
Office Action received for Japanese Patent Application No. 2016-557650, dated Apr. 13, 2018, 9 pages (5 pages of English Translation and 4 pages of Official copy).
Office Action received for Korean Patent Application No. 10-2016-7014577, dated Dec. 26, 2017, 14 pages (6 pages of English Translation and 8 pages of Official copy).
Razykdreviews, "In Depth Review of Apple Watch Activity and Workout App", available at: URL: https://www.youtube.com/watch?v=GkKl3qlK0ow, May 11, 2015, 1 page.
Rizknows, "Garmin Connect Mobile App—Review #2", https://www.youtube.com/watch?v=7my3wMpeRbE, Oct. 22, 2015, 1 page.
Search Report and Opinion received for Danish Patent Application No. PA201770423, dated Oct. 4, 2017, 10 pages.
Summons to Attend Oral Proceedings received for European Patent Application No. 13811085.3, dated Jan. 26, 2018, 14 pages.
Summons to Attend Oral Proceedings received for European Patent Application No. 15771747.1, mailed on May 25, 2018, 17 pages.
Utilization of Galaxy S4—S Health, Chaton and Samsung Hub, Jun. 12, 2013, 25 pages (Official copy only) (See Communication under 37 CFR § 1.98(a) (3)).
Decision to Refuse received for European Application No. 13811085.3, dated Sep. 11, 2018, 31 pages.
Minutes of the Oral Proceedings received for European Application No. 13811085.3, mailed on Sep. 11, 2018, 3 pages.
Office Action received for Chinese Patent Application No. 201580037927.5, dated Jul. 20, 2018, 21 pages (6 pages of English Translation and 15 pages of Official Copy).
Corrected Notice of Allowance received for U.S. Appl. No. 15/183,663, dated Mar. 27, 2019, 2 pages.
Notice of Allowance received for Japanese Patent Application No. 2016-557650, datedd Apr. 9, 2019, 4 pages (1 page of English Translation and 3 pages of Official Copy).
Office Action received for Chinese Patent Application No. 201380081349.6, dated Feb. 26, 2019, 12 pages (6 pages of English Translation and 6 pages of Official Copy).
Office Action received for Chinese Patent Application No. 201680047983.1, dated Mar. 18, 2019, 18 pages (6 pages of English Translation and 12 pages of Official Copy).
Office Action received for Chinese Patent Application No. 201810105846.X, dated Feb. 25, 2019, 10 pages (5 pages of English Translation and 5 pages of Official copy).
Office Action received for Danish Patent Application No. PA201770423, dated Mar. 29, 2019, 6 pages.
Office Action received for Germany Patent Application No. 112015002326.7, dated Feb. 20, 2019, 7 pages (2 pages of English Translation and 5 pages of Official Copy).
Supplemental Notice of Allowance received for U.S. Appl. No. 15/616,480, dated Mar. 28, 2019, 2 pages.

"Visual Pace Alarm app", Available Online at: https://apps.garmin.com/en-US/apps/3940f3a2-4847-4078-a911-d77422966c82, Oct. 19, 2016, 1 page.
Teunmo, "Data field: Visual Pace Alarm", Garmin Forum; Available online at: https://forunns.garmin.com/forum/developers/connect-iq/connect-iq-showcase/115996-data-field-visual-pace-alarm, Nov. 17, 2015, 10 pages.
"Multi-Set Bar Chart", The Data Visualization Catalogue, Available Online at: https://datavizcatalogue.com/methods/multiset_barchart.html, Feb. 8, 2014, 3 pages.
Office Action received for Chinese Patent Application No. 201580037927.5, dated Apr. 22, 2019, 9 pages(4 pages of English Translation and 5 pages of Official Copy).
Evergreen, et al., "Bar Chart", Better Evaluation, Available Online at: https://www.betterevaluation.org/en/evaluation-options/BarChart, Oct. 31, 2014, 8 pages.
Final Office Action received for U.S. Appl. No. 14/732,773, dated Jun. 21, 2019, 32 pages.
Final Office Action received for U.S. Appl. No. 15/608,848, dated Jun. 26, 2019, 27 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Intention to Grant received for Danish Patent Application No. PA201870379, dated May 2, 2019, 2 pages.
Non-Final Office Action Received for U.S. Appl. No. 16/144,864, dated Dec. 18, 2018, 19 pages.
Non-Final Office Action received for U.S. Appl. No. 15/627,069, dated Jun. 21, 2019, 22 pages.
Non-Final Office Action received for U.S. Appl. No. 16/144,849, dated Dec. 31, 2018, 28 pages.
Notice of Allowance received for Korean Patent Application No. 10-2016-7014577, dated May 30, 2019, 5 pages (2 pages of English Translation and 3 pages of Official Copy).
Office Action received for Danish Patent Application No. PA201870378, dated Feb. 25, 2019, 3 pages.
Office Action received for Danish Patent Application No. PA201870379, dated Feb. 28, 2019, 3 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Non-Final Office Action received for U.S. Appl. No. 15/600,243, dated Jun. 27, 2019, 17 Pages.
Office Action received for Japanese Patent Application No. 2018-014096, dated May 8, 2019, 14 pages (7 pages of English Translation and 7 pages of Official Copy).
Office Action Received for Danish Patent Application No. PA201670656, dated May 2, 2019, 4 pages.
Partial Supplementary European Search Report received for European Patent Application No. 17810749.6, dated Apr. 25, 2019, 8 pages.
Applicant Initiated Interview Summary received for U.S. Appl. No. 16/144,849, dated Jan. 21, 2020, 6 pages.
Corrected Notice of Allowance received for U.S. Appl. No. 15/600,243, dated Feb. 5, 2020, 3 pages.
Non-Final Office Action received for U.S. Appl. No. 16/144,864, dated Jan. 31, 2020, 29 pages.
Applicant Initiated Interview Summary received for U.S. Appl. No. 16/144,735, dated Jun. 18, 2020, 3 pages.
Applicant Initiated Interview Summary received for U.S. Appl. No. 16/144,753, dated Jun. 18, 2020, 3 pages.
Applicant-Initiated Interview Summary received for U.S. Appl. No. 16/144,864, dated Jun. 22, 2020, 3 pages.
Office Action received for Australian Patent Application No. 2017277971, dated Jun. 3, 2020, 3 pages.

(56) References Cited

OTHER PUBLICATIONS

Notice of Allowance received for Japanese Patent Application No. 2018-068846, dated Dec. 9, 2019, 4 pages (1 page of English Translation and 3 pages of Official Copy).
Notice of Allowance received for U.S. Appl. No. 14/732,773, dated Dec. 18, 2019, 21 pages.
Notice of Allowance received for U.S. Appl. No. 15/600,243, dated Dec. 12, 2019, 7 pages.
Office Action received for Chinese Patent Application No. 201680047983.1, dated Nov. 28, 2019, 9 pages (4 pages of English Translation and 5 pages of Official Copy).
Office Action received for Korean Patent Application No. 10-2019-7025781, dated Nov. 26, 2019, 10 pages (4 pages of English Translation and 6 pages of Official Copy).
Notice of Allowance received for Chinese Patent Application No. 201580037927.5, dated Oct. 17, 2019, 3 pages (1 page of English Translation and 2 pages of Official Copy).
Office Action received for Danish Patent Application No. PA201770191, dated Oct. 25, 2019, 4 pages.
Corrected Notice of Allowance received for U.S. Appl. No. 15/600,243, dated Mar. 13, 2020, 3 pages.
Final Office Action received for U.S. Appl. No. 15/627,069, dated Mar. 2, 2020, 22 pages.
Non-Final Office Action received for U.S. Appl. No. 16/138,809, dated Feb. 28, 2020, 22 pages.
Non-Final Office Action received for U.S. Appl. No. 16/144,753, dated Mar. 5, 2020, 9 pages.
Notice of Allowance received for Chinese Patent Application No. 201810105846.X, dated Feb. 18, 2020, 2 pages (1 page of English Translation and 1 page of Official Copy).
Notice of Allowance received for U.S. Appl. No. 16/144,849, dated Mar. 6, 2020, 9 pages.
Office Action received for Australian Patent Application No. 2019100495, dated Mar. 6, 2020, 3 pages.
Office Action received for Danish Patent Application No. PA201870380, dated Mar. 5, 2020, 2 pages.
Office Action received for Japanese Patent Application No. 2019-162293, dated Jan. 31, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy).
Wesley, "Apple Watch Series 1", Online available at: http://toolbox.info/blog/archives/1737-unknown.html, May 28, 2015, 5 pages (Official copy only) (See Communication under 37 CFR § 1.98(a) (3)).
Youtube, "Apple Watch Series 3", Online available at: https://www.youtube.com/watch?v=iBPr9gEti<K8, Nov. 21, 2017, 15 pages. (Official copy only) (See Communication under 37 CFR § 1.98(a) (3)).
Corrected Notice of Allowance received for U.S. Appl. No. 14/732,773, dated Mar. 24, 2020, 3 pages.
Corrected Notice of Allowance received for U.S. Appl. No. 15/600,243, dated Mar. 31, 2020, 5 pages.
Office Action received for Australian Patent Application No. 2019100495, dated Mar. 16, 2020, 3 pages.
Supplemental Notice of Allowance received for U.S. Appl. No. 16/144,849, dated Mar. 31, 2020, 2 pages.
Office Action received for Chinese Patent Application No. 20180105846.X, dated Aug. 27, 2019, 12 pages (5 pages of English Translation and 7 pagesof Official Copy).
Notice of Acceptance received for Australian Patent Application No. 2019201583, dated Jul. 15, 2019, 3 pages.
Advisory Action received for U.S. Appl. No. 16/144,864, dated Jul. 6, 2020, 6 pages.
Applicant-Initiated Interview Summary received for U.S. Appl. No. 15/705,849, dated Jun. 29, 2020, 3 pages.
Office Action Received for Danish Patent Application No. PA201670656, dated Jul. 1, 2020, 4 pages.

Office Action received for Japanese Patent Application No. 2019-044107, dated May 29, 2020, 6 pages (3 pages of English Translation and 3 pages of Official Copy).
Office Action received for Chinese Patent Application No. 201810105846.X, dated Nov. 28, 2019, 9 pages (5 pages of English Translation and 4 pages of Official Copy).
Office Action received for Danish Patent Application No. PA201870378, dated Jan. 6, 2020, 3 pages.
Office Action received for European Patent Application No. 16837432.0, dated Jan. 10, 2020, 7 pages.
Office Action received for European Patent Application No. 19721883.7, dated Jan. 10, 2020, 4 pages.
Applicant Initiated Interview Summary received for U.S. Appl. No. 15/608,848, dated May 12, 2020, 5 pages.
Final Office Action received for U.S. Appl. No. 15/705,849, dated May 1, 2020, 17 pages.
Final Office Action received for U.S. Appl. No. 16/144,735, dated May 4, 2020, 12 pages.
Non-Final Office Action received for U.S. Appl. No. 16/377,892, dated May 21, 2020, 9 pages.
Notice of Acceptance received for Australian Patent Application No. 2019222943, dated May 5, 2020, 3 pages.
Applicant-Initiated Interview Summary received for U.S. Appl. No. 16/138,809, dated Jun. 9, 2020, 7 pages.
Final Office Action received for U.S. Appl. No. 16/144,864, dated May 28, 2020, 29 pages.
Non-Final Office Action received for U.S. Appl. No. 15/627,069, dated May 26, 2020, 25 pages.
Non-Final Office Action received for U.S. Appl. No. 16/378,136, dated Jun. 2, 2020, 8 pages.
Office Action received for European Patent Application No. 19721883.7, dated May 28, 2020, 11 pages.
Applicant Initiated Interview Summary received for U.S. Appl. No. 16/144,864, dated Apr. 29, 2020, 4 pages.
Non-Final Office Action received for U.S. Appl. No. 16/418,786, dated Apr. 24, 2020, 16 pages.
Notice of Allowance received for U.S. Appl. No. 16/144,849, dated Apr. 17, 2020, 2 pages.
Office Action received for Chinese Patent Application No. 201710439448.7, dated Mar. 27, 2020, 13 pages (7 pages of English Translation and 6 pages of Official Copy).
Applicant-Initiated Interview Summary received for U.S. Appl. No. 15/705,849, dated Feb. 14, 2020, 3 pages.
Corrected Notice of Allowance received for U.S. Appl. No. 14/732,773, dated Feb. 10, 2020, 3 pages.
Non-Final Office Action received for U.S. Appl. No. 15/608,848, dated Feb. 6, 2020, 12 pages.
Non-Final Office Action received for U.S. Appl. No. 16/144,735, dated Feb. 19, 2020, 10 pages.
Notice of Allowance received for U.S. Appl. No. 16/144,671, dated Feb. 10, 2020, 17 pages.
Office Action received for Chinese Patent Application No. 201380081349.6, dated Jan. 16, 2020, 11 pages (6 pages of English Translation and 5 pages of Official Copy).
Office Action received for Japanese Patent Application No. 2018-014096, dated Jan. 6, 2020, 17 pages (8 pages of English Translation and 9 pages of Official Copy).
Advisory Action received for U.S. Appl. No. 16/144,864, dated Jul. 29, 2019, 6 pages.
Advisory Action received for U.S. Appl. No. 14/732,773, dated Aug. 23, 2019, 6 pages.
Advisory Action received for U.S. Appl. No. 16/144,849, dated Aug. 12, 2019, 5 pages.
Applicant Initiated Interview Summary received for U.S. Appl. No. 15/627,069, dated Nov. 4, 2019, 6 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Certificate of Examination received for Australian Patent Application No. 2018101855, dated Aug. 6, 2019, 2 pages.
Decision to Grant received for Danish Patent Application No. PA201870379, dated Jul. 5, 2019, 2 pages.

(56) References Cited

OTHER PUBLICATIONS

"Fitbit App", Available online at: <http://web.archive.org/web/20180114083150/https://www.fitbit.com/au/app>, Jan. 14, 2018, 8 pages.
International Search Report and Written Opinion received for PCT Patent Application No. PCT/US2019/024570, dated Aug. 8, 2019, 18 pages.
Non-Final Office Action received for U.S. Appl. No. 15/705,849, dated Nov. 12, 2019, 15 pages.
Non-Final Office Action received for U.S. Appl. No. 16/144,849, dated Sep. 17, 2019, 9 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081349.6, dated Jul. 15, 2019, 10 pages (5 pages of English Translation and 5 pages of Official copy).
Office Action received for European Patent Application No. 17810749.6, dated Aug. 20, 2019, 9 pages.
Supplementary European Search Report received for European Patent Application No. 17810749.6, dated Aug. 6, 2019, 6 pages.
International Preliminary Report on Patentability received for PCT Patent Application No. PCT/US2018/031662, dated Nov. 28, 2019, 12 pages.
Applicant Initiated Interview Summary received for U.S. Appl. No. 15/608,848, dated Oct. 26, 2020, 3 pages.
Applicant-Initiated Interview Summary received for U.S. Appl. No. 16/144,753, dated Nov. 4, 2020, 3 pages.
European Search Report received for European Patent Application No. 20182116.2, dated Oct. 21, 2020, 4 pages.
Final Office Action received for U.S. Appl. No. 15/627,069, dated Oct. 20, 2020, 25 pages.
Notice of Allowance received for U.S. Appl. No. 15/705,849, dated Oct. 16, 2020, 14 pages.
Notice of Allowance received for U.S. Appl. No. 16/144,735, dated Oct. 28, 2020, 13 pages.
Office Action received for Japanese Patent Application No. 2020-104679, dated Sep. 18, 2020, 13 pages (7 pages of English Translation and 6 pages of Official Copy).
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Korean Patent Application No. 10-2019-7025538, dated Aug. 15, 2020, 8 pages (4 pages of English Translation and 4 pages of Official Copy).
Office Action received for Australian Patent Application No. 2019250251, dated Aug. 6, 2020, 3 pages.
Summons to Attend Oral Proceedings received for European Patent Application No. 17810749.6, dated Aug. 12, 2020, 11 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
Non-Final Office Action received for U.S. Appl. No. 16/894,309, dated Oct. 15, 2020, 24 pages.
Notice of Allowance received for U.S. Appl. No. 16/144,864, dated Sep. 29, 2020, 2 pages.
Notice of Allowance received for U.S. Appl. No. 16/556,023, dated Oct. 15, 2020, 8 pages.
Result of Consultation received for European Patent Application No. 19721883.7, dated Oct. 7, 2020, 3 pages.
International Search Report and Written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Result of Consultation received for European Patent Application No. 18154145.9, dated Sep. 4, 2020, 3 pages.
Search Report and Opinion received for Danish Patent Application No. PA201970532, dated Nov. 8, 2019, 9 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Chinese Patent Application No. 201680047983.1, dated Jul. 1, 2020, 6 pages (3 pages of English Translation and 3 pages of Official Copy).
Applicant-Initiated Interview Summary received for U.S. Appl. No. 15/627,069, dated Jul. 20, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Notice of Allowance received for U.S. Appl. No. 16/144,735, dated Jul. 21, 2020, 13 pages.
Office Action received for Australian Patent Application No. 2018268972, dated Jul. 9, 2020, 4 pages.
Final Office Action received for U.S. Appl. No. 16/144,753, dated Sep. 22, 2020, 9 pages.
Invitation to Pay Additional Fees received for PCT Patent Application No. PCT/US2020/035199, dated Sep. 8, 2020, 12 pages.
Summons to Attend Oral Proceedings received for European Patent Application No. 18154145.9, mailed on Sep. 17, 2020, 11 pages.
Result of Consultation received for European Patent Application No. 18154145.9, dated Nov. 30, 2020, 17 pages.
Notice of Allowance received for Japanese Patent Application No. 2018-014096, dated Jan. 5, 2021, 3 pages (1 page of English Translation and 2 pages of Official Copy).
Intention to Grant received for Danish Patent Application No. PA201670656, dated Jan. 18, 2021, 2 pages.
Adeniyi Samuel, "How to connect a second PS4 controller to a PlayStation 4 console", Online available on: —https://www.youtube.com/watch?v=mOZX_SrNISE, May 28, 2017, 2 pages.
Allison Conor, "Working out with Fiit's wearable-powered boutique fitness classes", Online available at: —<https://www.wareable.com/wearable-tech/fiit-fitness-classes-review-3849>, May 14, 2018, 8 pages.

(56) References Cited

OTHER PUBLICATIONS

Applicant Initiated Interview Summary received for U.S. Appl. No. 16/894,309, dated Jan. 26, 2021, 3 pages.
Applicant-Initiated Interview Summary received for U.S. Appl. No. 15/627,069, dated Jan. 22, 2021, 4 pages.
Applicant-Initiated Interview Summary received for U.S. Appl. No. 16/138,809, dated Dec. 16, 2020, 7 pages.
Bagala et al., "Evaluation of Accelerometer-Based Fall Detection Algorithms on Real-World Falls", PloS One, vol. 7, No. 5, May 16, 2012, 9 pages.
Board Decision received for Chinese Patent Application No. 201380081349.6, dated Nov. 23, 2020, 2 pages (1 page of English Translation and 1 page of Official Copy).
Decision to Refuse received for European Patent Application No. 17810749.6, dated Jan. 29, 2021, 24 pages.
Extended European Search Report received for European Patent Application No. 20203526.7, dated Jan. 29, 2021, 13 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Final Office Action received for U.S. Appl. No. 16/418,786, dated Jan. 13, 2021, 14 pages.
Hamilton Jim, "Peloton Tips", Online available on: - <https://www.youtube.com/watch?app=desktop&v=OneXtB0kaD4>, Oct. 22, 2015, 3 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/035199, dated Oct. 30, 2020, 20 pages.
Minutes of the Oral Proceedings received for European Patent Application No. 17810749.6, dated Jan. 26, 2021, 8 pages.
Non-Final Office Action received for U.S. Appl. No. 16/820,383, dated Dec. 14, 2020, 11 pages.
Non-Final Office Action received for U.S. Appl. No. 17/031,859, dated Dec. 15, 2020, 13 pages.
Non-Final Office Action received for U.S. Appl. No. 17/031,874, dated Dec. 28, 2020, 14 pages.
Notice of Acceptance received for Australian Patent Application No. 2018268972, dated Dec. 18, 2020, 3 pages.
Notice of Allowance received for Chinese Patent Application No. 201710439448.7, dated Jan. 26, 2021, 2 pages (1 page of English Translation and 1 page of Official Copy).
Notice of Allowance received for Japanese Patent Application No. 2020-104679, dated Jan. 4, 2021, 4 pages (1 pages of English Translation and 3 pages of Official Copy).
Notice of Allowance received for U.S. Appl. No. 16/144,753, dated Dec. 4, 2020, 22 pages.
Notice of Allowance received for U.S. Appl. No. 16/556,023, dated Jan. 13, 2021, 8 pages.
Office Action received for Chinese Patent Application No. 201710439448.7, dated Oct. 10, 2020, 19 pages (8 pages of English Translation and 11 pages of Official Copy).
Office Action received for European Patent Application No. 16837432.0, dated Jan. 27, 2021, 7 pages.
Office Action received for European Patent Application No. 20182116.2, dated Nov. 6, 2020, 9 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7025781, dated Oct. 30, 2020, 10 pages (4 pages of English Translation and 6 pages of Official Copy).
Office Action received for Korean Patent Application No. 10-2019-7033834, dated Jan. 22, 2021, 13 pages (6 pages of English Translation and 7 pages of Official Copy).
Result of Consultation received for European Patent Application No. 17810749.6, dated Dec. 15, 2020, 3 pages.
Result of Consultation received for European Patent Application No. 17810749.6, dated Jan. 18, 2021, 3 pages.
Result of Consultation received for European Patent Application No. 17810749.6, dated Jan. 21, 2021, 18 pages.
Search Report and Opinion received for Danish Patent Application No. PA202070614, dated Jan. 14, 2021, 9 pages.
Supplemental Notice of Allowance received for U.S. Appl. No. 16/556,023, dated Feb. 3, 2021, 2 pages.
Vicky's Blog, "How to Log in to PS4 Automatically with Particular User?", Online available on: —https://www.youtube.com/watch?v=kqdlzXAvOkY, May 30, 2018, 3 pages.
Yoyodavid, "How to Use Multiple Accounts on the Playstation 4", Online available at: —https://www.youtube.com/watch?v=5V2lobRMeKE, Jan 9, 2014, 3 pages.

* cited by examiner

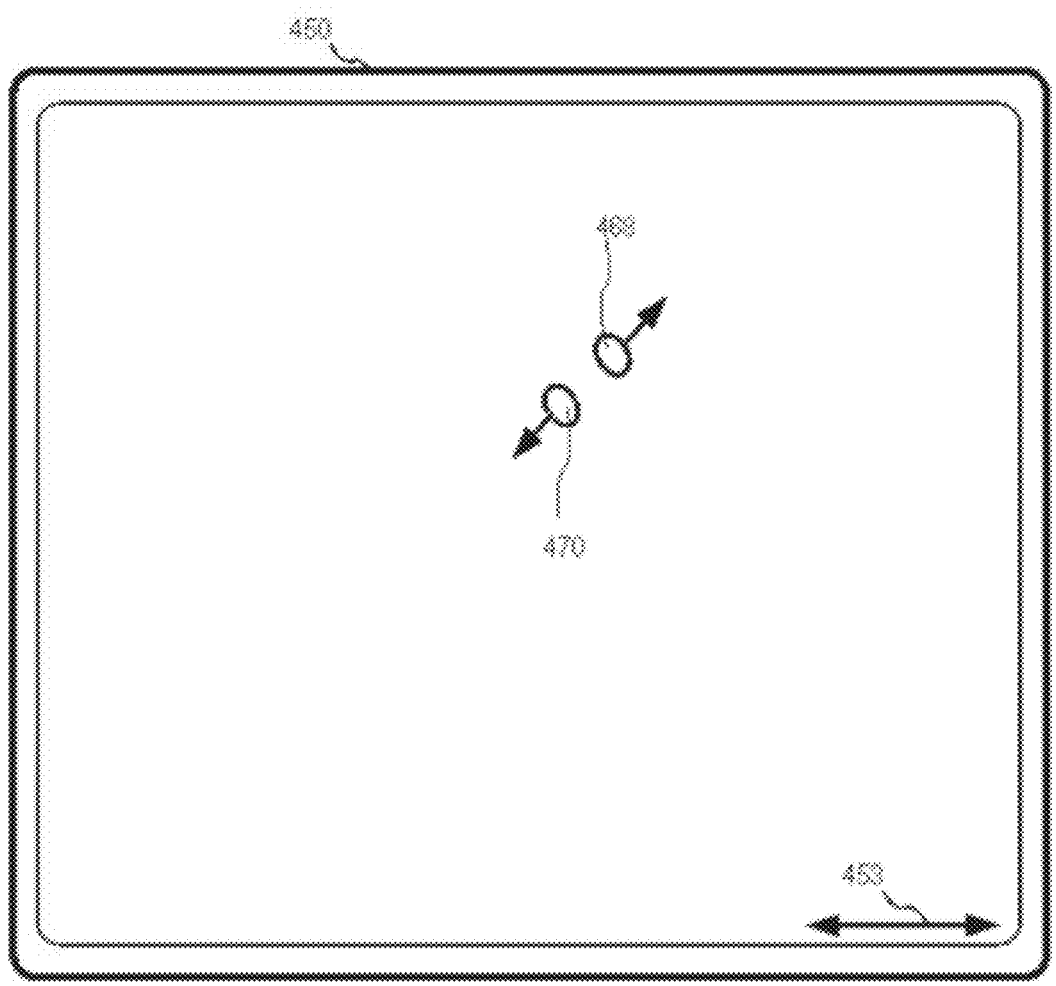
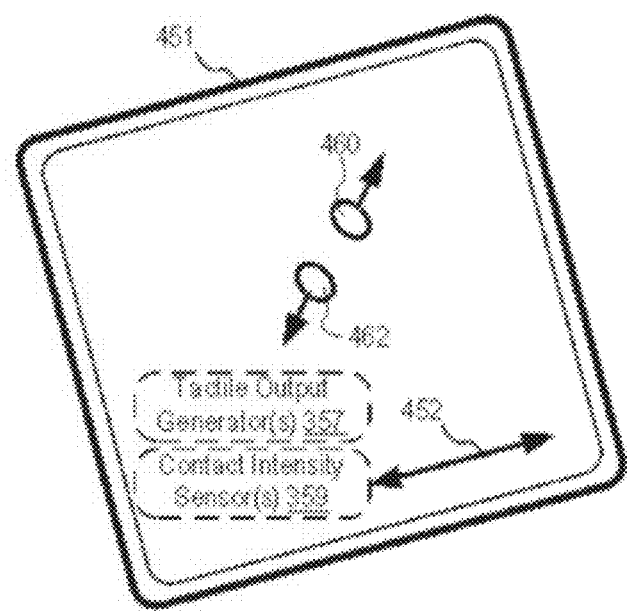
FIG. 4B

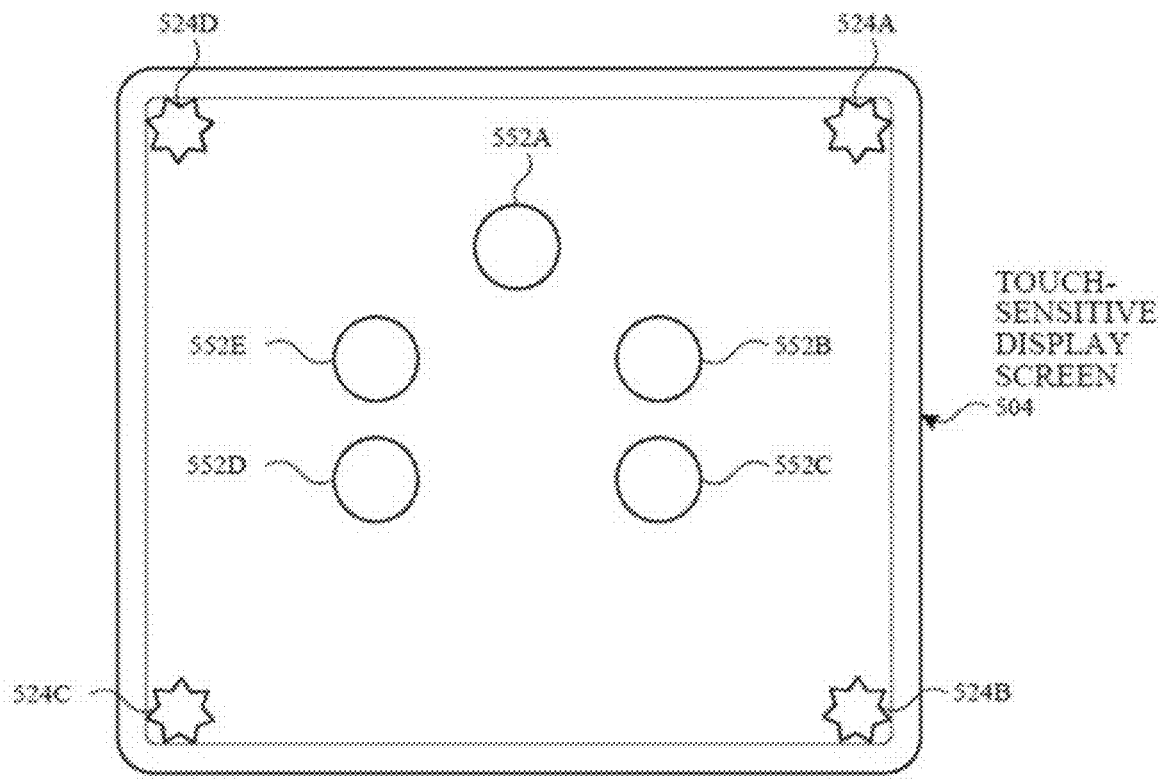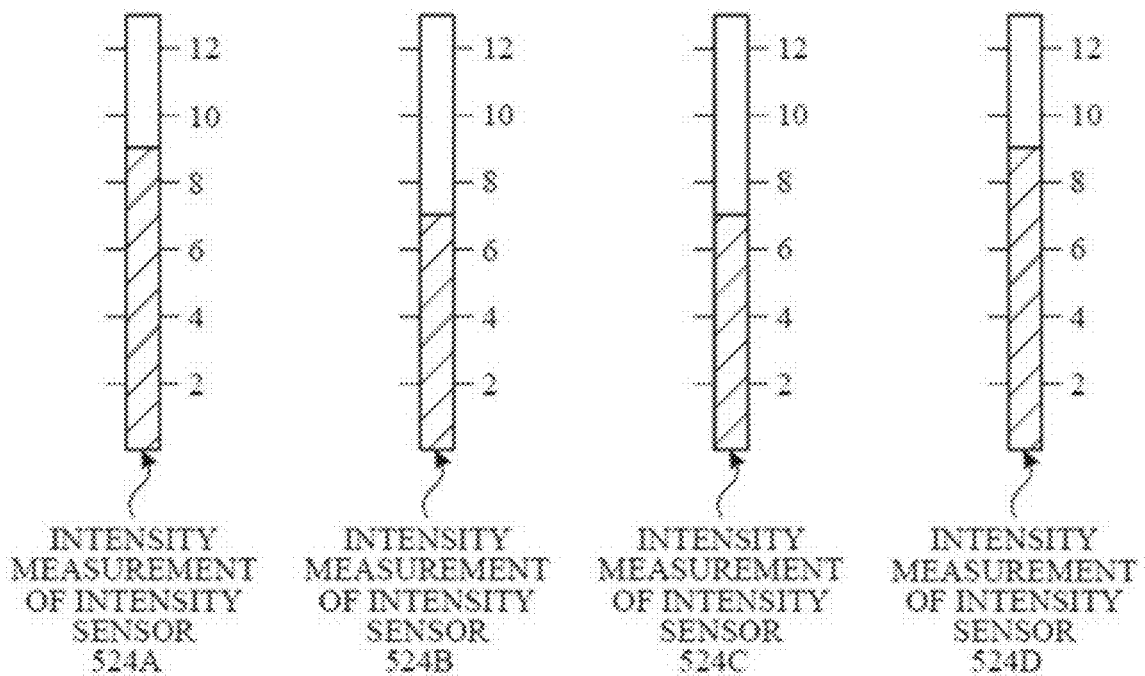
FIG. 5C

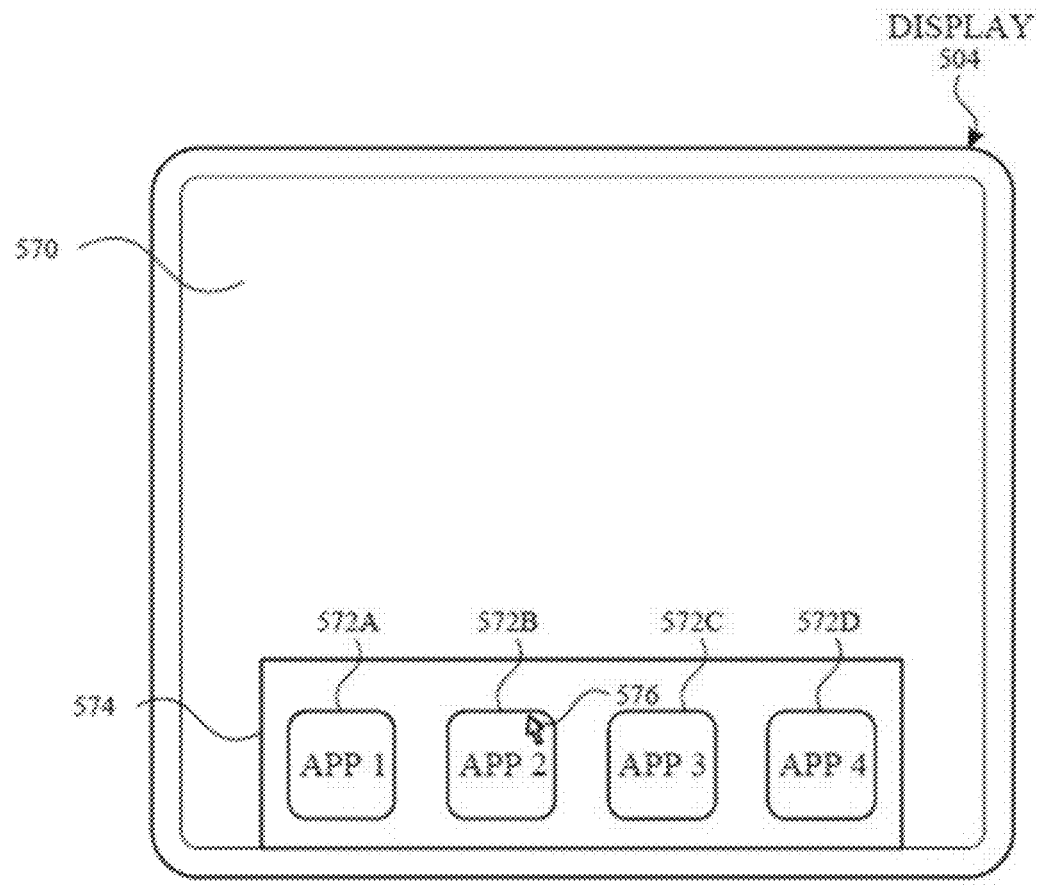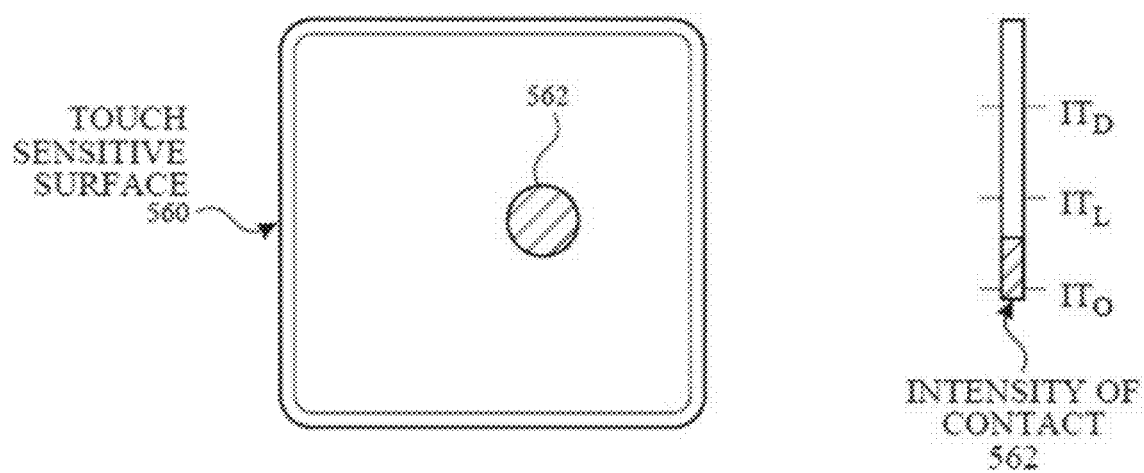
FIG. 5E

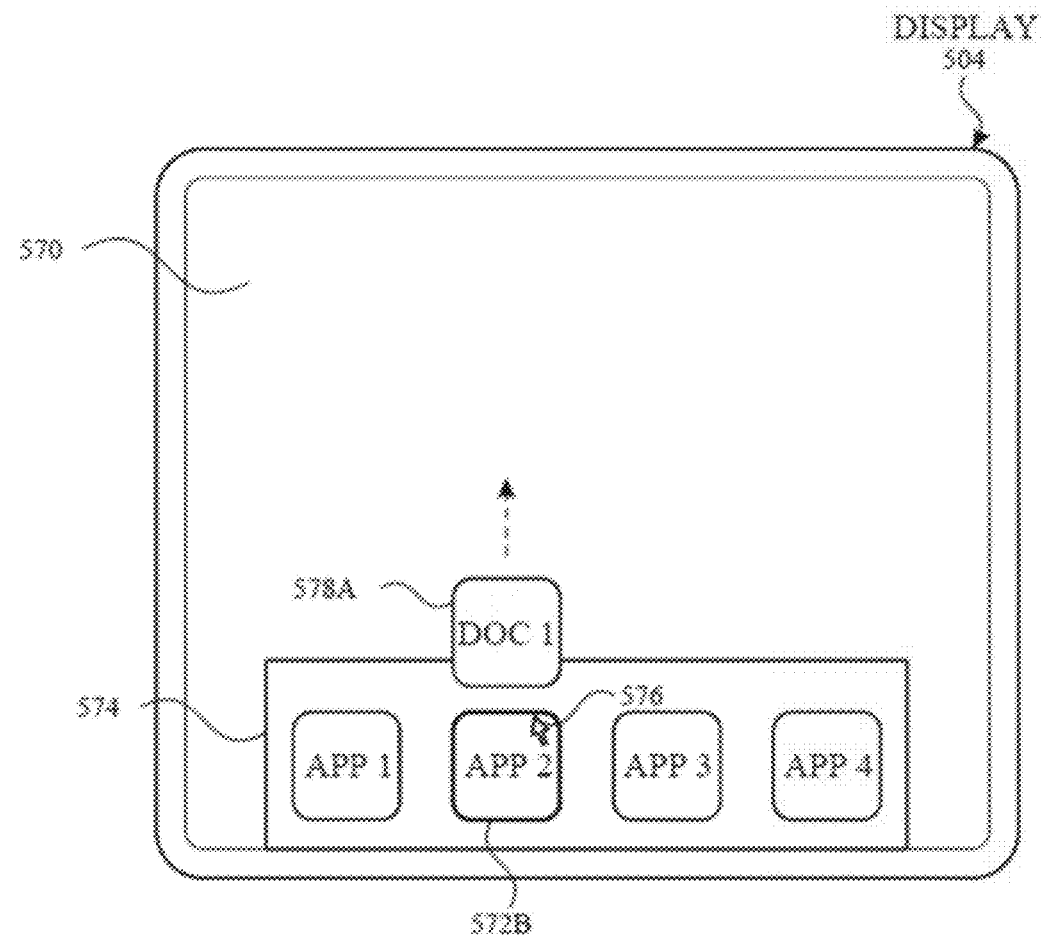
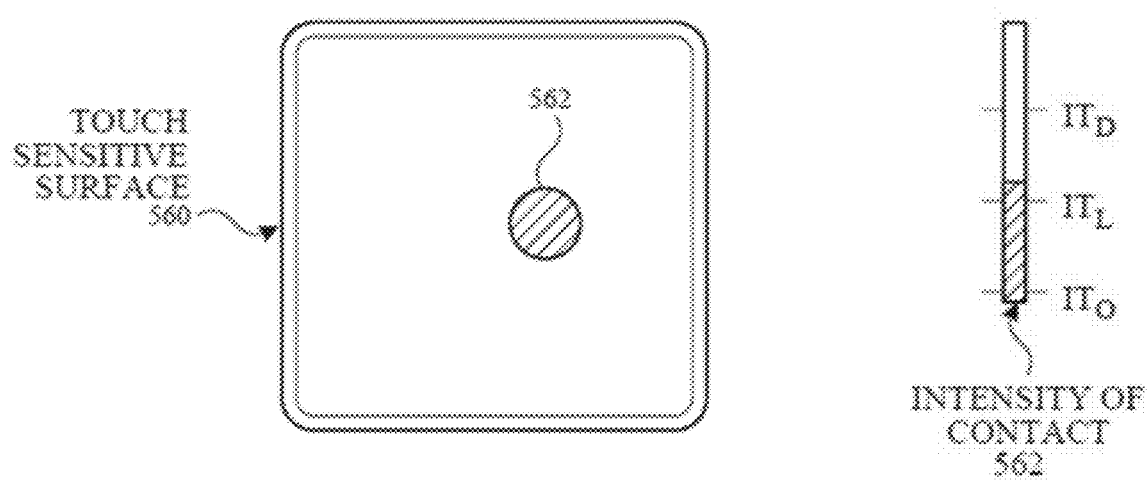
FIG. 5F

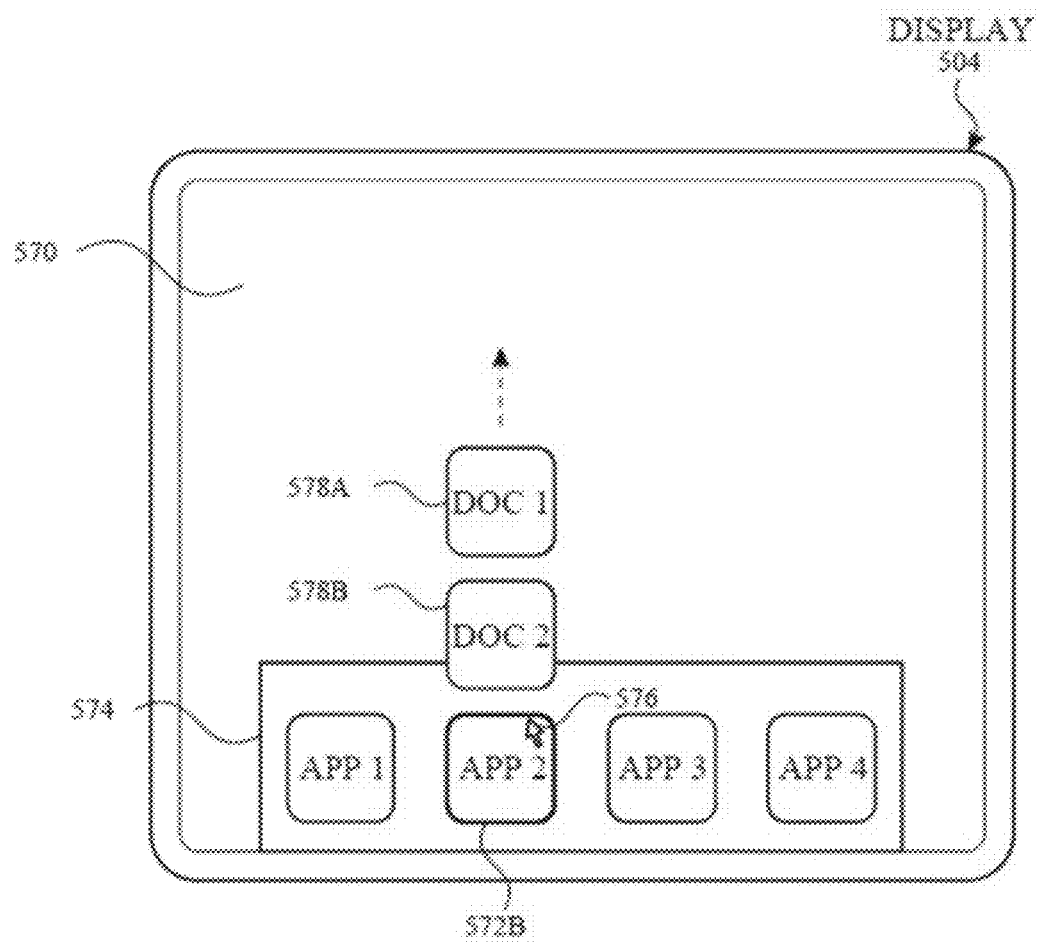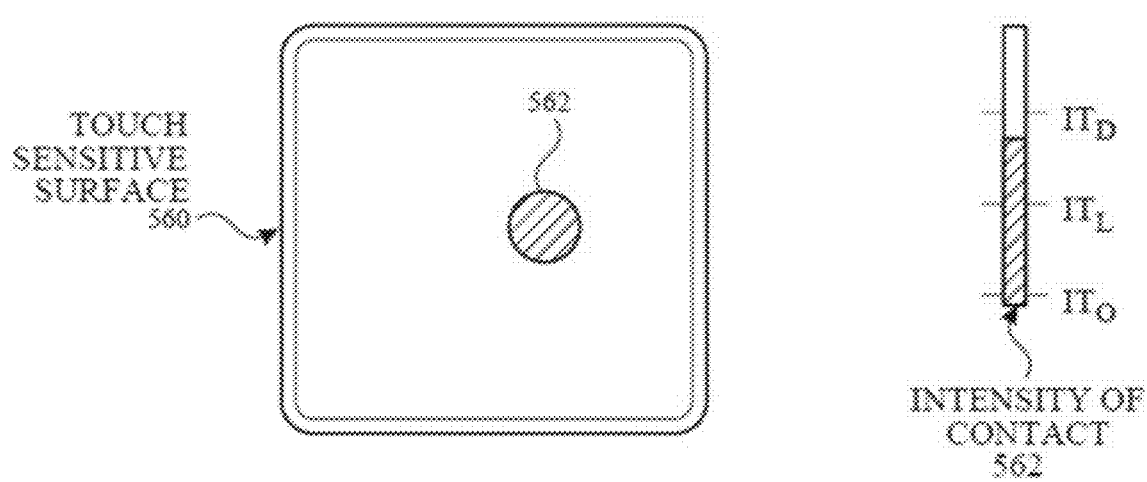
FIG. 5G

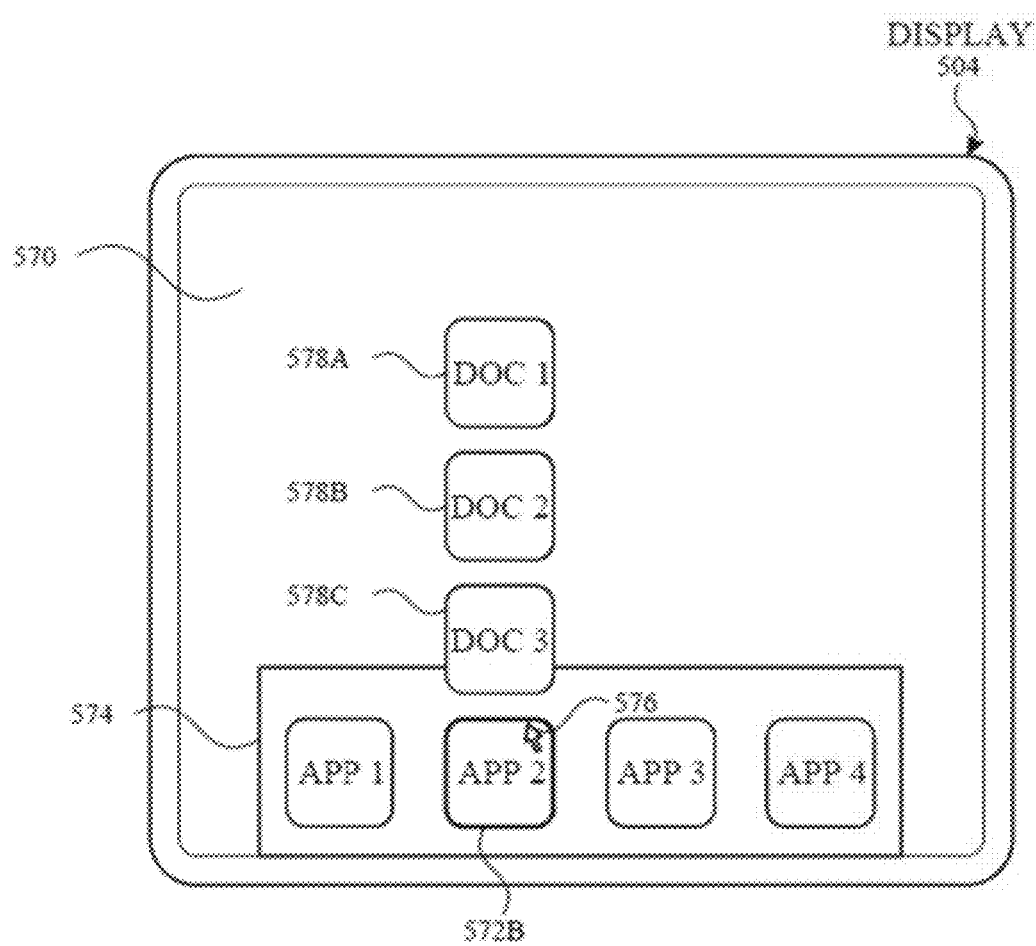
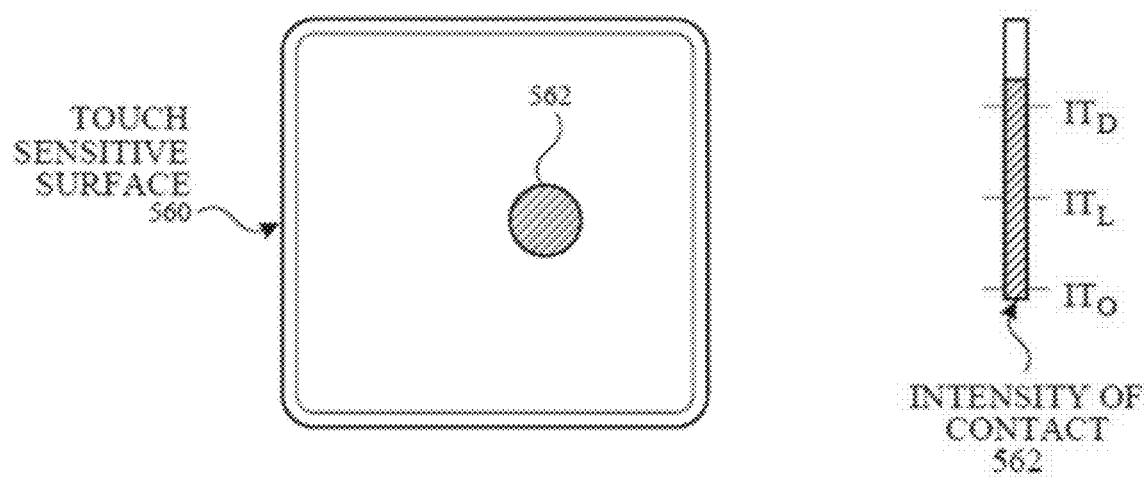
FIG. 5H

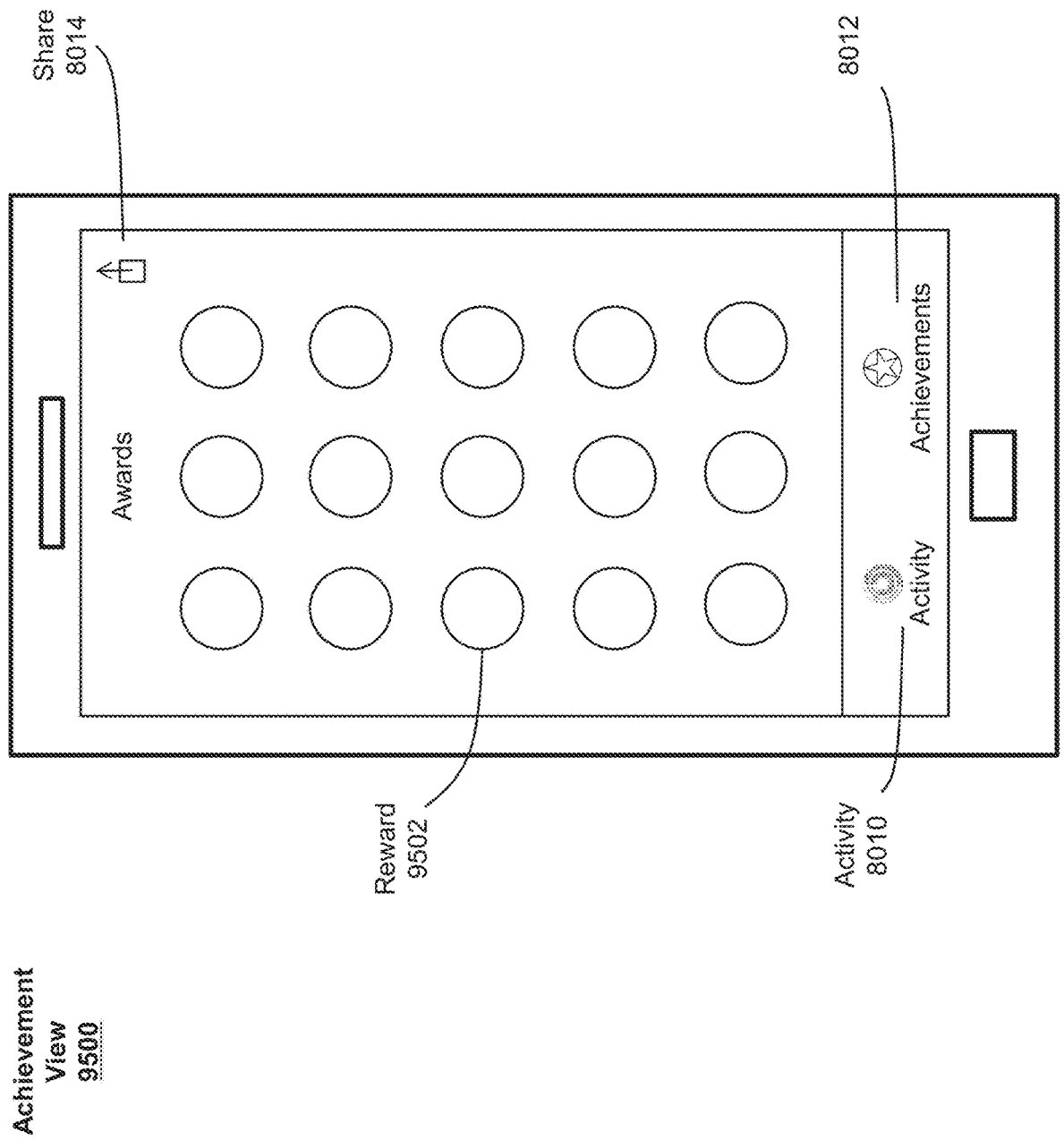

| Week | 1-2 Goal Days Achieved | 3 Goal Days Achieved (Daily Average>=75% Of Goal) | 3 Goal Days Achieved (Daily Average<75% Of Goal) | 4 Goal Days Achieved (Daily Average>=75% Of Goal) | 4 Goal Days Achieved (Daily Average<75% Of Goal) | 5-6 Days Achieved | 7 Days Achieved (Daily Average<125% Of Goal) | 7 Days Achieved (Daily Average>=125% Of Goal) |
|---|---|---|---|---|---|---|---|---|
| 1 | Goal Lowered To Average Of Lowest 4 Days | Goal Lowered By 10% | Goal Lowered To Average Of Lowest 4 Days | No Change | Goal Lowered To Average Of Lowest 3 Days | No Change | Goal Raised By 10% | Goal Raised To Average Of 7 Days |
| 2 | Goal Lowered To Average Of Lowest 4 Days | Goal Lowered By 10% | Goal Lowered To Average Of Lowest 4 Days | No Change | Goal Lowered To Average Of Lowest 3 Days | Goal Raised By 10% | Goal Raised By 10% | Goal Raised To Average Of 7 Days |
| 3 | Goal Lowered By 10% | Goal Lowered By 10% | Goal Lowered By 10% | Goal Raised By 10% | Goal Lowered By 10% | No Change | Goal Raised By 10% | Goal Raised By 10% |

FIG. 96

PHYSICAL ACTIVITY AND WORKOUT MONITOR

CROSS-REFERENCE TO RELATED APPLICATIONS

This application is a continuation of U.S. patent application Ser. No. 14/839,922, entitled "PHYSICAL ACTIVITY AND WORKOUT MONITOR," filed Aug. 29, 2015, which claims priority to U.S. Provisional Patent Application No. 62/044,990, entitled "PHYSICAL ACTIVITY AND WORKOUT MONITOR," filed Sep. 2, 2014, and U.S. Provisional Patent Application No. 62/129,828, entitled "PHYSICAL ACTIVITY AND WORKOUT MONITOR," filed Mar. 7, 2015, the content of each of which is hereby incorporated by reference in their entirety for all purposes.

FIELD

The following disclosure relates generally to a health monitor and, more specifically, to a physical activity and workout monitor.

BACKGROUND

Approximately 133 million Americans currently suffer from at least one chronic health condition. This number is expected to rise to approximately 165 million by the year 2020. This deterioration in health can be attributed largely to a sedentary lifestyle with little to no physical activity. For example, lack of sufficient physical activity can increase the risk of developing diabetes, hypertension, colon cancer, depression and anxiety, obesity, and weak muscles and bones. In addition, recent studies have found that extended periods of inactivity (e.g., sitting at a desk), can lead to serious health risks, such as an increased risk of a heart attack.

SUMMARY

The present disclosure relates to systems and processes for monitoring attributes of a user's physical activity or inactivity, and for generating user interfaces for displaying the same. One example user interface can include a first indicator that represents an attribute of a user's physical activity that is of a first type and a second indicator that represents an attribute of a user's physical activity that is of a second type. The first type of physical activity can be a physical activity that meets a first set of criteria and the second type of physical activity can be a physical activity that meets a second set of criteria. The user interface can further include a third indicator that represents an attribute of a user's inactivity, which can include the user not performing a specified type of physical activity or not performing a physical activity that meets a third set of criteria.

The present disclosure also relates to systems and processes for monitoring a user's workout, and for generating user interfaces for displaying the same. One example process can include monitoring a user's physical activity during a workout (e.g., a session of physical activity or exercise) using activity sensors selected based on the type of workout. The process can further include generating a user interface for displaying one or more attributes of the workout. One example user interface can include a first indicator (e.g., a visual representation) that represents a first attribute of the workout and a second indicator (e.g., a visual representation) that represents a second attribute of the workout. The process can further include providing notifications during the workout to notify the user of significant events associated with the workout.

In some embodiments, an electronic device comprises: a sensor configured to detect movement associated with the electronic device and generate activity data based on the detected movement; a display; a non-transitory computer readable storage medium comprising instructions for: determining that a physical activity has been performed by a user wearing the electronic device, based on the activity data received from the sensor; determining whether the physical activity corresponds to a first type based on a first set of criteria and determining whether the physical activity corresponds to a second type based on a second set of criteria; in response to determining that the physical activity corresponds to the first type, updating a first value stored in a memory based on the activity data; in response to determining that the physical activity corresponds to the second type, updating a second value stored in the memory based on the activity data; displaying a first indicator representative of the first value, the first value representing an aggregate amount of the first type of physical activity detected from the sensor over a period of time, and displaying a second indicator representative of the second value, the second value representing an aggregate amount of the second type of physical activity detected from the sensor over the period of time; and one or more processors operatively coupled to the sensor, the non-transitory computer readable storage medium, and the display, wherein the one or more processors are capable of executing the instructions of the non-transitory computer-readable storage medium.

In some embodiments, a computer-implemented method comprises: determining using one or more processors, that a physical activity has been performed by a user wearing an electronic device, based on activity data generated by a sensor of the electronic device; determining whether the physical activity corresponds to a first type based on a first set of criteria and determining whether the physical activity corresponds to a second type based on a second set of criteria; in response to determining that the physical activity corresponds to the first type, updating a first value, stored in a memory device, based on the activity data; in response to determining that the physical activity corresponds to the second type, updating a second value, stored in the memory device; and displaying the first value representing an aggregate amount of the first type of physical activity detected from the sensor over a period of time, and displaying the second value representing an aggregate amount of the second type of physical activity detected from the sensor over the period of time.

In some embodiments, an electronic device comprises: means for determining that a physical activity has been performed by a user wearing an electronic device based on activity data generated by a sensor of the electronic device; means for determining whether the physical activity corresponds to a first type based on a first set of criteria and determining whether the physical activity corresponds to a second type based on a second set of criteria; means for updating, in response to determining that the physical activity corresponds to the first type, a first value stored in a memory device based on the activity data; means for updating, in response to determining that the physical activity corresponds to the second type, a second value stored in the memory device; and means for displaying the first value representing an aggregate amount of the first type of physical activity detected from the sensor over a period of time, and displaying the second value representing an aggregate amount of the second type of physical activity detected from the sensor over the period of time.

In some embodiments, an electronic device comprises: a sensor unit configured to detect movement associated with the electronic device and generate activity data based on the detected movement; a memory unit configured to store values; a display unit configured to display graphic objects; and a processing unit coupled to the sensor unit, the memory unit, and the display unit, the processing unit configured to: determine that a physical activity has been performed by a user wearing the electronic device, based on activity data generated by the sensor unit; determine whether the physical activity corresponds to a first type based on a first set of criteria and determine whether the physical activity corresponds to a second type based on a second set of criteria; in response to determining that the physical activity corresponds to the first type, update a first value, stored in a memory unit, based on the activity data; in response to determining that the physical activity corresponds to the second type, update a second value, stored in the memory unit; and enable display, on the display unit, of the first value representing an aggregate amount of the first type of physical activity detected from the sensor unit over a period of time, and enable display, on the display unit, of the second value representing an aggregate amount of the second type of physical activity detected from the sensor unit over the period of time.

In some embodiments, an electronic device comprises: one or more processors; a memory; and one or more programs, wherein the one or more programs are stored in the memory and configured to be executed by the one or more processors, the one or more programs including instructions for: determining, using one or more processors, that a physical activity has been performed by a user wearing an electronic device, based on activity data generated by a sensor of the electronic device; determining whether the physical activity corresponds to a first type based on a first set of criteria and determining whether the physical activity corresponds to a second type based on a second set of criteria; in response to determining that the physical activity corresponds to the first type, updating a first value, stored in a memory device, based on the activity data; in response to determining that the physical activity corresponds to the second type, updating a second value, stored in the memory device; and displaying the first value representing an aggregate amount of the first type of physical activity detected from the sensor over a period of time and displaying the second value representing an aggregate amount of the second type of physical activity detected from the sensor over the period of time.

In some embodiments, a non-transitory computer readable storage medium stores one or more programs, the one or more programs comprising instructions, which when executed by one or more processors of an electronic device, cause the device to: determine that a physical activity has been performed by a user wearing an electronic device, based on activity data generated by a sensor of the electronic device; determine whether the physical activity corresponds to a first type based on a first set of criteria and determining whether the physical activity corresponds to a second type based on a second set of criteria; in response to determining that the physical activity corresponds to the first type, updating a first value, store in a memory device, based on the activity data; in response to determining that the physical activity corresponds to the second type, updating a second value, stored in the memory device; and display the first value representing an aggregate amount of the first type of physical activity detected from the sensor over a period of time, and display the second value representing an aggregate amount of the second type of physical activity detected from the sensor over the period of time.

In some embodiments, a transitory computer readable storage medium stores one or more programs, the one or more programs comprising instructions, which when executed by one or more processors of an electronic device, cause the device to: determine that a physical activity has been performed by a user wearing an electronic device, based on activity data generated by a sensor of the electronic device; determine whether the physical activity corresponds to a first type based on a first set of criteria and determining whether the physical activity corresponds to a second type based on a second set of criteria; in response to determining that the physical activity corresponds to the first type, updating a first value, store in a memory device, based on the activity data; in response to determining that the physical activity corresponds to the second type, updating a second value, stored in the memory device; and display the first value representing an aggregate amount of the first type of physical activity detected from the sensor over a period of time, and display the second value representing an aggregate amount of the second type of physical activity detected from the sensor over the period of time.

In some embodiments, a computer-implemented method comprises: receiving, from a sensor, activity data that is representative of physical activity performed by a user detected by the sensor; controlling an inactivity timer that measures a length of time that the user is inactive based on the activity data, wherein controlling the inactivity timer comprises resetting a value of the inactivity timer in response to determining, based on the activity data, that the user has performed a threshold amount of activity; and displaying an inactivity tracking interface, wherein the inactivity tracking interface comprises a visual representation of the value of the inactivity timer.

In some embodiments, an electronic device comprises: means for receiving, from a sensor, activity data that is representative of physical activity performed by a user detected by the sensor; means for controlling an inactivity timer that measures a length of time that the user is inactive based on the activity data, wherein controlling the inactivity timer comprises resetting a value of the inactivity timer in response to determining, based on the activity data, that the user has performed a threshold amount of activity; and means for displaying an inactivity tracking interface, wherein the inactivity tracking interface comprises a visual representation of the value of the inactivity timer.

In some embodiments, an electronic device comprises: a sensor unit configured to detect movement associated with the electronic device and generate activity data based on the detected movement; a display unit configured to display graphic objects; and a processing unit coupled to the sensor unit and the display unit, the processing unit configured to: receive, from the sensor unit, activity data that is representative of physical activity performed by a user detected by the sensor unit; control an inactivity timer that measures a length of time that the user is inactive based on the activity data, wherein controlling the inactivity timer comprises resetting a value of the inactivity timer in response to determining, based on the activity data, that the user has performed a threshold amount of activity; and enable display, on the display unit, of an inactivity tracking interface, wherein the inactivity tracking interface comprises a visual representation of the value of the inactivity timer.

In some embodiments, an electronic device comprises: one or more processors; a memory; and one or more programs, wherein the one or more programs are stored in the memory and configured to be executed by the one or more processors, the one or more programs including instructions for: receiving, from a sensor, activity data that is representative of physical activity performed by a user detected by the sensor; controlling an inactivity timer that measures a length of time that the user is inactive based on the activity data, wherein controlling the inactivity timer comprises resetting a value of the inactivity timer in response to determining, based on the activity data, that the user has performed a threshold amount of activity; and displaying an inactivity tracking interface, wherein the inactivity tracking interface comprises a visual representation of the value of the inactivity timer.

In some embodiments, a non-transitory computer readable storage medium stores one or more programs, the one or more programs comprising instructions, which when executed by one or more processors of an electronic device, cause the device to: receive, from a sensor, activity data that is representative of physical activity performed by a user detected by the sensor; control an inactivity tinier that measures a length of time that the user is inactive based on the activity data, wherein controlling the inactivity timer comprises resetting a value of the inactivity timer in response to determining, based on the activity data, that the user has performed a threshold amount of activity; and display an inactivity tracking interface, wherein the inactivity tracking interface comprises a visual representation of the value of the inactivity timer.

In some embodiments, a transitory computer readable storage medium stores one or more programs, the one or more programs comprising instructions, which when executed by one or more processors of an electronic device, cause the device to: receive, from a sensor, activity data that is representative of physical activity performed by a user detected by the sensor; control an inactivity timer that measures a length of time that the user is inactive based on the activity data, wherein controlling the inactivity timer comprises resetting a value of the inactivity timer in response to determining, based on the activity data, that the user has performed a threshold amount of activity; and display an inactivity tracking interface, wherein the inactivity tracking interface comprises a visual representation of the value of the inactivity timer.

In some embodiments, computer-implemented method comprises: determining, using one or more processors, that a physical activity has been performed by a user wearing an electronic device, based on activity data generated by a sensor of the electronic device; determining whether the physical activity corresponds to a first type based on a first set of criteria and determining whether the physical activity corresponds to a second type based on a second set of criteria; in response to determining that the physical activity corresponds to the first type, updating a first value, stored in a memory device, based on the activity data; in response to determining that the physical activity corresponds to the second type, updating a second value, stored in the memory device, based on the activity data; controlling an inactivity timer that measures a length of time that the user is inactive based on the activity data, wherein controlling the inactivity timer comprises: resetting a value of the inactivity tinier in response to determining, based on the activity data, that the user has performed a threshold amount of activity; incrementing the value of an inactivity counter in response to the value of the inactivity timer reaching an inactivity threshold; and resetting the value of the inactivity timer in response to the value of the inactivity timer reaching an inactivity threshold; and displaying: a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some embodiments, an electronic device comprises: means for determining, using one or more processors, that a physical activity has been performed by a user wearing an electronic device, based on activity data generated by a sensor of the electronic device; means for determining whether the physical activity corresponds to a first type based on a first set of criteria and determining whether the physical activity corresponds to a second type based on a second set of criteria; means for updating, in response to determining that the physical activity corresponds to the first type, a first value stored in a memory device based on the activity data; means for updating, in response to determining that the physical activity corresponds to the second type, a second value stored in the memory device based on the activity data; means for controlling an inactivity timer that measures a length of time that the user is inactive based on the activity data, wherein controlling the inactivity timer comprises: resetting a value of the inactivity timer in response to determining, based on the activity data, that the user has performed a threshold amount of activity; incrementing the value of an inactivity counter in response to the value of the inactivity timer reaching an inactivity threshold; and resetting the value of the inactivity timer in response to the value of the inactivity timer reaching an inactivity threshold; and means for displaying: a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some embodiments, an electronic device comprises: a sensor unit configured to detect movement associated with the electronic device and generate activity data based on the detected movement; a memory unit configured to store values; a display unit configured to display graphic objects; and a processing unit coupled to the sensor unit, the memory unit, and the display unit, the processing unit configured to: determine that a physical activity has been performed by a user wearing the electronic device, based on activity data generated by the sensor unit; determine whether the physical activity corresponds to a first type based on a first set of criteria and determine whether the physical activity corresponds to a second type based on a second set of criteria; in response to determining that the physical activity corresponds to the first type, update a first value, stored in the memory unit, based on the activity data; in response to determining that the physical activity corresponds to the second type, update a second value, stored in the memory unit, based on the activity data; control an inactivity timer that measures a length of time that the user is inactive based on the activity data, wherein controlling the inactivity timer comprises: resetting a value of the inactivity timer in response to determining, based on the activity data, that the user has performed a threshold amount of activity; incrementing the value of an inactivity counter in response to the value of the inactivity timer reaching an inactivity threshold; and resetting the value of the inactivity timer in response to the value of the inactivity timer reaching an inactivity threshold; and enable display, on the display unit, of: a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some embodiments, an electronic device comprises: one or more processors; a memory; and one or more programs, wherein the one or more programs are stored in the memory and configured to be executed by the one or more processors, the one or more programs including instructions for: determining that a physical activity has been performed by a user wearing an electronic device, based on activity data generated by a sensor of the electronic device; determining whether the physical activity corresponds to a first type based on a first set of criteria and determining whether the physical activity corresponds to a second type based on a second set of criteria; in response to determining that the physical activity corresponds to the first type, updating a first value, stored in a memory device, based on the activity data; in response to determining that the physical activity corresponds to the second type, updating a second value, stored in the memory device, based on the activity data; controlling an inactivity timer that measures a length of time that the user is inactive based on the activity data, wherein controlling the inactivity timer comprises: resetting a value of the inactivity timer in response to determining, based on the activity data, that the user has performed a threshold amount of activity; incrementing the value of an inactivity counter in response to the value of the inactivity timer reaching an inactivity threshold; and rescuing the value of the inactivity timer in response to the value of the inactivity timer reaching an inactivity threshold; and displaying: a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some embodiments, a non-transitory computer readable storage medium stores one or more programs, the one or more programs comprising instructions, which when executed by one or more processors of an electronic device, cause the device to: determine that a physical activity has been performed by a user wearing an electronic device, based on activity data generated by a sensor of the electronic device; determine whether the physical activity corresponds to a first type based on a first set of criteria and determining whether the physical activity corresponds to a second type based on a second set of criteria; in response to determining that the physical activity corresponds to the first type, updating a first value, store in a memory device, based on the activity data; in response to determining that the physical activity corresponds to the second type, update a second value, stored in the memory device, based on the activity data; control an inactivity timer that measures a length of time that the user is inactive based on the activity data, wherein controlling the inactivity tinier comprises: reset a value of the inactivity timer in response to determining, based on the activity data, that the user has performed a threshold amount of activity; increment the value of an inactivity counter in response to the value of the inactivity timer reaching an inactivity threshold; and reset the value of the inactivity timer in response to the value of the inactivity timer reaching an inactivity threshold; and display: a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some embodiments, a transitory computer readable storage medium stores one or more programs, the one or more programs comprising instructions, which when executed by one or more processors of an electronic device, cause the device to: determine that a physical activity has been performed by a user wearing an electronic device, based on activity data generated by a sensor of the electronic device; determine whether the physical activity corresponds to a first type based on a first set of criteria and determining whether the physical activity corresponds to a second type based on a second set of criteria; in response to determining that the physical activity corresponds to the first type, updating a first value, store in a memory device, based on the activity data; in response to determining that the physical activity corresponds to the second type, update a second value, stored in the memory device, based on the activity data; control an inactivity timer that measures a length of time that the user is inactive based on the activity data, wherein controlling the inactivity timer comprises: reset a value of the inactivity timer in response to determining, based on the activity data, that the user has performed a threshold amount of activity; increment the value of an inactivity counter in response to the value of the inactivity timer reaching an inactivity threshold; and reset the value of the inactivity timer in response to the value of the inactivity timer reaching an inactivity threshold; and display: a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some embodiments, a computer-implemented method comprises: at one or more processors of an electronic device: displaying an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time; receiving, from a sensor of the electronic device, activity data representing movement associated with the electronic device; and updating the aggregate amount of the first type of physical activity, the aggregate amount of the second type of physical activity, and the aggregate amount of the third type of physical activity based on the activity data.

In some embodiments, a system comprises: means for displaying an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time; means for receiving, from a sensor of the electronic device, activity data representing movement associated with the electronic device; and means for updating the aggregate amount of the first type of physical activity, the aggregate amount of the second type of physical activity, and the aggregate amount of the third type of physical activity based on the activity data.

In some embodiments, an electronic device comprises: a sensor unit configured to detect movement associated with the electronic device and generate activity data based on the detected movement; a display unit configured to display graphic objects; and a processing unit coupled to the sensor unit and the display unit, the processing unit configured to: enable display, on the display unit, of an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time; receive, from the sensor unit, activity data representing movement associated with the electronic device; and update the aggregate amount of the first type of physical activity, the aggregate amount of the second type of physical activity, and the aggregate amount of the third type of physical activity based on the activity data.

In some embodiments, an electronic device comprises: one or more processors; a memory; and one or more programs, wherein the one or more programs are stored in the memory and configured to be executed by the one or more processors, the one or more programs including instructions for: displaying an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time; receiving, from a sensor of the electronic device, activity data representing movement associated with the electronic device; and updating the aggregate amount of the first type of physical activity, the aggregate amount of the second type of physical activity, and the aggregate amount of the third type of physical activity based on the activity data.

In some embodiments, a non-transitory computer readable storage medium stores one or more programs, the one or more programs comprising instructions, which when executed by one or more processors of an electronic device, cause the device to: display an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time; receive, from a sensor of the electronic device, activity data representing movement associated with the electronic device; and update the aggregate amount of the first type of physical activity, the aggregate amount of the second type of physical activity, and the aggregate amount of the third type of physical activity based on the activity data.

In some embodiments, a transitory computer readable storage medium stores one or more programs, the one or more programs comprising instructions, which when executed by one or more processors of an electronic device, cause the device to: display an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time; receive, from a sensor of the electronic device, activity data representing movement associated with the electronic device; and update the aggregate amount of the first type of physical activity, the aggregate amount of the second type of physical activity, and the aggregate amount of the third type of physical activity based on the activity data.

In some embodiments, an electronic device comprises: one or more activity sensors configured to detect movement associated with the electronic device and generate activity data based on the detected movement; a display; a non-transitory computer readable storage medium comprising instructions for: receiving an identification of a type of workout to be performed, wherein the type of workout is associated with a plurality of workout attributes; receiving a goal for the type of workout, wherein the goal comprises an identification of a first workout attribute of the plurality of workout attributes and a goal value for the first workout attribute; determining a current value of the first workout attribute and a current value of a second workout attribute of the plurality of workout attributes based on activity data from at least a portion of the one or more activity sensors; displaying: a display of a first indicator representative of the current value of the first workout attribute relative to the goal value for the first workout attribute; and a display of a second indicator representative of the current value of the second workout attribute; and one or more processors operatively coupled to the one or more activity sensors, the non-transitory computer readable storage medium, and the display, wherein the one or more processors are capable of executing the instructions of the non-transitory computer-readable storage medium.

In some embodiments, a computer-implemented method comprises: receiving an identification of a type of workout to be performed, wherein the type of workout is associated with a plurality of workout attributes; receiving a goal for the type of workout, wherein the goal comprises an identification of a first workout attribute of the plurality of workout attributes and a goal value for the first workout attribute; determining a current value of the first workout attribute and a current value of a second workout attribute of the plurality of workout attributes based on activity data from one or more activity sensors; displaying a first indicator representative of the current value of the first workout attribute relative to the goal value for the first workout attribute; and displaying a second indicator representative of the current value of the second workout attribute.

In some embodiments, an electronic device comprises: means for receiving an identification of a type of workout to be performed, wherein the type of workout is associated with a plurality of workout attributes; means for receiving a goal for the type of workout, wherein the goal comprises an identification of a first workout attribute of the plurality of workout attributes and a goal value for the first workout attribute; means for determining a current value of the first workout attribute and a current value of a second workout attribute of the plurality of workout attributes based on activity data from one or more activity sensors; means for displaying a first indicator representative of the current value of the first workout attribute relative to the goal value for the first workout attribute; and means for displaying a second indicator representative of the current value of the second workout attribute.

In some embodiments, an electronic device comprises: one or more activity sensor units configured to detect activity and generate activity data based on the detected activity; a display unit configured to display graphic objects; and a processing unit coupled to the one or more sensor units and the display unit, the processing unit configured to: receive an identification of a type of workout to be performed, wherein the type of workout is associated with a plurality of workout attributes; receive a goal for the type of workout, wherein the goal comprises an identification of a first workout attribute of the plurality of workout attributes and a goal value for the first workout attribute; determine a current value of the first workout attribute and a current value of a second workout attribute of the plurality of workout attributes based on activity data from the one or more activity sensors units; enable display, on the display unit, of a first indicator representative of the current value of the first workout attribute relative to the goal value for the first workout attribute; and enable display, on the display unit, of a second indicator representative of the current value of the second workout attribute.

In some embodiments, an electronic device comprises: one or more processors; a memory; and one or more programs, wherein the one or more programs are stored in the memory and configured to be executed by the one or more processors, the one or more programs including instructions for: receiving an identification of a type of workout to be performed, wherein the type of workout is associated with a plurality of workout attributes; receiving a goal for the type of workout, wherein the goal comprises an identification of a first workout attribute of the plurality of workout attributes and a goal value for the first workout attribute; determining a current value of the first workout attribute and a current value of a second workout attribute of the plurality of workout attributes based on activity data from one or more activity sensors; displaying a first indicator representative of the current value of the first workout attribute relative to the goal value for the first workout attribute; and display a second indicator representative of the current value of the second workout attribute.

In some embodiments, a non-transitory computer readable storage medium stores one or more programs, the one or more programs comprising instructions, which when executed by one or more processors of an electronic device, cause the device to: receive an identification of a type of workout to be performed, wherein the type of workout is associated with a plurality of workout attributes; receive a goal for the type of workout, wherein the goal comprises an identification of a first workout attribute of the plurality of workout attributes and a goal value for the first workout attribute; determine a current value of the first workout attribute and a current value of a second workout attribute of the plurality of workout attributes based on activity data from one or more activity sensors; display a first indicator representative of the current value of the first workout attribute relative to the goal value for the first workout attribute; and display a second indicator representative of the current value of the second workout attribute.

In some embodiments, a transitory computer readable storage medium stores one or more programs, the one or more programs comprising instructions, which when executed by one or more processors of an electronic device, cause the device to: receive an identification of a type of workout to be performed, wherein the type of workout is associated with a plurality of workout attributes; receive a goal for the type of workout, wherein the goal comprises an identification of a first workout attribute of the plurality of workout attributes and a goal value for the first workout attribute; determine a current value of the first workout attribute and a current value of a second workout attribute of the plurality of workout attributes based on activity data from one or more activity sensors; display a first indicator representative of the current value of the first workout attribute relative to the goal value for the first workout attribute; and display a second indicator representative of the current value of the second workout attribute.

In some embodiments, a computer-implemented method comprises: at one or more processors of an electronic device: receiving historical activity data representing physical activity performed by a user; and displaying an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

In some embodiments, an electronic device comprises: means for receiving historical activity data representing physical activity performed by a user; and means for displaying an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

In some embodiments, an electronic device comprises: a display unit configured to display graphic objects; and a processing unit coupled to the display unit, the processing unit configured to: receive historical activity data representing physical activity performed by a user; and enable display, on the display unit, of an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

In some embodiments, an electronic device comprises: one or more processors; a memory; and one or more programs, wherein the one or more programs are stored in the memory and configured to be executed by the one or more processors, the one or more programs including instructions for: receiving historical activity data representing physical activity performed by a user; and displaying an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

In some embodiments, a non-transitory computer readable storage medium stores one or more programs, the one or more programs comprising instructions, which when executed by one or more processors of an electronic device, cause the device to: receive historical activity data representing physical activity performed by a user; and display an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

In some embodiments, a transitory computer readable storage medium stores one or more programs, the one or more programs comprising instructions, which when executed by one or more processors of an electronic device, cause the device to: receive historical activity data representing physical activity performed by a user; and display an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIGS. 4A and 4B illustrate an exemplary user interface for a menu of applications on a portable multifunction device in accordance with some examples.

FIGS. 5C-5D illustrate exemplary components of a personal electronic device having a touch-sensitive display and intensity sensors in accordance with some embodiments.

FIGS. 5E-5H illustrate exemplary components and user interfaces of a personal electronic device in accordance with some embodiments.

FIG. 95 illustrates an exemplary achievement view according to various examples.

FIG. 96 illustrates a table for calculating a new physical activity goal according to various examples.

DESCRIPTION OF EMBODIMENTS

Figure 1A:
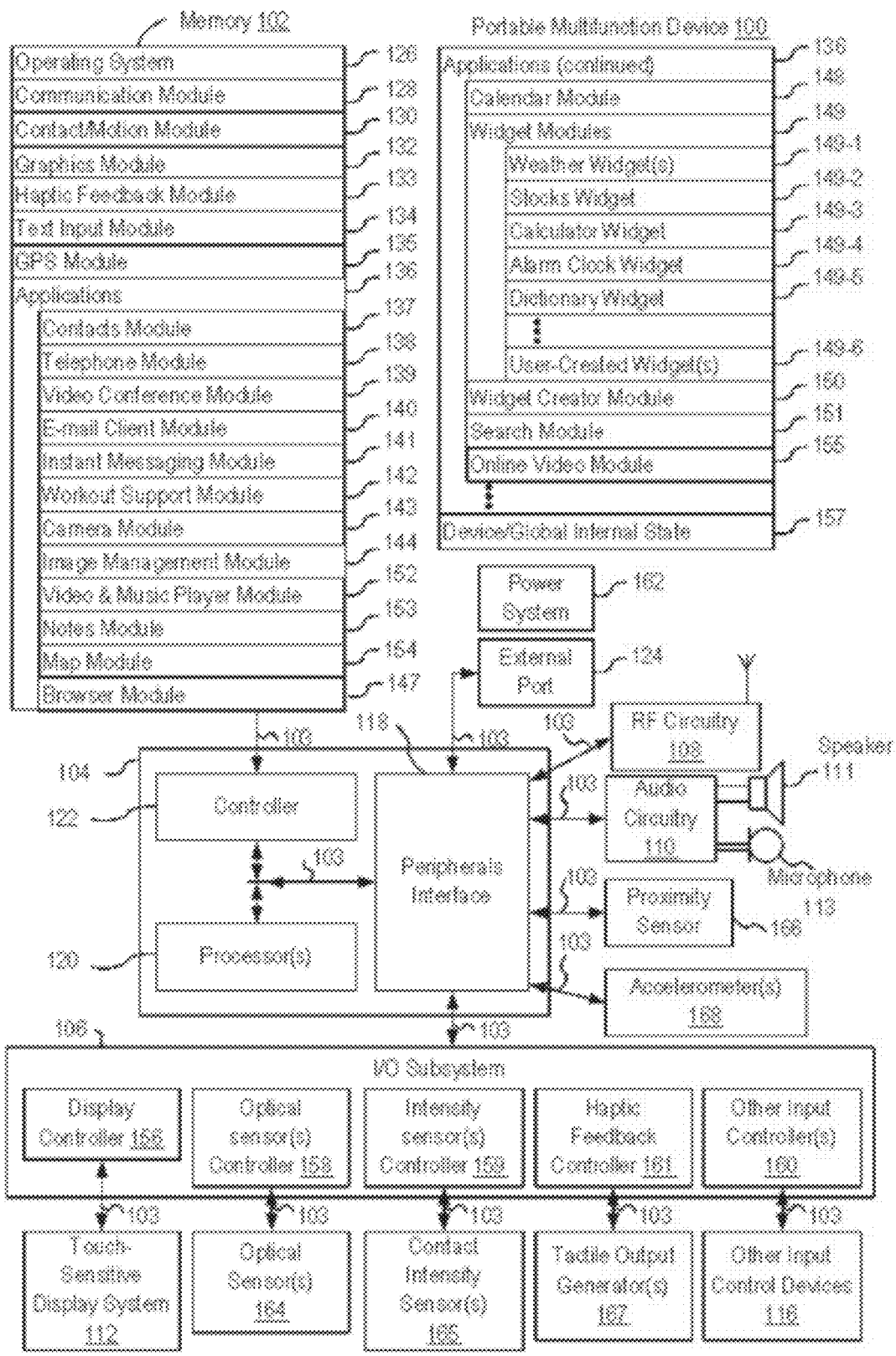
FIG. 1A is a block diagram illustrating a portable multifunction device with a touch-sensitive display in accordance with some examples.

The following description sets forth exemplary methods, parameters and the like. It should be recognized, however, that such description is not intended as a limitation on the scope of the present disclosure but is instead provided as a description of exemplary embodiments.

The present disclosure relates to a device for monitoring a user's physical activity or inactivity, and for generating user interfaces for displaying the same. The device can monitor various attributes of the user's physical activity and can generate a user interface for displaying some or all of the monitored attributes. One example user interface can include a first indicator (e.g., a visual representation) that represents one or more attributes of a user's physical activity that is of a first type and a second indicator (e.g., a visual representation) that represents one or more attributes of a user's physical activity that is of a second type. The first type of physical activity can be a physical activity that meets a first set of criteria and the second type of physical activity can be a physical activity that meets a second set of criteria. In some examples, the second set of criteria can encompass the first set of criteria, resulting in the second type of physical activity being a subset of the first type of physical activity. The user interface can further include a third indicator (e.g., a visual representation) that represents one or more attributes of a user's inactivity, which can include the user not performing a specified type of physical activity or the user not performing a physical activity that meets a third set of criteria.

The present disclosure also relates to a device for monitoring a user's workout, and for generating user interfaces for displaying the same. The device can monitor a user's physical activity during a workout (e.g., a session of physical activity or exercise) using activity sensors selected based on the type of workout. The device can further generate a user interface for displaying one or more attributes of the workout. One example user interface can include a first indicator (e.g., a visual representation) that represents a first attribute of the workout and a second indicator (e.g., a visual representation) that represents a second attribute of the workout. The device can further provide notifications during the workout to notify the user of significant events associated with the workout.

Electronic Devices

FIGS. 1A-1B, 2, 3, 4A-4B, and 5A-5B provide a description of exemplary devices for monitoring a user's physical activity. FIGS. 8-14, 17-21, 23, 25-39, 41-47, 49-78, 80-85, 87-88, 90-91, and 93-95 illustrate exemplary user interfaces that can be displayed on these exemplary devices. The user interfaces in the figures are also used to illustrate the processes described below, including the processes in FIGS. 15, 16, 22, 24, 40, 48, 79, 86, 89, and 92.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes one or more computer-readable storage mediums. The computer-readable storage mediums are optionally tangible and non-transitory. The computer-readable storage mediums are optionally transitory. Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), art intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

Figure 2:
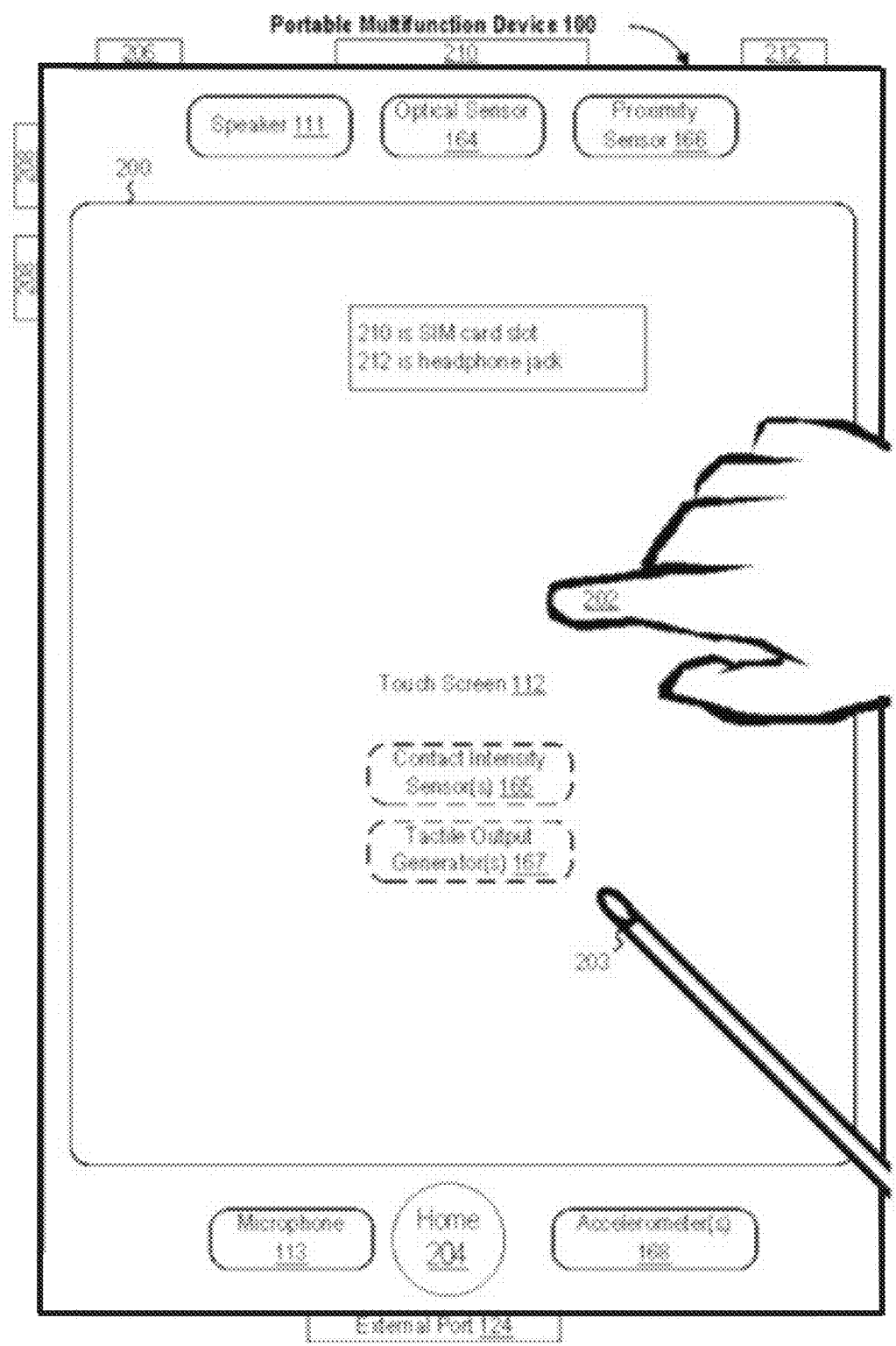
FIG. 2 illustrates a portable multifunction device having a touch-sensitive display in accordance with some examples

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161 and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206. FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005. U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touch-screen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad. (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
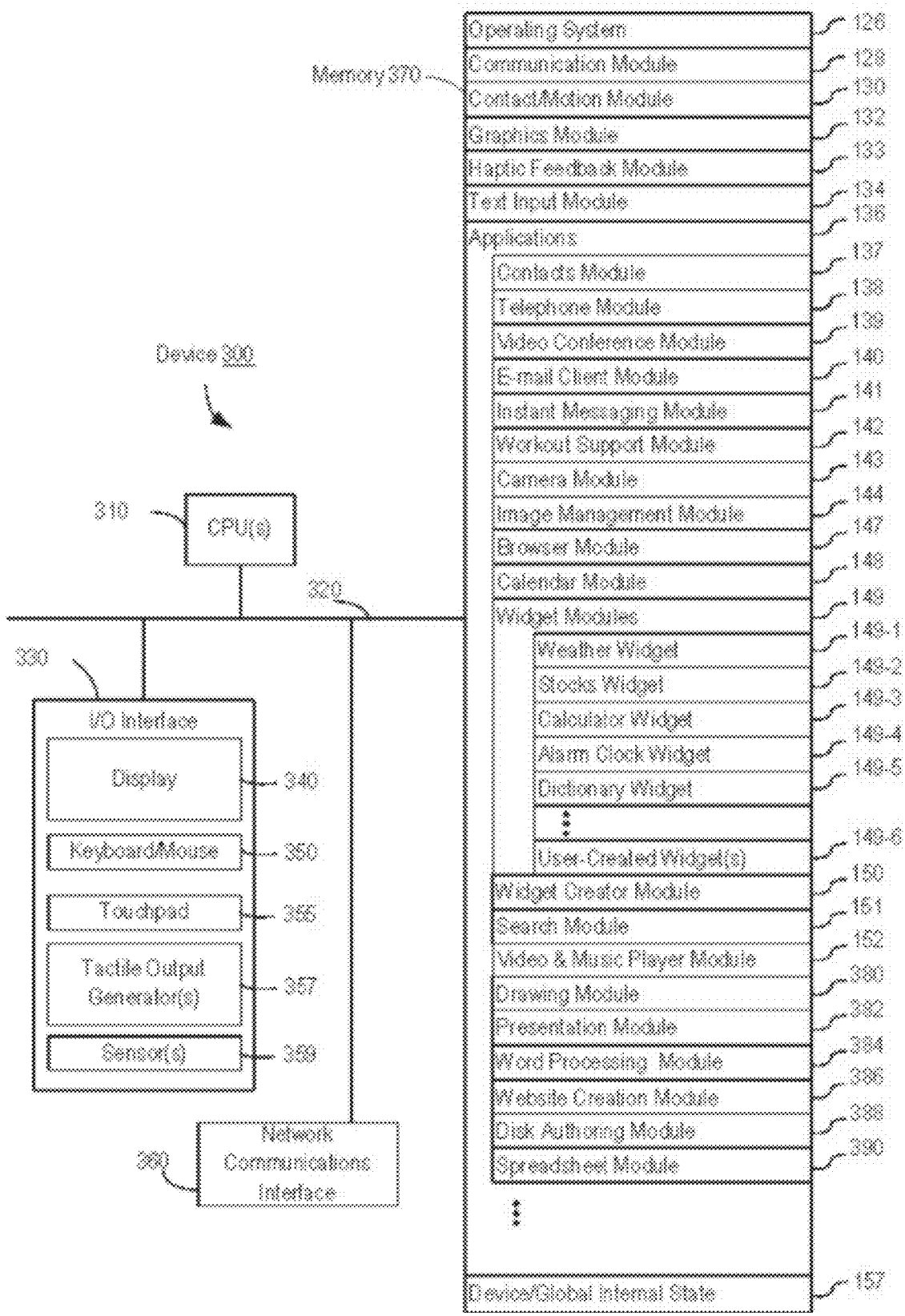
FIG. 3 is a block diagram of an exemplary multifunction device with a display and a touch-sensitive surface in accordance with some examples.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a linger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
   Contacts module 137 (sometimes called an address book or contact list);
   Telephone module 138;
   Video conference module 139;
   E-mail client module 140;
   Instant messaging (IM) module 141;
   Workout support module 142;
   Camera module 143 for still and/or video images;
   Image management module 144;
   Video player module;
   Music player module;
   Browser module 147;
   Calendar module 148;
   Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
   Widget creator module 150 for making user-created widgets 149-6;
   Search module 151;
   Video and music player module 152, which merges video player module and music player module;
   Notes module 153;
   Map module 154; and/or
   Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112 display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RE circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RE circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RE circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RE circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RE circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112 display controller 156, contact/motion module 130 graphics module 132, and text input module 134 notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen anchor a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
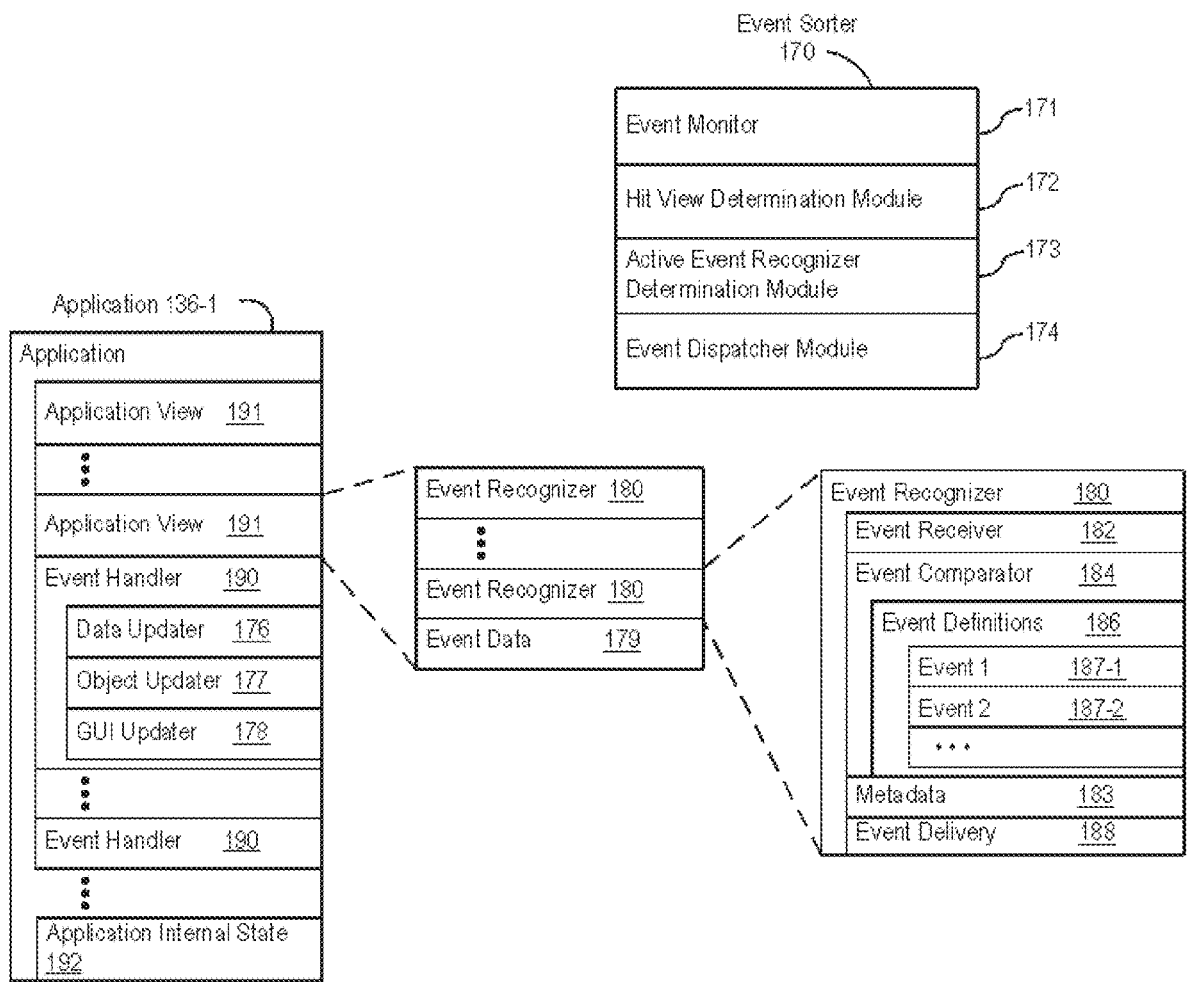
FIG. 1B is a block diagram illustrating exemplary components for event handling in accordance with some examples

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo; undo queue of previous actions taken by the user.

Event monitor 171 receives event information from peripherals interface 118. Event information includes information about a sub-event (e.g., a user touch on touch-sensitive display 112 as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs: and/or any combination thereof are optionally utilized as inputs corresponding to sub-events which define an event to be recognized.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices: and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 are, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that is, optionally, implemented on, for example, portable multifunction device 100.

Figure 4A:
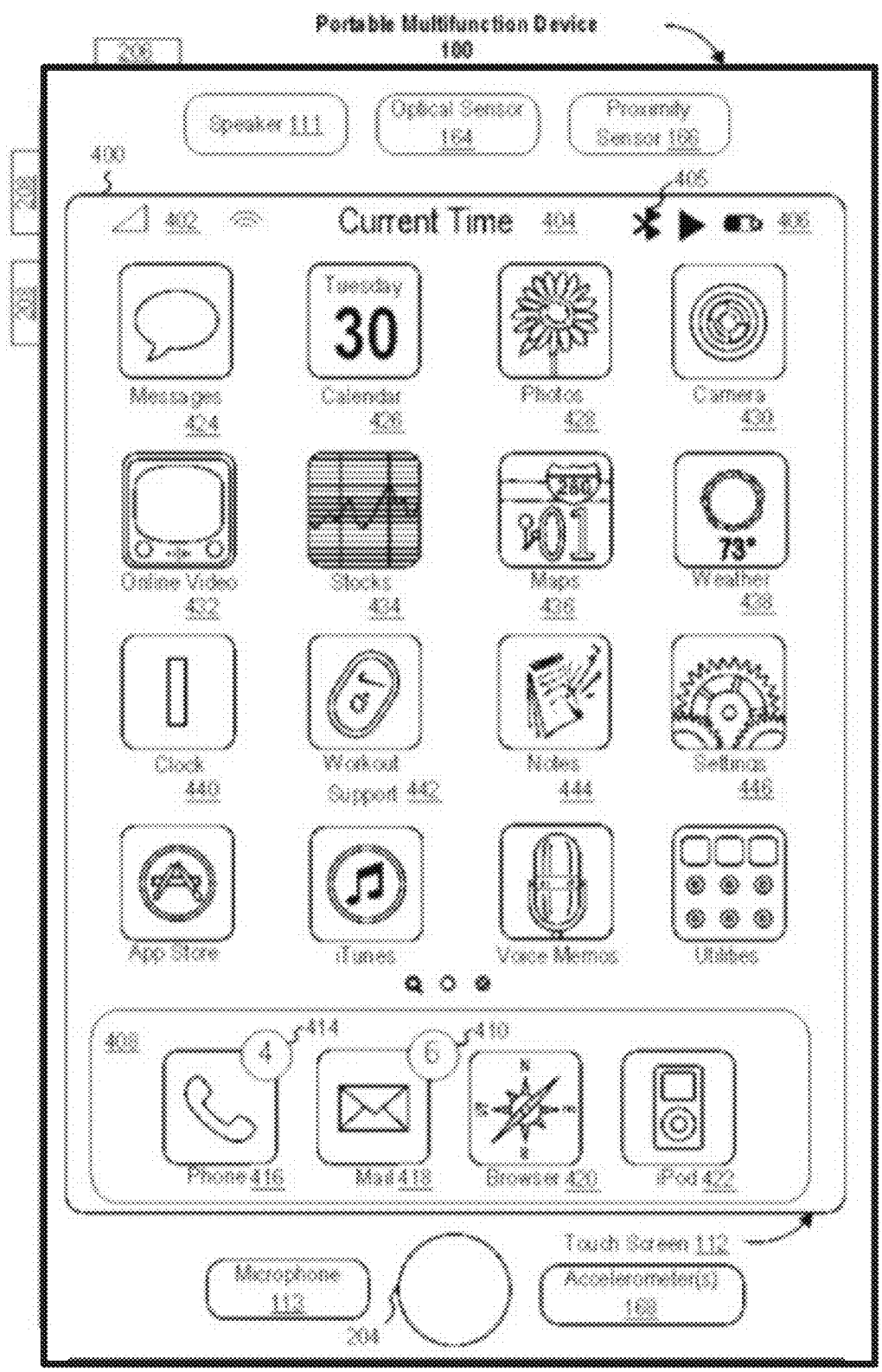

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages,"
  Icon 426 for calendar module 148, labeled "Calendar,"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps,"
  Icon 438 for weather widget 149-1, labeled "Weather;"
  Icon 440 for alarm clock widget 149-4, labeled "Clock,"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 are labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples which follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462 and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
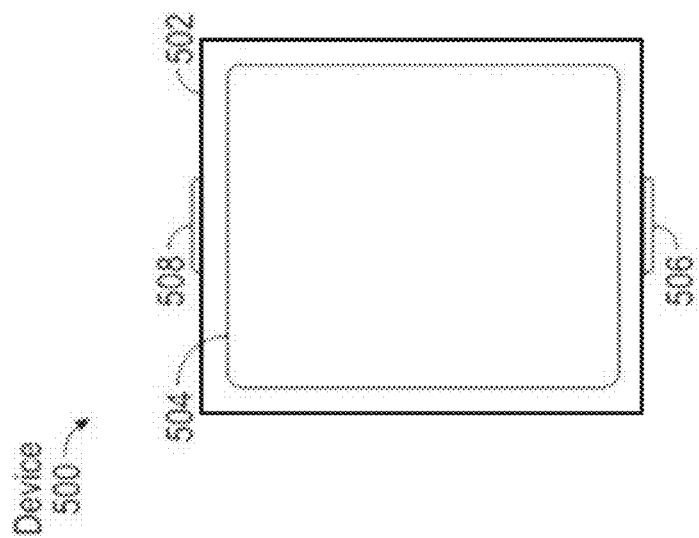
FIG. 5A illustrates a portable multifunction device having a touch-sensitive display in accordance with some examples.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Personal electronic device 500 can be used for detecting and monitoring various attributes of a user's physical activity, such as an amount, an intensity level, a duration, a progress relative to a set value, a trend over a time period, or the like, of the activity, and can generate user interfaces for displaying the same. Device 500 can further be used to monitor a user's inactivity, where the user can be categorized as being inactive when device 500 detects that the user is not engaged in a physical activity that meets a predetermined criteria. For example, inactivity can be characterized by the absence of the user engaging in a physical activity that meets a threshold intensity (e.g., movement that expends a threshold number of Calories per unit time, movement that exceeds a threshold distance per unit time, or the like), the absence of the user engaging in a specified type of activity (e.g., standing, walking, running, swimming, climbing stairs, or the like), or a combination thereof. As will be described in greater detail below, device 500 can include various activity sensors for detecting activity and inactivity of a user and can generate an interface on a display of the device to provide the user with information associated with their activity or inactivity.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, and International Patent Application Serial No. PCT/US2013/069483, titled "Device, Method, and Graphical User interface for Transitioning Between Touch input to Display Output Relationships," filed Nov. 11, 2013, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms may permit device 500 to be worn by a user.

In some examples, device 500 can further include an attachment mechanism (not shown) coupled to body 502 to permit device 500 to be worn by a user. The attachment mechanism can include a strap that permits device 500 to be worn around the user's wrist. However, it should be appreciated that the attachment mechanism can include other types of attachment mechanisms. For instance, in some examples, the attachment mechanism can include a string, a clip, a clasp, a metal loop, a toggle, a button, a snap, a hook, an interlocking part, a soldered part, or the like, that can be attached to or integrated with hats, eyewear, earrings, necklaces, shirts, jackets, bracelets, watch straps, chains, trousers, belts, shoes, purses, backpacks, hairbands, armbands, any other clothing, jewelry, or wearable accessories. In yet other examples, the attachment mechanism can include an adhesive, a weld metal, a polymer, a glue, or the like, that permits device 500 to be directly affixed to a user's body part, such as wrist, finger, toe, neck, head, arm, leg, ankle, waist, or the like.

Device 500 can further include one or more activity sensors for detecting physical activity of a user. The activity sensors can include one or more of global positioning system (GPS) sensors, pedometers, accelerometers, biometric sensors, gyroscope sensors, motion sensors, timer sensors, clock sensors, or the like, and can be operable to output activity data that represents various attributes of a detected activity of the user.

Figure 5B:
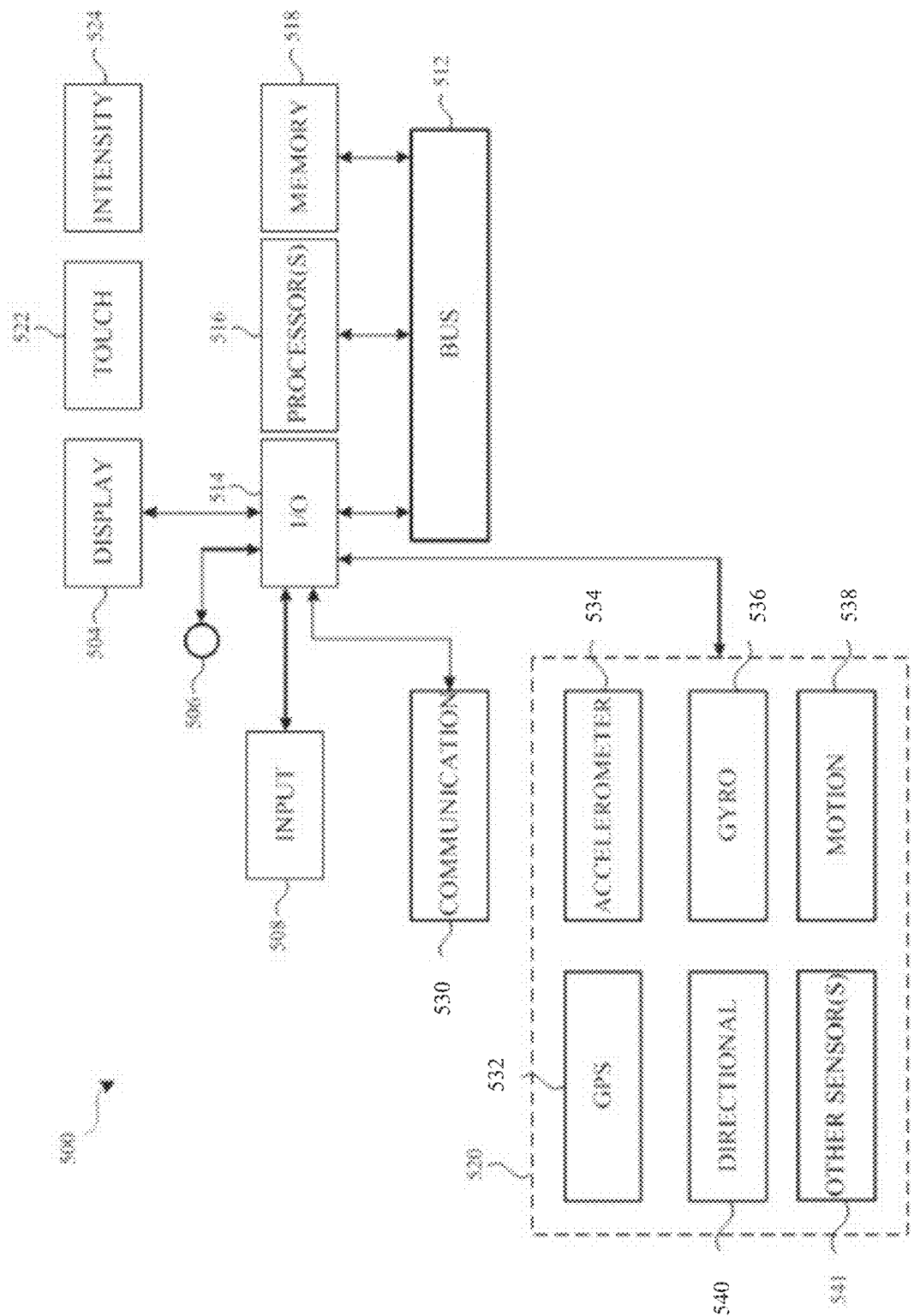
FIG. 5B is a block diagram illustrating a portable multifunction device with a touch-sensitive display in accordance with some examples.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various activity sensors 520 for detecting an activity of a user of device 500. Activity sensors 520 can include one or more of any desired type of sensor, such as GPS sensor 532, accelerometer 534, directional sensor 540 (e.g., compass), gyroscope 536, motion sensor 538, other sensor (s) 541, and/or a combination thereof, all of which can be operatively connected to I/O section 514. While not shown, other sensor(s) 541 can include any of a pedometer, a passive infrared sensor, an ultrasonic sensor, a microwave sensor, a tomographic motion detector, a camera, a biometric sensor, a light sensor, a timer, or the like.

In some examples, the biometric sensor can include one or more health-related optical sensors, capacitive sensors, thermal sensors, electric field (eField) sensors, and/or ultrasound sensors, such as photoplethysmogram (PPG) sensors, electrocardiography (ECG) sensors, and/or galvanic skin response (GSR) sensors. These sensors can generate data providing health-related information associated with the user. For example, PPG sensors can provide information regarding a user's respiratory rate, blood pressure, and/or oxygen saturation. ECG sensors can provide information regarding a user's heartbeats. GSR sensors can provide information regarding a user's skin moisture indicative of sweating and can prioritize a thermostat application to determine a user's body temperature. Using one or more of these sensors, device 500 can determine physiological characteristics of the user while performing a detected activity, such as a heart rate of a user associated with the detected activity, average body temperature of a user detected during the detected activity, any normal or abnormal physical conditions associated with the detected activity, or the like.

In some examples, GPS sensor 532 can be used to determine a user's location and movement, as well as a displacement of the user's motion. Accelerometer 534, directional sensor 540, and gyroscope 536 can further generate activity data that can be used to determine whether a user of device 500 is engaging in an activity, is inactive, or is performing a gesture. Device 500 can further include a timer that can be used, for example, to add time dimensions to various attributes of the detected physical activity, such as a duration of a user's physical activity or inactivity, time(s) of a day when the activity is detected or not detected, etc.

Activity sensors 520 can be embedded in body 502 of device 500, placed near a bottom surface of body 502 of device 500, or can be positioned at any other desirable location. In some examples, different activity sensors 520 can be placed in different locations inside or on the surfaces of device 500—e.g., some located inside body 502 and some attached to the attachment mechanism, or the like. In other examples, activity sensors 520 can be worn by a user separately from device 500. In such cases, the sensors can be configured to communicate with device 500 using a wired or wireless technology (e.g., via communication unit 531). In some examples, activity sensors 520 can be configured to communicate with each other and/or share data collected from one or more sensors. In some other examples, device 500 can be waterproof such that the sensors can detect a user's activity in water.

Memory 518 of personal electronic device 500 can be a non-transitory computer-readable storage medium, for storing computer-executable instructions, which, when executed by one or more computer processors 516, for example, can cause the computer processors to perform the techniques described above, including processes 1500, 1600, 2200, 2400, 4000, 4800, 7900, 8600, 8900, and 9200 (FIGS. 15, 16, 22, 24, 40, 48, 79, 86, and 89). The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

Device 500 can further include one or more computer processors 516 coupled to memory section 518 via bus 512, I/O section 514 can be coupled to bus 512 to allow processors 516 and memory 518 to transmit and receive data from other components of device 500. For example, processors 516 can be coupled to provide instructions to activity sensors 520 via. I/O section 514 and can be coupled to receive activity data from activity sensors 520 via I/O section 514.

Processors 516 can be configured to process the activity data to determine if the physical activity data represents a physical activity or a gesture being performed by the user, where a physical activity can generally refer to any bodily motion that can enhance or maintain physical fitness and overall health and wellness. Additionally, processors 516 can be configured to identify the type of physical activity represented by the activity data, such as whether the detected activity is standing, bicycling, jogging, walking, running, swimming, jumping, going up stairs, intense bodily movements, such as wrestling, or the like. Examples of gestures recognizable by device 500 include, but are not limited to, waving hands, moving fingers, such as typing, or the like. In some examples, processor 516 can determine a physical activity of a user based on one or more physical activity recognition algorithms. Some algorithms can instruct processor 516 to recognize movement of device 500 as being associated with a gesture if the detected movement does not have an intensity level greater than or equal to a physical activity threshold. The physical activity threshold can be represented as a distance traveled, a number of Calories burned, a number of steps taken, any one or more of these attributes calculated per unit time, or the like. The algorithms for storing such instructions for the one or more processors 516 can be stored in memory section 518.

Additionally, processors 516 can determine, based on the physical activity data received from the sensors, various attributes of the detected physical activity. Attributes of the detected physical activity can include physical, biological, physiological, or environmental characteristics associated with the detected physical activity. Examples of attributes determinable by device 500 upon detecting a physical activity can include, but are not limited to: duration of the detected physical activity; time(s) of a day when the user performs the detected physical activity; amount of Calories burned by a user of the device while performing the detected physical activity; distance traveled by a user of the device while performing the detected physical activity; steps taken by a user of the device while performing the detected physical activity; elevation climbed by a user of the device while performing the detected physical activity; highest/lowest/average velocity of a user of the device while performing the detected physical activity; highest/lowest/average heart rate of a user of the device while performing the detected physical activity; highest/lowest/average body temperature of a user of the device while performing the detected physical activity; or the like. For example, when device 500 categorizes a detected physical activity as walking, device 500 can further determine one or more attributes of the detected walking, such as a length of time for which the walking continues, highest/lowest/average speed of the user while walking, amount of Calories burned from the detected walking, or the like. In some examples, device 500 can further determine time dimensions associated with one or more attributes using a clock/timer sensor such as time(s) of a day when physical activity is detected, time(s) of a day when the most/least intensive physical activity is detected, time(s) of a day when a certain amount of Calories are burned, or the like.

In some examples, processors 516 in combination with activity sensors 520 of device 500 can detect when the system is placed into a viewing position. For instance, accelerometer 534, motion sensor 538, and/or gyroscope 536 can detect when device 500 is raised, lowered, and shaken. These sensors can also detect wrist rotation forward and backward. In some examples, the raising of device 500 can be interpreted as a placement of the device into viewing position. In other examples, the raising and rotation of device 500 can be interpreted as a placement of the device into viewing position. In yet other examples, the raising and rotation of device 500 within a threshold duration can be interpreted as a placement of the device into viewing position. When put into a viewing position, device 500 can adjust the display image according to the viewing positions and angles, and/or update the display image to reflect the most current data related to the user's physical activity. In some examples, device 500 can determine that when it is moving at a velocity that exceeds a threshold (e.g., 10 mph. 20 mph, 25 mph, 30 mph, 40 mph, 50 mph, 55 mph, 60 mph, 65 mph, etc.), the user of the device is commuting, and the movement associated with the user is not a result of the user's bodily movement or exercising. In other examples, device 500 can receive an input from a user indicating that he/she is engaging in a particular type of activity that causes them to move at a velocity exceeding the above-mentioned threshold (e.g., cycling), and that the associated movement should be interpreted as being a result of exercise.

In some other examples, device 500 can be globally turned off in response to a global turn-on/off signal. For instance, if globally turned off, device 500 can stop detecting and monitoring a physical activity from a user. This can advantageously save power in cases where the user intends to not use device 500 for a period of time. In some examples, a global turn-off signal can be inputted directly by a user of device 500 using an input mechanism of device 500. The user can set a period of time during which device 500 would be turned off and after which device 500 would automatically turn on. In other examples, a signal to turn off device 500 can be automatically generated in response to the processor determining, based on a contact temperature or other conditions detectable by the sensors, that device 100 is no longer being worn by a user.

Device 500 can track a user's physical activity over different lengths of time. For example, if device 500 monitors a user's daily activity, it can track one or more attributes of the user's physical activities performed on the same day and can store and reset the values of those attributes the next day. For instance, in some cases, device 500 can monitor a total amount of daily physical activity performed by the user, and this total amount can be updated in real time throughout the day for 24 hours as more activities are detected. After the 24 hours have passed, the total amount can be stored and reset. Device 500 can be configured to reset the attribute value at a specified time that is adjustable by a user. In other examples, device 500 can operate over different lengths of time, such as a half day, two days, a week, two weeks, a month, or the like, that can be adjustable by a user of device 500. Further, in some examples where device 500 monitors a user's physical activity over a relatively extended length of time, device 500 may not have enough memory capacity to track and store all of the attributes of the user's physical activities over such an extended length of time and can instead be configured to offload some or all of the data collected from the sensors on an external device (e.g., a remote server) that is remote from device 500. The external device can be configured to communicate with a plurality of devices 500, and store data collected from these devices. The external device can be further configured to execute computer instructions on the data and communicate the result with one or more of these devices 500.

As used here, the term "affordance" refers to a user-interactive graphical user interface object that is, optionally, displayed on the display screen of devices 100, 300, and/or 500 (FIGS. 1, 3, and 5). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation, in some embodiments, a comparison between the characteristic intensity and one or more thresholds is used to determine whether or not to perform one or more operations (e.g., whether to perform a respective operation or forgo performing the respective operation) rather than being used to determine whether to perform a first operation or a second operation.

Figure 5D:
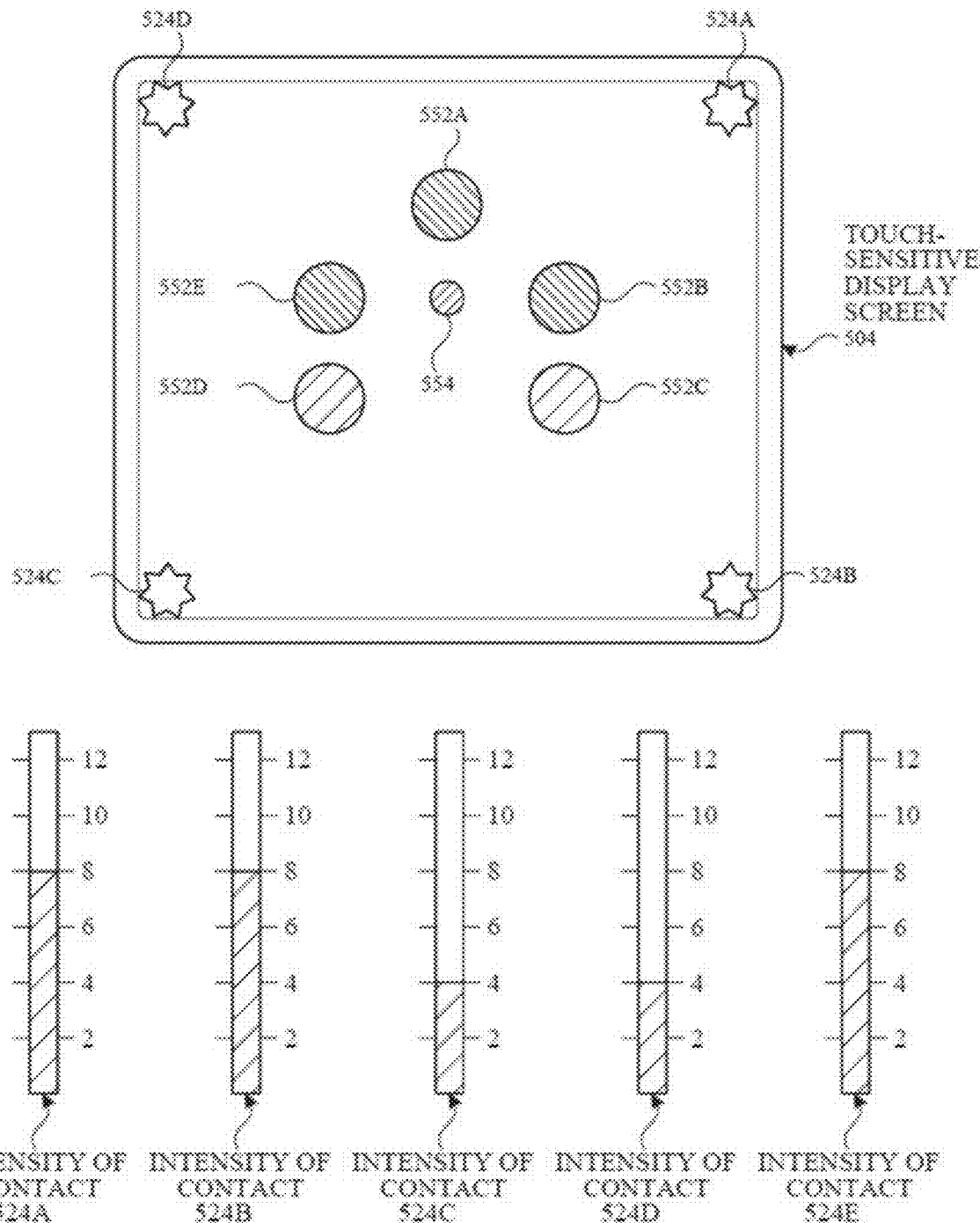

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, $Ij=A \cdot (Dj/\Sigma Di)$, where Dj is the distance of the respective contact j to the center of force, and $\Sigma Di$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

FIGS. 5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the term "open application" or "executing application" refers to a software application with retained state information (e.g., as part of device/global internal state 157 and/or application internal state 192). An open or executing application is, optionally, any one of the following types of applications:

- an active application, which is currently displayed on a display screen of the device that the application is being used on;
- a background application (or background processes), which is not currently displayed, but one or more processes for the application are being processed by one or more processors; and
- a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

System Overview

Figure 6:
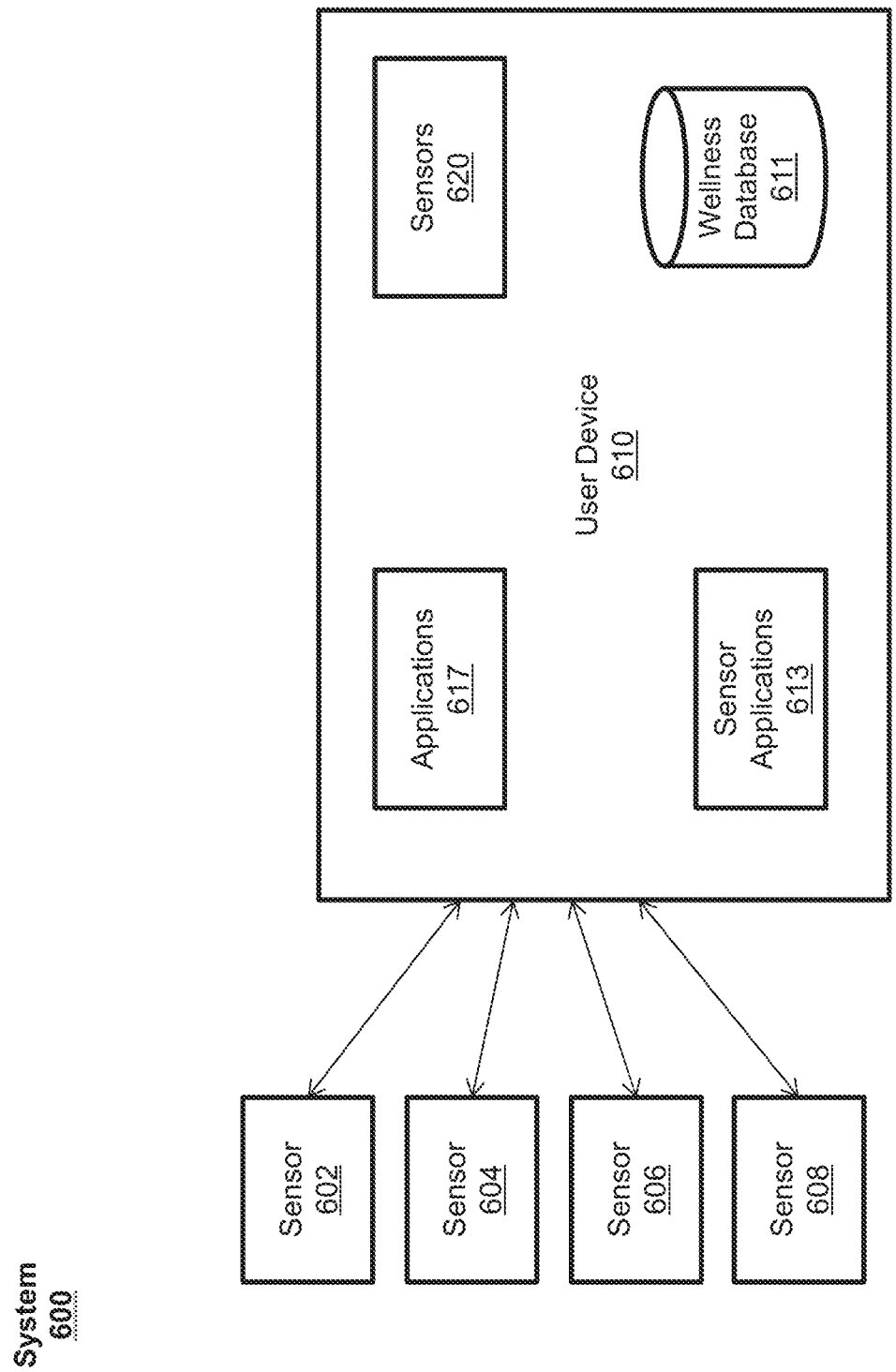
FIG. 6 illustrates a block diagram of an exemplary system for aggregating wellness data according to various examples.

FIG. 6 illustrates an example system 600 for aggregating wellness and other types of data. Wellness data can include, but is not limited to, any type of data associated with a person's health, such as their physical activity data, workout data, weight, heart rate, blood pressure, blood glucose level, medication compliance, or the like. System 600 can be used to collect wellness data associated with a user, store the wellness data, present the wellness data to the user in useful ways, and selectively share the user's wellness data with other users or entities based on permissions set by the user. In addition, in some examples, system 600 can further be used to collect non-wellness data along with wellness data, correlate the non-wellness data with the wellness data, and display the non-wellness data with the wellness data.

System 600 can include one or more user devices 610, which can include any type of electronic device, such as a mobile phone, tablet computer, desktop computer, laptop computer, PDA, or the like. In some examples, user device 610 can include a device similar or identical to devices 100, 300, or 500, described above. User device 610 can include an operating system and a wellness database 611 (e.g., memory 102, 370, or 518) for securely storing wellness or non-wellness data along with associated metadata, such as the time the data was recorded, type of data, device used to record the data, user associated with the data, and the like. User device 610 can further include application programming interfaces (APIs) with access controls for storing data in the wellness database 611 and for accessing data stored in the wellness database 611.

User device 610 can be configured to receive wellness or non-wellness data from various sources and can store the received data in the wellness database 611. For example, user device 610 can be configured to receive wellness or non-wellness data from sensors 602, 604, 606, and 608. These sensors can include any type of sensor capable of obtaining wellness data, such as a biometric sensor, activity tracker, or the like. For example, sensors 602, 604, 606, and 608 can include, but are not limited to, a scale, blood pressure cuff, blood glucose monitor, electrocardiogram, step counter, gyroscope, accelerometer. SpO2 sensor, respiration sensor, posture sensor, stress sensor, photoplethysmogram, galvanic skin response sensor, temperature sensor, or the like. Sensors 602, 604, 606, and 608 can also include other types of sensors, such as audio sensors, ambient light sensors, electromagnetic sensors, touch sensors, capacitive sensors, and the like, for obtaining non-wellness data, such as situational data, temporal data, personal data, contact data, and the like data. In some examples, each sensor can be a separate device, while, in other examples, any combination of two or more of the sensors can be included within a single device. For example, the gyroscope, accelerometer, photoplethysmogram, galvanic skin response sensor, and temperature sensor can be included within a wearable electronic device, such as a smart watch, while the scale, blood pressure cuff, blood glucose monitor, SpO2 sensor, respiration sensor, posture sensor, stress sensor, and asthma inhaler can each be separate devices. While specific examples are provided, it should be appreciated that other sensors can be used and other combinations of sensors can be combined into a single device.

Sensors 602, 604, 606, and 608 can be used to measure wellness or non-wellness data continuously, intermittently, periodically, or at any other desired frequency or interval of time. For example, sensors 602, 604, 606, and 608 can be used to obtain a single measurement or multiple measurements over a length of time. Sensors 602, 604, 606, and 608 can be configured to measure wellness or non-wellness data at the same intervals of time, or can be configured to measure wellness or non-wellness data at different intervals of time. These intervals may be set by a user or may be a default setting for each sensor. Additionally, sensors 602, 604, 606, 608 can be used to measure wellness or non-wellness data at any time or location desired by the user. Moreover, sensors 602, 604, 606, and 608 can be used with or without the supervision of a healthcare provider. For example, a user can use sensors 602, 604, 606, and 608 to obtain sensor measurements at home without the supervision of a medical professional.

In some examples, user device 610 can include software sensor applications 613 (e.g., third party applications) associated with each of sensors 602, 604, 606, and 608 for interfacing with the sensors to allow user device 610 to receive the wellness or non-wellness data. In these examples, the applications 613 can use the device's APIs to store the wellness or non-wellness data in the wellness database 611 of user device 610. In some examples, device 610 can be a smart phone, tablet computer, or the like, and the software sensor applications 613 can include software applications downloadable onto device 610. It should be understood that "third party" can correspond to an entity different than the manufacturer of device 610 and/or the entity that created and/or maintains the operating system of device 610. In these instances, third party applications and their corresponding sensors can communicate and function within the operating system of device 610 according to a predefined device protocol associated with device 610.

The applications 613 can similarly use the device's APIs to access data stored in the wellness database 611. In other examples, user device 610 can be configured to share one or more communication formats with sensors 602, 604, 606, and 608 to allow user device 610 to receive and interpret the wellness or non-wellness data from the sensors. The received data can then be stored in the wellness database 611 of user device 610.

User device 610 can further receive wellness or non-wellness data from its own wellness or non-wellness data sensors 620 (e.g., sensors 168, 359, and 520), from a user interacting with user device 610, from another entity, such as a physician, or from other non-sensor sources. For example, using the device's APIs, wellness or non-wellness data can be received from applications 617 (third party or first party applications) on user device 610, such as a clock application, a calendaring application, a gaming application, an application from a healthcare provider, a messaging application, a physical activity application, a workout application, or the like. The wellness or non-wellness data from the applications 617 can originate from sensors 620, a user interacting with the applications, a remote database (e.g., database for a medical website), a healthcare provider institution (e.g., via the institution's application 617), or the like. In these examples, the usage of the application 617 (e.g., how long you play a video game application, when you play the video game, number of times interacting with a stock application, number of times interacting with a social networking application, length of time interacting with a social networking application, etc.), usage of user device 610 (e.g., length of time on the phone or number of text messages sent as determined from a phone payment application, time spent browsing the Internet as determined from the device's browser, etc.), time spent listening to music as determined from a music or streaming radio application, time spent using a remote application for controlling a television, amount of time or money spent on shopping websites, weather data from a weather application (e.g., to determine how weather affects a user's health), type of events occurring in the user's life as determined from a calendar (e.g., meetings, birthdays, holidays, etc.), interactions with certain people as determined from a contact list and/or calendar application and/or a messaging application and/or phone of user device 610, or the like, can be received by user device 610 and stored in the wellness database 611.

In some examples, default or user-selected settings can be provided to restrict the access that at least one application (e.g., at least one of applications 613 and 617) on user device 610 has to the wellness database 611 of user device 610 (for both storage and retrieval purposes) and to the sensor data generated by sensors 620 within user device 610 and/or sensor data generated by sensors 602, 604, 606, and 608. For example, an application for tracking a user's running sessions can be granted access to the data generated by the GPS sensor of user device 610, but can be prevented from accessing the user's blood pressure data stored in the wellness database 611. In some examples, an entity other than the owner of user device 610 can set the authorization settings for various applications on user device 610. For example, the manufacturer of user device 610 and/or the entity that created and/or maintains the operating system of user device 610 can evaluate the applications to determine if they should be given access to the user's wellness data and/or sensor data generated or received by user device 610. In some examples, these settings can be overridden by the user. User device 610 can further include a display for displaying the stored wellness data or non-wellness data.

Figure 7:
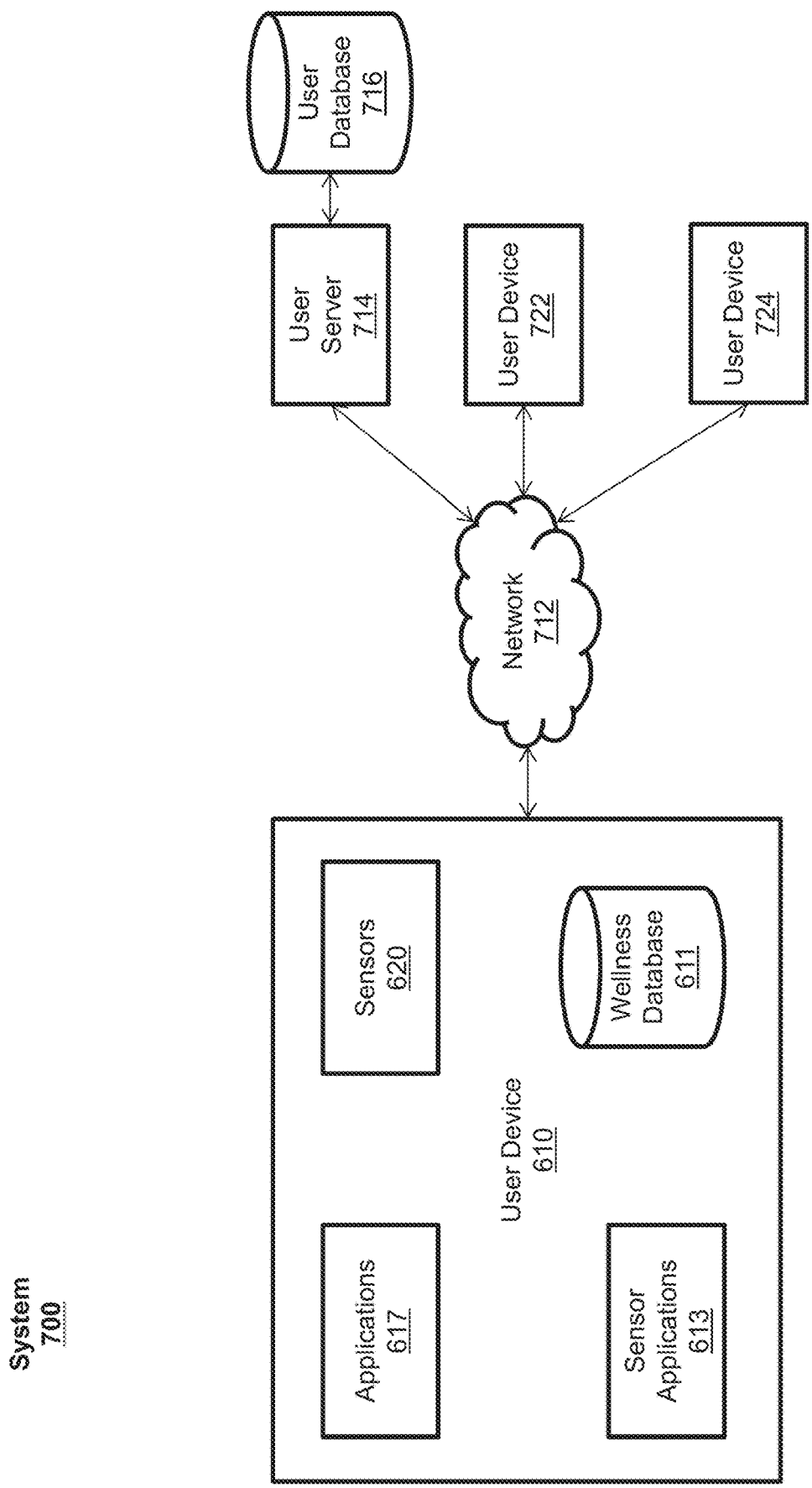
FIG. 7 illustrates a block diagram of another exemplary system for aggregating wellness data according to various examples.

FIG. 7 illustrates system 700 for sharing user wellness data. System 700 can include user server 714 communicatively coupled to user device 610 via network 712, which can include the Internet, an intranet, or any other wired or wireless public or private network. User device 610 can be configured to securely transmit the aggregated wellness or non-wellness data and associated metadata stored on the device to user server 714 for storage in user database 716. In some examples, the wellness or non-wellness data and associated metadata can be transmitted to user server 714 for storage in user database 716 in response to an explicit request for such a transfer by the user of device 610, while, in other examples, the wellness or non-wellness data can be synced with the data in user database 716 continuously, periodically, intermittently, or at any desired frequency. In yet other examples, the user's wellness or non-wellness data can be stored only on user device 610 and may not be stored in an external database.

In some examples, user server 714 and user database 716 can be configured to securely store a user's wellness or non-wellness data using a public/private key system that only allows the owner of the wellness or non-wellness data to decrypt the data. Additionally, the wellness or non-wellness data stored in user database 716 can be stored anonymously (e.g., without identifying and/or personal information about the user, such as a legal name, username, time and location data, or the like). In this way, other users, hackers, and the owner/operator of user database 716 cannot determine the identity of the user associated with the data stored in database 716. In some examples, a user can access their wellness or non-wellness data stored in user database 716 from a user device that is different than the one used to upload the wellness or non-wellness data to user server 714. In these instances, the user can be required to provide login credentials to access their wellness or non-wellness data. User server 714 can be configured to perform the authorization process to restrict access to the data within user database 716.

System 700 can further include any number of other user devices 722 and 724 coupled to network 712. In some examples, user devices 722 and 724 can be operated by the same user as user device 610. In these instances, the user can access their wellness or non-wellness data stored in user database 716 by providing user server 714 with the appropriate credentials. In some examples, wellness and non-wellness data can be synced between user database 716 and one or more of user device 610, 722, and 724. In other examples, the user of user devices 722 and 724 can be a person that is different than the user of user device 610. In these examples, the users of devices 722 and 724 cannot access the wellness or non-wellness data of the user of user device 610 without the authorization of the user of user device 610. If authorization is given, wellness or non-wellness data can be shared with the users of user devices 722 and 724.

In some examples, any of the above described sources of wellness or non-wellness data can be configured to measure, generate, or receive wellness or non-wellness data continuously, intermittently, periodically, or at any other desired frequency or interval of time. As such, the wellness or non-wellness data can similarly be stored or updated in wellness database 611 or user database 716 continuously, intermittently, periodically, or at any other desired frequency or interval of time. The frequencies and intervals of time used for measuring, generating, receiving, or storing wellness or non-wellness can be the same or they can be different. Additionally, these frequencies and intervals can be default values or they can be set by a user to provide the user with wellness or non-wellness data that has been updated within a desired length of time.

While not shown, it should be appreciated that many other user devices can be coupled to user server 714 through network 712 to collect and store wellness or non-wellness data for other users in a manner similar to that described above.

Activity Monitor

Figure 8:
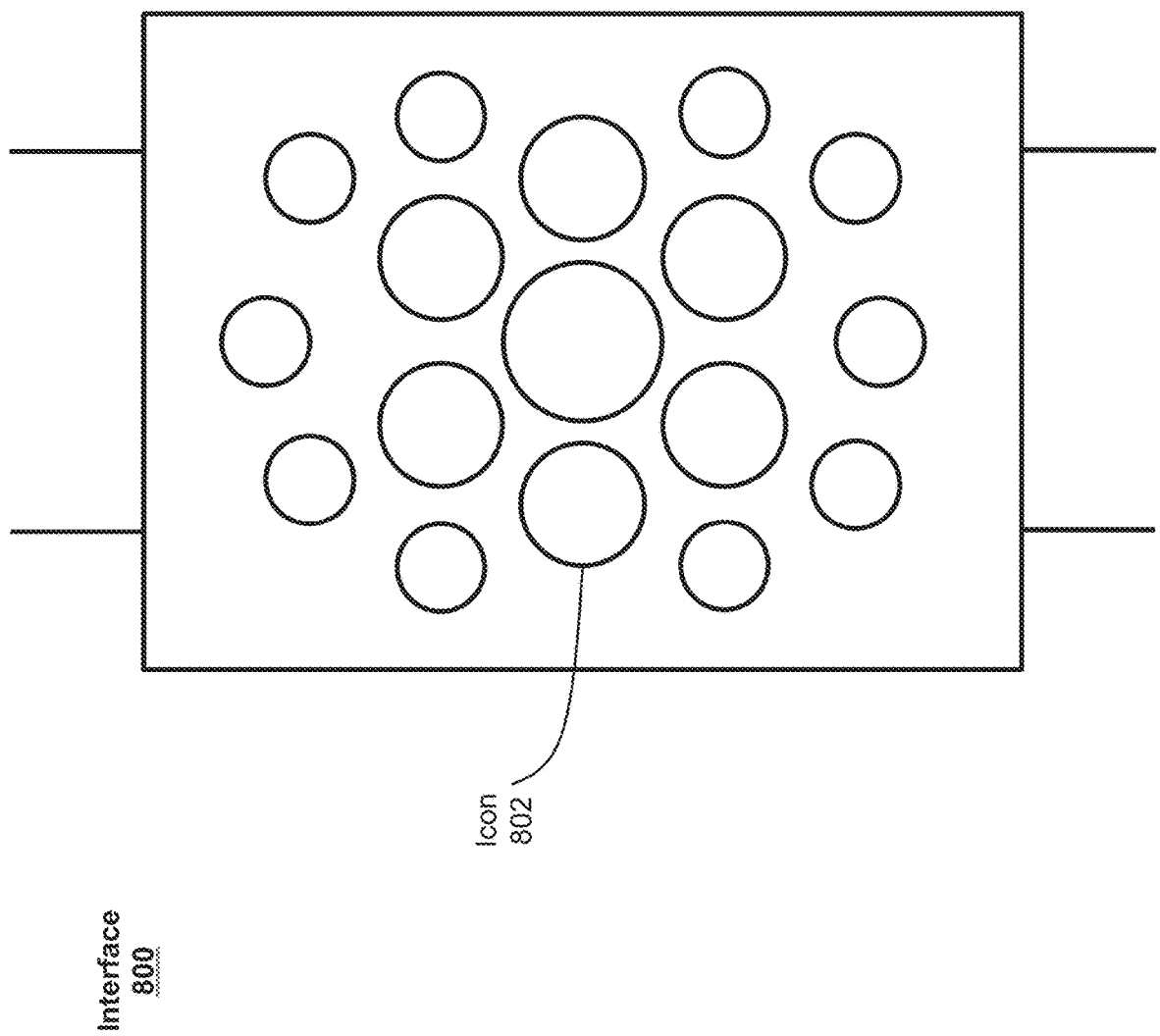
FIG. 8 illustrates an exemplary physical interface for displaying a menu of applications according to various examples.
Figure 9:
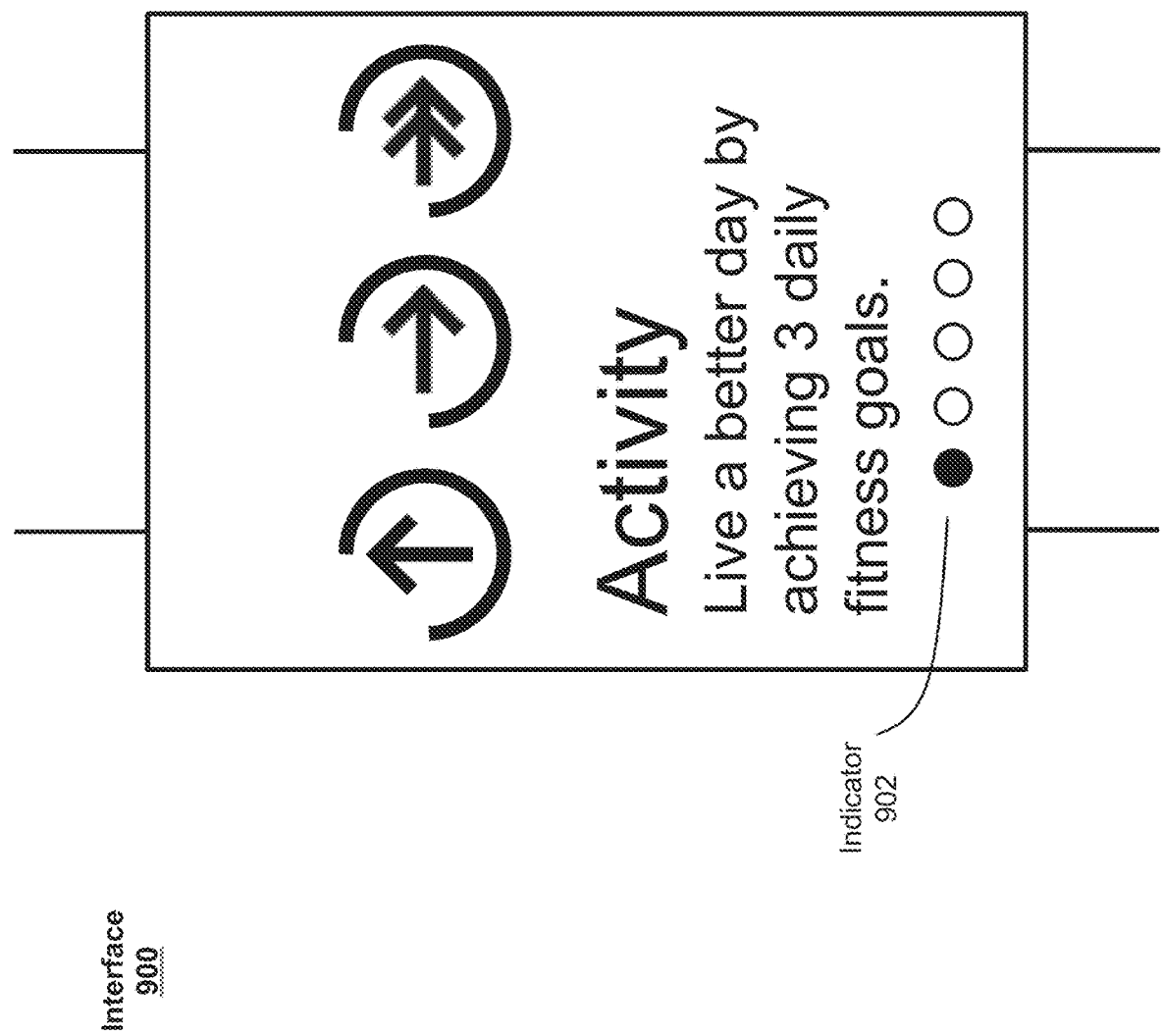
FIGS. 9-14 illustrate exemplary interfaces of a physical activity application according to various examples.
Figure 10:
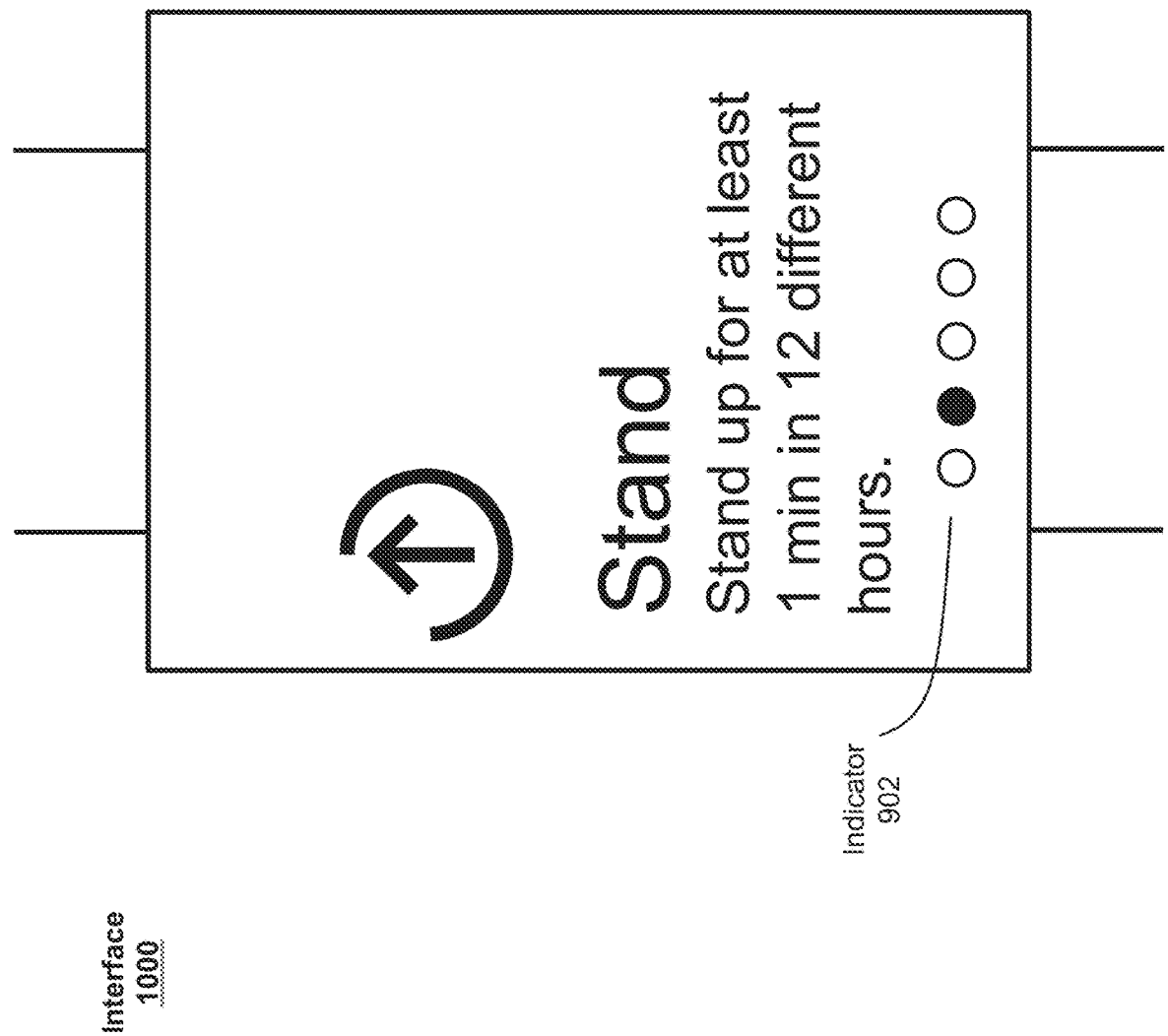
Figure 11:
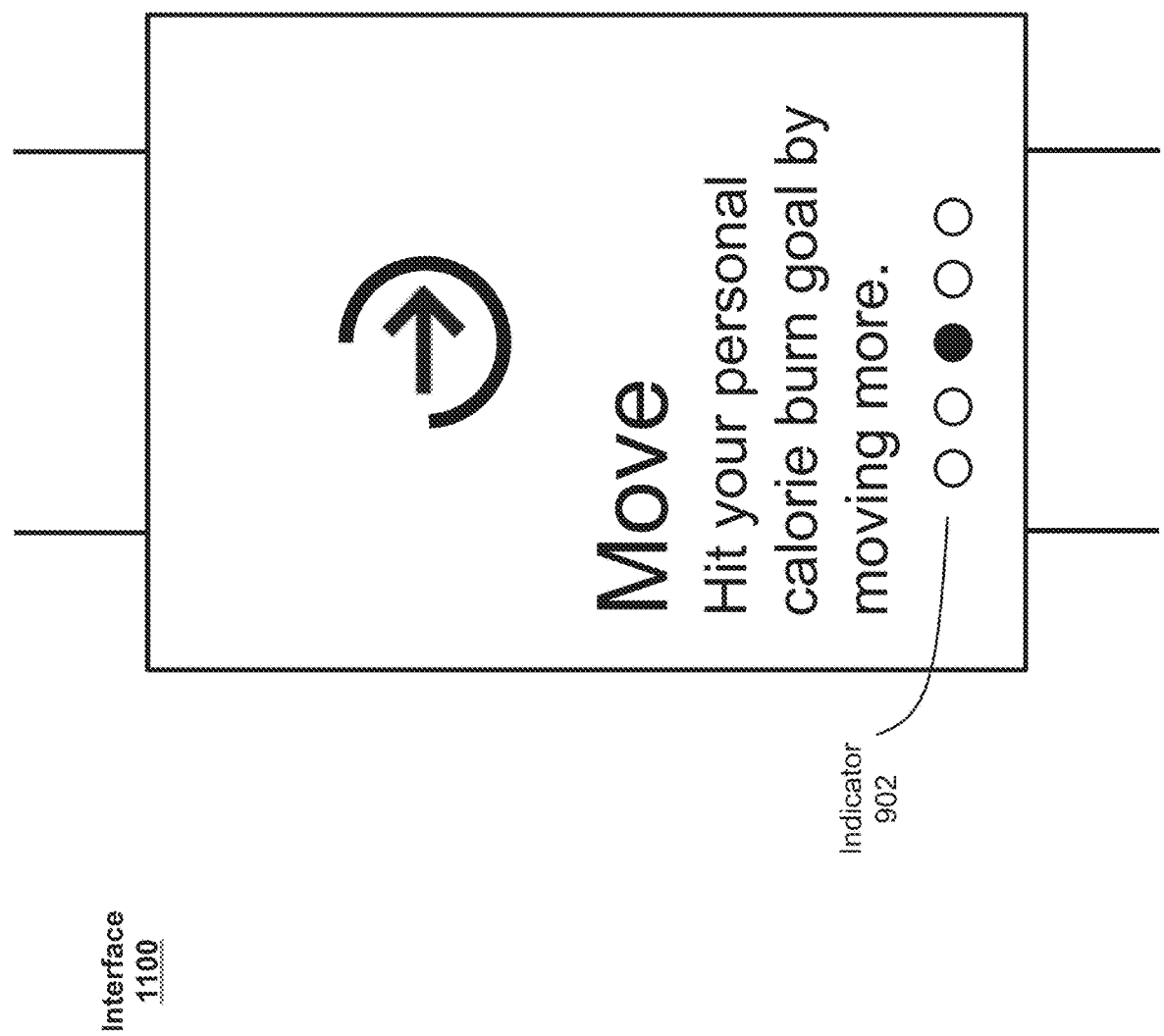
Figure 12:
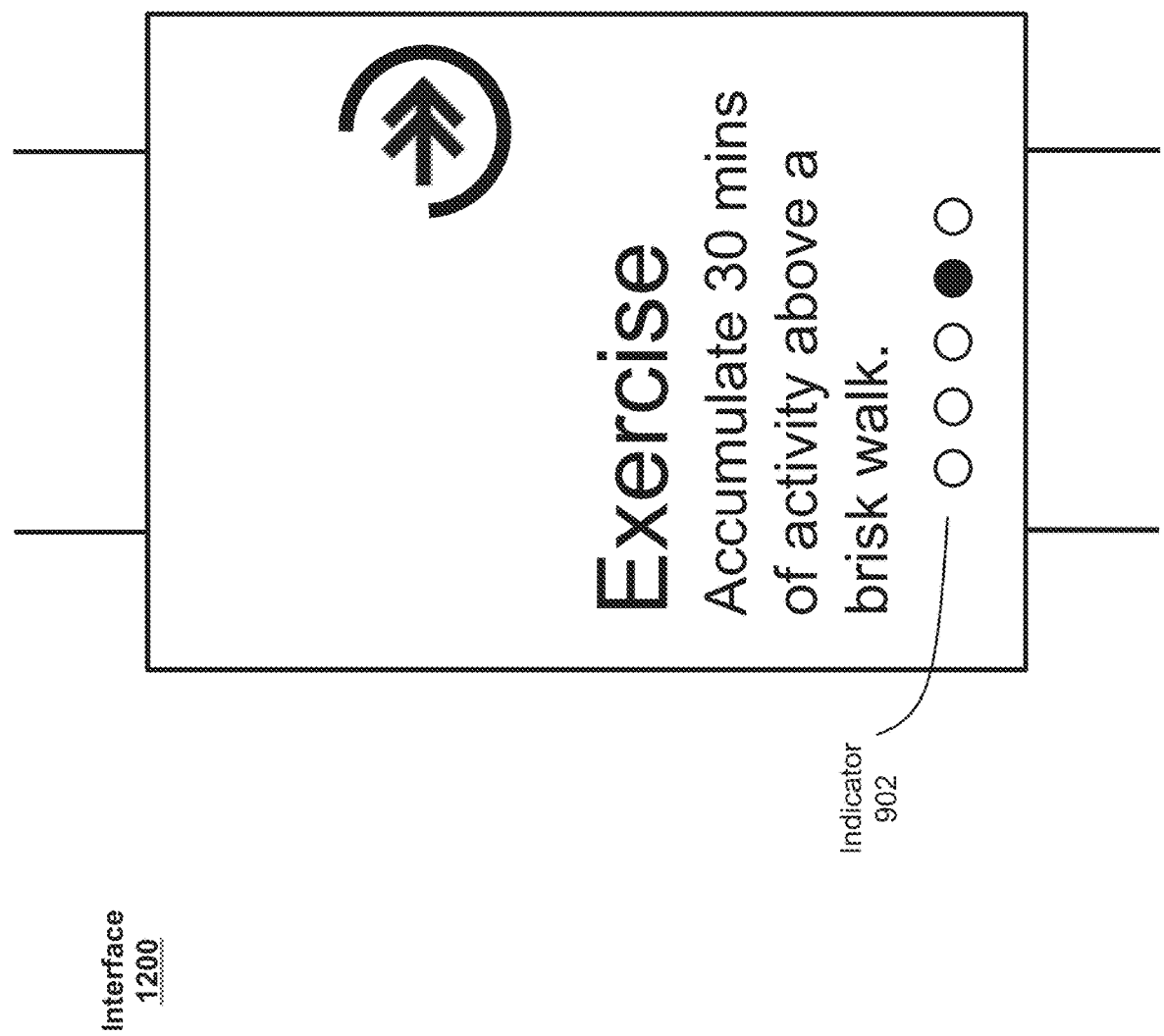
Figure 13:
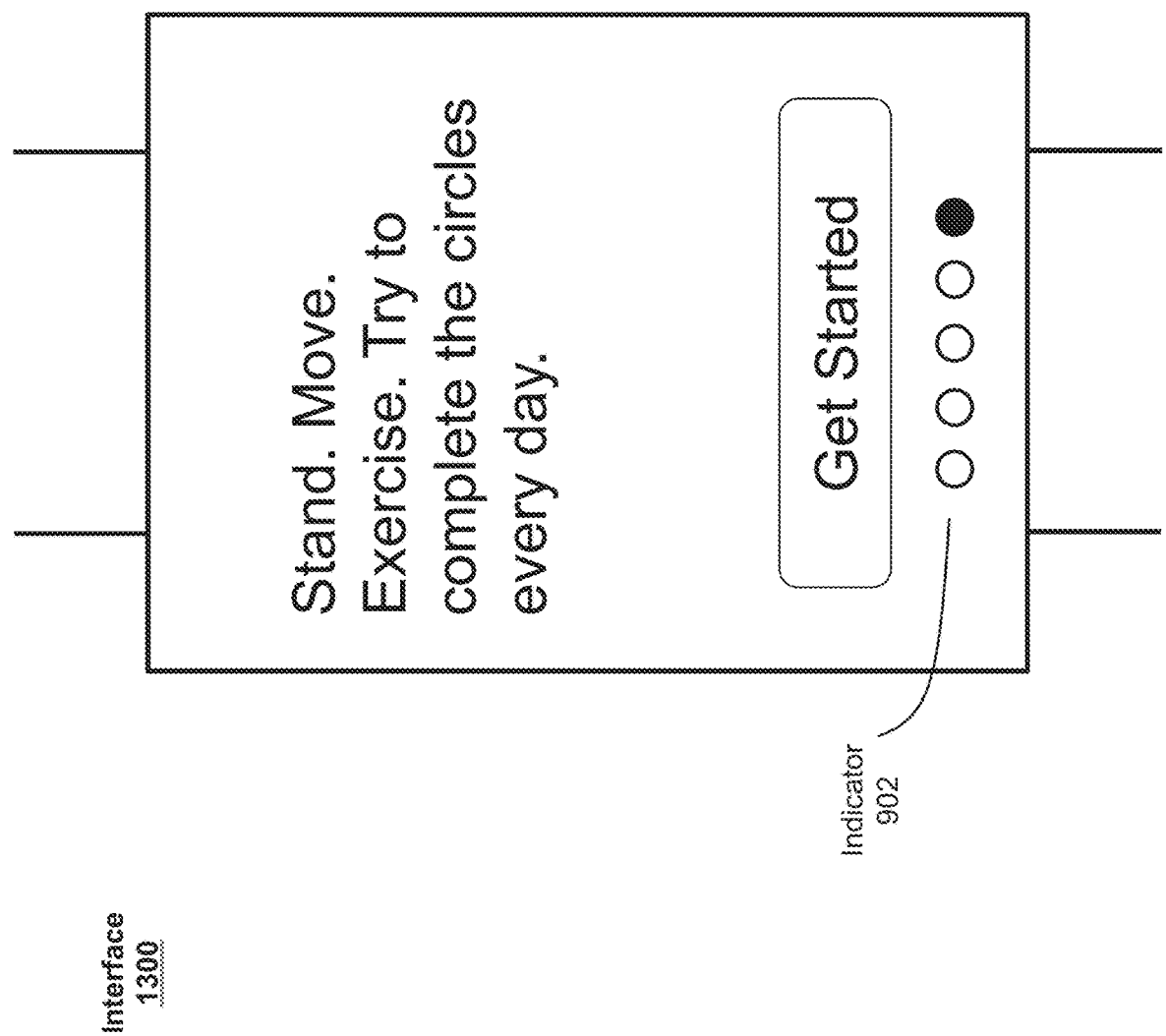

FIG. 8 illustrates an exemplary interface 800 for displaying a menu of applications on an electronic device, such as device 100, 300, 500, or 610. As shown, interface 800 includes multiple application icons 802 that, when selected by a user, causes the electronic device to open the associated application. For example, in response to a user selection of an application icon 802 corresponding to an application for monitoring a user's physical activity, an interface similar to interface 900, shown in FIG. 9, can be displayed. As shown, interface 900 can include a description of the physical activity application and a page indicator 902 indicating that other pages are available for viewing. In response to a user selection to view another page, such as a swipe gesture from the right of the display to the left of the display, interface 1000, shown in FIG. 10, can be displayed. As shown, interface 1000 can include a description of a first goal of the physical activity application and the page indicator 902. In response to a user selection to view another page, such as a swipe gesture from the right of the display to the left of the display, interface 1100, shown in FIG. 11, can be displayed. As shown, interface 1100 can include a description of a second goal of the physical activity application and the page indicator 902. In response to a user selection to view another page, such as a swipe gesture from the right of the display to the left of the display, interface 1200, shown in FIG. 12, can be displayed. As shown, interface 1200 can include a description of a third goal of the physical activity application and the page indicator 902. In response to a user selection to view another page, such as a swipe gesture from the right of the display to the left of the display, interface 1300, shown in FIG. 13, can be displayed. As shown, interface 1300 can include a summary description of the three goals of the physical activity application and the page indicator 902.

Figure 14:
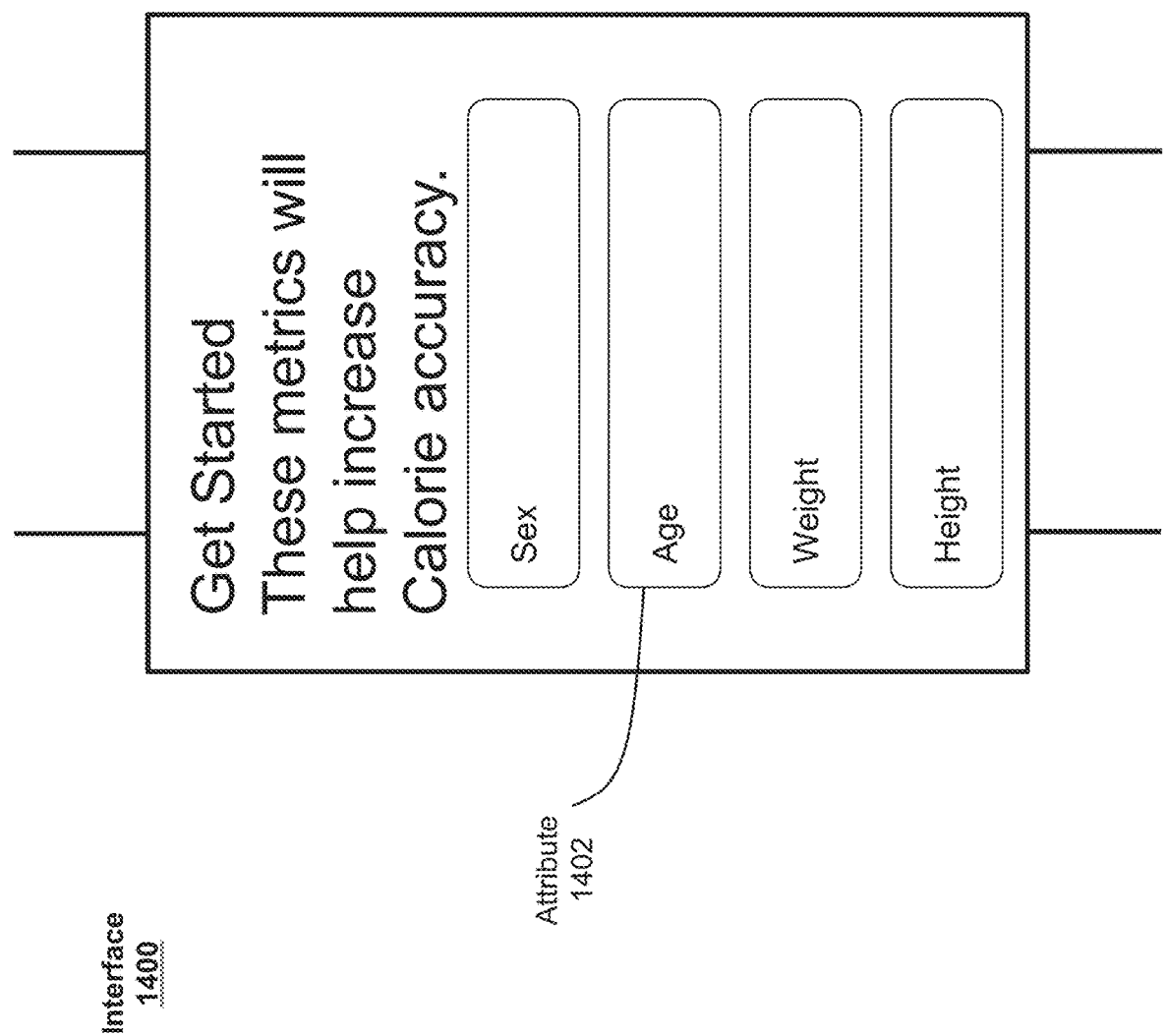
Figure 15:
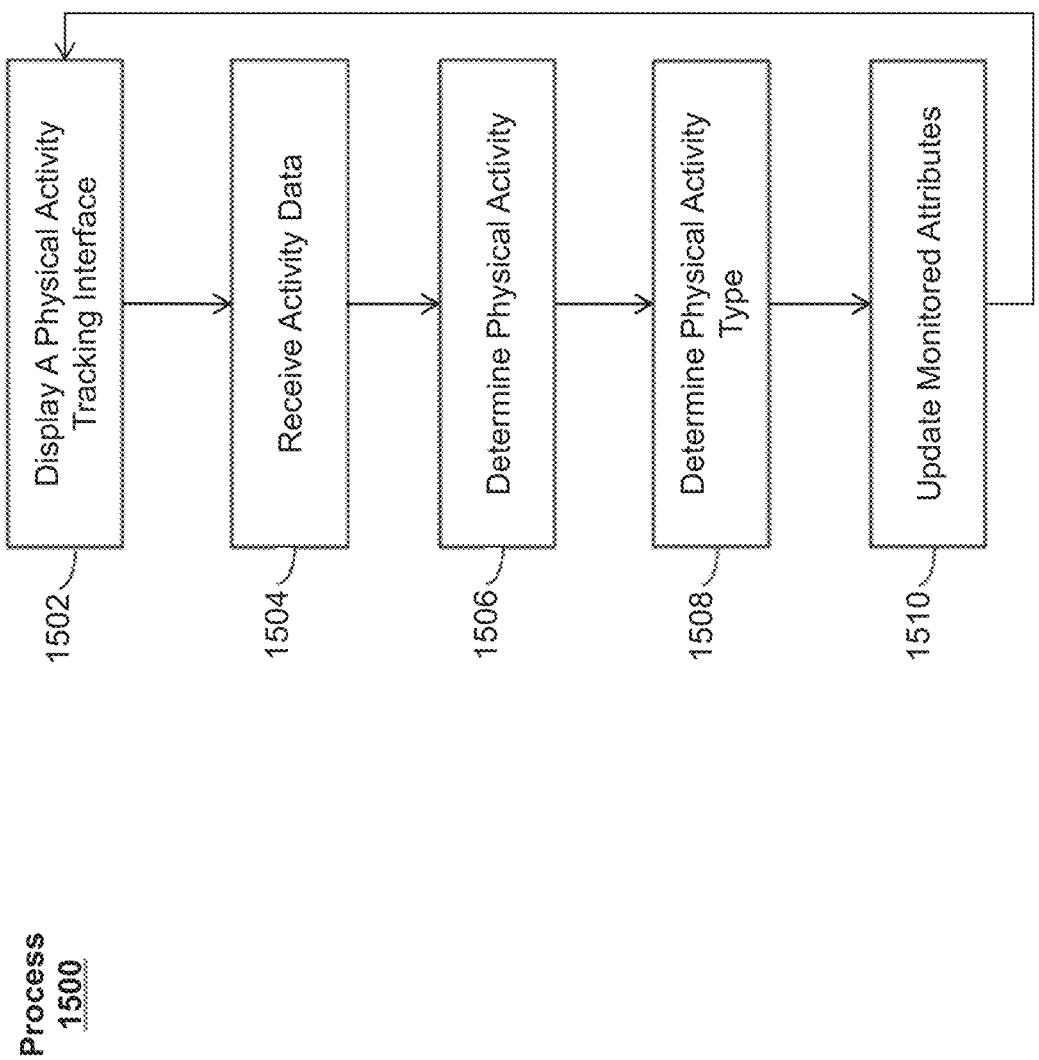
FIG. 15 illustrates an exemplary process for generating a physical activity tracking interface for monitoring a user's physical activity according to various examples.

In some examples, in response to a user selection of the "Get Started" option of interface 1300, an interface similar to interface 1400, shown in FIG. 14, can be displayed. As shown, interface 1400 can include selectable attribute elements 1402 for entering various user attributes, such as the user's sex, age, weight, and height. In response to a selection of any of elements 1402, the electronic device can display an interface to allow the user to enter the desired attribute value. The interface can include any type of input mechanism, such as a text box, a list of values, a pull-down menu, or the like. In response to the user entering a particular attribute value, the electronic device can store the entered information in the memory of the device and/or in a remote database.

In some examples, the interfaces shown in FIGS. 9-13 can be displayed each time the physical activity application is opened. In other examples, the interfaces shown in FIGS. 9-13 can only be displayed the first time that the physical activity application is opened. In some examples, the electronic device can determine, before displaying interface 1400, whether the user attributes (e.g., sex, age, weight, and height) are available on the electronic device or an accessible remote database. If it is determined that the user attributes are available, the electronic device may not display interface 1400. If it is instead determined that some or all of the user attributes are unavailable, the electronic device can display interface 1400. Since the electronic device can store the user attributes entered using interface 1400, interface 1400 may only be displayed the first time that physical activity application is opened.

In some examples, after displaying some or all of the interfaces shown in FIGS. 9-13 (or directly after displaying interface 800 if the interfaces shown in FIGS. 9-13 are not displayed), the electronic device can perform process 1500, shown in FIG. 1.5, for generating and updating a physical activity tracking interface. Process 1500 can be performed using a device similar or identical to device 100, 300, 500, or 610 and can include detecting movement associated with the device, recognizing it as being associated with a physical activity performed by the user using the device, monitoring various attributes of the detected physical activity, and displaying one or more attributes of the physical activity on a display of the device. Some operations in process 1500 may be combined, the order of some operations may be changed, and some operations may be omitted.

As described below, process 1500 provides an intuitive way to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 1502, the one or more processors of the device can cause, on the display of the device, a display of a physical activity tracking interface. The physical activity tracking interface can include any number of indicators representing any number of monitored attributes of a user's physical activity. The indicators of the physical activity tracking interface can be updated in real-time in response to updates to the values of the monitored attributes of physical activity. In this way, the display of the device can provide real-time information about the user's monitored physical activity. The indicator can include a text, an image, or combination thereof. For example, an animated image can be used to show a progression or otherwise changing status of a monitored attribute. In some examples, block 1502 can further include displaying additional indicators to provide more information about the monitored attributes, such as a goal value for each of the monitored values, a progressive measure of the monitored values compared to respective goal values, an automatically adjusting goal value based on a passage of time (e.g., 10% of a whole goal value in the morning gradually being adjusted to increase the percentage as the time passes, etc.), a history of past physical activity (e.g., the highest/lowest, or daily average over a month, a week, two days, last day, etc.), any of the above information associated with other users (e.g., the highest/lowest, or daily average amount of physical activity performed by other users different from the user of the device), or the like. Information associated with other users wearing devices other than the device performing process 1500 can be collected through an external server that is configured to communicate with such devices. FIGS. 17-21, discussed in greater detail below, illustrate example physical activity tracking interfaces that can be displayed at block 1502 of process 1500.

At block 1504, one or more processors of the device can receive activity data that is representative of sensed physical activity of a user from an activity sensor (e.g., sensors 168, 359, and 520). At block 1506, the one or more processors can process the received activity data to determine whether the activity data indicates that a physical activity, as opposed to a gesture, has been performed by the user of the device. In some examples, the occurrence of a physical activity by the user can be determined by analyzing the activity data and determining whether it reflects one or more characteristics that are associated with a user performing a physical activity while wearing the device. Such characteristics can include a minimum displacement per unit time, a speed, a rate of change of body temperature, or the like.

After determining that a physical activity has been performed by the user, the processor(s) can determine, at block 1508, a type of the detected physical activity. This determination can be based on at least the activity data and a predetermined set of criteria for a certain type of activity. The device can categorize detected physical activities into any number of categories (e.g., 1 or more) and monitor different attributes for each category. For example, the device can categorize detected physical activities of a user of the device into two categories a first type and a second type. In some examples, the first type of physical activity can refer to all detected physical activities of a user of the device. The second type of physical activity can refer to physical activities that satisfy certain required conditions that, for example, can include having activity intensities equal to or greater than a threshold intensity. Alternatively, the second type of physical activity can refer to physical activities that have intensities less than a threshold intensity. A threshold intensity can be represented as a distance traveled, a number of Calories burned, a number of steps taken, any one or more of these attributes calculated per unit time, or the like. In some examples, the device can adjust a threshold for one or more categories of activities depending on the identified type of the detected physical activity. For instance, the device can categorize activities as being of a second type if they have an activity intensity equal to or greater than a threshold intensity (e.g., a high intensity, an intensity corresponding to a brisk walk, etc.). This threshold intensity can vary depending on whether the detected activity is a walking activity (in which case the threshold can be represented as a minimum number of steps taken per unit time), a running activity (in which case the threshold can be represented as a minimum distance traveled per unit time), or all other types of activity (in which case the threshold can be represented as a minimum number of Calories burned per unit time). It should be appreciated that conditions other than the intensity level can be used to categorize physical activities, for example, time(s) of a day when physical activity is detected (e.g., a category for morning activities, another category for day activities, or another category for evening activities, etc.), predetermined type(s) of physical activity (e.g., a category for standing activities, walking activities, running activities, etc.), or the like. One or more conditions can be used alone or in combination to define a category or a type of physical activity.

In some examples, the first type of activity can refer to activity that meets a first set of criteria, a second type of activity can refer to activity that meets a second set of criteria, a third type of activity can refer to activity that meets a third set of criteria, and so on. In the determination process, the processor(s) of the device can determine whether the activity data indicates that the associated physical activity meets the first set of criteria, the second set of criteria, and/or the third set of criteria (or other sets of criteria). The criteria can include any information detectable by the activity sensors, such as a speed greater than or equal to a threshold, a minimum number of steps taken per unit time, a minimum amount of Calories burned per unit time, etc. In some examples, the different sets of criteria can be nested such that the third type of activity is a subset of the second type, which can be a subset of the first type. In other examples, the different sets of criteria can cause the types of activity to be mutually exclusive. In yet other examples, the different sets of criteria can cause the types of activity to be partially overlapping.

In some examples, the processor(s) can categorize a user's activity as being a first type of activity representing all forms of physical activity or a second type of activity representing physical activity equal to or greater than a threshold intensity (or, alternatively, less than the threshold intensity). In such cases, a first set of criteria for the first type can simply require that the activity be a physical activity (rather than a gesture) and a second set of criteria for the second type can require having an intensity greater than or equal to (or, alternatively, less than) the threshold intensity. Intensity can be measured using any number of attributes of an activity, including but not limited to, a distance traveled, a speed, a number of Calories burned, a number of steps taken, any one or more of these attributes calculated per unit time, or the like. Intensity can also be associated with a biological condition detectable by biometric sensors, including but not limited to, a heart rate, an amount of heat, or a rate of change in any of the foregoing conditions, etc. In some examples, the threshold intensity of the second set of criteria can correspond to the intensity of a brisk walk or 3 Metabolic Equivalent of Tasks (METs). According to the Centers for Disease Control and Prevention (CDC), a brisk walk is walking at a pace of three to three and a half miles per hour or roughly 20 minutes per mile. That equates to approximately five kilometers per hour or 12 minutes per kilometer. While example types of physical activity are provided above, it should be appreciated that other types of physical activity can be used (e.g., standing, running, climbing, etc.).

In some examples, the criteria used by the device to determine type(s) of activity can be pre-set in the device. In other examples, the criteria can be directly input by a user, such that the user can customize which activities are going to be monitored separately from others. In yet other examples, the criteria can be automatically calculated by the device based on the user's health information. The user's health information can be input by a user and can refer to user's age, weight, gender, body mass index (BMI), average heart rate, average blood pressure, or the like. Alternatively, the user's health information can be stored in an external device configured to communicate with the device such that the device can receive the data to generate customized criteria for the user of the device. In other examples, the external device can determine the customized criteria for the user of the device and can transmit the determined criteria to the device.

At block 1510, the processor(s) can update the monitored attributes of the detected physical activity. The monitored attributes of the detected activity can be expressed in any standard, arbitrary, or other unit of measurement, such as Calories burned, amount of time spent, distance traveled, number of steps, etc. The monitored attributes of different types of physical activity can be the same or different. Additionally, the monitored attributes can be stored as values in a memory or storage, and updating the monitored attributes at block 1510 can include updating these stored values. For example, if the detected movement of the device corresponds to a physical activity of a first type and not of any other type, a stored value representing the aggregate amount of the first type of activity can be updated at block 1510, and other stored values representing other types of activity may not be updated. The updating process can be performed in real-time in response to a detection of any new physical activity to the extent that the detected physical activity has attributes that are being monitored by the device.

Blocks 1502, 1504, 1506, 1508, and 1510 can be repeated any number of times and at any desired interval of time to detect a user's physical activity and to update the display of the physical activity tracking interface accordingly. Additionally, it should be appreciated that while blocks 1502, 1504, 1506, 1508, and 1510 are shown in a particular order, blocks 1502, 1504, 1506, 1508, and 1510 can be performed in any order, at the same time, or some of the blocks can be omitted. For example, the physical activity tracking interface can be repeatedly updated at block 1502 while activity data is being received at block 1504 and processed to update the monitored attributes at blocks 1506, 1508, and 1510 to provide the user with current or real-time physical activity information. In other examples where the physical activity application is running in the background of the device or while the display of the device is deactivated, block 1502 can be omitted and blocks 1504, 1506, 1508, and 1510 can repeatedly be performed to monitor the user's physical activity and update the monitored attributes such that an accurate display of the attributes can later be provided to the user when the physical activity application is reopened or the display of the device is activated.

Note that details of the processes described above with respect to method 1500 (e.g., FIG. 15) are also applicable in an analogous manner to the methods described below. For example, methods 1600, 2200, 2400, 4000, 4800, 7900, 8600, and 9200 may include one or more of the characteristics of the various methods described above with reference to method 1500. For example, the activity data, activity types, displayed values and other elements described above with reference to method 1500 optionally have one or more of the characteristics of the activity data, activity types, displayed values and other elements described herein (e.g., methods 1600, 2200, 2400, 4000, 4800, 7900, 8600, and 9200). For brevity, these details are not repeated below.

Figure 16:
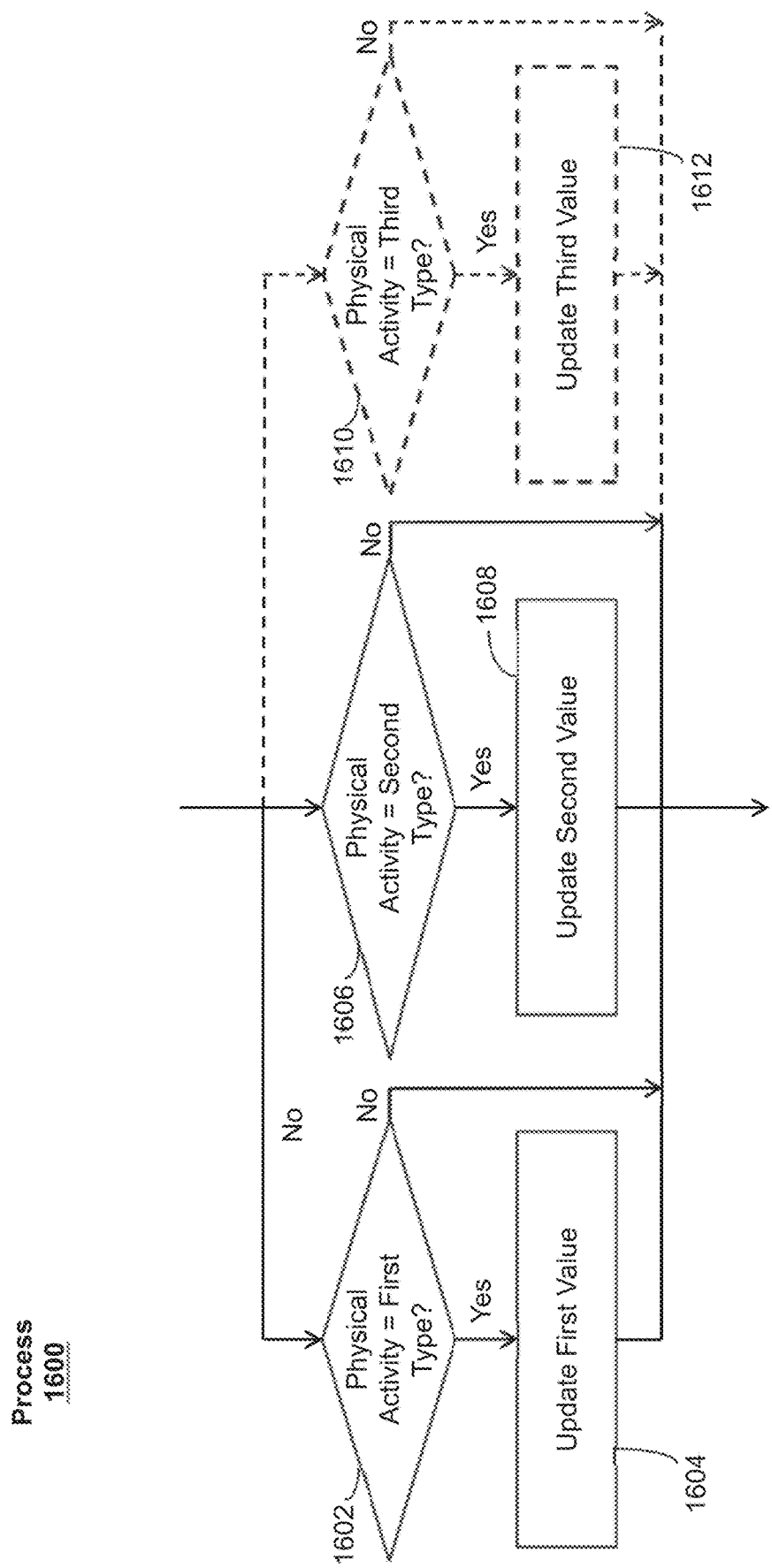
FIG. 16 illustrates an exemplary process for determining a physical activity type and updating monitored attributes of the physical activity type according to various examples.

FIG. 16 illustrates an exemplary process 1600 for determining a type physical activity and updating monitored attributes of the type physical activity. Process 1600 can be performed using a device similar or identical to device 100, 300, 500, or 610 and can be used to perform blocks 1604, 1608, and 1612 of process 1600. In the illustrated example, process 1600 can be used to determine if a physical activity falls within one or both of two types of physical activities—a first type and a second type. The first type of physical activity can be a physical activity that meets a first set of criteria, and the second type of physical activity can be a physical activity that meets a second set of criteria. In some examples, the first type of activity can be a physical activity detectable by the device, and the second type of activity can be a physical activity that has an intensity greater than or equal to a threshold intensity. Some operations in process 1600 may be combined, the order of some operations may be changed, and some operations may be omitted.

As described below, process 1600 provides an intuitive way to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 1602, the activity data received at block 1504 of process 1500 can be used to determine whether the physical activity represented by the activity data corresponds to a first type based on a predetermined first set of criteria. This can include determining whether the physical activity meets each criterion of the first set of criteria. For example, the first set of criteria can simply require that the physical activity be a physical activity (as opposed to a gesture). In this example, block 1602 can include determining whether the activity data represents a physical activity rather than a gesture. If it is determined that the physical activity represented by the activity data meets the first set of criteria, process 1600 can proceed to block 1604. Alternatively, if it is determined at block 1602 that the physical activity represented by the activity data does not meet the first set of criteria, process 1600 can bypass the updating of the first value of block 1604.

At block 1604, a first value representing an attribute of the first type of activity can be updated. The attribute can include any desired attribute, such as an amount, an intensity level, a duration, a progress relative to a set value, a trend over a time period, or the like, of the activity. For example, the first value can represent an aggregate amount of active and/or resting Calories expended by the user in performing the first type of activity over a predetermined period of time (e.g., a day). In this example, the updating process performed at block 1604 can include adding, to a previously stored first value (representing previously measured Calories expended by the user), a value calculated from the activity data that represents an amount of Calories expended by the user in performing the recently detected physical activity.

Before, during, or after performing blocks 1602 and 1604, block 1606 can be performed to determine whether the physical activity represented by the activity data corresponds to a second type based on a predetermined second set of criteria. Block 1606 can be similar to block 1602, except that block 1606 can include determining whether the physical activity meets each criterion of the second set of criteria. In some examples, the second set of criteria can cause the second type of physical activity to be mutually exclusive from the first type of physical activity. In other examples, the second set of criteria can cause the second type of physical activity to be partially overlapping with the first type of physical activity. In yet other examples, the second set of criteria can encompass the first set of criteria, such that the second type of physical activity can be a subset of the first type of physical activity. For example, the second set of criteria can require that the physical activity have an intensity that is equal to or greater than a threshold intensity (e.g., 3 METs, a threshold movement speed of 3.5 miles per hour or a brisk walk, etc.). In this example, block 1606 can include determining whether the activity data represents the user moving at a speed that is greater than or equal to 3.5 miles per hour. If it is determined that the physical activity represented by the activity data meets the second set of criteria, process 1600 can proceed to block 1608. Alternatively, if it is determined at block 1606 that the physical activity represented by the activity data does not meet the second set of criteria, process 1600 can bypass the updating of the second value of block 1608.

At block 1608, a second value representing an attribute of the second type of activity can be updated. The attribute can include any desired attribute, such as an amount, an intensity level, a duration, a progress relative to a set value, a trend over a time period, or the like, of the activity. For example, the second value can represent a duration of time that the user performs the second type of activity over a predetermined period of time (e.g., a day). In this example, the updating process performed at block 1608 can include adding, to a previously stored second value (representing a previously measured duration of time that the user was performing the second type of activity), a value calculated from the activity data that represents a duration of time that the user was engaged in the second type of activity in performing the recently detected physical activity.

The attributes being monitored and updated for each of the types of activities can be the same or different. For example, the monitored attribute of both the first and second types of activities can be Calories expended. Alternatively, the monitored attribute of the first type of activity can be Calories expended, while the monitored attribute of the second type of activity can be a duration of time performing the second type of activity. Additionally, the period of time over which the first and second types of activities are monitored can be the same or different. For example, if different periods are used, the amount of the first type of physical activity can be aggregated over a day, while the amount of the second type of physical activity can be aggregated over two days. It should be appreciated that many other different periods of time can be used to monitor each of the attributes.

In some examples, process 1600 can include additional determination paths (e.g., a third determination path represented by the dotted path attached to blocks 1610 and 1612) to determine whether the physical activity corresponds to other types of activity. For example, block 1610 can be performed before, during, or after performing blocks 1602, 1604, 1606, and/or 1608 and can include determining whether the physical activity represented by the activity data corresponds to a third type based on a predetermined third set of criteria. In some examples, the third set of criteria can include both the first set of criteria and the second set of criteria, causing the third type of physical activity to be a subset of the second type and a subset of the first type of physical activities. In other examples, the third set of criteria can be only partially overlapping with the second set of criteria and/or the first set of criteria, or entirely mutually exclusive with respect to both or either set. For example, the first, second, and third sets of criteria can be configured such that the first type includes a physical activity detectable (and recognizable as a physical activity rather than a gesture) by the device, the second type includes only a physical activity that has an intensity equal to or greater than a first threshold intensity (or an activity in which the user is standing), and the third type includes only physical activities that have an intensity lower than a second threshold intensity. It should be appreciated that there can be numerous other ways to configure the criteria.

While FIG. 16 shows the detection of only three types of activities, it should be appreciated that process 1600 can be used to determine any number of physical activity types and to update monitored attributes for those physical activity types. For example, process 1600 can continue to determine whether a physical activity corresponds to a fourth type, a fifth type, sixth type, and so one, each followed by their respective updating process, similar to the process shown in the illustrated example. Additionally, while the blocks of process 1600 are shown and described in a particular order, it should be appreciated that the blocks can be performed in other orders or at the same time. For example, the activity data can be used to determine whether the physical activity corresponds to the first, second, and third types at blocks 1602, 1606, and 1610, respectively, at the same time or in any sequential order.

Referring back to FIG. 15, after performing process 1600 at blocks 1508 and 1510, process 1500 can return to block 1502. At block 1502, the processor(s) may cause, on the display of the device, an updated display of the indicators representative of each of the monitored values—e.g., the first value, the second value, and the third value (if one exists). In some examples, the indicator may include a first indicator representing attributes of only the first value, a second indicator representing attributes of only the second value, and a third indicator representing attributes of only the third value. The first, second, and third indicators can be simultaneously displayed on the display or alternatingly displayed. Each of the indicators can include one or more of graphic images, animations, texts or other visual representations. In some other examples, the indicators can include sound effects, haptic effects, or any other non-visual effects. Further, one or more indicators can be used to alert the user for occurrence of certain conditions, such as a continued inactivity of the user for a certain length of time, a detection of a new physical activity, or an achievement of a daily goal, or the like. These indicators advantageously provide a user glancing at the indicators with an overview of their physical activity.

Note that details of the processes described above with respect to method 1600 (e.g., FIG. 16) are also applicable in an analogous manner to the other methods described herein. For example, methods 1500, 2200, 2400, 4000, 4800, 7900, 8600, and 9200 may include one or more of the characteristics of the various methods described above with reference to method 1600. For example, the activity data, activity types, displayed values and other elements described above with reference to method 1600 optionally have one or more of the characteristics of the activity data, activity types, displayed values and other elements described herein (e.g., methods 1500, 2200, 2400, 4000, 4800, 7900, 8600, and 9200). For brevity, these details are not repeated.

FIGS. 17-21 illustrate different example interfaces that can be displayed on the device at block 1502 of process 1500. In these examples, the device is assumed to be a daily activity monitor that categorizes a user's physical activity into a first type (based on a first set of criteria) and a second type (based on a second set of criteria), and monitors a daily aggregate amount of each type of the user's activity. The first type can include a physical activity detectable (e.g., recognizable as a physical activity as opposed to a gesture) by the device, and the second type can include a physical activity that has an intensity equal to or greater than a threshold intensity. While specific example parameters are described below, it should be appreciated that different parameters can be used to configure the device. For example, the device can monitor a user's activity over different periods of time (e.g., 5 hours, 6 hours, 12 hours, 48 hours, a week, etc.), can monitor a different number of types of activities (e.g., one, three, four, etc.), and/or can monitor different types of activities. Further, the device can monitor attributes other than an aggregate amount for each of the monitored types, such as an average amount over a period of time, a frequency of activity, a maximum or a minimum amount, etc.

Figure 17:
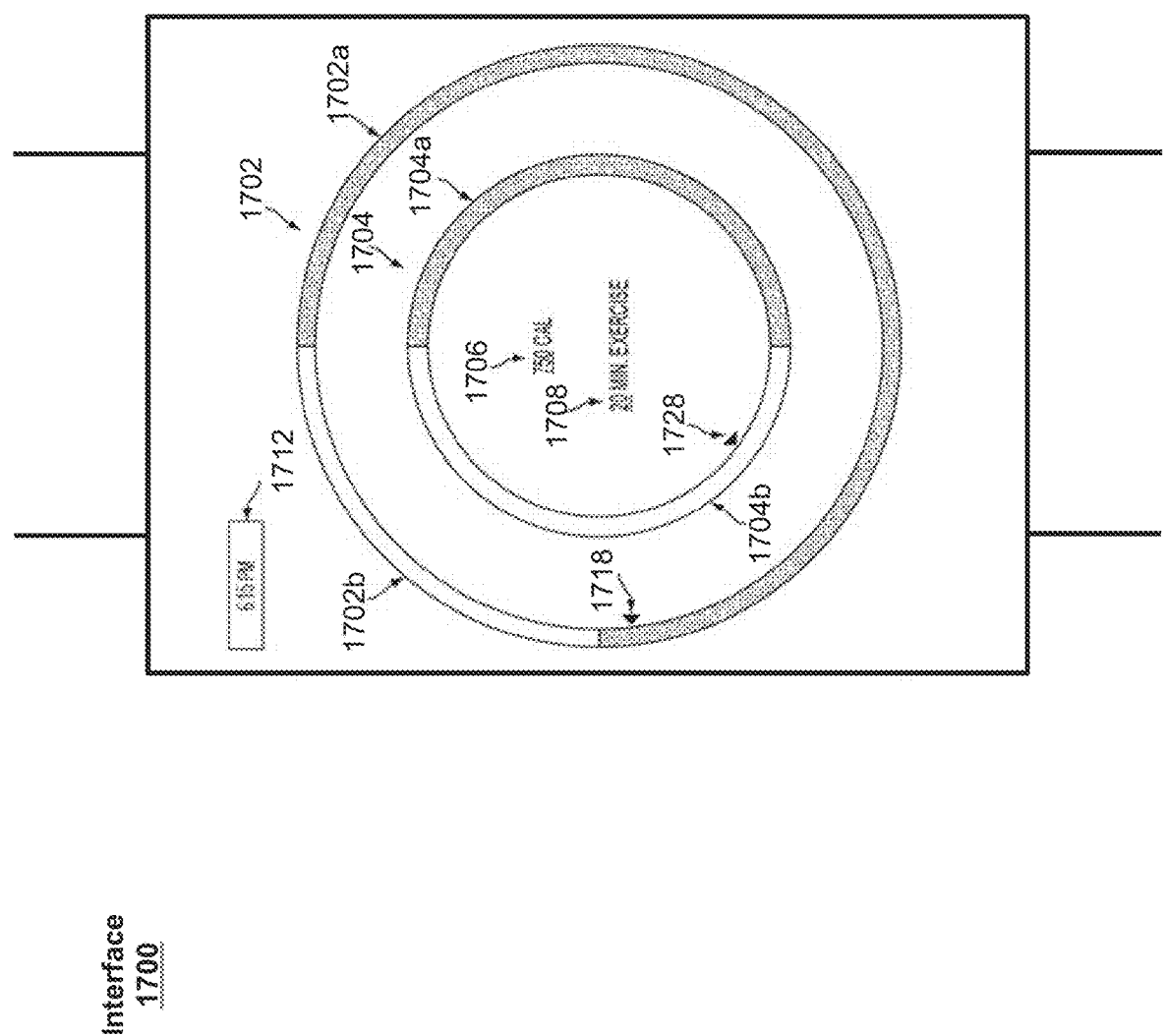
FIGS. 17-21 illustrate exemplary physical activity tracking interfaces according to various examples.

FIG. 17 illustrates an example physical activity tracking interface 1700 that can be displayed at block 1502 of process 1500. Interface 1700 can be updated in real time or any other desired interval of time to reflect current values of the monitored attributes of the user's physical activity that are updated at block 1510 of process 1500. In some examples, interface 1700 can reflect the values representative of the daily total amount of the first type and the second type of physical activities that are stored in the memory and updated in response to detection of any new physical activity, as explained above in reference to blocks 1508 and 1510 of process 1500.

In the illustrated example of FIG. 17, interface 1700 can include a first indicator representative of the daily total amount of the first type of physical activity including all physical activities detected from the user, and a second indicator representative of the daily total amount of the second type of activity including only physical activities at or above a threshold intensity. The first indicator can include both graphic/image representation 1702 and textual representation 1706 and similarly, the second indicator can include both graphic/image representation 1704 and textual representation 1708. The first and second indicators can be updated in real time or any other desired interval of time in response to an update to the corresponding values stored in the memory as explained above in reference to blocks 1508 and 1510 of process 1500.

In some examples, the memory of the device can store a first goal value representative of a daily goal amount for the first type and a second goal value representative of a daily goal amount for the second type of physical activities. In some examples, the first goal value can be represented in the same measurement metric used to quantify the first type, and the second goal value can be represented in the same measurement metric used to quantify the second type of physical activity. In the illustrated example, the amount of the first type of activity is represented using the amount of Calories burned, and thus, the numeric value of the first goal value stored in the memory represents the goal amount of Calories to be burned by the user per day (e.g., 300 Calories, 500 Calories, 1000 Calories, 2000 Calories, etc.). On the other hand, the amount of the second type of activity can be represented using the amount of time spent performing the second type of physical activity, and thus, the numeric value of the second goal value stored in the memory represents the goal amount of time to be spent by the user for performing high intensity activities per day (e.g., 30 minutes, 40 minutes, 60 minutes, etc.).

In some examples, as the aggregate amounts of the first and second types of activities are updated, the one or more processors can compare these updated aggregate amounts to the respective goal values stored in the memory and cause, on the display, a display of the result of the comparison. For example, graphic representation 1702 can represent a first goal value and/or the user's progress toward reaching this goal. The size of graphic representation 1702 can be scaled such that its size represents the first goal amount, and a portion of graphic representation 1702 can be marked such that the marked portion represents the actual amount of the first type of activity performed by the user. Alternatively or additionally, graphic representation 1702 can include a first portion (e.g., part 1702a) that is representative of the total amount of the first type of activity (e.g., all activity) performed by the user and a second portion (e.g., part 1702b) that is representative of a difference between the total amount of the first type of activity and the first goal value. In other words, part 1702a shows what user has achieved and part 1702b shows what user needs to achieve to complete their goal. As shown, the first portion can be given a color or shading that differs from that of the second portion. In some examples, the leading edge of the completed portion 1702a of the ring can be displayed having a different appearance or texture than the trailing parts of the completed portion 1702a of the ring. For example, the leading edge of the completed portion 1702a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by portion 1702a exceeds the goal value, the leading edge of the completed portion 1702a of the ring can continue to traverse the ring and overlap a previously completed portion of the ring. By displaying the leading edge using a different shade or texture, the user can distinguish the leading edge from a previously completed portion of the ring. Further, a ratio between a size of the first portion and a size of the second portion can be equal to a ratio between the total amount of the first type of activity performed by the user and the difference between the total amount of the first type of activity performed by the user and the first goal value.

In some examples, graphic representation 1704 can also represent a second goal value and/or a user's progress toward reaching this goal. The size of graphic representation 1704 can be scaled such that its size represents the second goal amount, and a portion of graphic representation 1704 can be marked such that the marked portion represents the actual amount of the second type of activity performed by the user. Alternatively or additionally, graphic representation 1704 can include a third portion (e.g., part 1704a) that is representative of the total amount of the second type of activity (e.g., activity above a threshold intensity) performed by the user and a fourth portion (e.g., part 1704b) that is representative of a difference between the total amount of the second type of activity and the second goal value. In other words, part 1704a shows what user has achieved and part 1704b shows what user needs to achieve to complete their goal. In some examples, the leading edge of the completed portion 1704a of the ring can be displayed having a different appearance or texture than the trailing parts of the completed portion 1704a of the ring. For example, the leading edge of the completed portion 1704a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by portion 1704a exceeds the goal value, the leading edge of the completed portion 1704a of the ring can continue to traverse the ring and overlap a previously completed portion of the ring. By displaying the leading edge using a different shade or texture, the user can distinguish the leading edge from a previously completed portion of the ring. Further, a ratio between a size of the third portion and a size of the fourth portion can be equal to a ratio between the total amount of the second type of activity performed by the user and the difference between the total amount of the second type of activity performed by the user and the second goal value.

In the illustrated example of FIG. 17, graphic representation 1702 is an outer ring and graphic representation 1704 is an inner ring that is concentric to the outer ring. Each ring has two visually distinct parts. The outer ring has visually distinct parts 1702a and 1702b, and the inner ring has visually distinct parts 1704a and 1704b. These parts can be scaled to visually indicate relative progressive measures of the total amount of the first and second types of activities compared to their respective goal values, in the illustrated example, outer ring 1702 can be scaled such that the entire length of its circumference (1702a+1702b) represents the daily goal for the all activity (the first goal value). Part 1702a of the ring can be configured to represent the actual amount of activity performed by the user (e.g., the first value updated at block 1604), and the second part 1702b can be configured to represent the amount of activity remaining to be completed by the user to achieve the goal. Respective size of parts 1702a and 1702b can be updated in real-time to reflect the most current progressive measure of the total amount of all activity, as compared to the first goal value. For example, as additional activity is detected, part 1702a can be increased in size and part 1702b can be decreased in size to give the appearance that the leading edge of part 1702a is traveling in a clockwise direction along outer ring 1702. Ring parts 1702a and 1702b can be scaled such that a ratio between the entire circumference of ring 1702 and ring part 1702a is equal to a ratio between the first goal value and the total amount of activity performed by the user.

Similarly, inner ring 1704 can be scaled such that the entire length of its circumference (1704a+1704b) represents the second goal value (e.g., the daily goal amount for activity above a threshold intensity). Part 1704a of the ring can represent the actual amount of activity above the threshold intensity performed by the user while the second part 1704b can represent the amount of activity above the threshold intensity remaining to be completed by the user to achieve the second goal value. Respective size of parts 1704a and 1704b can be updated in real-time to reflect the most current progressive measure of the user's total amount of activity above the threshold intensity, as compared to the second goal value. For example, as additional activity above the threshold intensity is detected and monitored at blocks 1504, 1506, 1508, and 1510 of process 1500 by the device, part 1704*a* can be increased in size while part 1704*b* can be decreased in size to give the appearance that the leading edge of part 1704*a* is traveling in a clockwise direction along inner ring 1704. Ring parts 1704*a* and 1704*b* can be scaled such that a ratio between the entire circumference of ring 1704 and ring part 1704*a* is equal to a ratio between the second goal value and the total amount of activity above the threshold intensity performed by the user.

In the illustrated example of FIG. 17, the first goal value can be 1000 Calories and the second goal value can be 40 minutes. In other words, the user's goal is to burn at least 1000 Calories per day regardless of the types of physical activity performed, and to perform at least 40 minutes of exercise or activity above the threshold intensity per day. Text indicator 1706 shows that the user has burned a total of 750 Calories by 6:15 p.m., which is the time shown by time indicator 1712. There can be another text indicator to indicate the actual value of the first goal or a text indicator to indicate the amount of the first type of activity remaining (e.g., 250 Calories in this example) before achieving the first goal. Text indicator 1708 shows that the user has spent a total of 20 minutes exercising or performing activity above the threshold intensity by 6:15 p.m. There can be another text indicator to indicate the actual value of the second goal or a text indicator to indicate the amount of the second type of activity remaining (e.g., 20 minutes in this example) before achieving the second goal. Since the user has completed three-fourths of the first goal for all activity (e.g., burned 750 Calories out of the 1000 Calorie goal), part 1702*a* can be configured to occupy approximately three-fourths of the entire circumference of ring 1702. Similarly, since the user has completed half of the second goal for activity having an intensity equal to or greater than a threshold intensity (e.g., spent 20 minutes out of the 40 minute goal), part 1704*a* can be configured to occupy approximately half of the entire circumference of ring 1704. As more activity or activity having an intensity equal to or greater than the threshold intensity, part 1702*a*/1704*a* can be animated to be increased in size while part 1702*b*/1704*b* can be animated to be decreased in size.

Visually distinct parts of rings 1702 and 1704 permit a user of the device to readily recognize relative progressive measures of the monitored activity. The visual distinction is, in the illustrated example, filled area (e.g., parts 1702*a* and 1704*a*) versus empty area (e.g., parts 1702*b* and 1704*b*). However, it is noted that different effects may be used to make the visual distinction, examples of which effects include, but are not limited to, applying different colors, hues, shapes, images, animations, intensity, brightness, or other effects of the same sort. Further, as shown in the illustrated example, interface 1700 can include text indicators 1706, 1708, and 1712. The fonts, sizes, and locations of the text indicators can vary depending on the display specifications and any other desired visual configurations.

The goal values (e.g., the first goal value and the second goal value) can be directly inputted by a user of the device before the monitoring starts. In other examples, the goal values can be automatically set by the device based at least on user's health data (e.g., received using interface 1400), which may be stored in the device or in an external device configured to communicate with the device. Health data can include information relating to the user's age, weight, gender, BMI, blood pressure, heart rate, or any other physical conditions. The device and/or the external device can perform predetermined computing instructions (e.g., algorithms) on any portion of the user's health data to automatically determine the goal values. The goal values can be determined based on the user's progress over a certain period of time and/or the training level selected by the user. Moreover, the goal can be recalculated periodically based on the user's performance over each previous period of time. An example process that can be used to calculate the goal values is described below with respect to FIG. 96.

In some examples, there can be additional goal values stored in the device's memory, such as a time-based goal so that the one or more processors can compare the aggregate amounts of the first and second type of activities performed by the user to such goal values and cause, on the display, a display of the comparison. For example, interface 1700 can further include one or more additional reference indicators representing supplemental information relevant to the user's activity. In the illustrated example, the additional reference indicators are shown as carets 1718 and 1728 provided along the rings. Examples of supplemental information that can be additionally provided on the display include, non-exclusively, timed-based goals that are adjusted in accordance with a passage of time (e.g., certain percentage(s) of the goal to be completed by certain time(s) of a day, such as 10% to be completed by 10:00 am, 80% to be completed by 9:00 pm, etc, such that the indicator would be moving along the ring throughout the day to indicate the changing percentage of the goal to be completed depending on the tune of a day), history of a user's past activity (e.g., activity performed by a user of the device on a particular day of the week, a highest/lowest or daily average amount of activity of a certain category performed by the user of the device over a month, a week, two days, last day, etc.), activity data of other users different from the user of the device (e.g., a highest/lowest or daily average amount of activity of certain category performed by other users different from the user of the device, average amount of activity of a certain category performed by other users at a given time during the day, etc.), or the like. Indicators representing the information about the user's total amount of all activity are provided on ring 1702, whereas indicators representing the information about the user's total amount of activity above a threshold intensity are provided on ring 1704.

In some examples, the device can obtain the activity data of other users from an external device that is configured to communicate with a plurality of monitors monitoring activity of the other users. Examples of information the device can obtain from an external storage device include, non-exclusively, highest/lowest/average amount of activity performed by other users over a certain time period, certain percentile amount of activity performed by other users, average progressive measure of amount of activity performed by other users which may be updated as time passes, or the like. In some other examples, device 100 can request to receive data associated with only a particular group of users having common conditions (e.g., physical conditions) as the user of device 100 or other groups known or unknown to the user.

Referring to the example of FIG. 17, carets 1718 provided on outer ring 1702 can represent a global average progressive measure of the total amount of activity performed by a group of users. Since caret 1718 is placed inside part 1702*a*, the user of the device can see that he has burned more Calories than other users in the group have done on average by 6:15 p.m. Similarly, caret 1728 may also be provided on inner ring 1704, representing a global average progressive measure of the total amount of high intensity activity performed by a group of users. Since caret 1728 is placed outside part 1704*a*, the user of the device can see that other users in the group have spent more than 20 minutes on average exercising or performing activity above the threshold intensity by 6:15 p.m. Providing such information can motivate a user of the device to engage in more activities and exercises. As explained above, the display can display either one or both indicators 1718 and 1728.

The device can display some or all of indicators 1702, 1704, 1706, 1708, 1712, 1718, and 1728. In some examples, the device can determine which indicators the display will display based on a signal entered by a user of the device. Upon receiving a first input signal, the display can display rings 1702 and 1704. Upon receiving a second input signal, the display can additionally display texts 1706 and 1708. Upon receiving a third input signal, the display can additionally display reference indicators 1718 and 1728, and so forth. Input signals can be triggered by a user of the device using various input mechanisms of the device, such as pressing a mechanical button of the device, detecting a movement of a rotatable input mechanism, touching a touch-sensitive display of the device, combinations of any of the input mechanisms, or the like. In other examples, the display can display only indicators relating to one of the monitored features, e.g., the total amount of all activity, and display indicators 1702, 1706, and 1718. Then, upon receiving a trigger signal from a user of the device, the display can additionally display indicators relating to the activity above the threshold intensity. Any other variations in display configuration can be employed without departing from the core of this disclosure.

In some examples, the device can provide rewards to a user of the device when the user achieves one or more goals. Examples of rewards include, but are not limited to, visual rewards, such as animations, glowing or pulsating graphics, 3D images, lighting effects, badges, or the like; sound rewards, such as alerts, ringtones, music, voice, or the like; vibrations; or any combinations of rewards thereof. The visual rewards can be displayed over the indicators as complications (e.g., a smaller display within the larger interface) with desired information. As used herein, consistent with its accepted meaning in art, a complication can refer to any clock face feature other than those used to indicate the hours and minutes of a time (e.g., clock hands or hour/minute indications). Complications can provide different types of information to a user, such as data obtained from an application, and the information conveyed to a user by a complication can be customizable. Alternatively, the indicators themselves can be displayed as a complication overlaid on other visual displays. For example, the indicators can be displayed within a circular icon displayed over a conventional watch display showing a date and time. In the illustrated example of FIG. 17, rings 1702 and 1704 can start glowing and/or pulsating once completed by the user. The same or different visual effects can be displayed to the user in response to one of rings 1702 and 1704 being completed additional times. For example, a brighter glow or pulsating effect can be displayed to the user for each subsequent completion of a ring. Further, in some examples, different types of rewards can be used for rewarding different levels of achievements. If a user achieves the first goal without achieving the second goal (e.g., completes ring 1702 without completing ring 1704), the display can provide a first effect. If a user achieves the second goal without achieving the first goal (e.g., completes ring 1704 without completing ring 1702), the display can provide a second effect that is the same or different from the first effect. If a user achieves both the first and second goals (e.g., completes both rings 1702 and 1704), the display can provide a third effect which is the same or different from the first and second effects. By providing rewards that are exciting give feedback to the user, a user of the device can be motivated to engage in more activities and exercises.

Figure 18:
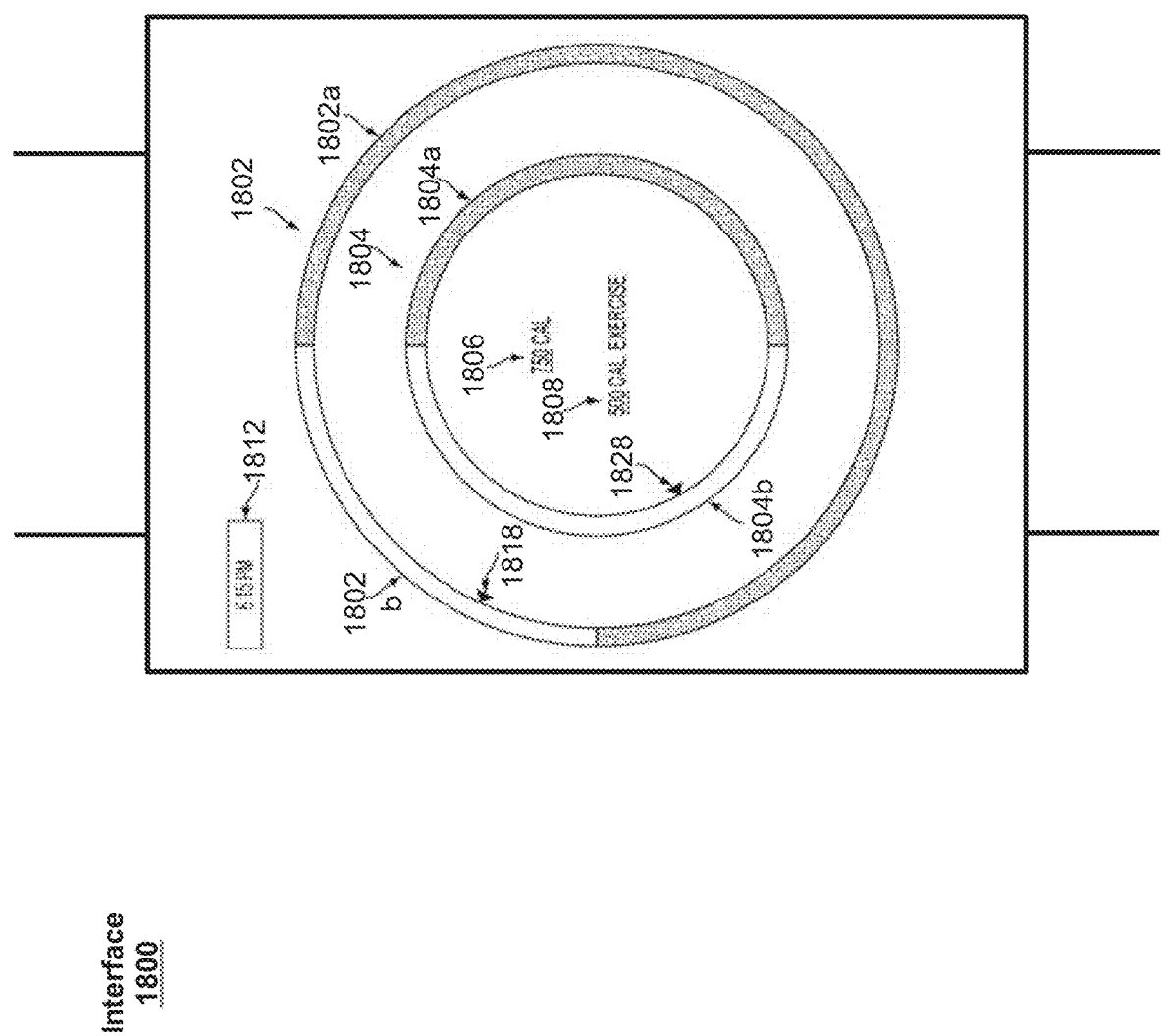

FIG. 18 illustrates another example physical activity tracking interface 1800 that can be displayed at block 1502 of process 1500. Interface 1800 is similar to interface 1700, except that the same measurement metric is used to measure the first and second types of physical activities. As will be apparent to a person of ordinary skill in the art, different metrics can be used, such as, non-exclusively, amount of time spent, distance traveled, steps taken, or the like. In the illustrated example of FIG. 18, the goal values (e.g., the first and the second goal values) are both represented using the same measurement metric—the amount of Calories burned, and have the identical numerical value of 1000 Calories. However, in other examples, the first and second goal values can have different numerical values.

In the illustrated example of FIG. 18, interface 1800 includes a first indicator representative of the daily total amount of all activity and a second indicator representative of the daily total amount of activity above a threshold intensity. The first indicator includes graphic representation 1802 and textual representation 1806, each representing the daily total amount of activity performed by the user. The second indicator includes graphic representation 1804 and textual representation 1808, each representing the daily total amount of activity above a threshold intensity performed by the same user. Optionally, interface 1800 can further include indicators 1818 and 1828. The configuration, functionalities, and possible variations of interface 1800 are similar to those of interface 1700 explained with reference to FIG. 17, and therefore, the overlapping descriptions are omitted herein.

Similar to the example shown in FIG. 17, rings 1802 and 1804 are configured to represent respective progressive measures of the total amount of all activity performed by the user compared to the first goal value and the total amount of activity above a threshold intensity performed by the user compared to the second goal value. Indicators 1802 and 1812 show that the user has performed three fourths of the daily goal amount for all activity (the first goal value) by 6:15 p.m. Indicators 1804 and 1812 show that the user has performed one half of the daily goal amount for activity above a threshold intensity (the second goal value) by 6:15 p.m. As more activity is detected, part 1802*a* can be increased in size and part 1802*b* can be decreased in size, and as more activity above a threshold intensity is detected, part 1804*a* can be increased in size and part 1804*b* can be decreased in size. In certain examples, ring parts 1802*a* and 1802*b* can be scaled such that the ratio of the entire circumference of ring 1802 to filled part 1802*a* matches the ratio of the first goal value to the actual amount of all activity performed by the user. Similarly, ring parts 1804*a* and 1804*b* can be scaled such that the ratio of the entire circumference of ring 1804 to filled pail 1804*a* matches the ratio of the second goal value to the actual amount of activity above a threshold intensity performed by the user.

If the amount of all activity and the amount of activity above a threshold intensity are measured using the same metric unit (e.g., the unit of Calories burned) as shown in the illustrated example, a user can see how much each type of activity contributes to another. Referring to FIG. 18, a user can see that out of 750 Calories he has burned in total by 6:15 p.m., 500 of those were burned from exercising or performing activity above a threshold intensity. Further, if the first and second goal values are the same (e.g., 1000 Calories) as is the case in the example of FIG. 18, a user can always achieve the first goal (e.g., completes outer ring 1802) if the user achieves the second goal. If the first and second goal values are different, it may not necessarily be true that the user achieves the first goal automatically if the user achieves the second goal.

In some examples, the amount of one type of activity can be measured using more than one measurement metric. For example, the amount of activity above a threshold intensity can be measured using a first metric and a second metric. In such cases, the display of the device can alternatingly display an indicator representing the amount measured in the first metric and another indicator representing the amount measured in the second metric. For example, the display can alternatingly display indicator 1800 and indicator 1700 if the activity above a threshold intensity is measured using both the amount of Calories burned and amount of time spent performing the activity.

Figure 19:
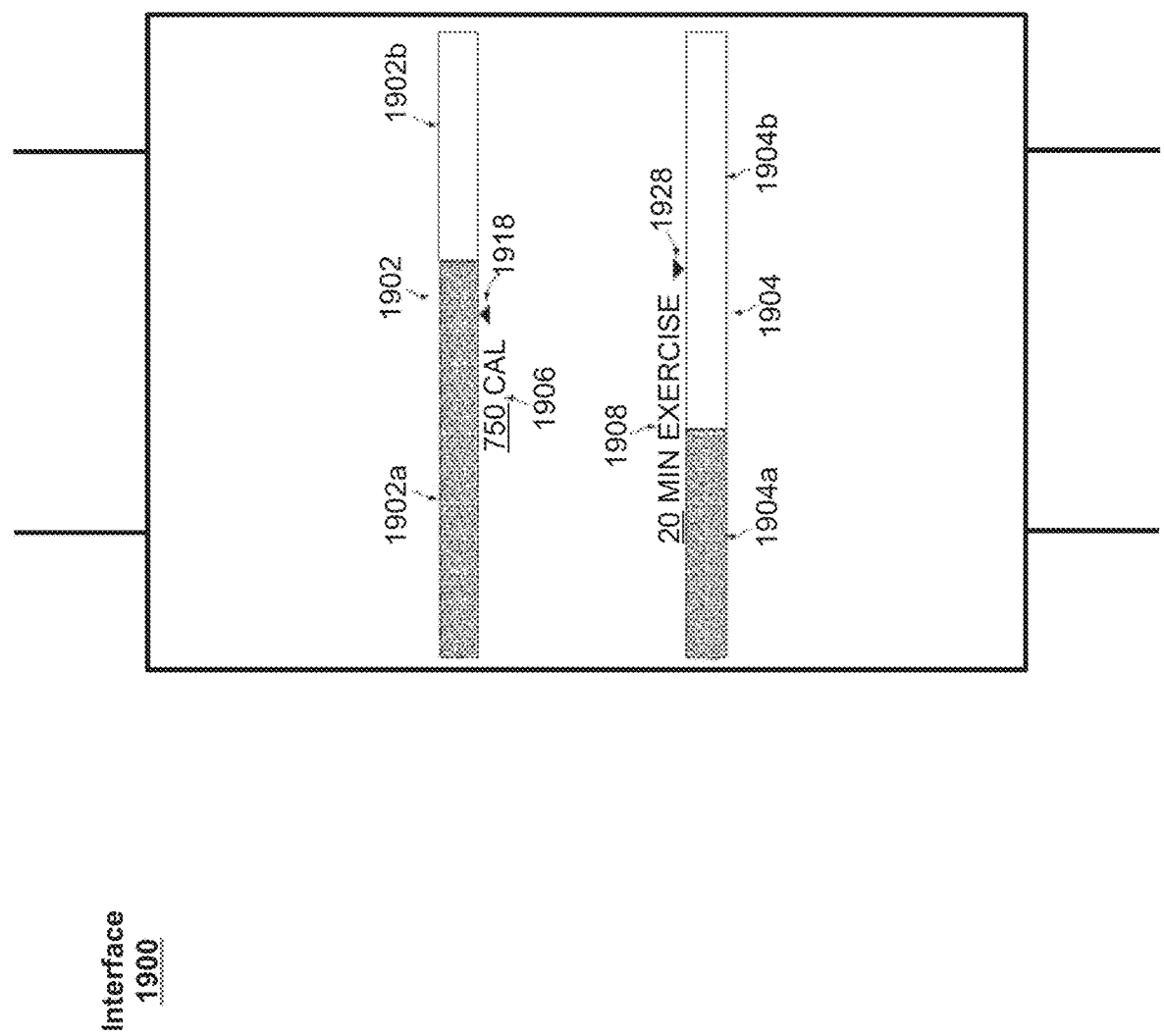
Figure 20:
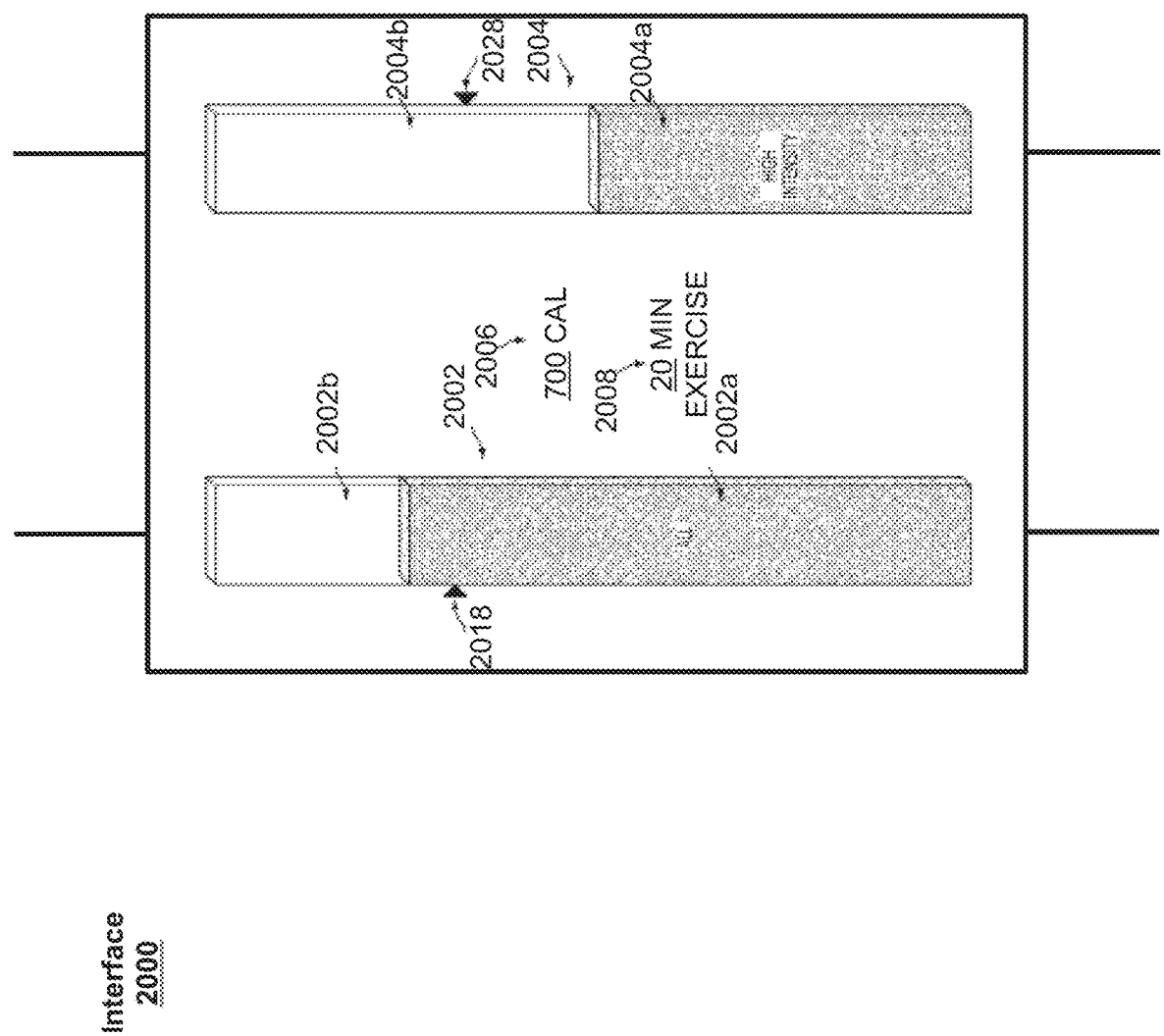
Figure 21:
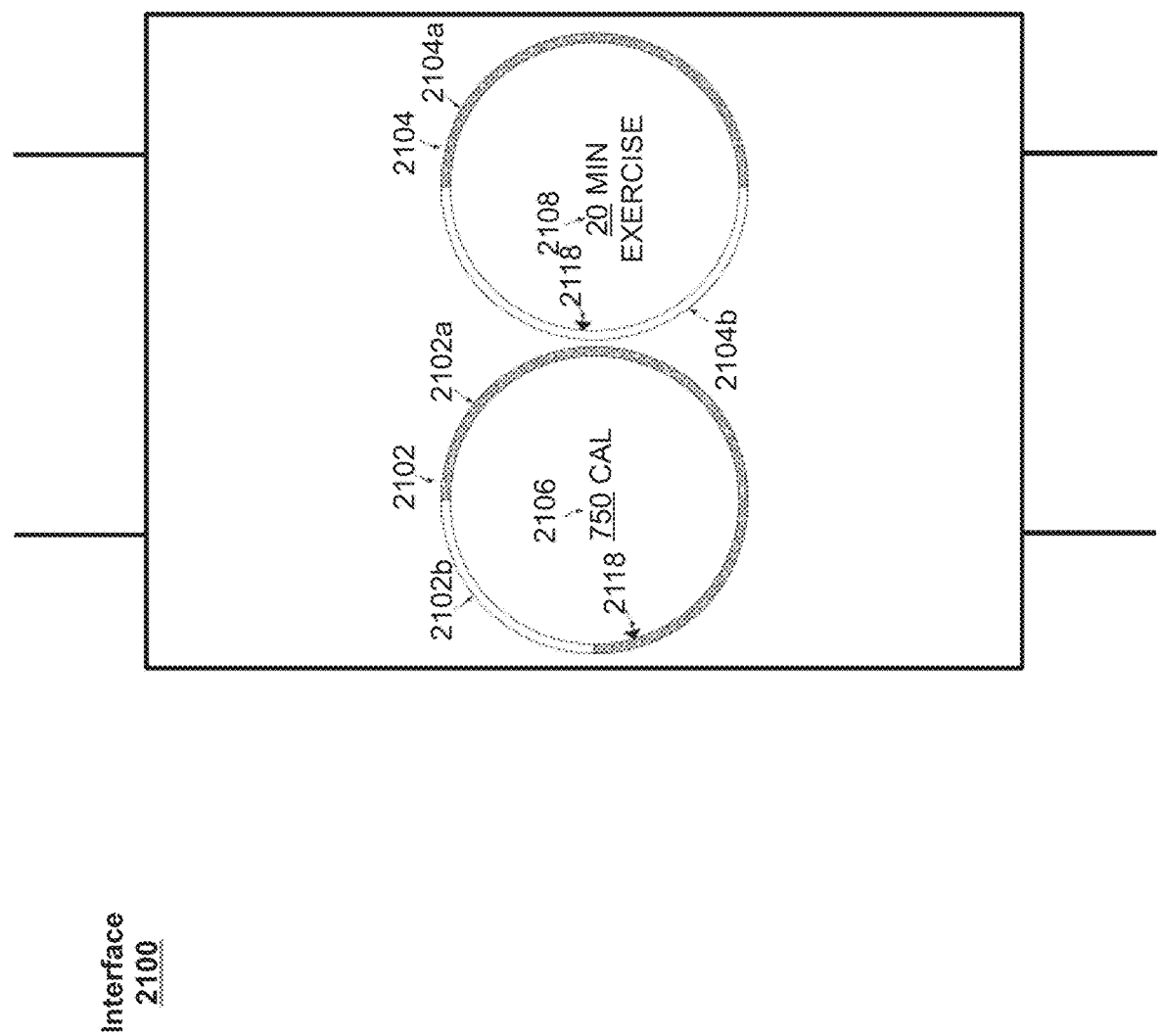

It is noted that indicators 1700 and 1800 disclosing two concentric rings are provided herein only as examples. As will be apparent to a person of ordinary skill in the art, numerous other visual representations may be used instead such as, non-exclusively, two parallel lines, two vertical bars, two line graphs, side by side circles, or the like. FIGS. 19-21 illustrate such examples.

FIG. 19 illustrates an example physical activity tracking interface 1900 having two parallel lines that can be displayed at block 1502 of process 1500. In the illustrated example, line 1902 represents an attribute of a first type of activity, such as the total amount of all activity performed by a user of the device, and line 1904 represents an attribute of a second type of activity, such as the total amount of activity above a threshold intensity performed by the same user. Line 1902 can be scaled such that the entire length represents the goal amount of all activity (the first goal value), while solid part 1902a represents the actual amount of activity performed by the user. Empty part 1902b represents the amount of activity remaining to be performed by the user to achieve the goal. As more activity is detected, solid part 1902a can be increased in size and empty part 1902b can be decreased in size. Similarly, line 1904 can be scaled such that the entire length represents the goal amount for activity above a threshold intensity (the second goal value), while solid part 1904a represents the actual amount of activity above a threshold intensity performed by the user. Empty part 1904b represents the amount of activity above a threshold intensity remaining to be performed by the user to achieve the goal. As more activity above a threshold intensity is detected, solid part 1904a can be increased in size and empty part 1904b can be decreased in size. Thus, lines 1902 and 1904 can represent progressive measures of the total amount of all activity and the total amount of activity above a threshold intensity performed by the user. In certain examples, lines 1902 and 1904 can be scaled such that the ratio of the entire length of the line to the solid part matches the ratio of the goal value to the actual amount performed by the user. Optionally, texts 1906 and 1908 and/or carets 1918 and 1928, which have similar configuration, functionalities, and possible variations as texts 1706 and 1708 and/or carets 1718 and 1728, explained above in reference to the example of FIG. 17, can be provided.

FIG. 20 illustrates another example physical activity tracking interface 2000 having two vertical bars that can be displayed at block 1502 of process 1500. Bar 2002 having parts 2002a and 2002b and bar 2004 having parts 2004a and 2004b can be configured and displayed in a manner similar to line 1902 having parts 1902a and 1902b and line 1904 having parts 1904a and 1904b in FIG. 19, respectively. Similar to FIG. 19, texts 2006 and 2008 and/or carets 2018 and 2028 can optionally be provided.

FIG. 21 illustrates another example physical activity tracking interface 2100 having two non-concentric rings that can be displayed at block 1502 of process 1500. In the illustrated example, two side-by-side rings 2102 and 2104 are provided. Left ring 2102 having parts 2102a and 2102b and right ring 2104 having parts 2104a and 2104b can be configured and displayed in a manner similar to ring 1702 having parts 1702a and 1702b and ring 1704 having parts 1704a and 1704b in FIG. 17, respectively. Texts 2106 and 2108 and/or carets 2118 and 2128, which can have similar configurations, functionalities, and possible variations as texts 1706 and 1708 and/or carets 1718 and 1728 explained above in reference to the example of FIG. 17, can be provided. As will be apparent to a person of ordinary skill in the art, the examples shown in FIGS. 19-21 are not exhaustive, and various modifications can be made with respect to, for example, shapes, visual effects, fonts, sizes, locations of each element on the display, graph dimensions, color effects, intensity, brightness, or the like.

Figure 22:
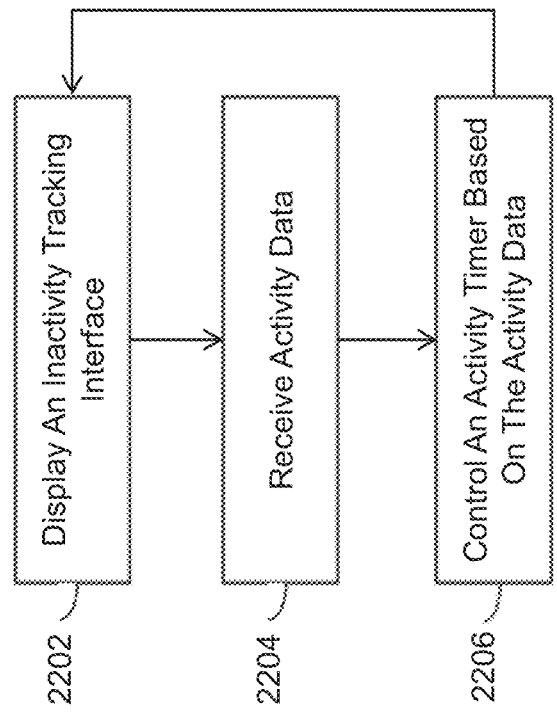
FIG. 22 illustrates an exemplary process for generating an inactivity tracking interface for monitoring the inactivity of a user according to various examples.
Figure 24:
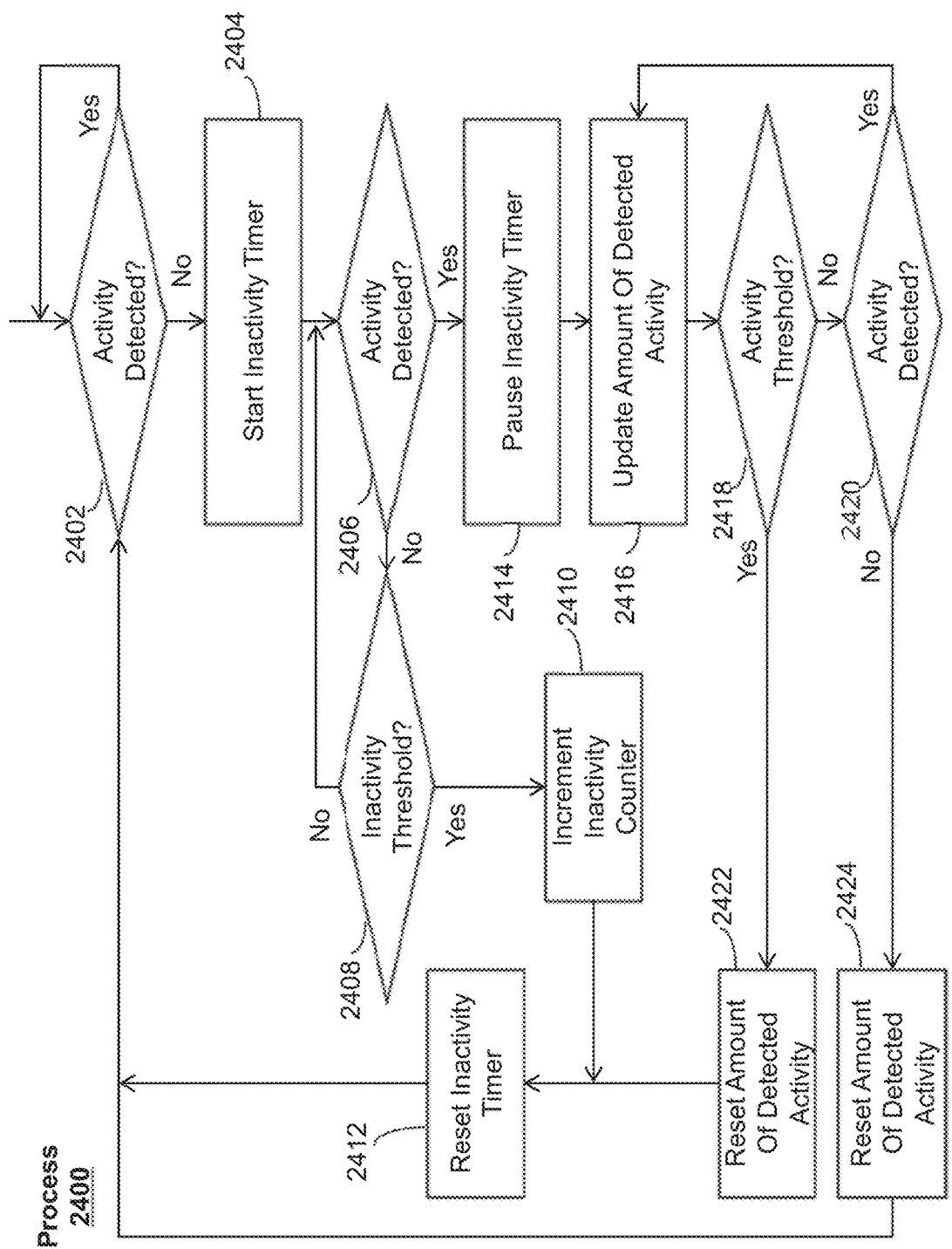
FIG. 24 illustrates a process for controlling an inactivity timer according to various examples.

In some examples, after displaying some or all of the interfaces shown in FIGS. 9-13 (or directly after displaying interface 800 if the interfaces shown in FIGS. 9-13 are not to be displayed), the electronic device can perform process 2200 and/or process 2400, shown in FIGS. 22 and 24 for generating and updating an inactivity tracking interface. Processes 2200 and 2400 can be performed using a device similar or identical to device 100, 300, 500 or 610, and can be performed at the same or a different time than process 1500. Some operations in process 2200 and/or 2400 may be combined, the order of some operations may be changed, and some operations may be omitted.

As described below, process 2200 and/or 2400 provide intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 2202, a display of an inactivity tracking interface can be displayed. As mentioned above, recent studies have found that extended periods of inactivity (e.g., sitting at a desk) can lead to serious health risks, such as an increased risk of heart attack. Some healthcare providers recommend that individuals move at least once every hour (e.g., by getting up out of their chair to walk or to stand). The inactivity tracking interface can be used to track the number of hour-long segments (or segments of other lengths) that a user is inactive and prompt users to be active before the hour (or other length of time) elapses. To do so, the inactivity tracking interface can include a visual representation of an amount of a user's inactivity (e.g., a length of time the user is inactive as measured by an inactivity timer), an amount of detected user activity (e.g., a length of time the user is active, a number of steps taken by the user, a number of Calories expended, or the like), or a combination thereof. The user can be categorized as being inactive when the device detects that the user is not engaged in a physical activity that meets a predetermined criteria. For example, inactivity can be characterized by the absence of the user engaging in a physical activity that meets a threshold intensity (e.g., movement that expends a threshold number of Calories per unit time, movement that exceeds a distance per unit time threshold, or the like), the absence of the user engaging in specified type of activity (e.g., standing, walking, running, swimming, climbing stairs, or the like), or a combination thereof.

Figure 23:
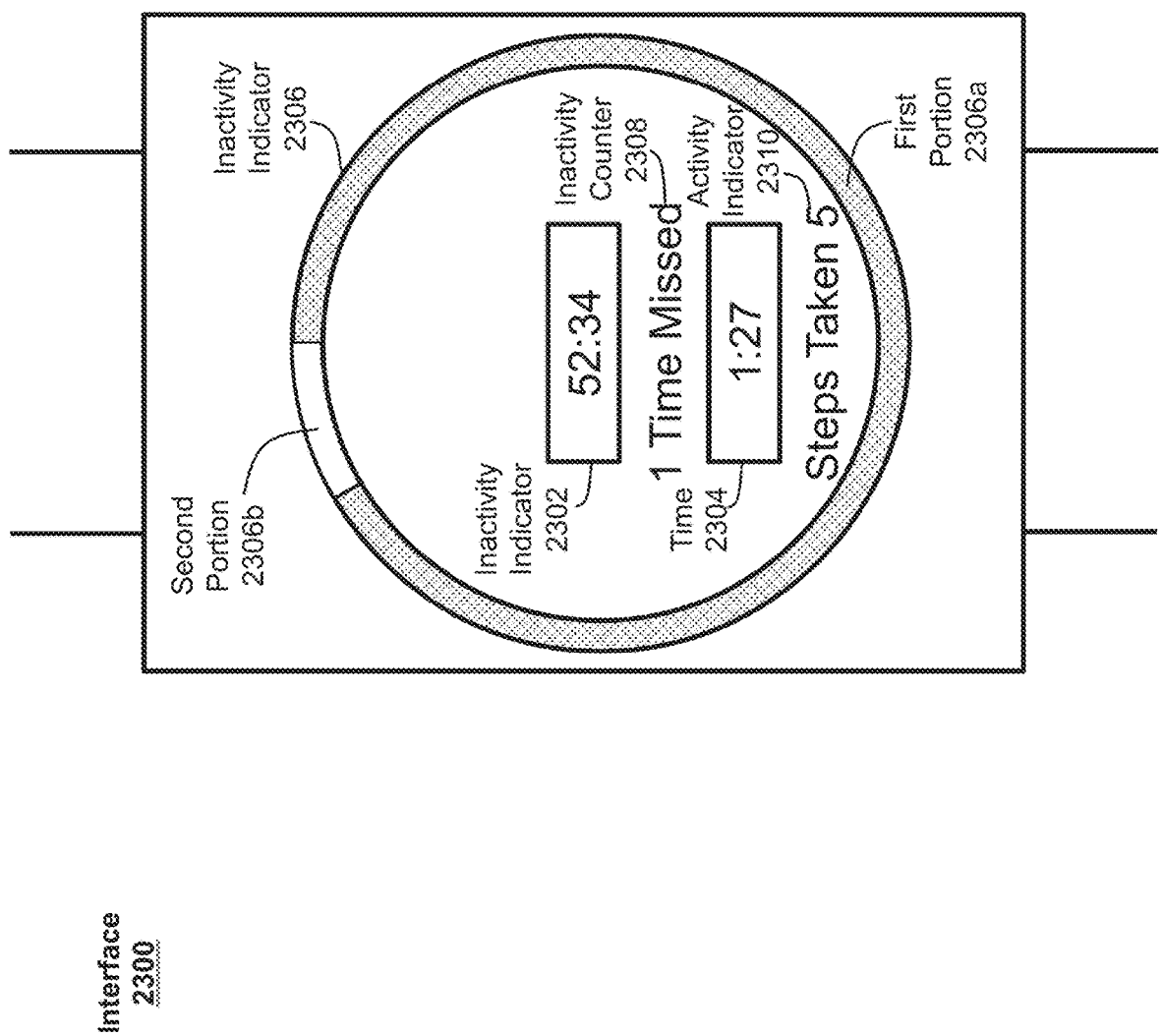
FIG. 23 illustrates an exemplary inactivity tracking interface according to various examples.

FIG. 23 illustrates an exemplary inactivity tracking interface 2300 that can be displayed at block 2202 of process 2200. Interface 2300 can include a first visual representation of an amount of a user's inactivity in the form of first inactivity indicator 2302, a second visual representation of the user's inactivity in the form of second inactivity indicator 2306, and a third visual representation of the user's inactivity in the form of inactivity counter 2308.

First inactivity indicator 2302 can include a numerical representation of a length of time that the user has been inactive (e.g., as indicated by a timer of the device). For instance, in the illustrated example, first inactivity indicator 2302 indicates that the user has been inactive for 52 minutes and 34 seconds. Second inactivity indicator 2306 can include a graphical representation of the length of time that the user has been inactive (e.g., a graphical representation of the numerical value of first inactivity indicator 2302).

In some examples, first inactivity indicator 2302 and second inactivity indicator 2306 can represent a length of time that a user has been inactive, up to an inactivity threshold duration. Upon reaching the inactivity threshold duration, the value represented by first inactivity indicator 2302 and second inactivity indicator 2306 can be reset (e.g., to zero), and the value represented by inactivity counter 2308 (which can include a numerical value representing the number of times cycles a user has been inactive for the inactivity threshold duration) can be incremented. The inactivity threshold duration can have any predetermined or user-selectable value, such as 10 minutes, 20 minutes, 30 minutes, 1 hour, or the like. In this way, first inactivity indicator 2302 and second inactivity indicator 2306 can display a length of time that the user has been inactive, and inactivity counter 2308 can indicate the number of times that the user was inactive for a length of time equal to the inactivity threshold duration.

In some examples, as shown in FIG. 23, second inactivity indicator 2306 can include a ring that can include a completed first portion 2306a representative of the length of time the user has been inactive and an uncompleted second portion 2306b representative of a difference between the inactivity threshold duration and the length of the time the user has been inactive. For example, when the user has not been inactive (e.g., inactive for a length of time equal to zero), the ring may be entirely incomplete and absent from the display. As the length of inactivity increases, the outline of the ring can be darkened, starting at one point along the ring (e.g., the top of the ring) and progressing in a clockwise direction around the ring to give the appearance that the ring is being drawn on the display. The percentage of the ring that is completed can be equal to the length of time the user has been inactive divided by the inactivity threshold duration. For example, if the user has been inactive for 30 minutes and the inactivity threshold duration is one hour, then half of the ring can be completed. In other examples, second inactivity indicator 2306 can include other visual representations, such as a line, bar, rectangle, or the like, where the portion of the visual representation that is displayed can be representative of the length of time the user has been inactive. In yet other examples, second portion 2306b can instead be representative of the number of times that the user remained inactive for a continuous segment of time equal to the inactivity threshold duration and first portion 2306a can instead be representative of a difference between the number of times that the user remained inactive for a continuous segment of time equal to the inactivity threshold and the length of time over which the inactivity is being monitored (e.g., elapsed time in the day or other period of time).

Interface 2300 can further include activity indicator 2310, which can include a numerical representation of an amount of consecutive activity (e.g., activity performed without stopping for more than a threshold length of time) that has been performed, up to an activity threshold. Upon reaching the activity threshold, the value represented by activity indicator 2310 can be reset (e.g., to zero), and the values represented by first inactivity indicator 2302 and second inactivity indicator 2306 can also be reset (e.g., to zero). The threshold activity threshold can have any predetermined or user-selectable value represented in any desired unit of measurement, such as 50 steps, 75 steps, 100 steps, 1 Calorie, 5 Calories, 30 seconds, 60 seconds, or the like. In some examples, as shown in FIG. 23, activity indicator 2310 can include a numerical value of the amount of activity performed by the user (e.g., duration standing, steps taken, length of time active, or the like). In other examples, activity indicator 2310 can include a graphical representation of the amount of detected activity relative to the activity threshold. The graphical representation can include a ring similar to that used for second inactivity indicator 2306 that is concentric to the ring of second inactivity indicator 2306, or any other graphical representation, such as a line, a bar, a rectangle, or the like. In this way, activity indicator 2310 can display an amount of detected activity performed by the user and can show the user's progress toward reaching the activity threshold required to reset first inactivity indicator 2302 and second inactivity indicator 2306. In particular, the completed portion of the ring can be representative of the amount of detected activity and the missing portion of the ring can be representative of the difference between the activity threshold and the amount of detected activity. In other examples, such as when the activity threshold is relatively small (e.g., 25 steps, 60 seconds, etc.), activity counter 2310 may not be included within the inactivity tracking interface.

Interface 2300 can further include time 2304 containing a numerical or graphical representation of the time of day. For example, time 2304 in interface 2300 indicates that the time is 1:27 a.m. In other examples, time 2304 may be excluded from interface 2300 and can be displayed in another interface.

While interface 2300 is shown as occupying a majority of the display, interface 2300 can similarly be displayed as a complication on another interface display with varying levels of information. As mentioned above, consistent with its accepted meaning in art, a complication can refer to any clock face feature other than those used to indicate the hours and minutes of a time (e.g., clock hands or hour/minute indications). Complications can provide different types of information to a user, such as data obtained from an application, and the information conveyed to a user by a complication can be customizable. For example, a user may select an option to cause interface 2300 to be displayed as a complication to cause a smaller version of interface 2300 to be displayed overlaid on a display of a conventional watch face showing a date and time. As a result of occupying a smaller portion of the display, some of the elements of interface 2300, such as time 2304 or activity indicator 2310, can be removed from the interface to allow the other elements to be displayed in a size sufficient to be viewed by the user.

Referring back to FIG. 22, at block 2204, activity data that is representative of sensed physical activity of a user may be received from an activity sensor (e.g., sensors 168, 359, and 520). For example, processor(s) of the device can receive activity data from the activity sensors and can process the data to determine whether the user is active (e.g., performing a physical activity, such as standing, bicycling, jogging, walking, running, stepping side to side, swimming, jumping, going up stairs, intense bodily movements, such as wrestling, or the like), whether the user is inactive, or whether the user is performing a gesture (e.g., waving hands, moving fingers, such as typing, or the like). The processor(s) can additionally or alternatively determine attributes of a detected physical activity, such as a duration of the detected activity, time(s) of a day when the user performs the detected activity, amount of Calories burned by a user of the device while performing the detected activity, distance travelled by a user of the device while performing the detected activity, steps taken by a user of the device while performing the detected activity, elevation climbed by a user of the device while performing the detected activity, highest/lowest/average velocity of a user of the device while performing the detected activity, highest/lowest/average heart rate of a user of the device while performing the detected activity, highest/lowest/average body temperature of a user of the device while performing the detected activity, other contextual information (to quantity if it is activity data or not), or the like.

At block 2206, an activity timer that measures a length of time that the user is inactive can be controlled based on the activity data received at block 2204. For example, processor(s) of the device can be configured to a control timer such that the timer starts in response to the received activity data indicating that the user is inactive, pauses in response to the received activity data indicating that the user is active, and is reset in response to either the value of the inactivity timer reaching the inactivity threshold or the activity data indicating that the user has performed an activity threshold amount of activity. The value of the inactivity timer can be the length of time that the user is inactive that is represented by first and second inactivity indicators 2302 and 2306 of inactivity tracking interface 2300.

Blocks 2202, 2204, and 2206 can be repeated any number of times at and at any desired interval of time to detect a user's activity/inactivity and to update the display of the inactivity tracking interface accordingly. Additionally, it should be appreciated that while blocks 2202, 2204, and 2206 are shown in a particular order, blocks 2202, 2204, and 2206 can be performed in any order or at the same time. For example, the inactivity tracking interface can be repeatedly updated at block 2202 while activity data is being received at block 2204 and processed to control the inactivity timer at block 1006 to provide the user with current or real-time inactivity information. In some examples where the physical activity application is running in the background of the device or while the display of the device is deactivated, block 2202 can be omitted and blocks 2204 and 2206 can repeatedly be performed to monitor the user's activity and control the activity timer such that an accurate display of the attributes can later be provided to the user when the physical activity application is reopened or the display of the device is activated.

FIG. 24 illustrates an exemplary process 2400 that can be used to perform block 2206 of process 2200. The operations of the blocks of processes 2200 and 2400 will be described below with reference to the example inactivity tracking interfaces shown in FIGS. 25-39.

Figure 25:
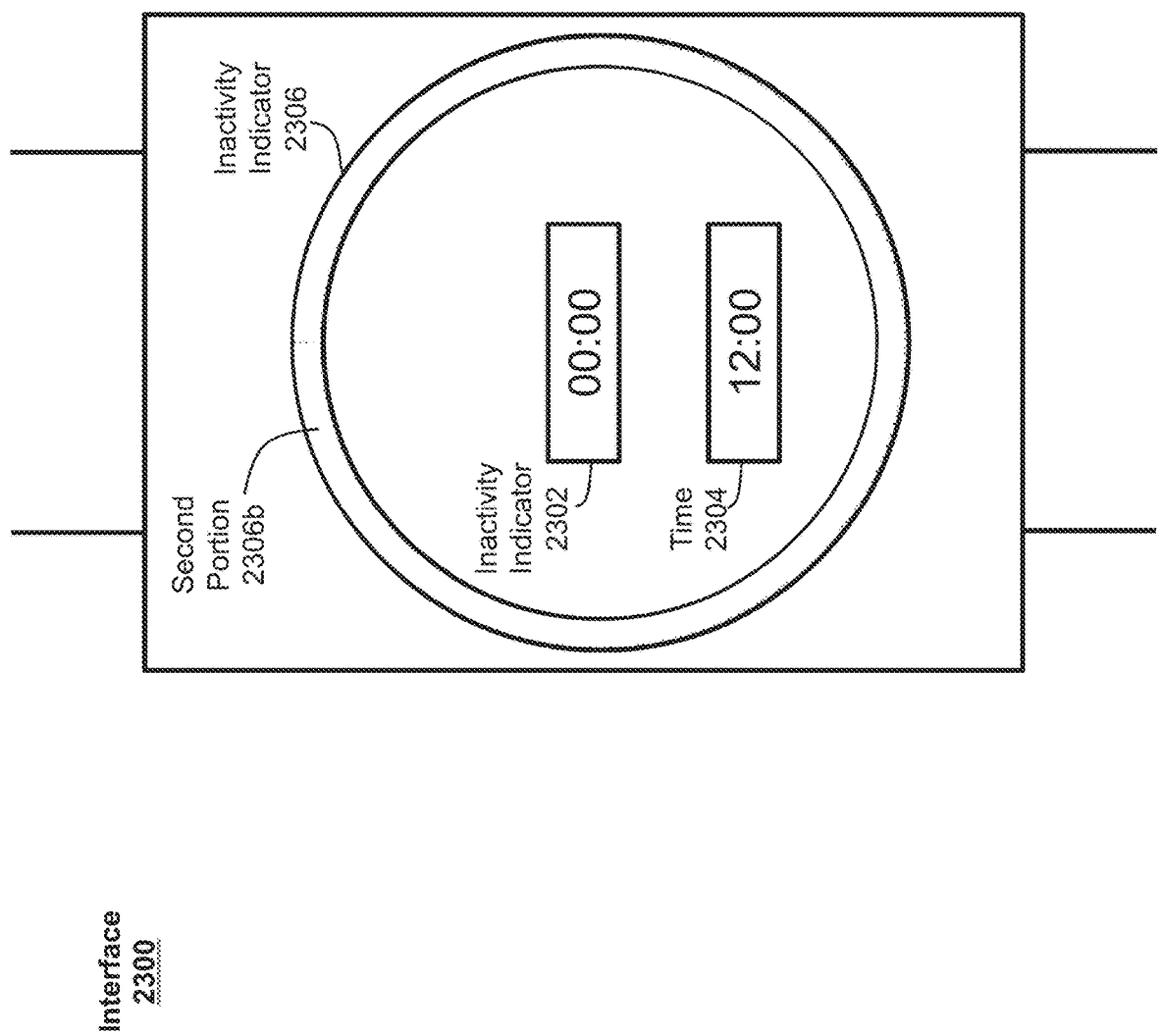
FIGS. 25-39 illustrate exemplary inactivity tracking interfaces according to various examples.

At block 2202 of process 2200, a device similar or identical to device 100, 300, 500, or 610 can cause a display of an inactivity tracking interface similar or identical to interface 2300 shown in FIG. 25. As illustrated, interface 2300 includes a first inactivity indicator 2302 that indicates that the user has been inactive for a length of time equal to zero and a time indicator 2304 that indicates that the current time is 12:00 p.m. Additionally, inactivity indicator 2306 can include only second portion 2306b, indicating that the user has been inactive for a length of time equal to zero. At block 2204 of process 2200, activity data that is representative of sensed physical activity of a user of the device can be received as well as other data.

Proceeding to block 2402 of process 2400, it can be determined whether the activity data received at block 2204 indicates that the user is active (e.g., performing an activity). In some examples, the determination made at block 2402 can include determining whether the user is performing a predefined type of activity (e.g., standing, walking, running, swimming, or the like) or is performing any type of activity with an intensity greater than a threshold amount (e.g., performing an activity that expends more than a threshold number of Calories per minute, traveling at a speed greater than a threshold amount, or the like). For purposes of explanation, the determination made at block 2402 will be described herein as determining whether the user is walking. However, it should be appreciated that any other criteria, such as whether the user is standing, jumping, climbing, performing a physical activity meeting a threshold intensity, or the like, can similarly be used. If it is determined from the activity data from an activity sensor, such as an accelerometer, that the user is walking, or has taken a step within a threshold length of time (e.g., 5-10 seconds), the process can return to block 2402 where the activity data can continue to be monitored to detect when the user becomes inactive. Alternatively, if it is determined that the user is not walking, or has not taken a step within the threshold length of time, the process can proceed to block 2404. In some examples, the absence of data from the activity sensors can cause a negative determination to be made at block 2402 and the process to proceed to block 2404.

At block 2404, an inactivity timer that measures a length of time that the user is inactive can be started. For example, processor(s) of the device can start a timer to begin recording the length of time that the user is inactive. The Value of the inactivity tinier can represent the length of time that the user is inactive and can be visually represented by the first and second inactivity indicators 2302 and 2306 in the inactivity tracking interface 2300.

At block 2406, it can be determined whether or not updated activity data has been received at block 2204 and if that activity data indicates that the user is performing an activity. This determination can be similar or identical to the determination made at block 2402. If it is determined that the user is not performing an activity (or is not performing the predefined type of activity), or has not performed an activity within the threshold length of time, the process can proceed to block 2408. In some examples, the absence of data from the activity sensors can cause a negative determination to be made at block 2406 and the process to proceed to block 2408.

Figure 26:
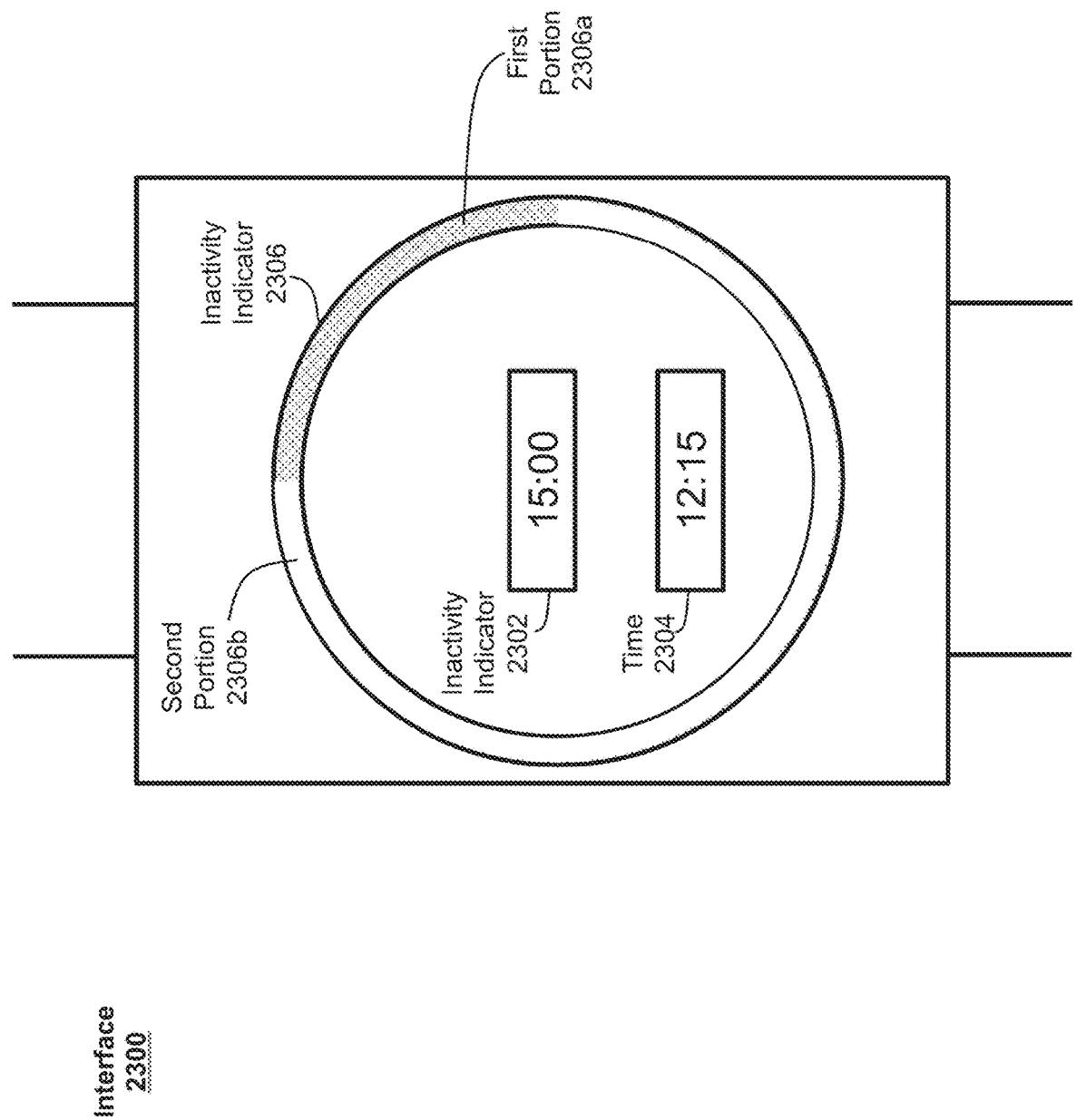
Figure 27:
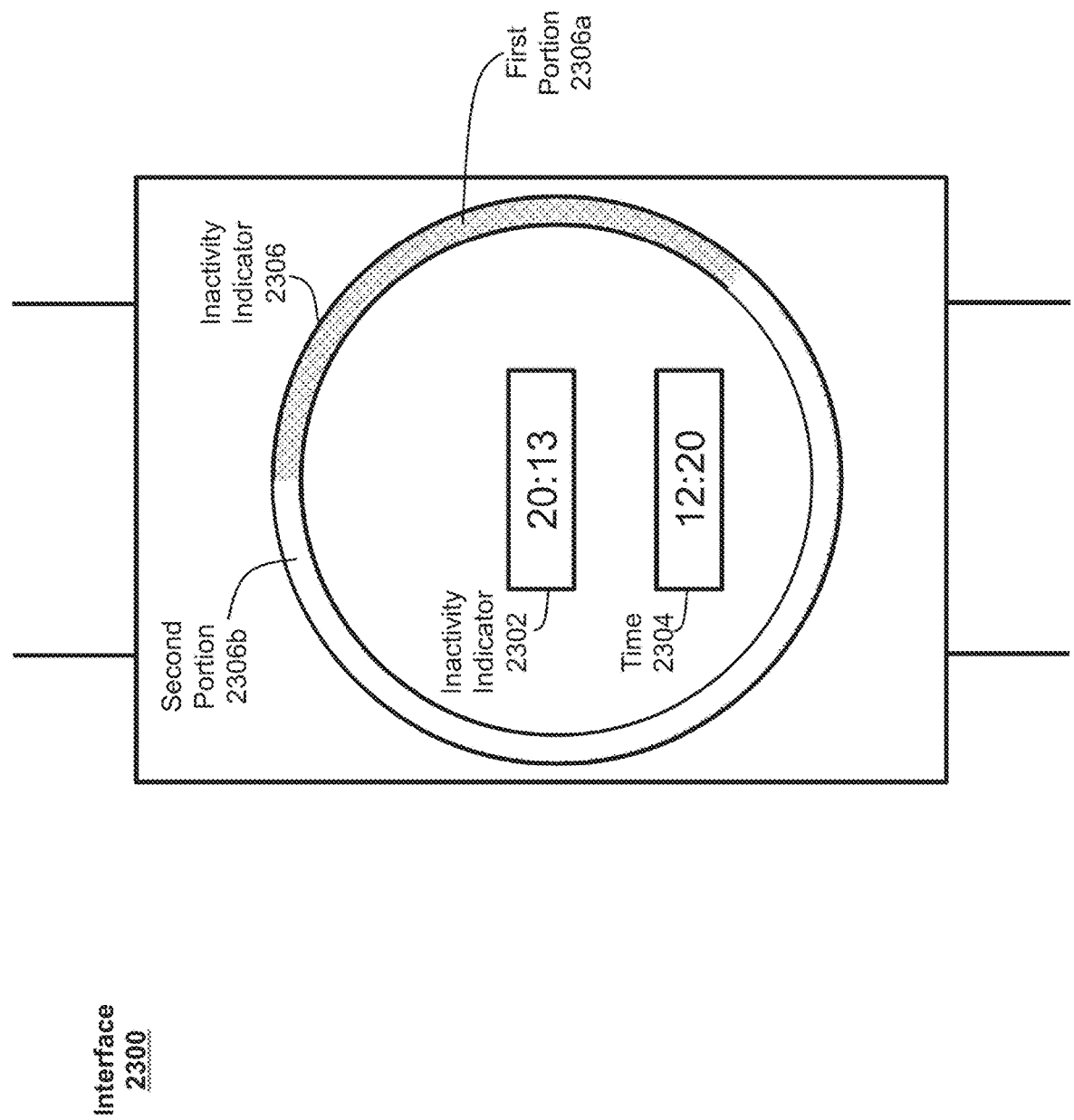
Figure 28:
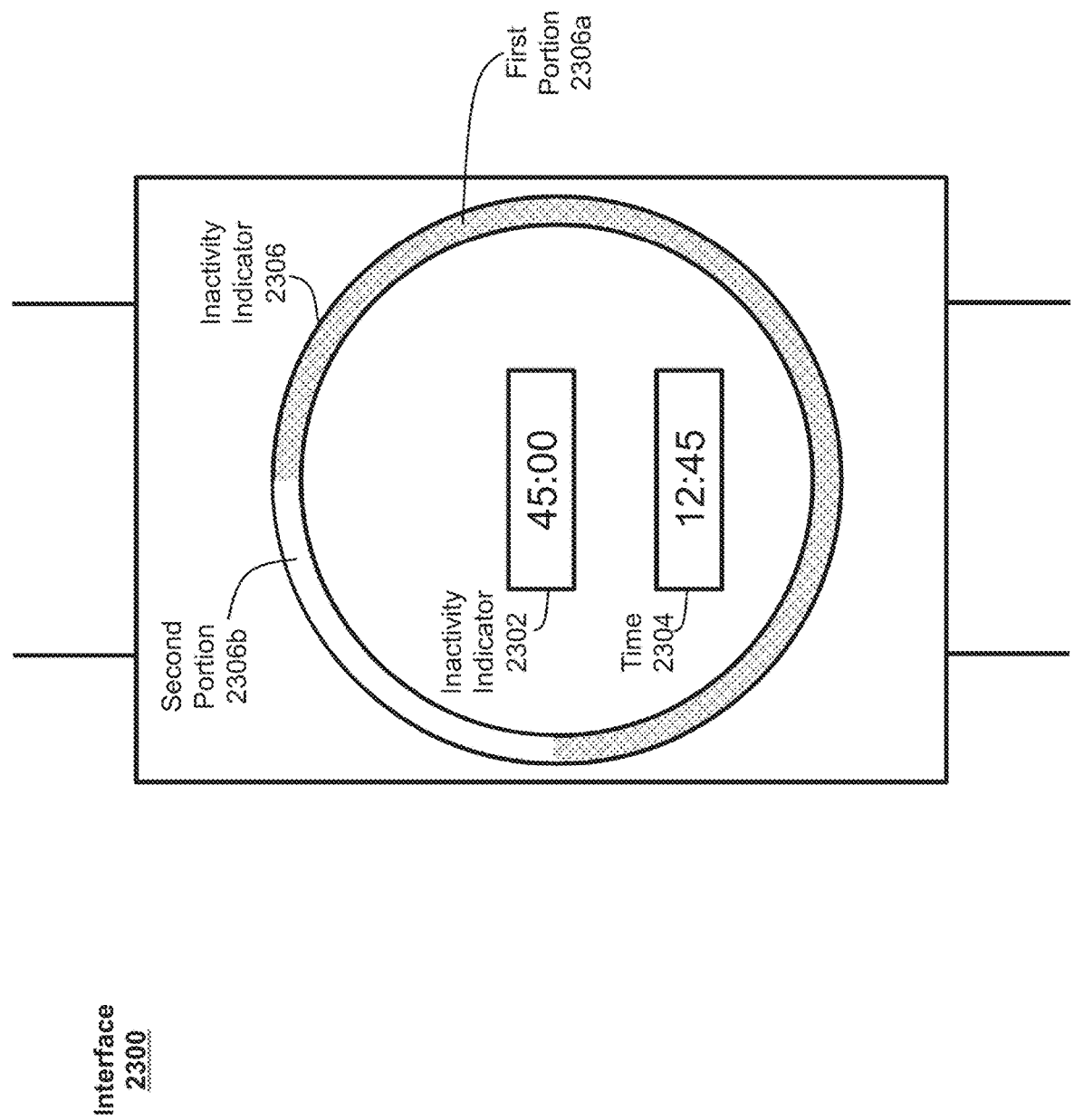
Figure 29:
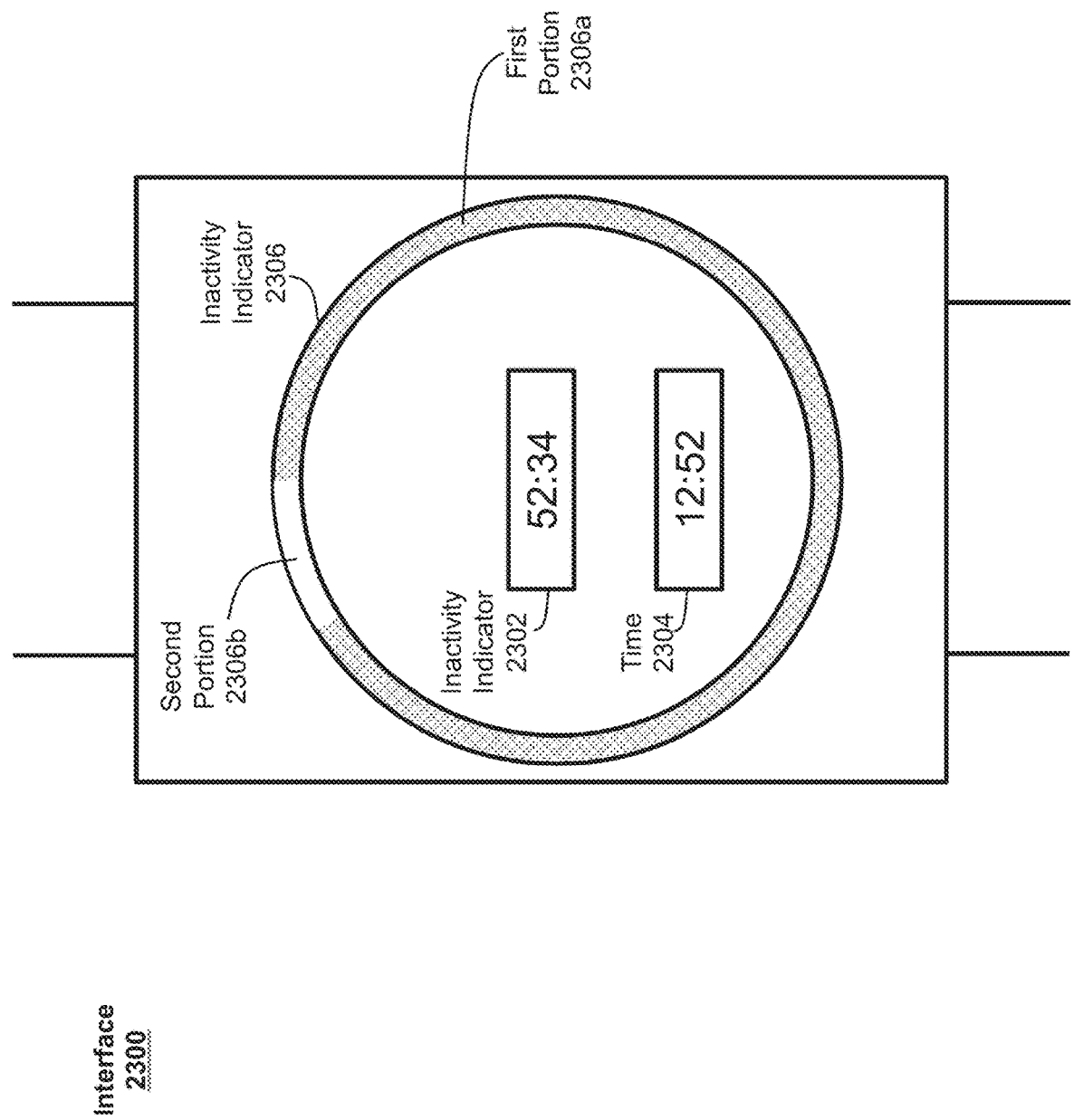

At block 2408, it can be determined whether the value of the inactivity timer has reached an inactivity threshold. As mentioned above, the inactivity threshold can have any predetermined or user-selectable value, such as 10 minutes, 20 minutes, 30 minutes, 1 hour, or the like. If it is determined that the value of the inactivity timer has not reached the inactivity threshold, the process can return to block 2406. While the user remains inactive, blocks 2406 and 2408 can be repeated, causing the inactivity timer to continue counting. For example, FIG. 26 shows an example view of interface 2300 after the user has remained inactive for 15 minutes after interface 2300 in FIG. 25 was displayed. As shown, first inactivity indicator 2302 indicates that the length of time the user has been inactive (e.g., as determined by the inactivity timer) is 15 minutes. Similarly, a quarter of the ring (e.g., one-fourth of indicator 2306 is first portion 2306*a* and three-fourths of indicator 2306 is second portion 2306*b*) of second inactivity indicator 2306 has been completed to indicate that the user has been inactive for one-fourth of the 60 minute inactivity threshold. FIG. 27 shows interface 2300 after the user has remained inactive for 20 minutes and 13 seconds. As shown, first inactive indicator 2302 has been updated with the length of inactivity (e.g., as determined by the inactivity tinier) and second inactivity indicator 2306 has been animated to include a larger portion of a ring (e.g., approximately one-third of indicator 2306 is first portion 2306*a* and two-thirds of indicator 2306 is second portion 2306*b*), with the portion of the completed ring being representative of the length of inactivity relative to the inactivity threshold. FIG. 28 shows interface 2300 after the user has remained inactive for 45 minutes. As shown, first inactive indicator 2302 has been updated with the length of inactivity (e.g., as determined by the inactivity timer) and second inactivity indicator 2306 has been animated to have first portion 2306*a* occupy a larger portion of the ring and to have second portion 2306*b* occupy a smaller portion of the ring, with the portion of the completed ring (e.g., first portion 2306*a*) being representative of the length of inactivity relative to the inactivity threshold. FIG. 29 shows interface 2300 after the user has remained inactive for 52 minutes and 34 seconds. As shown, first inactive indicator 2302 has been updated with the length of inactivity (e.g., as determined by the inactivity timer) and second inactivity indicator 2306 has been animated to have first portion 2306*a* occupy a larger portion of the ring and to have second portion 2306*b* occupy a smaller portion of the ring, with the portion of the completed ring (e.g., first portion 2306*a*) being representative of the length of inactivity relative to the inactivity threshold.

Figure 30:
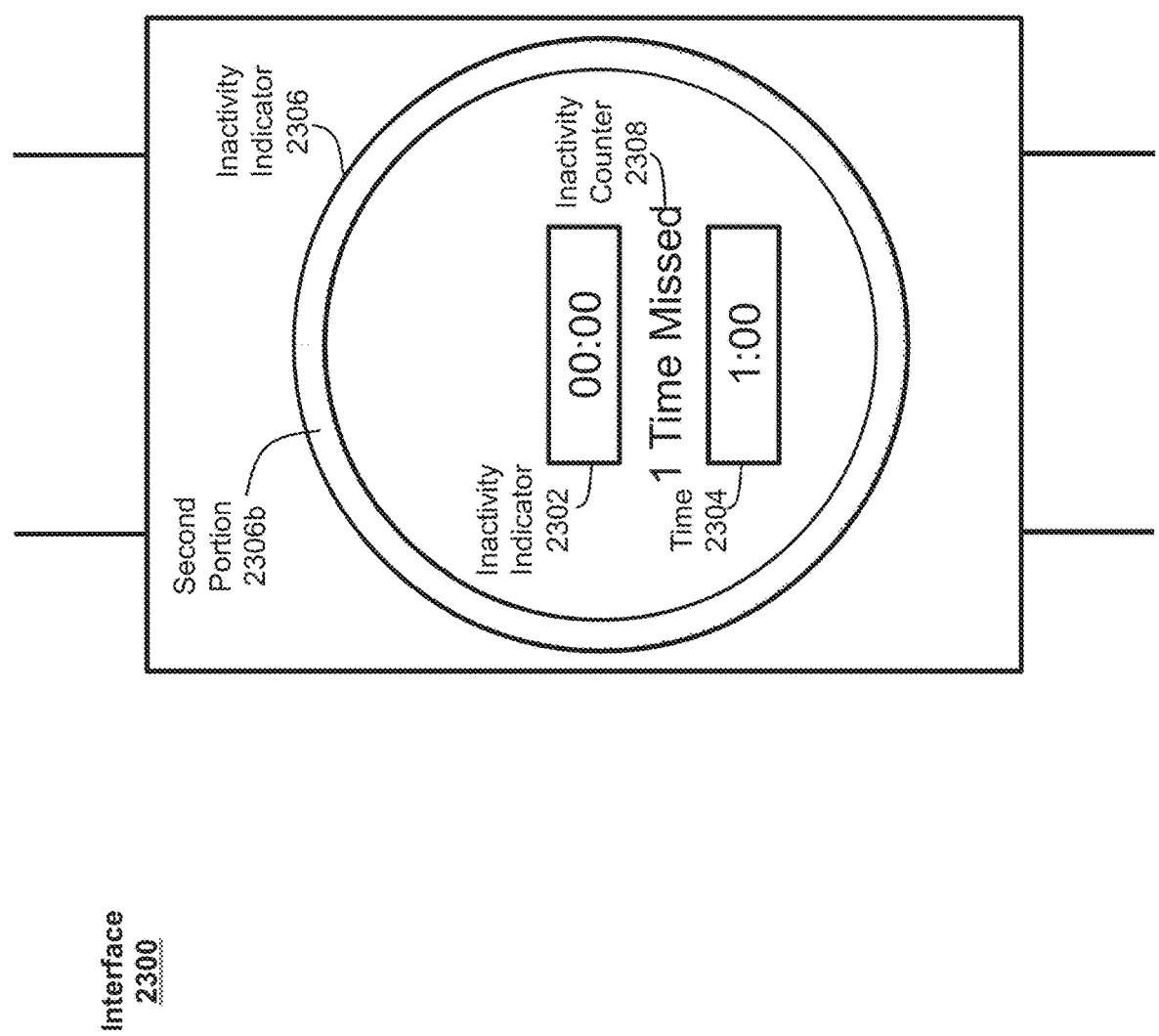

Referring back to FIG. 24, once the inactivity timer reaches the inactivity threshold, a positive determination can be made at block 2408 and the process can proceed to block 2410. At block 2410, the value of an inactivity counter can be incremented. The inactivity counter can be used to track the number of times that the user remained inactive for a continuous segment of time equal to the inactivity threshold. The value of the inactivity counter can be visually represented in the inactivity tracking interface by inactivity counter 2308. Process 2400 can then proceed to block 2412 where the inactivity timer can be reset to a value of zero. To illustrate, FIG. 30 shows an example view of interface 2300 after the user has remained inactive for 60 minutes after interface 2300 in FIG. 25 was displayed. As shown, inactivity counter 2308 indicates that the user has missed one segment of time as a result of block 2410 being performed in response to the user continuously remaining inactive for 60 minutes. Additionally, first inactivity indicator 2302 indicates that the length of time the user has been inactive (e.g., as determined by the inactivity timer) is zero minutes as a result of the inactivity timer being reset at block 2412. Similarly, indicator 2306 has been modified to include only second portion 1106*b* to indicate that the user has been inactive for zero minutes of the 60 minute inactivity threshold.

After resetting the inactivity timer at block 2412 process 2400 can return to block 2402 where it can be determined whether or not updated activity data has been received at block 2204 and if that activity data indicates that the user is active (e.g., by performing an activity). If it is determined that the user is performing an activity, or has performed an activity within a threshold length of time (e.g., 5-10 seconds), the process can return to block 2402 where the activity data can continue to be monitored to detect when the user becomes inactive. Alternatively, if it is determined that the user is not performing an activity (or is not performing the predefined type of activity), or has not performed an activity within the threshold length of time, the process can proceed to block 2404. By resetting the inactivity timer at block 2412 and starting the inactivity timer at block 2404 once it is determined that the user is again inactive, process 2400 can be used to identify hour-long (or any other desired duration) segments of time during which the user is inactive (e.g., segments that can start at any time), rather than identify predefined hour-long segments (e.g., segments from 1 pm to 2 pm, 2 pm to 3 pm, etc.) during which the user is inactive.

Figure 31:
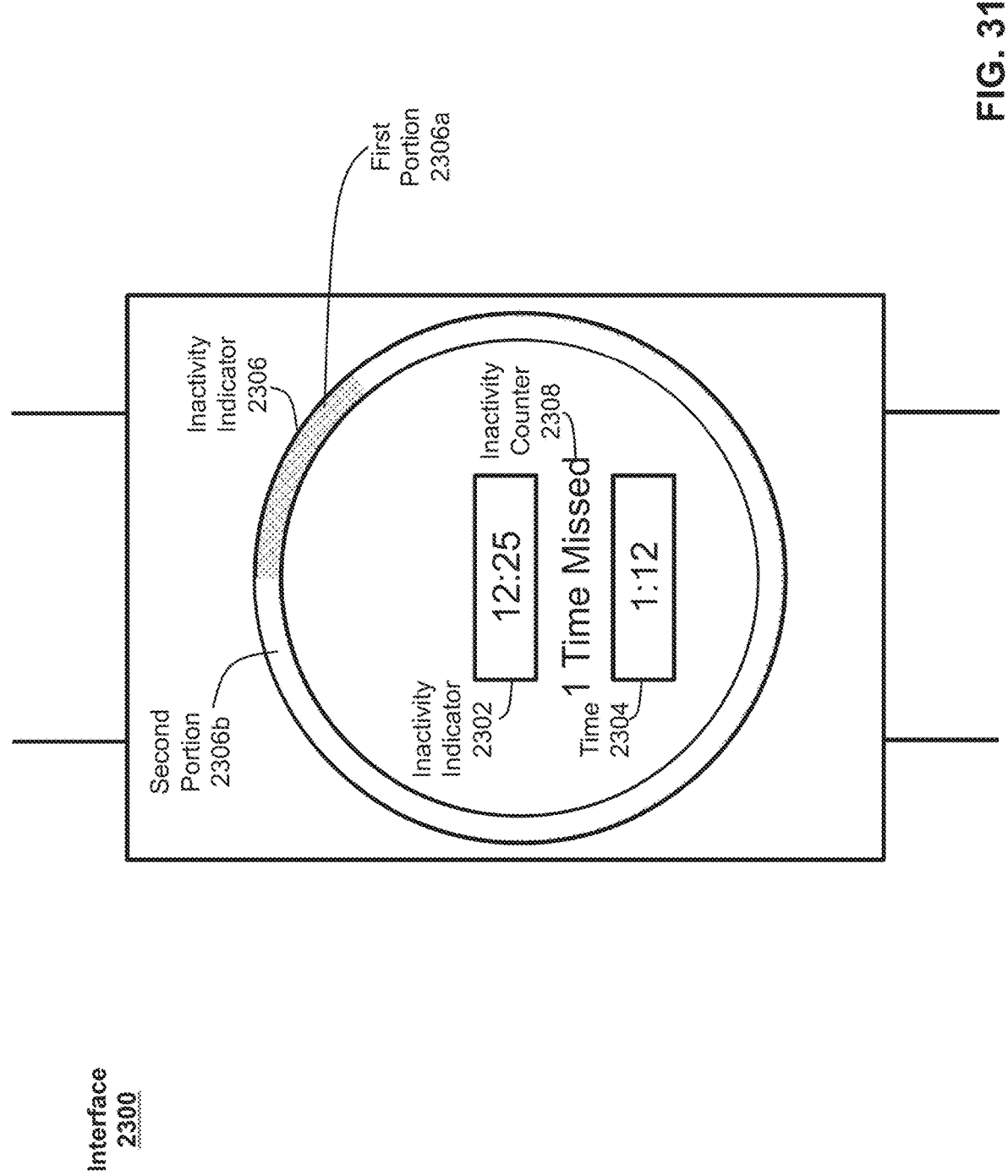

At block 2404, the inactivity timer can again be started. While the user remains inactive, process 2400 can proceed to repeatedly perform blocks 2406 and 2408, as discussed above. To illustrate, FIG. 31 shows an example view of interface 2300 after the user has remained inactive for 12 minutes and 25 seconds after interface 2300 in FIG. 30 was displayed (and 72 minutes and 25 seconds after interface 2300 in FIG. 25 was displayed). As shown, inactivity counter 2308 indicates that the user has missed one segment of time by continuously remaining inactive for 60 minutes. Additionally, first inactivity indicator 2302 indicates that the length of time the user has been inactive during the current segment of time (e.g., as determined by the inactivity timer) is 12 minutes and 25 seconds. Similarly, the ring of second inactivity indicator 2306 has been animated to have first portion 2306*a* occupy a larger portion of the ring and to have second portion 2306*b* occupy a smaller portion of the ring, with the portion of the completed ring (e.g., first portion 2306*a*) being representative of the 12 minutes and 25 seconds that the user has been inactive.

Figure 32:
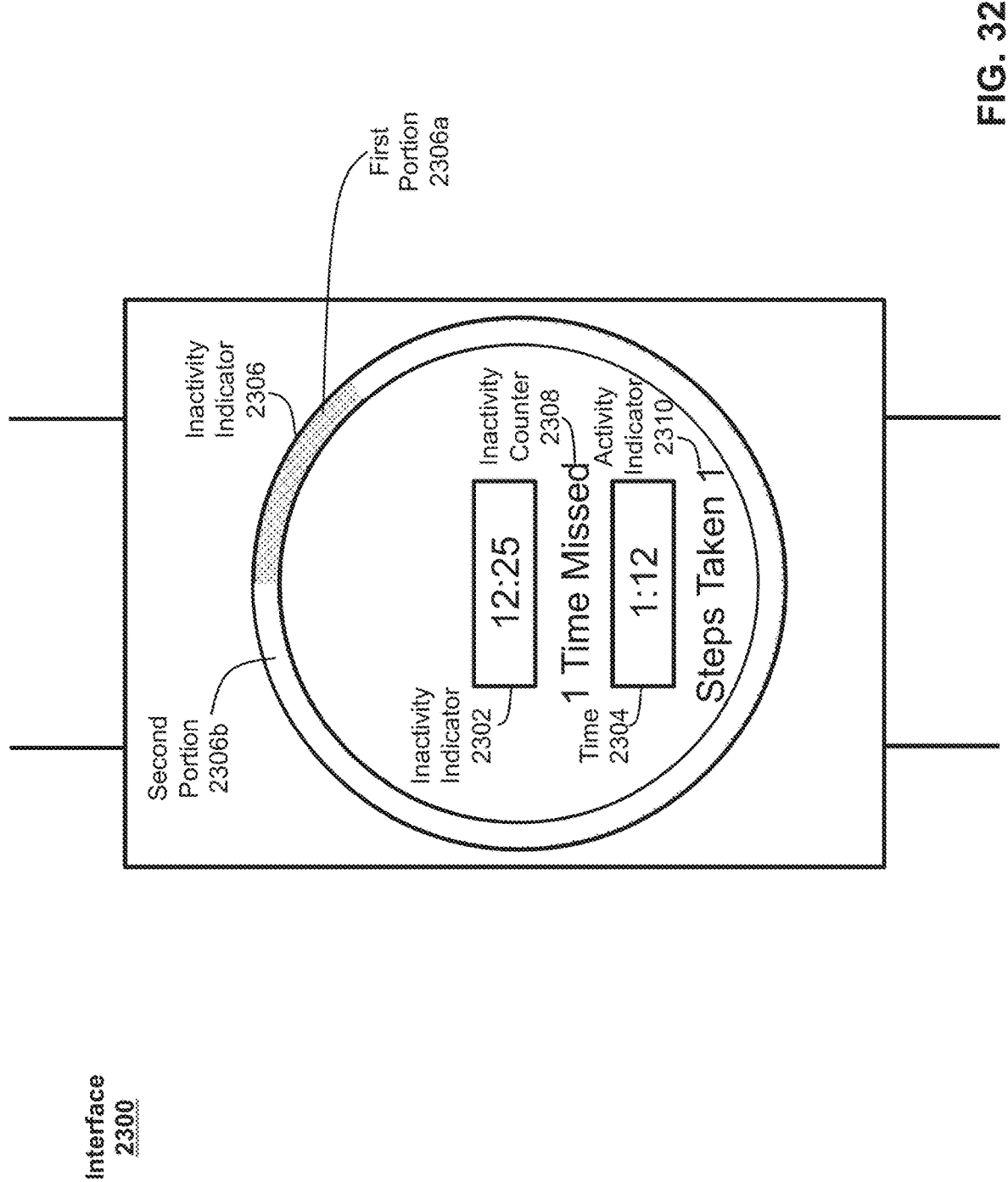

If, at block 2406, it is instead determined that the user is performing an activity, or has performed an activity within a threshold length of time (e.g., 5-10 seconds), the process can proceed to block 2414. For example, in response to the user taking a step as determined by the activity sensor, it can be determined at block 2406 that the user is performing an activity and is active. At block 2414, the inactivity timer can be paused. For example, the processor(s) of the device can pause the timer to cause the value of the timer to remain constant. Process 2400 can then proceed to block 2416 where the activity detected at block 2406 can be used to update an amount of detected activity. The amount of detected activity can represent the physical activity performed by the user using any desired metric, such as Calories expended, steps taken, distance traveled, or the like, and can be visually represented by activity indicator 2310 in the inactivity tracking interface. Continuing with the examples above that use walking as the activity being detected at blocks 2402 and 2406, the amount of detected activity can be measured using steps taken. Thus, the amount of detected activity can be updated to include the number of steps taken by the user as indicated by the activity data received from the activity sensors. To illustrate, FIG. 32 shows an example view of interface 2300 after the user has taken one step after interface 2300 in FIG. 31 was displayed. As shown, the values of inactivity counter 2308, first inactivity indicator 2302, and second inactivity indicator 2306 have not changed from that shown in FIG. 31 as a result of the inactivity timer being paused at block 2414. However, activity indicator 2310 has been displayed within interface 2300 and indicates that the user has taken one step (e.g., based on the value of the amount of detected activity that was updated at block 2416).

At block 2418, it can be determined whether the amount of detected activity updated at block 2416 has reached an activity threshold. As discussed above, the activity threshold can have any predetermined or user-selectable value represented in any desired unit of measurement, such as Calories expended, steps taken, distance traveled, or the like. For example, the activity threshold can have a value of 100 steps. Since the user has only taken one step, it can be determined at block 2418 that the amount of detected activity has not reached the activity threshold. As a result, the process can proceed to block 2420.

Figure 33:
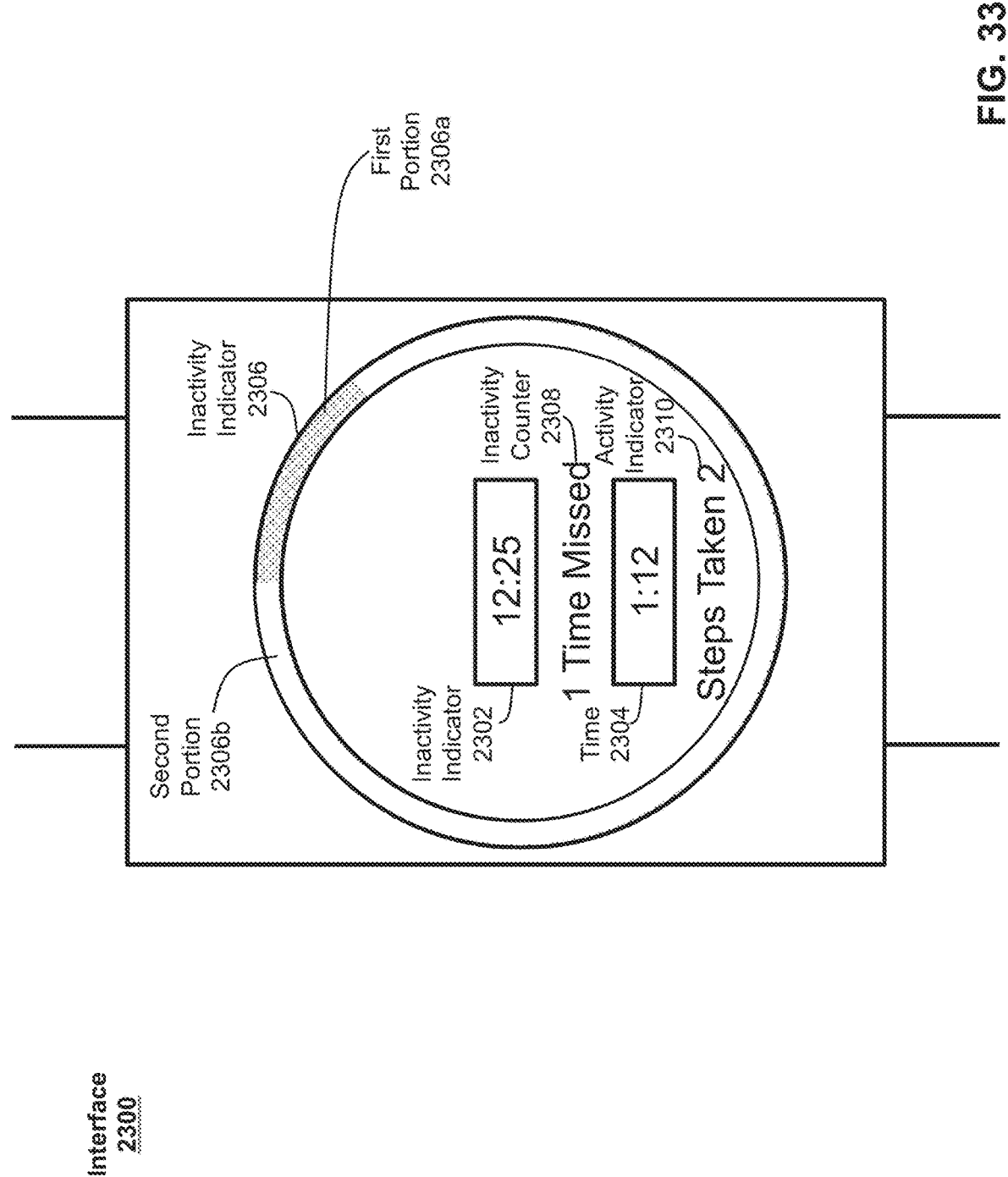
Figure 34:
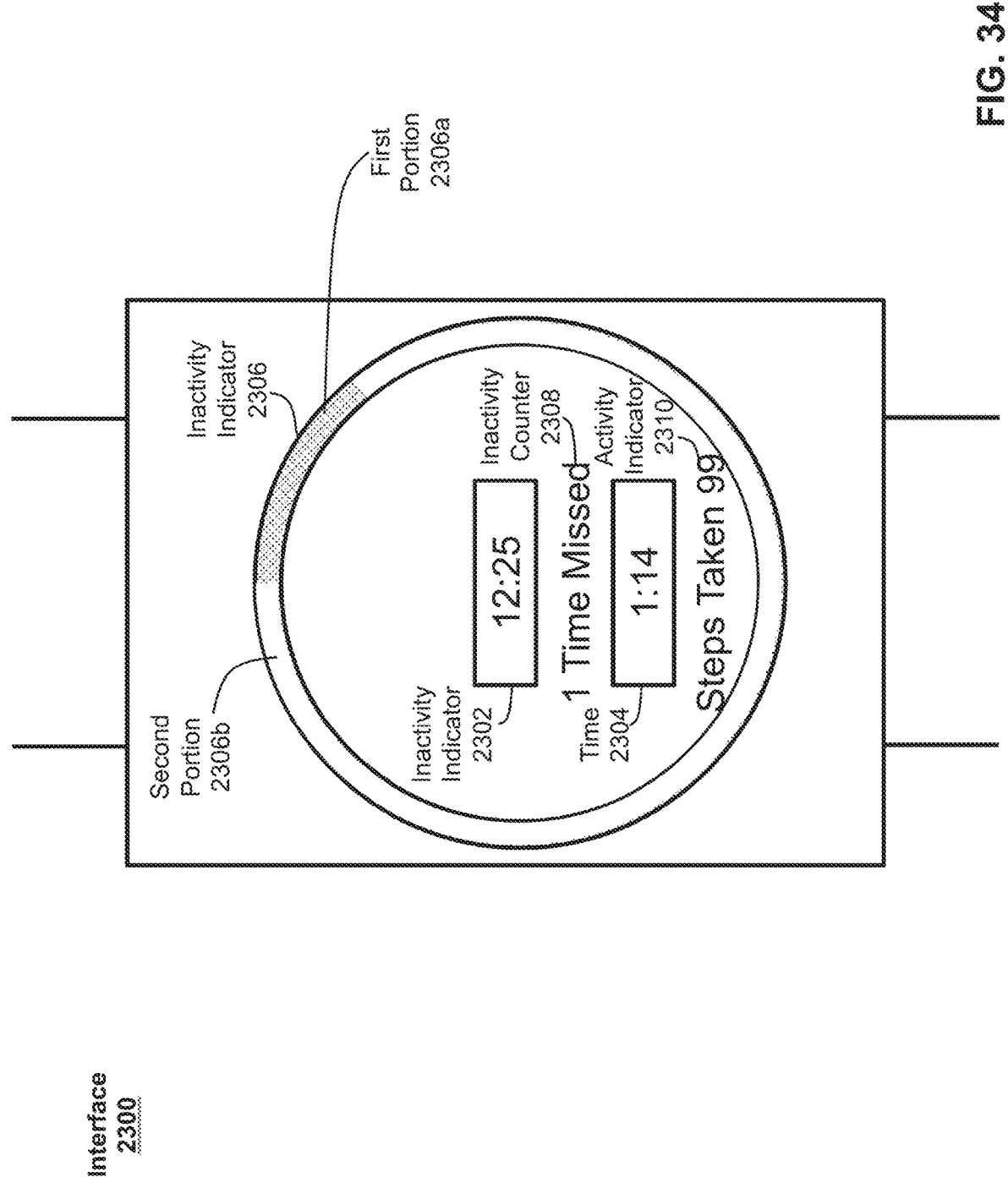

At block 2420, it can be determined whether or not updated activity data has been received at block 2204 and if that activity data indicates that the user is performing an activity. This determination can be similar or identical to the determination made at blocks 2402 and 2406. If it is determined that the user is performing an activity (or is performing the predefined type of activity), or has performed an activity within the threshold length of time, the process can return to block 2416. While the user continues to perform a physical activity (e.g., walking), or continues to perform the physical activity without stopping for more than a threshold length of time (e.g., 5-10 seconds), and while the amount of physical activity remains less than the activity threshold, blocks 2416, 2418, and 2420 can be repeated to detect and record the physical activity using the amount of detected activity value. To illustrate, FIG. 33 shows an example view of interface 2300 after the user has taken two steps after interface 2300 in FIG. 31 was displayed. As shown, the values of inactivity counter 2308, first inactivity indicator 2302, and second inactivity indicator 2306 have not changed from that shown in FIGS. 31 and 32 as a result of the inactivity timer being paused at block 2414. However, activity indicator 2310 has been updated to indicate that the user has taken two steps (e.g., based on the value of the amount of detected activity that was updated at block 2416). FIG. 34 shows an example view of interface 2300 after the user has taken 99 steps after interface 2300 in FIG. 31 was displayed. As shown, the values of inactivity counter 2308, first inactivity indicator 2302, and second inactivity indicator 2306 have not changed from that shown in FIGS. 31, 32, and 33 as a result of the inactivity timer being paused at block 2414. However, activity indicator 2310 has been updated to indicate that the user has taken 99 steps (e.g., based on the value of the amount of detected activity that was updated at block 2416).

Figure 35:
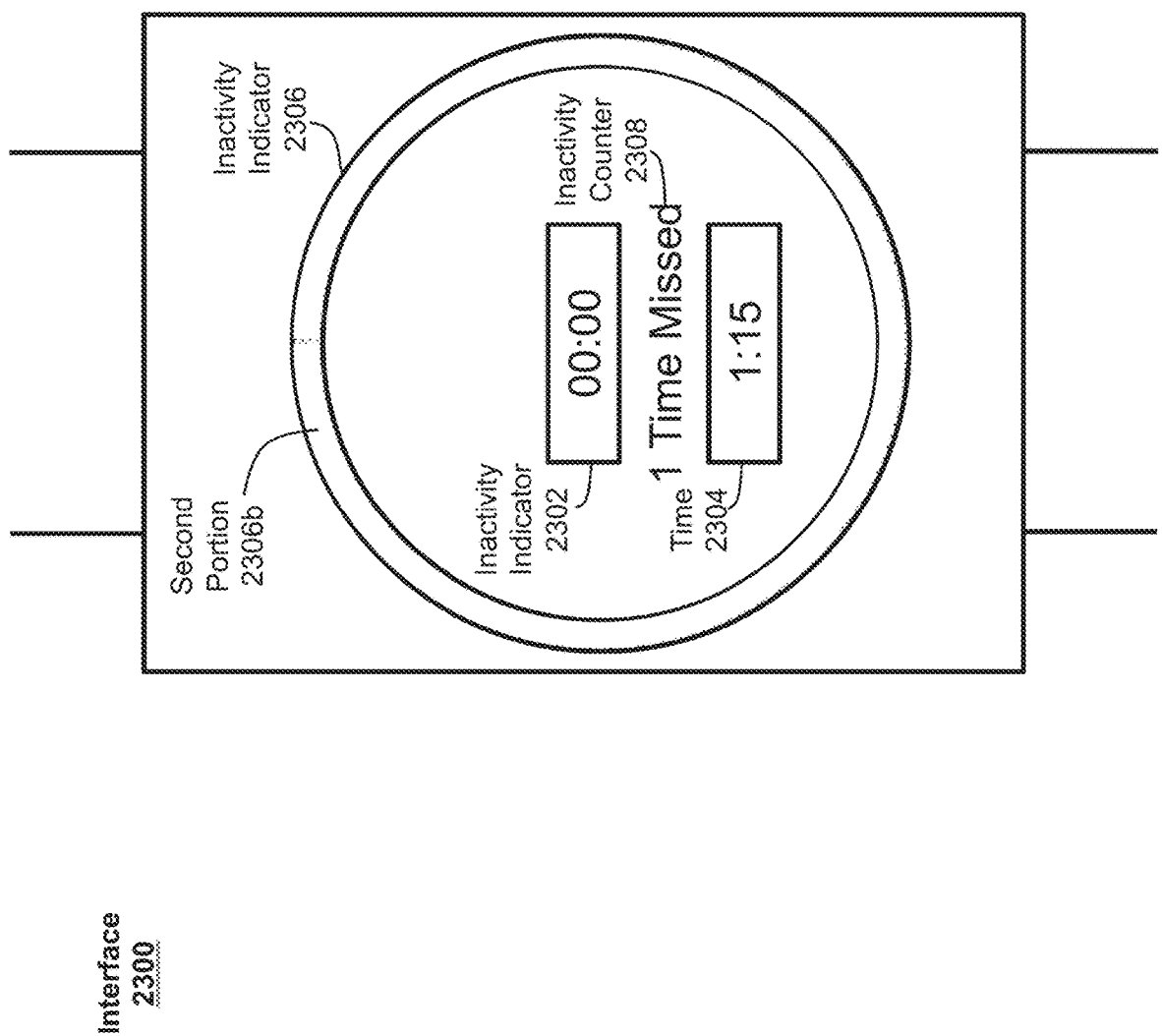

If, at block 2418, it is instead determined that the amount of detected activity has reached the activity threshold, the process can proceed to block 2422. At block 2422, the amount of detected activity can be reset to zero and the process can proceed to block 2412 where the inactivity timer can also be reset to zero. For example, the processor(s) of the device can reset the value of the amount of detected activity and can reset the timer to a value of zero. To illustrate, FIG. 35 shows an example view of interface 2300 after the user has taken 100 steps after interface 2300 in FIG. 31 was displayed. As a result of performing an amount of activity equal to or greater than the activity threshold, the inactivity timer has been reset at block 2412, causing first inactivity indicator 2302 to indicate that the length of time the user has been inactive (e.g., as determined by the inactivity timer) is zero minutes. Similarly, the ring of second inactivity indicator 2306 has been animated to include only second portion 2306*b* to indicate that the user has been inactive for zero minutes of the 60 minute inactivity threshold. Additionally, activity indicator 2310 has been removed from the display in response to the amount of detected activity being reset at block 2422.

Figure 36:
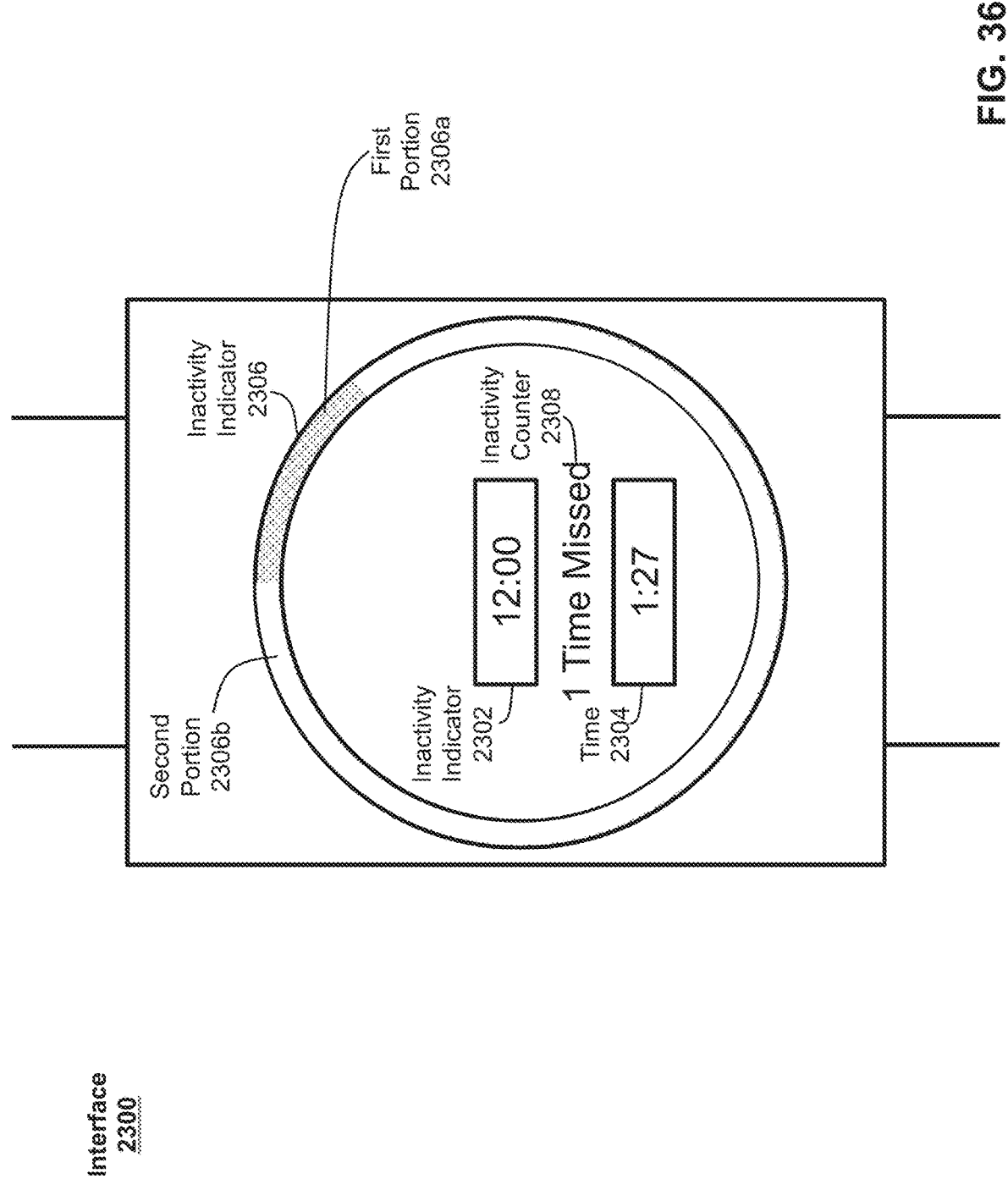

After resetting the inactivity timer at block 2412, process 2400 can return to block 2402 where it can be determined whether or not updated activity data has been received at block 2204 and if that activity data indicates that the user is performing an activity. If it is determined that the user is performing an activity, or has performed an activity within a threshold length of time (e.g., 5-10 seconds), the process can return to block 2402 where the activity data can continue to be monitored to detect when the user becomes inactive. Alternatively, if it is determined that the user is not performing an activity (or is not performing the predefined type of activity), or has not performed an activity within the threshold length of time, the process can proceed to block 2404. At block 2404, the inactivity timer can again be started. While the user remains inactive, process 2400 can proceed to repeatedly perform blocks 2406 and 2408, as discussed above. To illustrate, FIG. 36 shows an example view of interface 2300 after the user has remained inactive for 12 minutes after interface 2300 in FIG. 35 was displayed. As shown, inactivity counter 2308 indicates that the user has missed one segment of time by continuously remaining inactive for 60 minutes. Additionally, first inactivity indicator 2302 indicates that the length of time the user has been inactive during the current segment of time (e.g., as determined by the inactivity timer) is 12 minutes. Similarly, the ring of second inactivity indicator 2306 has been animated to have first portion 2306*a* occupy a larger portion of the ring and to have second portion 2306*b* occupy a smaller portion of the ring, with the portion of the completed ring (e.g., first portion 2306*a*) being representative of the 12 minutes that the user has been inactive.

Figure 37:
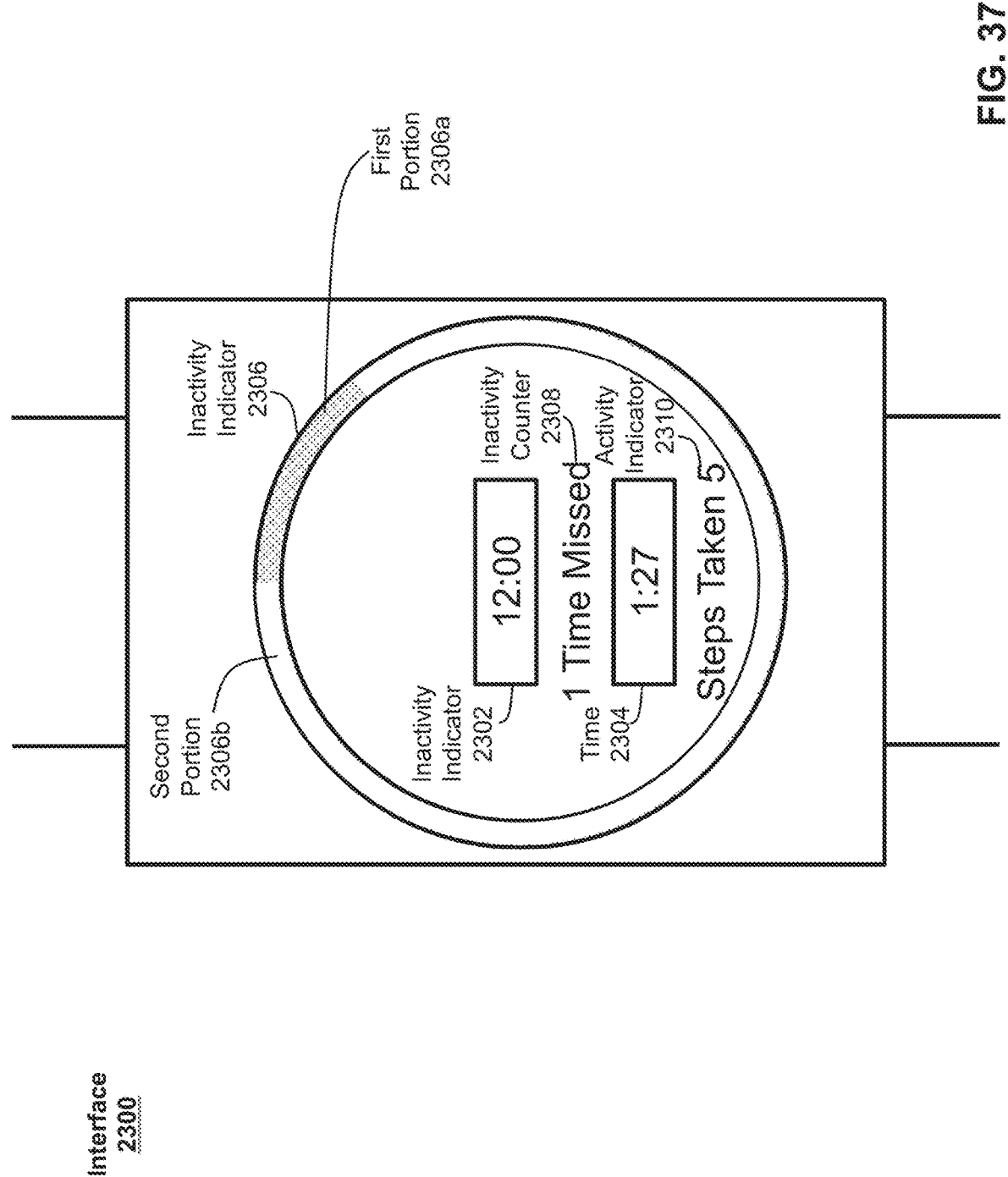

As discussed above, if the user begins to perform an activity, such as walking five steps, a positive determination can be made at block 2406 and the process can proceed to block 2414. At block 2414 the activity timer can be paused, and at block 2416 the amount of detected activity can be updated to include the five steps taken by the user. To illustrate, FIG. 37 shows an example view of interface 2300 after the user has taken five steps after interface 2300 in FIG. 36 was displayed. As shown, the values of inactivity counter 2308, first inactivity indicator 2302, and second inactivity indicator 2306 have not changed from that shown in FIG. 36 as a result of the inactivity timer being paused at block 2414. However, activity indicator 2310 has been displayed within interface 2300 and indicates that the user has taken five steps (e.g., based on the value of the amount of detected activity that was updated at block 2416).

Figure 38:
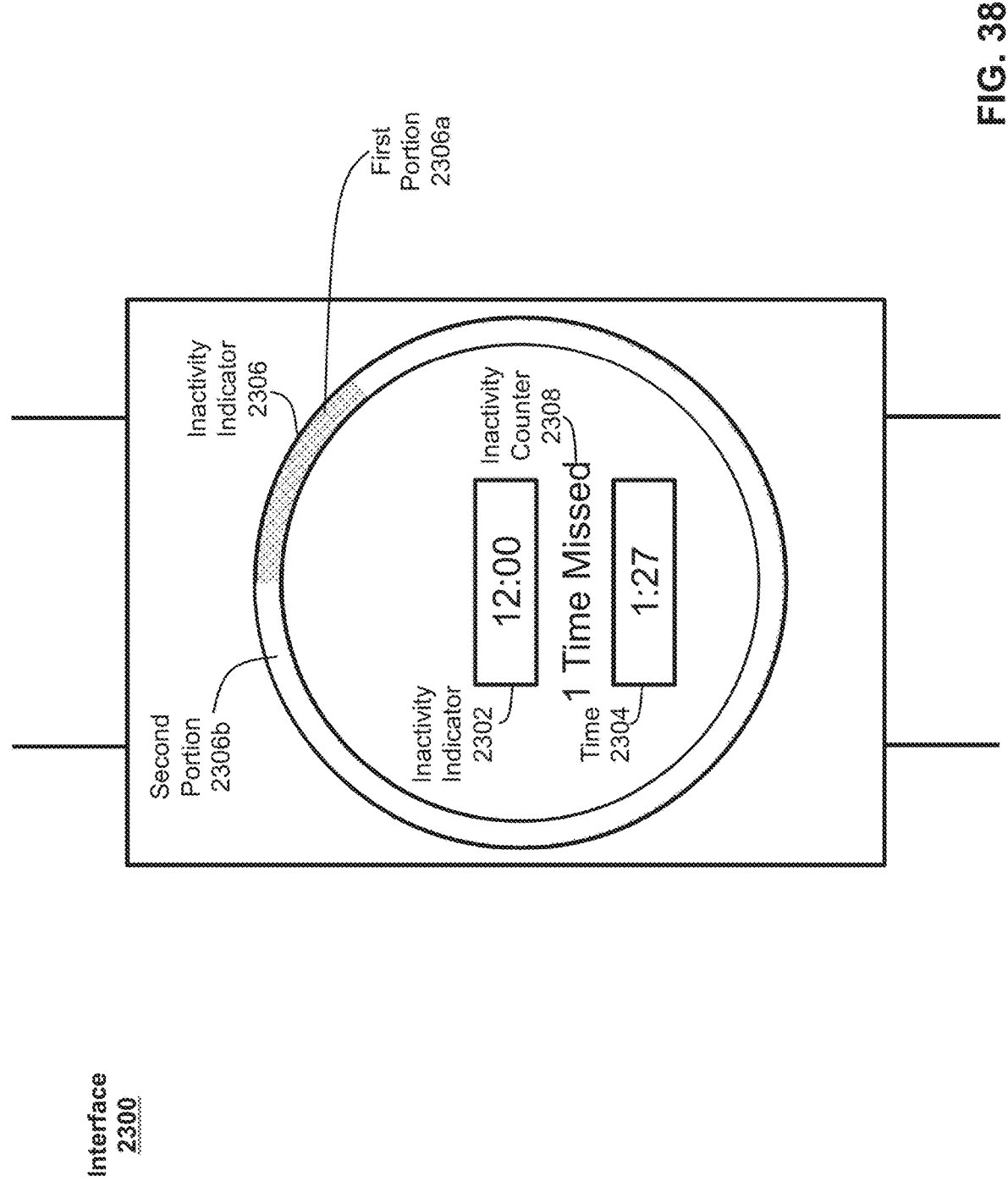

Since the five steps taken by the user is less than the 100 step activity threshold, a negative determination can be made at block 2418 and the process can proceed to block 2420. If, at block 2420, the user stops performing a physical activity, or stops performing the physical activity for more than a threshold length of time (e.g., 5-10 seconds), a negative determination can be made at block 2420 and the process can proceed to block 2424. In some examples, the absence of data from the activity sensors can cause a negative determination to be made at block 2420 and the process to proceed to block 2424. At block 2424, the amount of detected activity can be reset in a manner similar or identical to block 2422 without resetting the inactivity timer. To illustrate, FIG. 38 shows an example view of interface 2300 after the user has stopped walking, or has stopped walking for more than a threshold length of time, after interface 2300 in FIG. 37 was displayed. As a result of stopping the physical activity, the amount of detected activity has been reset at block 2424 and activity indicator 2310 has been removed from the display. Additionally, since the activity timer was not reset, the values of first inactivity indicator 2302 and second inactivity indicator 2306 have not changed from those shown in FIG. 37.

Figure 39:
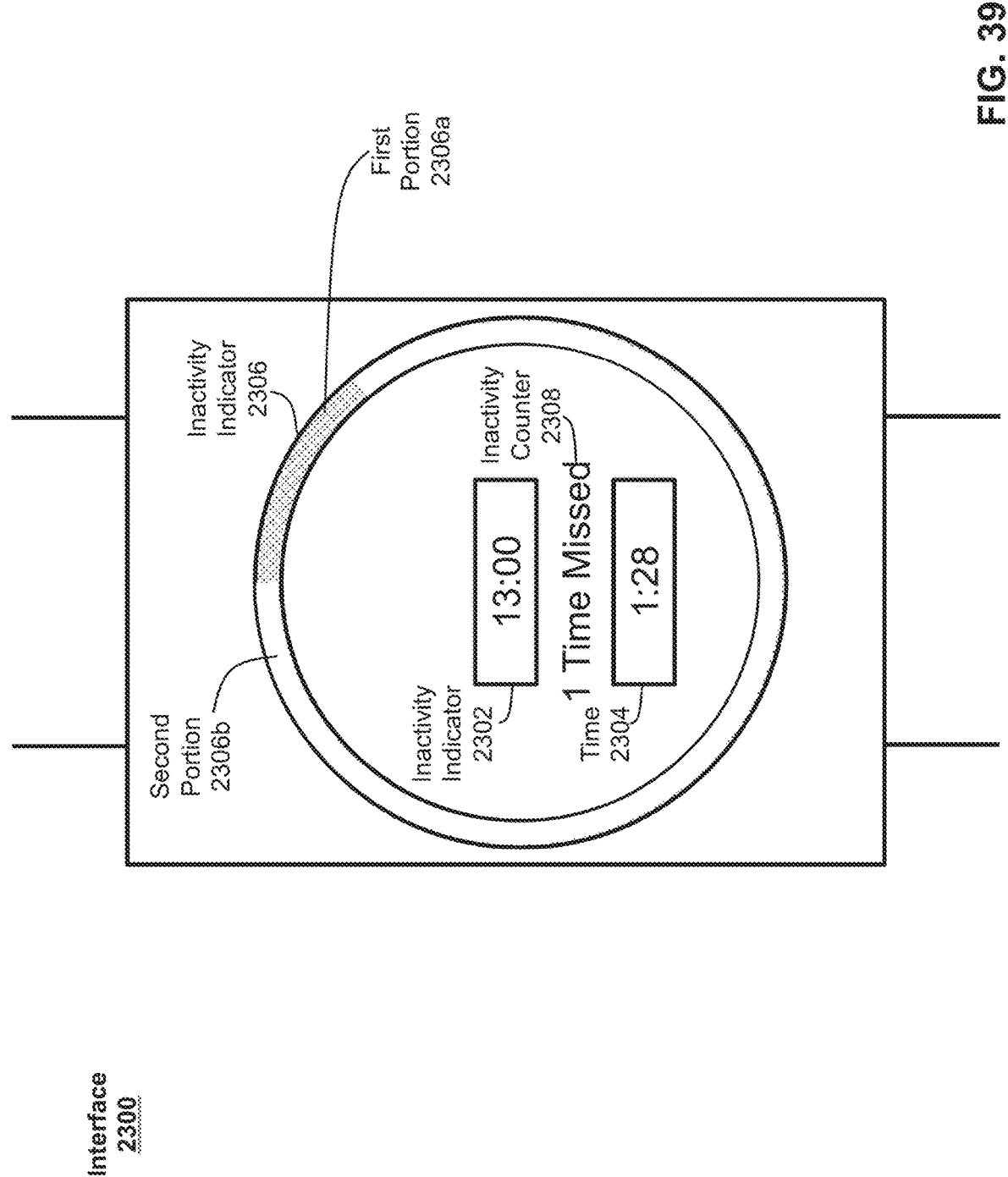

If the user remains inactive, blocks 2402, 2404, 2406, and 2408 can be performed to continue to record the amount of time that the user is inactive using the inactivity timer. To illustrate, FIG. 39 shows an example view of interface 2300 one minute after interface 2300 in FIG. 38 was displayed. As shown, first inactivity indicator 2302 and second inactivity indicator 2306 have been updated to reflect the 13 minute value of the inactivity timer caused by the activity timer being started at block 2404.

In some examples, process 2400 can further include resetting the values of the inactivity counter periodically or at predetermined times (e.g., once each day, week, month, or the like). In these examples, the value of the inactivity counter can be stored prior to being reset to track the number of times the user continuously remains inactive for a length of time equal to the inactivity threshold over time. For example, the value of the inactivity counter can be stored and then reset at the end of each day (e.g., at midnight). The recorded values of the inactivity counter can allow the user to view the number of times that the user remained continuously inactive for 60 minutes from day to day.

In some examples, process 2200 or 2400 can further include generating a notification in response to the inactivity timer reaching a value that is a threshold length of time less than the inactivity threshold. The notification can include any desired visual, audio, haptic, or other notification to the user to indicate that the inactivity threshold is nearly expired. For example, a text notification can be displayed on the display of the device when the inactivity timer reaches a value of 50 minutes (10 minutes before the 60 minute inactivity threshold). This advantageously gives the user the ability to preemptively get up before the inactivity threshold duration has passed.

In some examples, process 2200 or 2400 can further include generating images (e.g., badges) on the display of the device that represent achievements attained by the user, such as reducing the number of times the user is continuously inactive for a length of time equal to the inactivity threshold (e.g., the recorded value of the inactivity counter) by a threshold amount, reducing the number of times the user is continuously inactive for a length of time equal to the inactivity threshold (e.g., the recorded value of the inactivity counter) to less than a predefined number, or the like. Other rewards, including visual rewards, such as animations, glowing or pulsating graphics, 3D images, lighting effects, badges, or the like; sound rewards, such as alerts, ringtones, music, voice, or the like; vibrations; or any combinations of rewards thereof, can be provided to the user for other tasks completed by the user. For example, rewards can be given in response to the inactivity timer being reset, a time period ending and the user having an inactivity counter value below a threshold amount, or the like.

In some examples, prior to resetting the inactivity timer at block 2412, the value of the inactivity tinier can be added to a total length of inactivity value that represents the total amount of time that the user is inactive. The total length of inactivity can be stored and reset at predetermined times (e.g., once each day, week, month, or the like). For example, the total length of inactivity can be stored and then reset at the end of each day (e.g., at midnight). The recorded values of the total length of inactivity can allow the user to view length of time that the user is inactive (rather than or in addition to the number of times that the user remained continuously inactive for 60 minutes) from day to day.

While the blocks of processes 2200 and 2400 are shown and described in a particular order, it should be appreciated that the blocks of these processes can be performed in different orders or at the same time. For example, while controlling the inactivity timer using process 2400, additional activity data can be received at block 2204 of process 2200 and the inactivity tracking interface can be repeatedly updated at block 2202.

Note that details of the processes described above with respect to processes 2200 and 2400 (e.g., FIGS. 22 and 24) are also applicable in an analogous manner to the other processes described herein. For example, processes 1500, 1600, 4000, 4800, 7900, 8600, and 9200 may include one or more of the characteristics of the various methods described above with reference to processes 2200 and 2400. For example, the activity data, activity types, displayed values and other elements described above with reference to processes 2200 and 2400 optionally have one or more of the characteristics of the activity data, activity types, displayed values and other elements described herein (e.g., processes 1500, 1600, 4000, 4800, 7900, 8600, and 9200). For brevity, these details are not repeated.

Figure 40:
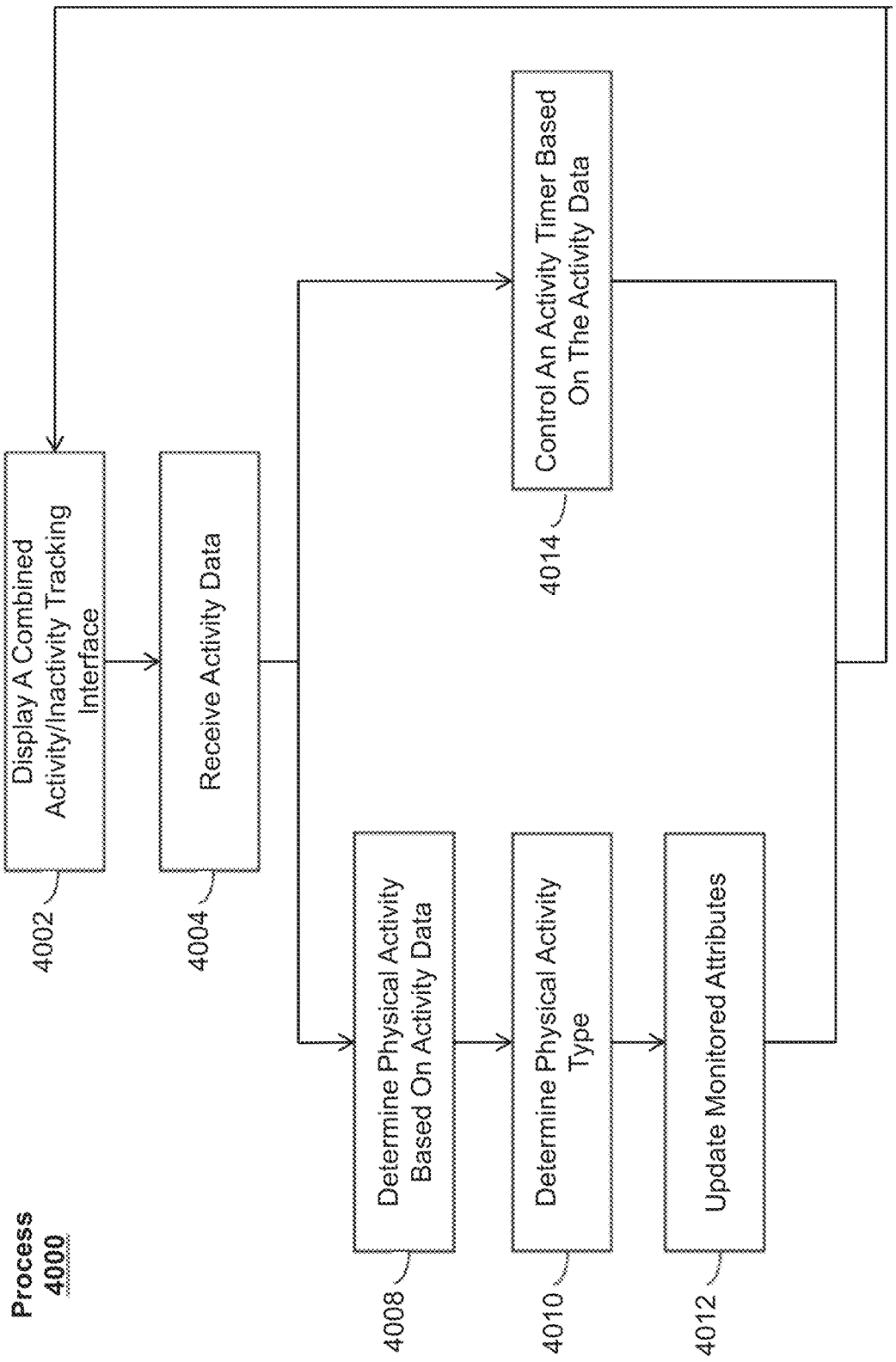
FIG. 40 illustrates a process for generating a combined physical activity/inactivity tracking interface for monitoring the activity and inactivity of a user according to various examples.

FIG. 40 illustrates an exemplary process 4000 for generating and updating a combined physical activity/inactivity tracking interface that can be used to monitor attributes of a user's physical activity and inactivity. In some examples, process 4000 can be performed using a device similar or identical to device 100, 300, 500, or 610. At block 4002, a display of a combined physical activity/inactivity tracking interface can be displayed. The combined physical activity/inactivity tracking interface can include visual representations of attributes of any number of physical activity types similar to the indicators of interface 1700, shown in FIG. 17, as well as visual representations of attributes of a user's inactivity similar to the indicators of interface 2300, shown in FIG. 23. Some operations in process 4000 may be combined, the order of some operations may be changed, and some operations may be omitted.

As described below, process 4000 provides intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

Figure 41:
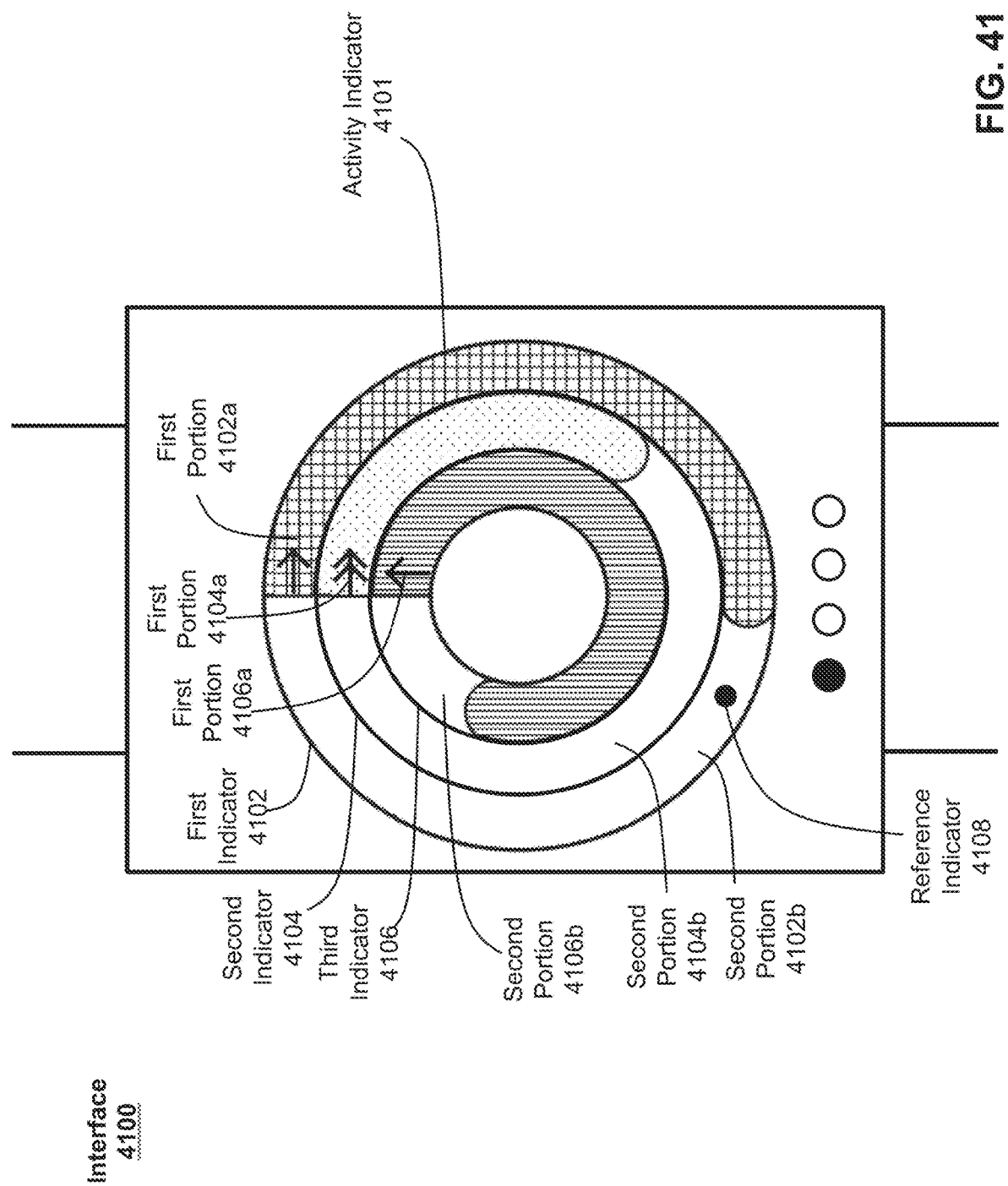
FIG. 41 illustrates an exemplary combined physical activity/inactivity tracking interface according to various examples.
Figure 42:
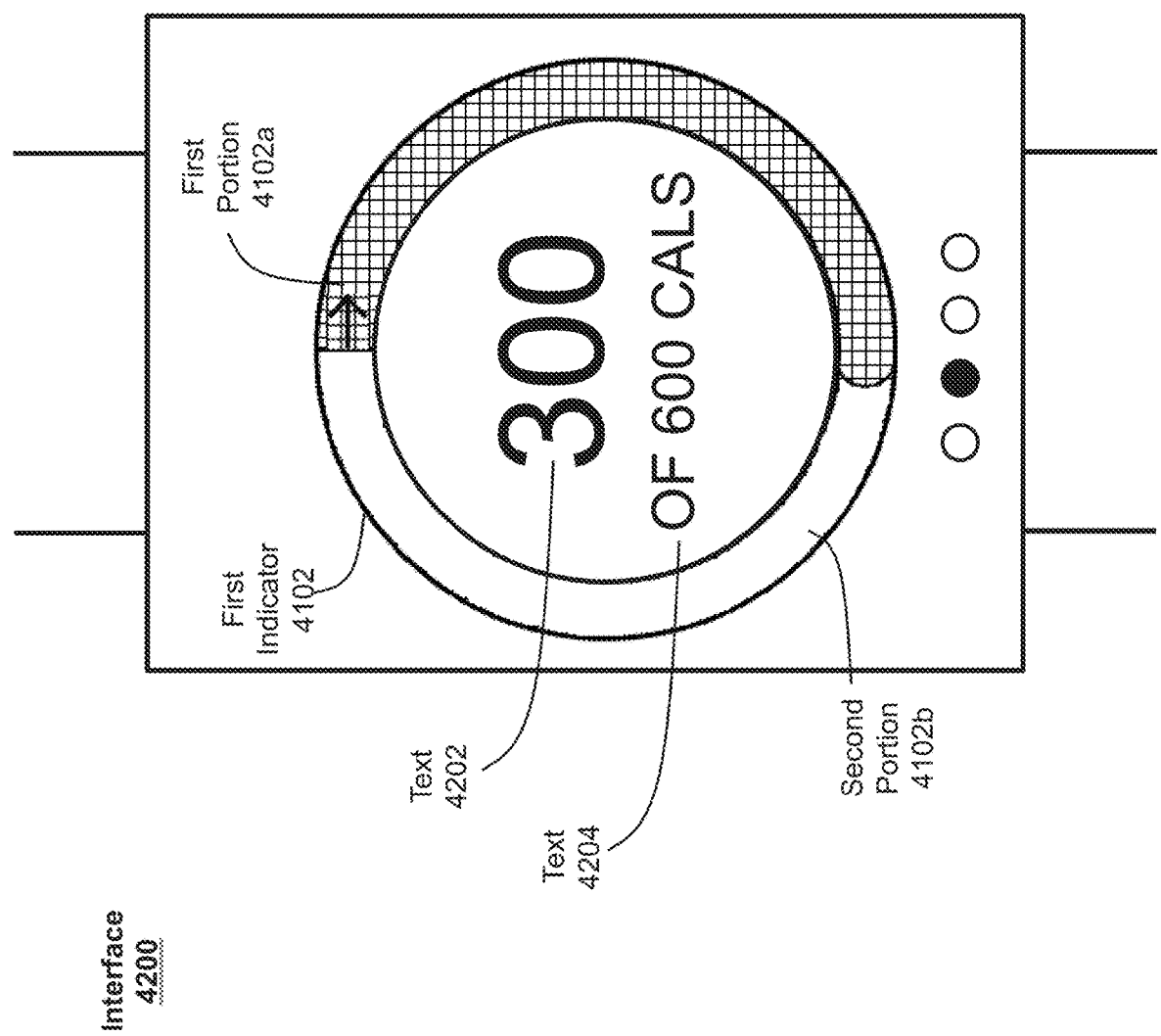
FIGS. 42-47 illustrate exemplary interfaces for displaying information about a user's physical activity and/or inactivity according to various examples.

For example, FIG. 41 illustrates an exemplary activity/inactivity tracking interface 4100 that can be displayed at block 4002 of process 4000. Interface 4100 can include a combined activity indicator 4101 having a first visual representation of an attribute of a first type of user activity in the form of first indicator 4102. In some examples, first indicator 4102 can be controlled and displayed in a manner similar or identical to that of indicator 1702 of interface 1700 to represent an attribute of the first type of activity. For example, as discussed above with respect to FIGS. 15-21, a physical activity can be categorized into any number of types based on a predetermined set of criteria for each type. The criteria can include any attribute of the physical activity or information detectable by the activity sensors, such as a speed greater than or equal to a threshold, a minimum number of steps taken per unit time, a minimum amount of Calories burned per unit time, etc. For example, the first set of criteria for the first type of physical activity can simply require that the activity be a physical activity (rather than a gesture) Additionally, similar to indicators 1702 and 1704 of interface 1700, first indicator 4102 can represent a first value of any attribute of the physical activity, such as an amount, an intensity level, a duration, a progress relative to a set value, a trend over a time period, or the like, of the activity. For example, the first value can represent an aggregate amount of active and/or resting Calories expended by the user in performing the first type of activity over a predetermined period of time (e.g., a day).

In some examples, first indicator 4102 can further represent a first goal value for the represented attribute of the first type of physical activity. In these examples, the size of first indicator 4102 can be scaled such that its size represents the first goal amount, and a portion of first indicator 4102 can be marked such that the marked portion represents the actual value of the represented attribute of the first type of activity performed by the user. Alternatively or additionally, first indicator 4102 can include a first portion (e.g., portion 4102a) that is representative of the value of the represented attribute of the first type of activity performed by the user and a second portion (e.g., portion 4102b) that is representative of a difference between the value of the represented attribute of the first type of activity and the first goal value. As shown, the first portion 4102a can be given a color or shading that differs from that of the second portion 4102b. Further, a ratio between a size of the first portion 4102a and a size of the second portion 4102b can be equal to a ratio between the total amount of the first type of activity performed by the user and the difference between the total amount of the first type of activity performed by the user and the first goal value.

In some examples, first indicator 4102 can include a visual indicator representative of the type of activity that it represents (e.g., the right-facing arrow at the top of the ring). Additionally, in some examples, the leading edge of the completed portion 4102a of the ring can be displayed having a different appearance or texture than the trailing parts of the completed portion 4102a of the ring. For example, the leading edge of the completed portion 4102a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by first indicator 4102 exceeds the goal value, the leading edge of the completed portion 4102a of the ring can continue to traverse the ring and overlap a previously completed portion of the ring. By displaying the leading edge using a different shade or texture, the user can distinguish the leading edge from a previously completed portion of the ring.

Activity indicator 4101 can further include a second visual representation of an attribute of a second type of user activity in the form of second indicator 4104. In some examples, second indicator 4104 can be controlled and displayed in a manner similar or identical to that of indicator 1704 of interface 1700 to represent an attribute of the second type of activity. For example, as discussed above with respect to FIGS. 15-21, a physical activity can be categorized into any number of types based on a predetermined set of criteria for each type. The criteria can include any attribute of the physical activity or information detectable by the activity sensors, such as a speed greater than or equal to a threshold, a minimum number of steps taken per unit time, a minimum amount of Calories burned per unit time, etc. For example, the second set of criteria for the second type of physical activity can require that the physical activity have an intensity greater than or equal to (or, alternatively, less than) a threshold intensity, such as an intensity corresponding to a brisk walk or moving at a speed equal to or greater than 3 miles per hour. Additionally, similar to indicators 1702 and 1704 of interface 1700, second indicator 4104 can represent a second value of any attribute of the physical activity, such as an amount, an intensity level, a duration, a progress relative to a set value, a trend over a time period, or the like, of the activity. For example, the second value can represent an aggregate duration of time that the user performed the second type of activity over a predetermined period of time (e.g., a day).

In some examples, second indicator 4104 can further represent a second goal value for the represented attribute of the second type of physical activity. In these examples, the size of second indicator 4104 can be scaled such that its size represents the second goal amount, and a portion of second indicator 4104 can be marked such that the marked portion represents the actual value of the represented attribute of the second type of activity performed by the user. Alternatively or additionally, second indicator 4104 can include a first portion (e.g., portion 4104a) that is representative of the value of the represented attribute of the second type of activity performed by the user and a second portion (e.g., portion 4104b) that is representative of a difference between the value of the represented attribute of the second type of activity and the second goal value. As shown, the first portion 4104a can be given a color or shading that differs from that of the second portion 4104b. Further, a ratio between a size of the first portion 4104a and a size of the second portion 4104b can be equal to a ratio between the total amount of the second type of activity performed by the user and the difference between the total amount of the second type of activity performed by the user and the second goal value.

In some examples, second indicator 4104 can include a visual indicator representative of the type of activity that it represents (e.g., the double right-facing arrow at the top of the ring). Additionally, in some examples, the leading edge of the completed portion 4104a of the ring can be displayed having a different appearance or texture than the trailing parts of the completed portion 4104a of the ring. For example, the leading edge of the completed portion 4104a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by first indicator 4104 exceeds the goal value, the leading edge of the completed portion 4104a of the ring can continue to traverse the ring and overlap a previously completed portion of the ring. By displaying the leading edge using a different shade or texture, the user can distinguish the leading edge from a previously completed portion of the ring.

Activity indicator 4101 can further include a third visual representation of an attribute of a user's inactivity in the form of third indicator 4106. In some examples, third indicator 4106 can be controlled and displayed in a manner similar or identical to that of indicator 2306 of interface 2300 to represent an attribute of the second type of activity. For example, as discussed above, the user can be categorized as being inactive when the device detects that the user is not engaged in a physical activity that meets a predetermined criteria. For example, inactivity can be characterized by the absence of the user engaging in a physical activity that meets a threshold intensity (e.g., movement that expends a threshold number of Calories per unit time, movement that exceeds a threshold distance per unit time, or the like), the absence of the user engaging in a specified type of activity (e.g., standing, walking, running, swimming, climbing stairs, or the like), or a combination thereof. Additionally, similar to indicator 2306 of interface 2300, third indicator 4106 can represent a third value of any attribute of the user's inactivity, such as an amount, a duration, a progress relative to a set value, a trend over a time period, or the like. For example, the third value can represent the length of time that the user has been inactive.

In some examples, third indicator 4106 can further represent an inactivity threshold duration value for the represented attribute of the user's inactivity. The inactivity threshold can have any predetermined or user-selectable value, such as 10 minutes, 20 minutes, 30 minutes, 1 hour, or the like. In these examples, the size of third indicator 4106 can be scaled such that its size represents the inactivity threshold value, and a portion of third indicator 4106 can be marked such that the marked portion represents the actual value of the represented attribute of the user's inactivity. Alternatively or additionally, third indicator 4106 can include a first portion (e.g., portion 4106a) that is representative of the value of the represented attribute of the user's inactivity and a second portion (e.g., portion 4106b) that is representative of a difference between the value of the represented attribute of the user's inactivity and the inactivity threshold value. As shown, the first portion 4106a can be given a color or shading that differs from that of the second portion 4106b. Further, a ratio between a size of the first portion 4106a and a size of the second portion 4106b can be equal to a ratio between the total amount of the user's inactivity and the difference between the total amount of the user's inactivity and the inactivity threshold value.

In other examples, third indicator 4106 can instead represent the number of times that the user remained inactive for a continuous segment of time equal to the inactivity threshold duration (e.g., the value of the inactivity counter controlled at block 2410 of process 2400). In these examples, the size of third indicator 4106 can be scaled such that its size represents the number of time segments equal to the inactivity threshold duration that have passed during a certain period of time, and a portion of third indicator 4106 can be marked such that the marked portion represents the number of times that the user remained inactive for a continuous segment of time equal to the inactivity threshold duration during the same period of time. For example, if the inactivity threshold duration is equal to one hour and the period of time that is being monitored is one day, third indicator 4106 can include a second portion (e.g., portion 4106b) that is representative of a number of times that the user remained inactive for one continuous hour in the day and a first portion (e.g., portion 4106a) that is representative of the difference between the number of times that the user remained inactive for one continuous hour in the day and the number of hours that have occurred in the day. Thus, if four hours have elapsed in the day (e.g., it is 4:00 am) and the user has been inactive for one continuous hour only once, second portion 4106b can occupy one-fourth of third indicator 4106, and first portion 4106a can occupy three-fourths of third indicator 4106 to signify that the user avoided being inactive for a continuous hour for three-fourths of the hours in the day. In this way, a third indicator 4106 that is fully occupied by first portion 4106a can indicate that the user was never inactive for a continuous hour during the day. The completed percentage of third indicator 4106 (e.g., percentage of third indicator 4106 occupied by first portion 4106a) can decrease or increase as the user becomes inactive for segments of time equal to the inactivity threshold or avoids being inactive for segments of time equal to the inactivity threshold. As shown, the first portion 4106a can be given a color or shading that differs from that of the second portion 4106b. Further, a ratio between a size of the second portion 4106b and a size of the second portion 4106a can be equal to a ratio between the number of time segments equal to the inactivity threshold that have passed during a certain period of time and the difference between the number of time segments equal to the inactivity threshold that have passed during a certain period of time and the number of times that the user remained inactive for a continuous segment of time equal to the inactivity threshold during the same period of time.

In yet other examples, third indicator 4106 can instead represent a number of segments of time during which the user performed a threshold amount of a predetermined type of activity. In these examples, the size of third indicator 4106 can be scaled such that its size represents a predetermined (or goal) number of time segments that are each equal to a predetermined duration of time. In these examples, a portion of third indicator 4106 can be marked such that the marked portion represents the number of segments of time during which the user performed the threshold amount of the predetermined type of activity. For example, the predetermined number of time segments can be equal to 12 and the predetermined duration of each of these segments can be 1 hour. Additionally, the threshold amount of the predetermined type of activity can be 60 seconds (within a continuous 90 second segment of time) of standing. Thus, for each hour-long segment of time (e.g., 12-1 a.m., 1-2 a.m., 2-3 a.m., etc.) that the user stands for at least 60 seconds within a continuous 90 second segment of time, the size of first portion 4106a can be increased in size to occupy an additional 1/12 of third indicator 4106. Second portion 4106b can be representative of a number of segments of time equal to a difference between the predetermined number of time segments (12) and the number of time segments during which the user performed the threshold amount of the predetermined type of activity. Thus, if the user stood for at least 60 seconds within a 90 second segment of time during 4 hours during the day, first portion 4106a can occupy one-third of third indicator 4106 (4 segments out of 12 segments), and second portion 4106b can occupy two-thirds of third indicator 4106 (8 segments out of 12 segments). In this way, as the user stands for at least 60 seconds within a 90 second segment of time in an hour, first portion 4106a of a third indicator 4106 can grow in size and traverse third indicator 4106 in a clockwise direction. A third segment 4106 that is fully occupied by first portion 4106*a* can indicate that the user reached their goal of standing at least 60 seconds within a 90 second segment of time during the predetermined number of segments of time (12). As shown, the first portion 4106*a* can be given a color or shading that differs from that of the second portion 4106*b*.

In some examples, third indicator 4106 can include a visual indicator representative of the type of activity that it represents (e.g., the upward-facing arrow at the top of the ring). Additionally, in some examples, the leading edge of the completed portion 4106*a* of the ring can be displayed having a different appearance or texture than the trailing parts of the completed portion 4106*a* of the ring. For example, the leading edge of the completed portion 4106*a* of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by indicator 4106 exceeds the goal value, the leading edge of the completed portion 4106*a* of the ring can continue to traverse the ring and overlap a previously completed portion of the ring. By displaying the leading edge using a different shade or texture, the user can distinguish the leading edge from a previously completed portion of the ring.

Interface 4100 can further include a reference indicator representing supplemental information relevant to the user's activity on any of the first, second, or third indicators 4102, 4104, or 4106. In the illustrated example, the additional reference indicators are shown as reference indicator 4108 along the rings of first indicator 4102. Examples of supplemental information that can be additionally provided on the display include, non-exclusively, timed-based goals that are adjusted in accordance with a passage of time (e.g., certain percentage(s) of the goal to be completed by certain time(s) of a day, such as 10% to be completed by 10:00 am, 80% to be completed by 9:00 pm, etc. such that the indicator would be moving along the ring throughout the day to indicate the changing percentage of the goal to be completed depending on the time of a day), history of user's past activity (e.g., activity performed by a user of device 100 on a particular day of the week, a highest/lowest or daily average amount of activity of a certain category performed by the user of the device over a month, a week, two days, last day, etc.), activity data of other users different from the user of the device (e.g., a highest/lowest, or daily average amount of activity of certain category performed by other users different from the user of the device), or the like.

While not shown, interface 4100 can further include text representations of the values of the attributes represented by indicators 4102, 4104, and 4106. Additionally, in some examples, each indicator can be displayed in a different color. In these examples, the first portion of each indicator can be displayed in a different shade of color than the second portion of the same indicator. For example, the first portion 4102*a* can be displayed as bright green, while the second portion 4102*b* can be displayed as a dark or grayed-out green.

Referring back to FIG. 40, at block 4004, one or more processors of the device can receive activity data that is representative of sensed physical activity of a user from an activity sensor. Block 4004 can be similar or identical to blocks 1504 and 2204. At block 4008 the one or more processors can process the received activity data to determine whether the activity data indicates that a physical activity, as opposed to a gesture, has been performed by the user of the device in a manner similar or identical to that of block 1506, described above. At block 4010, the one or more processors can determine a type of the detected physical activity in a manner similar or identical to that of block 1508 of process 1500 and to that of process 1600, described above. At block 4012, the one or more processors can update the monitored attributes of the detected physical activity in a manner similar or identical to that of block 1510 of process 1500 and to that of process 1600, described above. At block 4014, the one or more processors can control an activity timer that measures a length of time that the user is inactive based on the activity data received at block 4004 in a manner similar or identical to that of block 2206 of process 2200 and to that of process 2400, described above.

The blocks of process 4000 can be repeated any number of times at and at any desired interval of time to detect a user's activity/inactivity and to update the display of the combined activity/inactivity tracking interface accordingly. Additionally, it should be appreciated that while the blocks of process 4000 are shown in a particular order, the blocks can be performed in any order or at the same time. For example, the combined activity/inactivity tracking interface can be repeatedly updated at block 4002 at any desired interval of time while activity data is being received at block 4004 and processed to control the at block 4004 and processed at blocks 4008, 4010, and 4010 to update the attributes of the various types of physical activity being monitored to provide the user with current or real-time activity and inactivity information. In other examples where the physical activity application is running in the background of the device or while the display of the device is deactivated, block 4002 can be omitted and the remaining blocks of process 4000 can repeatedly be performed to monitor the user's physical activity and update the monitored attributes such that an accurate display of the attributes can later be provided to the user when the physical activity application is reopened or the display of the device is activated.

Note that details of the processes described above with respect to processes 4000 (e.g., FIG. 40) are also applicable in an analogous manner to the other processes described herein. For example, processes 1500, 1600, 2200, 2400, 4800, 7900, 8600, and 9200 may include one or more of the characteristics of the various methods described above with reference to processes 4000. For example, the activity data, activity types, displayed values and other elements described above with reference to processes 4000 optionally have one or more of the characteristics of the activity data, activity types, displayed values and other elements described herein (e.g., processes 1500, 1600, 2200, 2400, 4800, 7900, 8600, and 9200). For brevity, these details are not repeated.

Other interfaces can be displayed to provide additional information associated with the attributes represented by the indicators of interface 4100. These other interfaces can be displayed in response to a tap, swipe, or other gesture performed while interface 4100 is displayed on the device. For example, interface 4200, shown in FIG. 42, can be displayed in response to a swipe gesture performed from right to left of the display while interface 4100 is displayed. Interface 4200 can include first indicator 4102 of interface 4100 having first portion 4102*a* and second portion 41028. Unlike in interface 4100, first indicator 4102 can be displayed within interface 4200 without second and third indicators 4104 and 4106. Interface 4200 can further include a text representation 4202 of the current value of the attribute represented by first portion 4102a and a text representation 4204 of the goal value attribute represented by first indicator 4102. For example, text representation 4202 indicates that first portion 4102a represents 300 Calories and text representation 4204 indicates that the entire first indicator 4102 represents a goal value of 600 Calories. Thus, interface 4200 indicates that the user has expended 300 Calories and has a goal of 600 Calories. Interface 4100 can be displayed again in response to a swipe gesture performed from left to right of the display while interface 4200 is being displayed.

Figure 43:
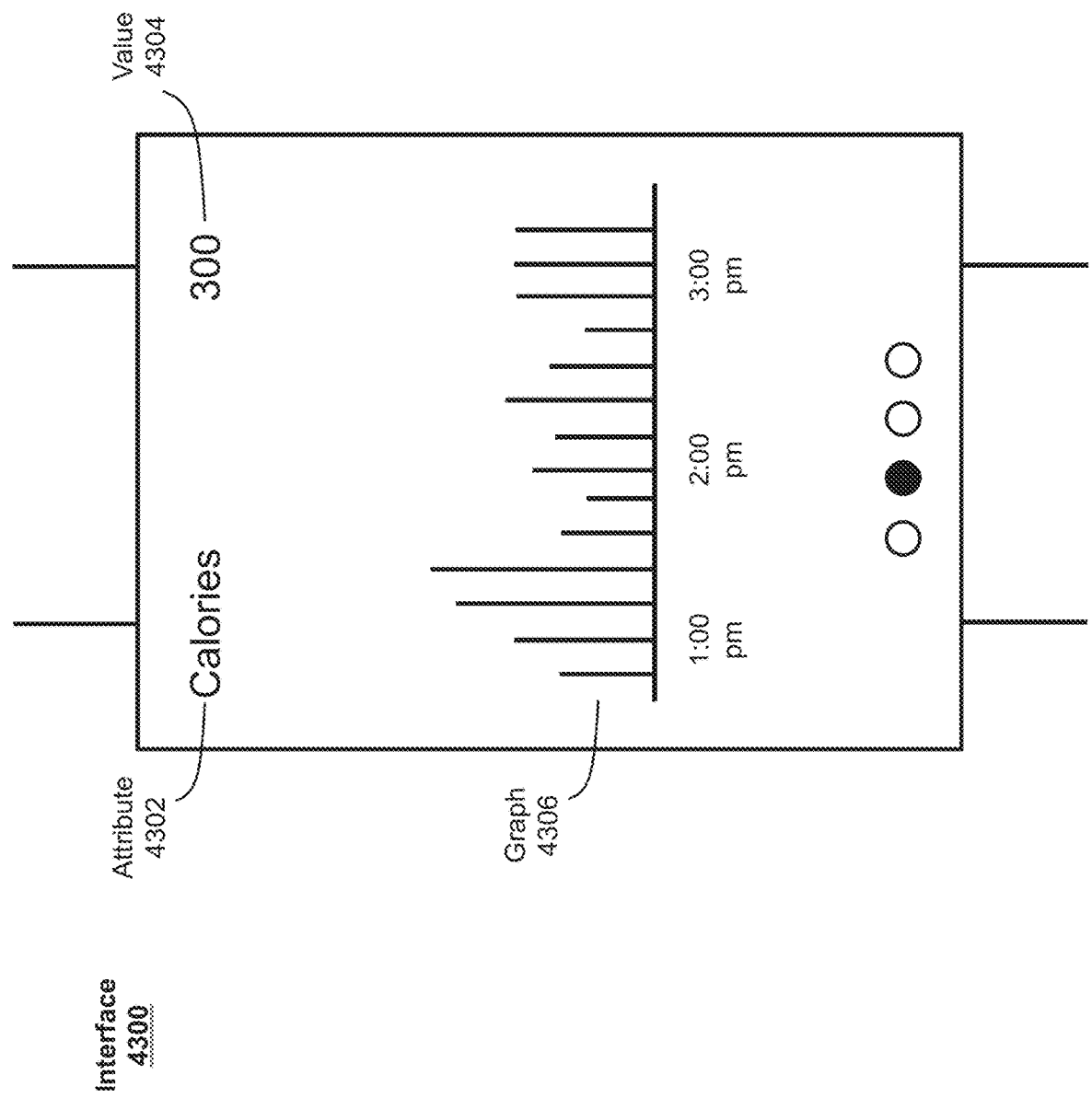

FIG. 43 illustrates another example interface 4300 that can be displayed in response to a swipe gesture performed from the bottom to the top of the display while interface 4200 is displayed. Interface 4300 can represent a more detailed view of the information displayed in interface 4200 and can include attribute label 4302 indicating the type of information being displayed within interface 4300, value 4304 indicating the value of the attribute (e.g., represented by first portion 4102a in FIGS. 41 and 42), and graph 4306 showing the value of the measured attribute over time. For example, attribute label 4302 indicates that the attribute being displayed is Calories expended, value 4304 indicates that 300 Calories have been expended, and graph 4306 shows the amount of Calories expended at various times throughout the day. Interface 4200 can be displayed again in response to a swipe gesture performed from the top to the bottom of the display while interface 4300 is being displayed.

Figure 44:
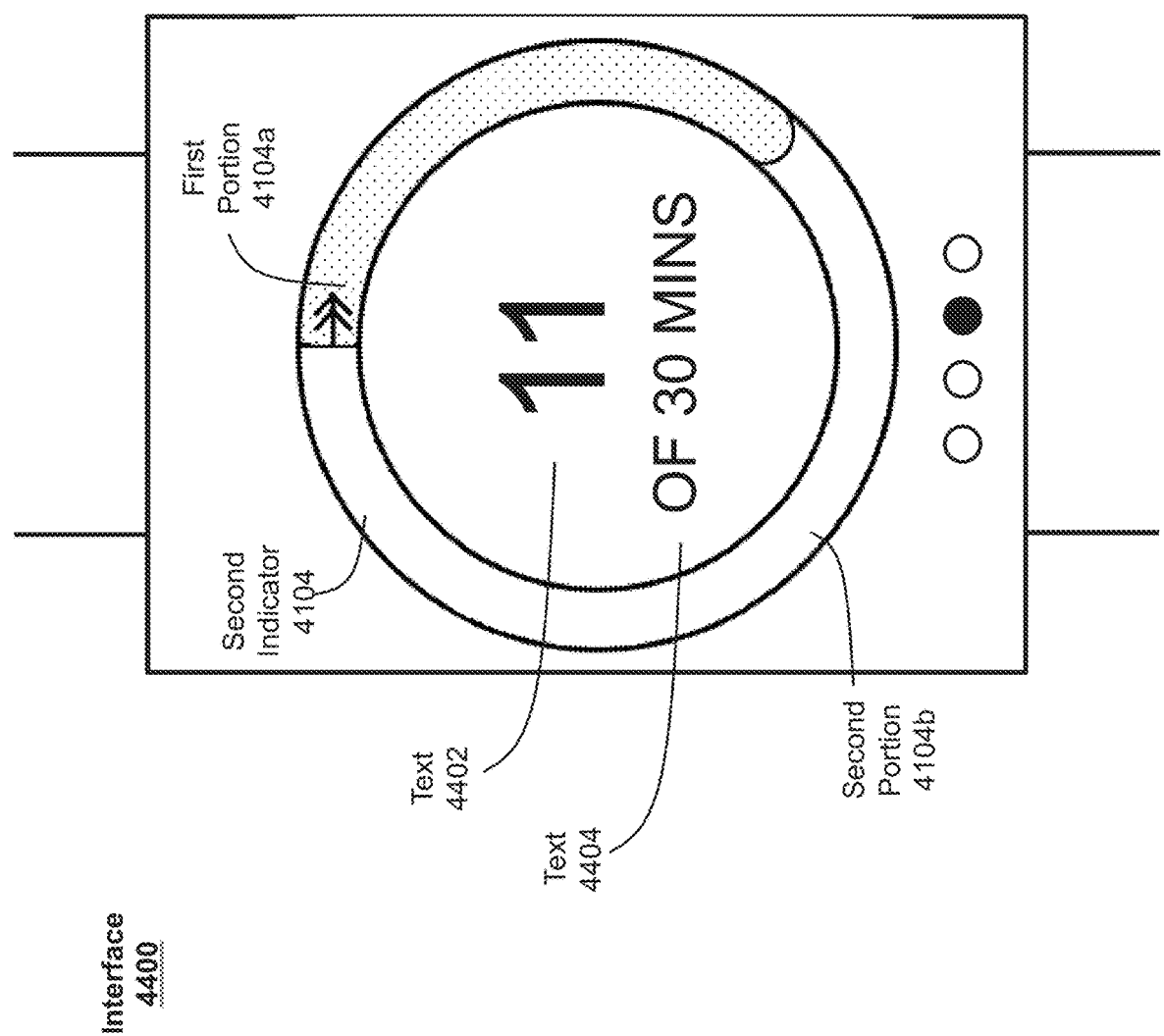

FIG. 44 illustrates another example interface 4400 that can be displayed in response to a swipe gesture performed from right to left of the display while interface 4200 is being displayed. Interface 4400 can include second indicator 4104 of interface 4100 having first portion 4104a and second portion 4104b. Unlike in interface 4100, second indicator 4104 can be displayed within interface 4400 without first and third indicators 4102 and 4106. Interface 4400 can further include a text representation 4402 of the value of the attribute represented by first portion 4104a and a text representation 4404 of the goal value represented by second indicator 4104. For example, text representation 4402 indicates that first portion 4104a represents 11 minutes and text representation 4404 indicates that the entire second indicator 4104 represents a goal value of 30 minutes. Thus, interface 4400 indicates that the user has performed 11 minutes of a second type of physical activity (represented by second indicator 4104) and has a goal of performing 30 minutes of this second type of physical activity. Interface 4200 can be displayed again in response to a swipe gesture performed from left to right of the display while interface 4300 is being displayed.

Figure 45:
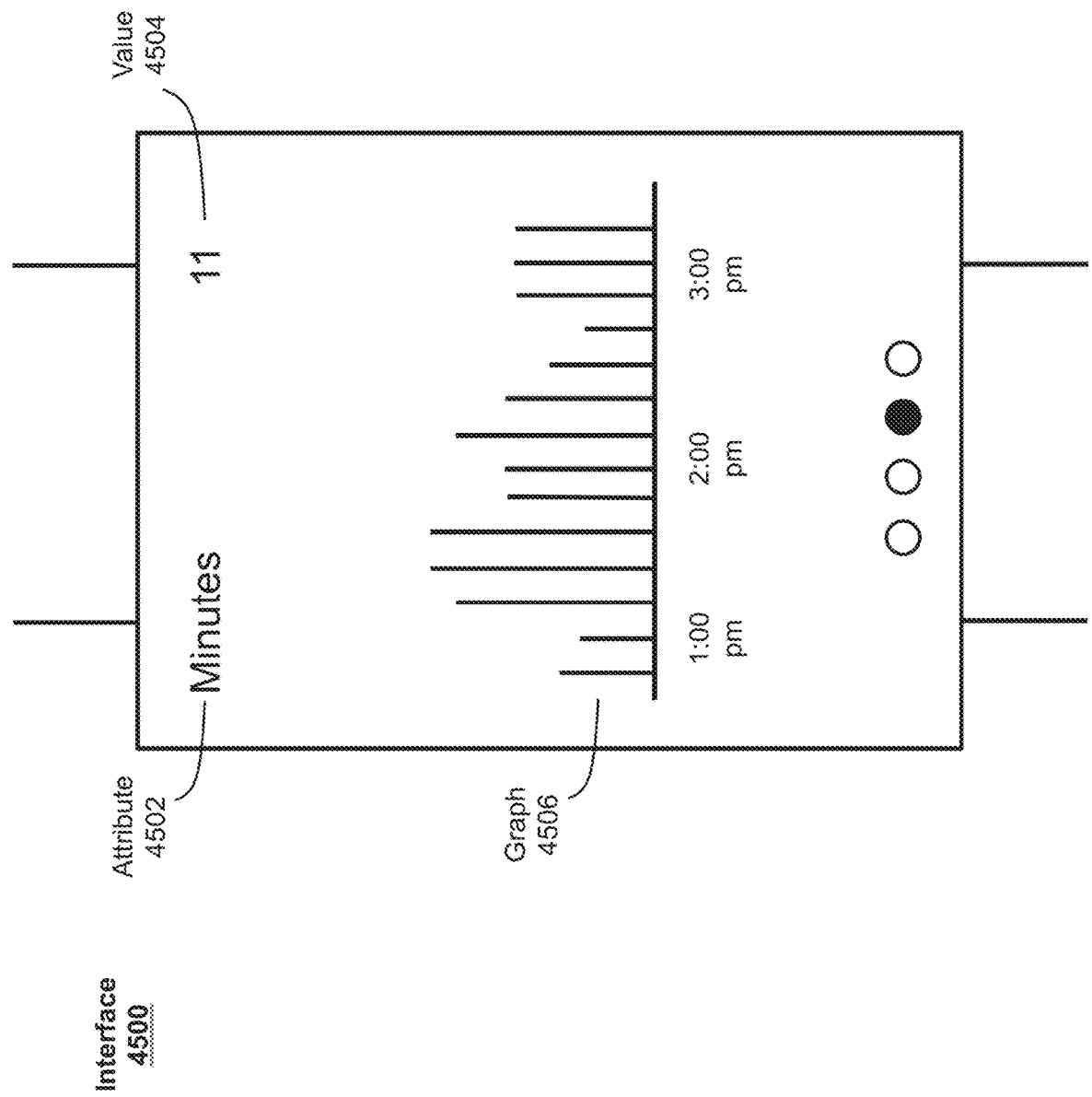

FIG. 45 illustrates another example interface 4500 that can be displayed in response to a swipe gesture performed from the bottom to the top of the display while interface 4400 is displayed. Interface 4500 can represent a more detailed view of the information displayed in interface 4400 and can include attribute label 4502 indicating the type of information being displayed within interface 4500, value 4504 indicating the value of the attribute (e.g., represented by first portion 4104a in FIGS. 41 and 42), and graph 4506 showing the value of the measured attribute over time. For example, attribute label 4502 indicates that the attribute being displayed is minutes performing the second type of activity, value 4504 indicates that the user has performed 11 minutes of the second type of activity, and graph 4506 shows the amount of time performing the second type of activity at various times throughout the day. Interface 4400 can be displayed again in response to a swipe gesture performed from the top to the bottom of the display while interface 4500 is being displayed.

Figure 46:
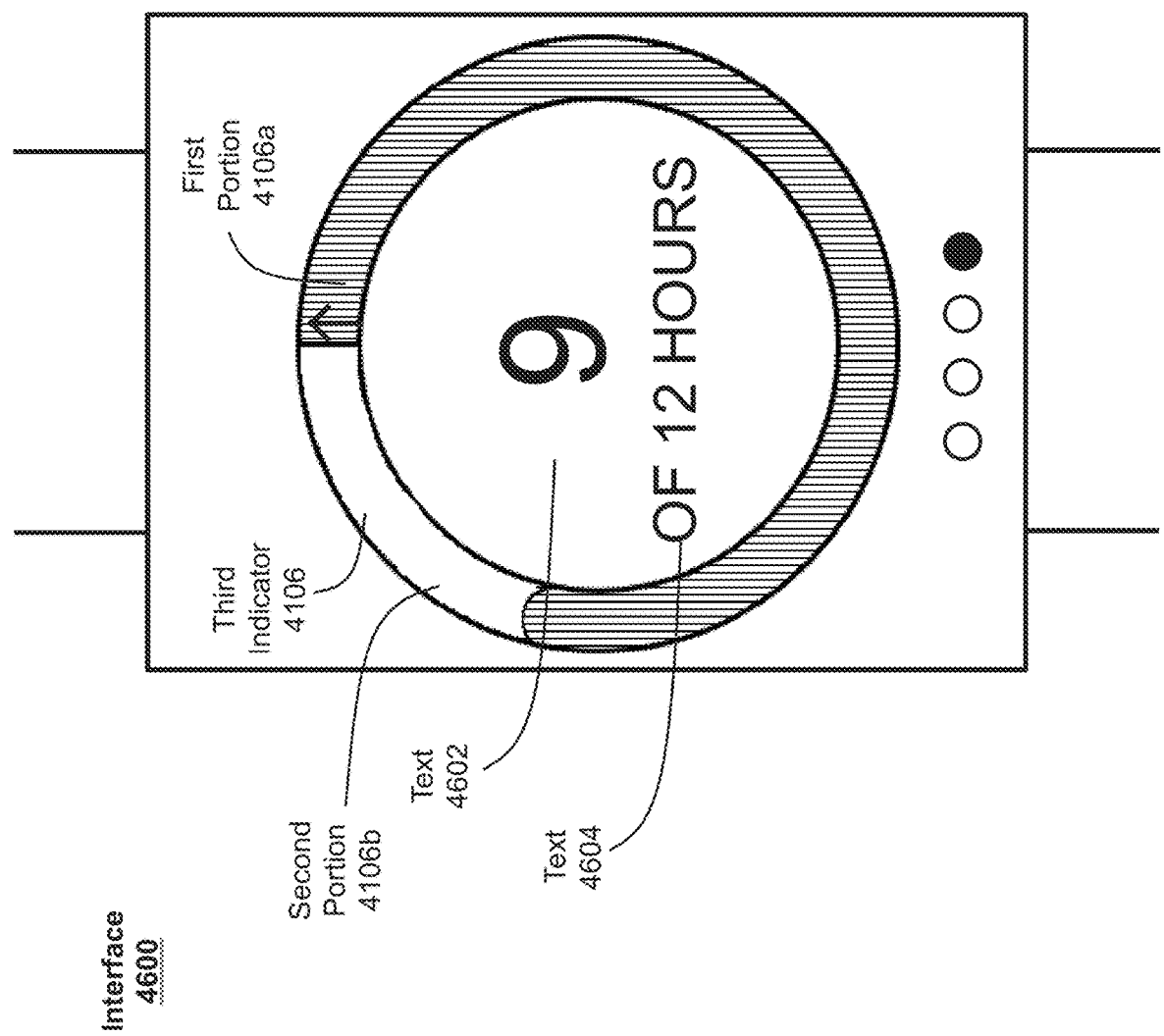

FIG. 46 illustrates another example interface 4600 that can be displayed in response to a swipe gesture performed from right to left of the display while interface 4400 is being displayed. Interface 4600 can include third indicator 4106 of interface 4100 having first portion 4106a and second portion 4106b. Unlike in interface 4100, third indicator 4106 can be displayed within interface 4600 without first and second indicators 4102 and 4104. Interface 4600 can further include a text representation 4602 of the value represented by first portion 4106a and a text representation 4604 of the value represented by third indicator 4106. For example, text representation 4602 indicates that first portion 4106a represents 9 hour-long segments of time and text representation 4604 indicates that the entire third indicator 4106 represents 12 hour-long segments of time. Thus, interface 4600 indicates that the user has performed a threshold amount of a predetermined type of activity during 9 hour-long segments of time and has a goal of performing the threshold amount of the predetermined type of activity during 12 hour-long segments. Interface 4400 can be displayed again in response to a swipe gesture performed from left to right of the display while interface 4600 is being displayed.

Figure 47:
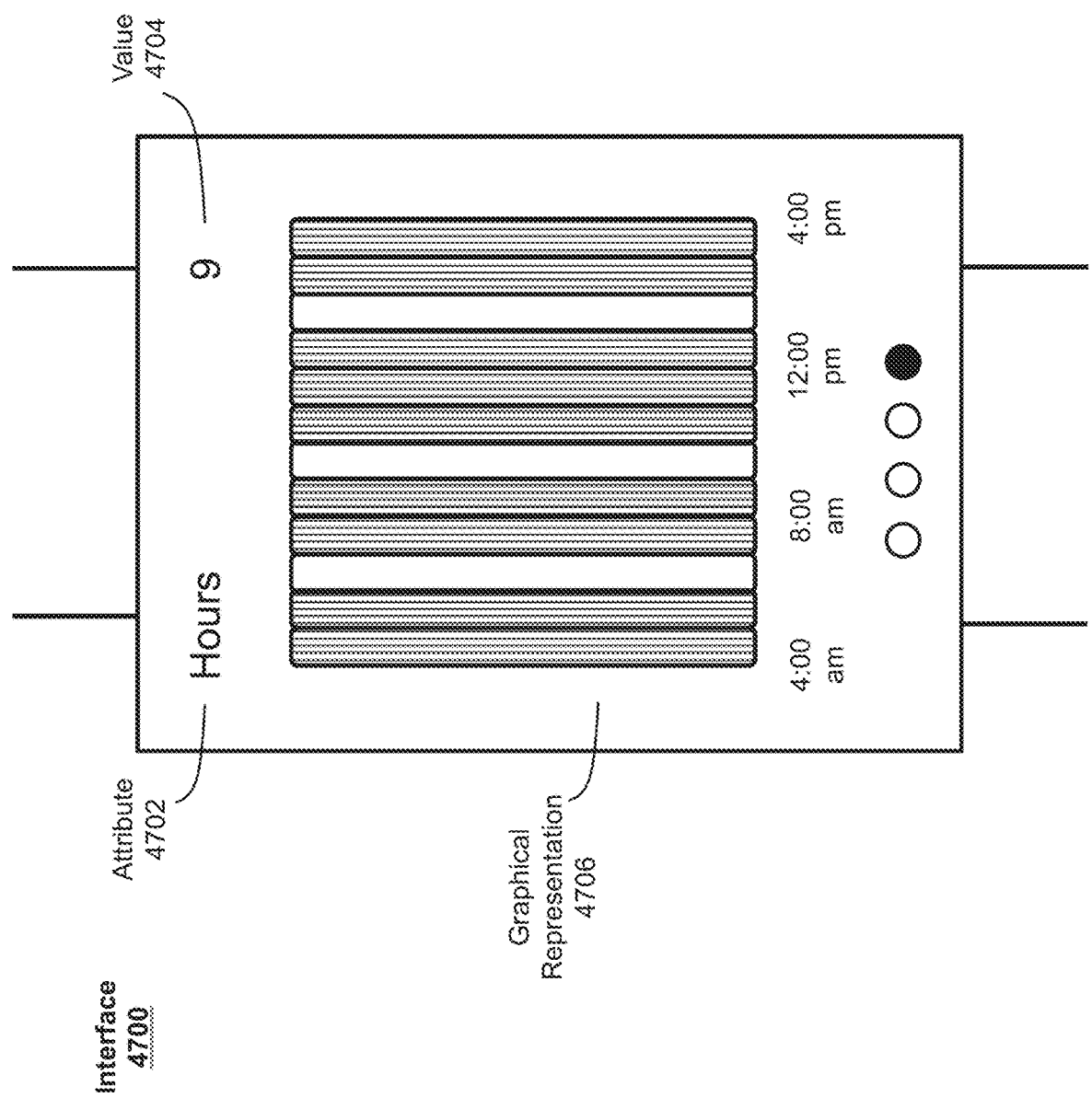

FIG. 47 illustrates another example interface 4700 that can be displayed in response to a swipe gesture performed from the bottom to the top of the display while interface 4600 is displayed. Interface 4700 can represent a more detailed view of the information displayed in interface 4600 and can include attribute label 4702 indicating the type of information being displayed within interface 4700, value 4704 indicating the value of the attribute (e.g., represented by first portion 4106a in FIGS. 41 and 42), and graphical representation 4706 showing the hours during the day counting toward the value represented by first portion 4106a in FIGS. 41 and 42. For example, attribute label 4702 indicates that the attribute being displayed is hour-long segments of time during which the user performed the threshold amount of the predetermined type of activity, value 4704 indicates that the user performed the threshold amount of the predetermined type of activity during 9 hour-long segments of time, and graphical representation 4706 shows the hours during the day during which the user performed the threshold amount of the predetermined type of physical activity (represented by shaded bars). Interface 4600 can be displayed again in response to a swipe gesture performed from the top to the bottom of the display while interface 4700 is being displayed.

While the examples provided above recite specific lengths of time, amounts of activity, and the like, it should be appreciated that those values are provided only as examples and that any other values can be used.

Workout Monitor

Figure 48:
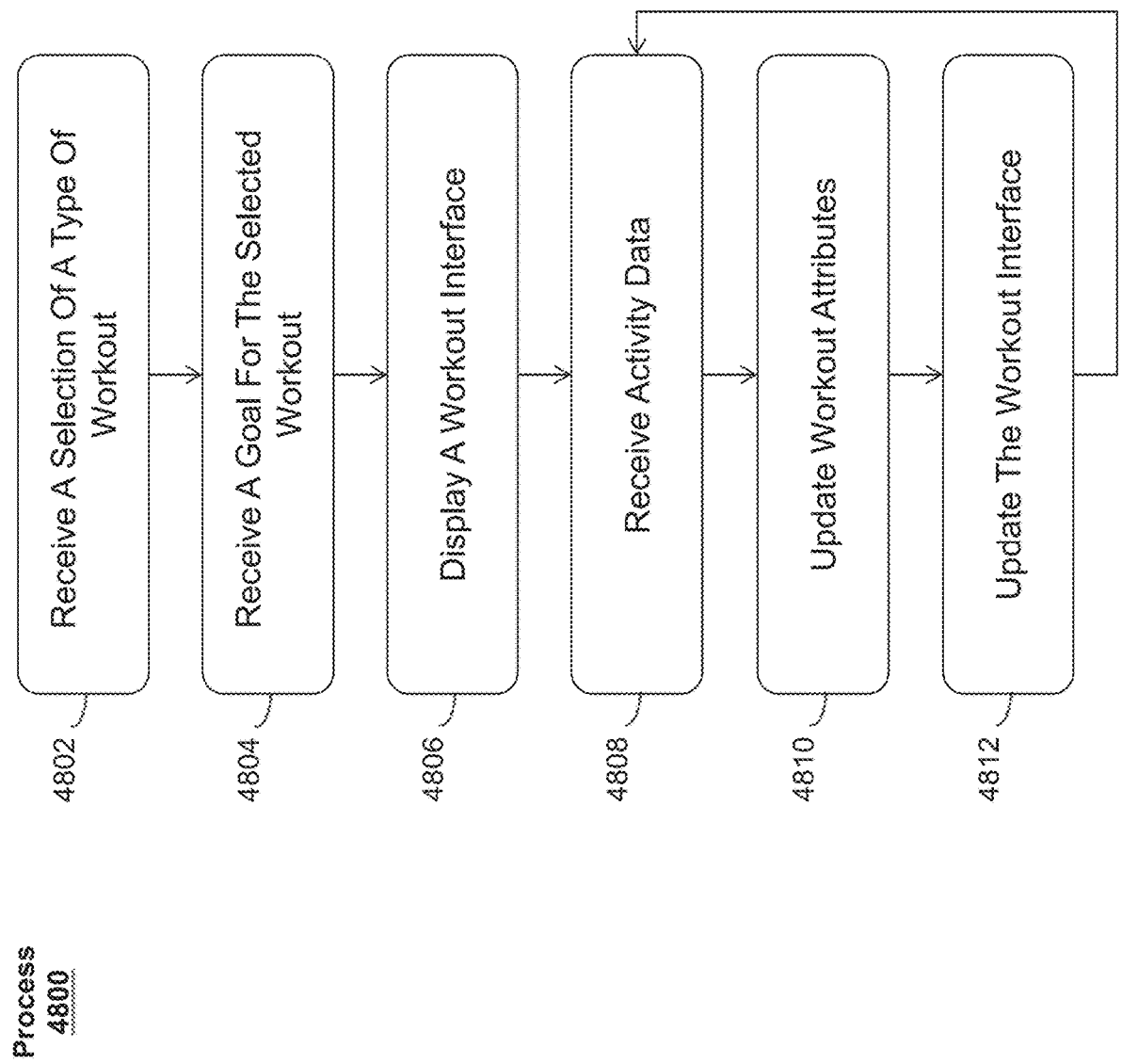
FIG. 48 illustrates a process for generating a workout interface for monitoring a user's workout according to various examples.

Referring back to FIG. 8, in some examples, in response to a user selection of an application icon 802 corresponding to a workout application for monitoring a user's workout, the workout application can be opened and process 4800, shown in FIG. 48, can be performed. Process 4800 can be performed by device 100, 300, 500, or 610 to detect movement associated with the device during a workout, recognizing it as being associated with a physical activity performed by the user using the device, monitoring various attributes of the detected physical activity, determining attributes of the workout based on the monitored attributes of the detected physical activity, and displaying one or more of the attributes of the workout on a display of the device. Some operations in process 4800 may be combined, the order of some operations may be changed, and some operations may be omitted.

As described below, process 4800 provides intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 4802, the one or more processors of the device can receive a selection of a type of workout. The selected type of workout can include any type of workout, such as running, walking, cycling, swimming, yoga, dancing, climbing, cross-training, rowing, or the like. In some examples, the one or more processors of the device can cause, on the display of the device, a display of a list of available types of workouts that a user can select. In these examples, the selection of the type of workout can be received by the one or more processors of the device in response to a user indicating a selection of one of the displayed available types of workouts (e.g., via mouse click, touch on a touch sensitive display, or the like).

Figure 49:
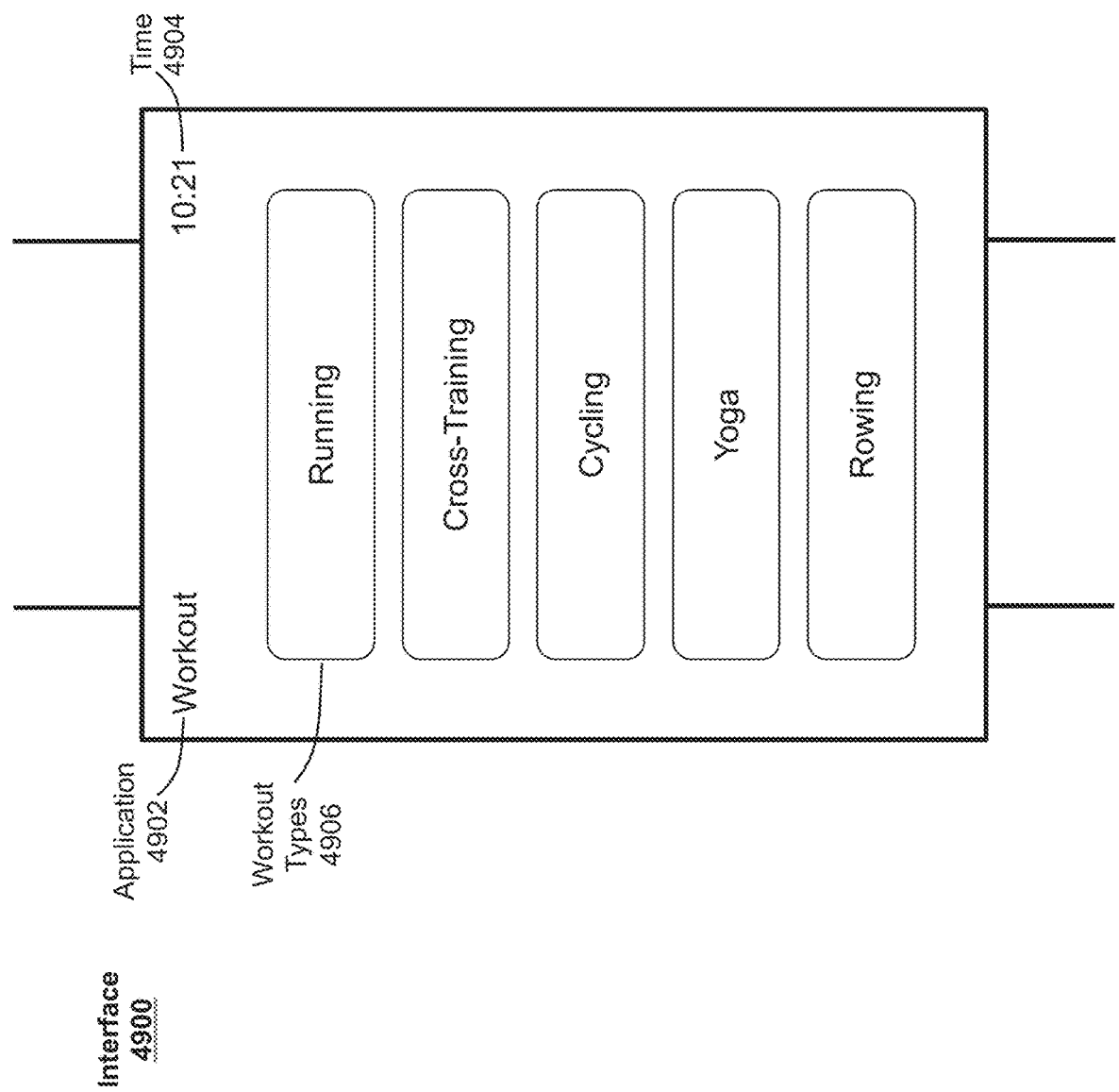
FIG. 49 illustrates an exemplary interface for selecting a type of workout according to various examples.

For example, FIG. 49 illustrates an example interface 4900 that can be displayed at block 4802 of process 4800. As shown, interface 4900 can include an application identifier 4902 indicating that the "Workout" application is being displayed, a time indicator 4904 indicating the current time, and a list of workout types 4906 that includes a list of selectable objects associated with available workouts that can be selected by a user. The types of workouts contained in the list of workout types 4906 can be ordered in any desired manner, such as alphabetically, by frequency of performance, by time since last performed, in a user-selected order, or combinations thereof. For example, the first selectable object can correspond to the workout that was most recently performed by the user ("Running"), and the remaining selectable objects can be ordered based on a frequency that the corresponding workouts have been performed. In some examples, the list of workout types 4906 can include more types of workouts than can be displayed at one time on the display of the device. In these examples, the device can display the other types of workouts in response to a user initiating a scroll operation (e.g., by making a swipe or touch and drag motion on the touch sensitive display). While FIG. 49 shows an example list of workout types 4906, it should be appreciated that the list of workout types 4906 can include any number and types of workouts.

Figure 50:
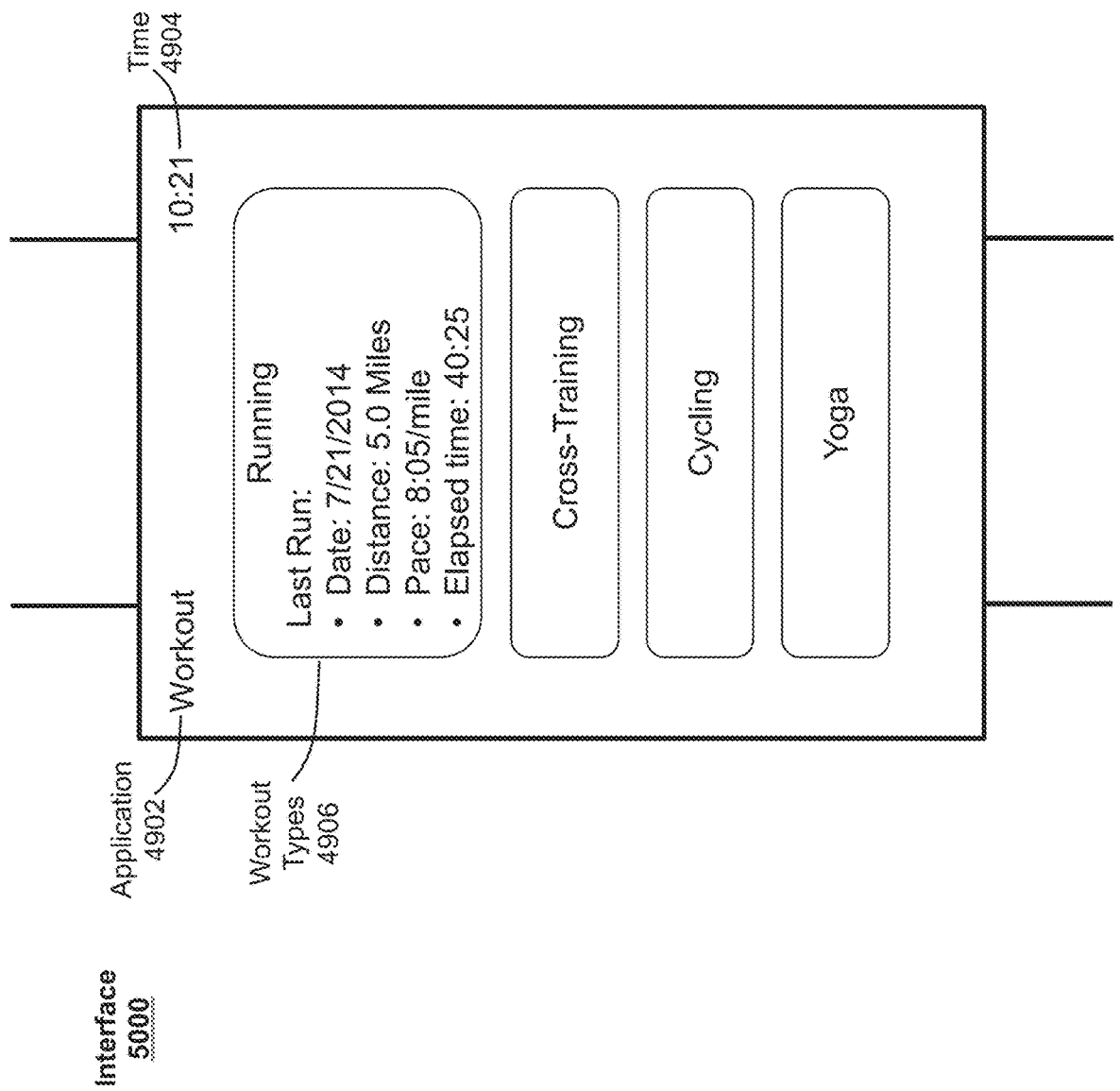
FIG. 50 illustrates another exemplary interface for selecting a type of workout according to various examples.

FIG. 50 illustrates another example interface 5000 that can be displayed at block 4802 of process 4800. Similar to interface 4900, interface 5000 can include an application identifier 4902, a time indicator 4904, and a list of workout types 4906. However, in interface 5000, one selectable object associated with a type of workout in the list of workout types 4906 can be larger than the selectable objects associated with other types of workouts and can include additional information about the workout type. This selectable object can correspond to the workout that was most recently performed by the user. For example, as shown in FIG. 50, the selectable object for the "Running" workout type can be twice as large as the other selectable objects and can include information associated with the most recent workout of that type. In particular, information about the date, distance, pace, and elapsed time of the most recent run is displayed on the selectable object for the "Running" type of workout. The selectable objects below the larger selectable object can be ordered based on a frequency that the corresponding workouts are performed. Alternatively, the objects may be ordered by recency, or a combination of recency and frequency. In some examples, an interface similar to interface 4900 can be displayed the first time that a user is using the workout application on the device, while an interface similar to interface 5000 can be displayed during any subsequent use of the application.

At block 4804, a goal for the type of workout selected at block 4802 can be received. The goal can include an identification of an attribute of the selected workout (e.g., a distance, a duration, a number of Calories burned, a pace, or the like) and a goal value for the attribute. For example, for a running type of workout, the goal received at block 4804 can include a distance attribute and a value of 10 kilometers. Another example goal can include a duration attribute and a value of 45 minutes, or a Calorie attribute and a value of 500 Calories. In some examples, the one or more processors of the device can cause, on the display of the device, a display of an interface that allows the user to select an attribute of the workout and to enter a desired value for that attribute.

Figure 51:
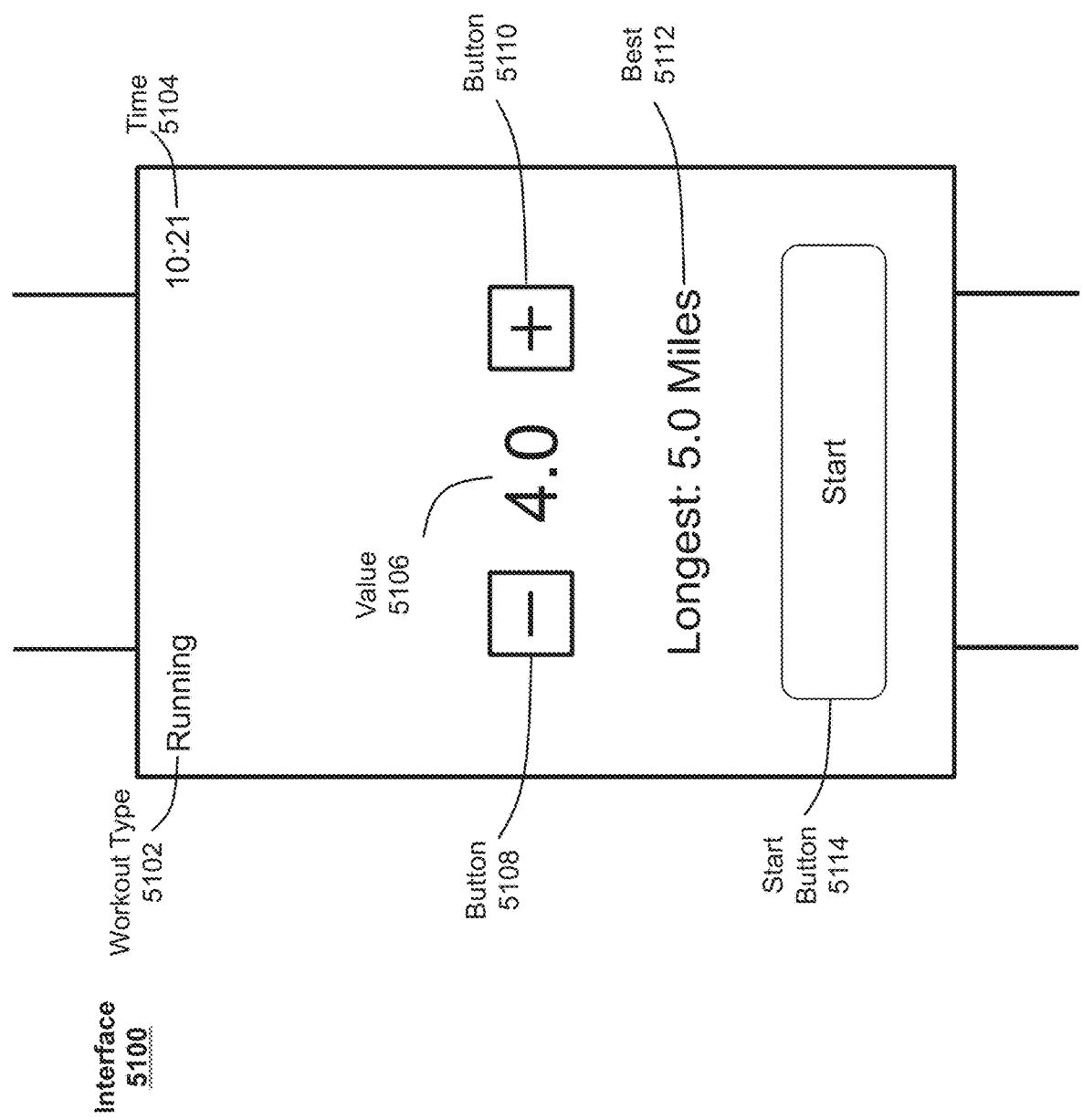
FIGS. 51-55 illustrate exemplary interfaces for selecting a workout goal according to various examples.

For example, FIG. 51 illustrates an example interface 5100 that can be displayed at block 4804 of process 4800 in response to receiving a selection of a "Twining" type of workout at block 4802 (e.g., by a user selecting the "Running" option in either interface 4900 or 5000). As shown, interface 5100 can include a workout type identifier 5102 indicating that the "Running" type of workout was selected, a time indicator 5104 indicating the current time, a value 5106 for the attribute of the workout, buttons 5108 and 5110 for adjusting the value 5106, a best value 5112 of the attribute of the workout, and a start button 5114 for selecting the goal and beginning the workout. In this example, the distance attribute of the workout is being selected and the value for that attribute can be selected by adjusting value 5106 up or down using buttons 5110 or 5108, respectively. In other examples, the value for that attribute can be selected by moving (e.g., rotating) a rotatable input mechanism of the device. The initial value 5106 displayed in interface 5100 can be a default value (e.g., 0), a value used in a previous workout, an average value from two or more previous workouts, or any other desired value. Once the desired value 5106 is displayed, a user can select the start button 5114 to set the workout goal to be a distance goal having the value of value 5106. In some examples, best value 5112 can be selectable and can cause the goal of the workout to be the attribute and value of the displayed best value 5112. For example, in response to a selection of best value 5112 made by a user tapping on the touch-sensitive display at a location corresponding to best value 5112, the goal of the workout can be set to a distance goal of 5.0 miles. In other examples, best value 5112 can represent a value determined based on past performance of the user, the user's contacts, the user's friends, a predefined group of users, or the like. For example, best value 5112 can instead represent the longest distance run by the user over a predetermined length of time (e.g., the last week), an average distance run by the user, an average distance run by the user over a predetermined length of time (e.g., the last week), a longest distance run by the user's contacts/friends/running group, a longest distance run by the user's contacts/friends/running group over a predetermined length of time (e.g., the last week), an average distance run by the user's contacts/friends/running group, an average distance run by the user's contacts/friends/running group over a predetermined length of time (e.g., the last week), or the like. In some examples, the device can allow a user to select a different attribute of the workout as the goal by displaying a different interface associated with a different attribute of the workout in response to a request from the user. In some examples, the request can be made by a vertical or horizontal swipe gesture across the touch sensitive display of the device, a button press, a movement of a rotatable input mechanism of the device, a user contact having a characteristic intensity above an intensity threshold on a display of the device, or any other desired form of input.

Figure 52:
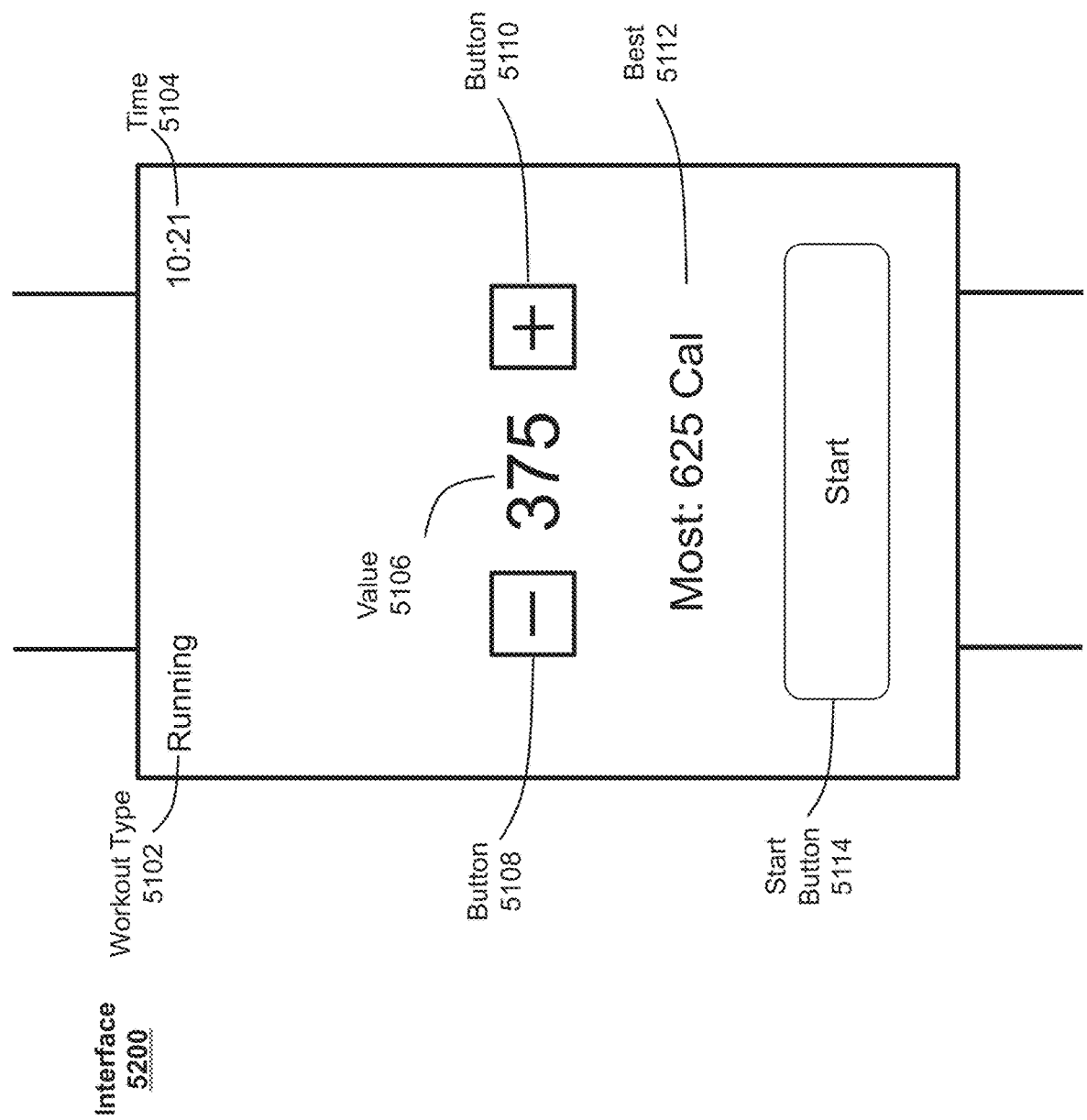

FIG. 52 illustrates another example interface 5200 that can be displayed at block 4804 of process 4800 in response to receiving a selection of a "running" type of workout at block 4802 (e.g., by a user selecting the "Running" option in either interface 4900 or 5000) or in response to a request to select a different workout attribute from interface 5100. Similar to interface 5100, interface 5200 can include a workout type identifier 5102 indicating that the "Running" type of workout was selected, a time indicator 5104 indicating the current time, a value 5106 for the attribute of the workout, buttons 5108 and 5110 for adjusting the value 5106, a best value 5112 of the attribute of the workout, and a start button 5114 for selecting the goal and beginning the workout. In this example, the Calories burned attribute of the workout is being selected and the value for that attribute can be selected by adjusting value 5106 up or down using buttons 5110 or 5108, respectively. In other examples, the value for that attribute can be selected by moving (e.g., rotating) a rotatable input mechanism of the device. The initial value 5106 displayed in interface 5200 can be a default value (e.g., 0), a value used in a previous workout, an average value from two or more previous workouts, or any other desired value. Once the desired value 5106 is displayed, a user can select the start button 5114 to set the workout goal to be a Calorie goal having the value of value 5106. In some examples, best value 5112 can be selectable and can cause the goal of the workout to be the attribute and value of the displayed best value 5112. For example, in response to a selection of best value 5112 made by a user tapping on the touch-sensitive display at a location corresponding to best value 5112, the goal of the workout can be set to a Calorie goal of 625 Calories. In other examples, best value 5112 can represent a value determined based on past performance of the user, the user's contacts, the user's friends, a predefined group of users, or the like. For example, best value 5112 can instead represent the most Calories burned by the user over a predetermined length of time (e.g., the last week), an average number of Calories burned by the user, an average number of Calories burned by the user over a predetermined length of time (e.g., the last week), the most Calories burned by the user's contacts/friends/running group, a most Calories burned by the user's contacts/friends/running group over a predetermined length of time (e.g., the last week), an average number of Calories burned by the user's contacts/friends/running group, an average number of Calories burned by the user's contacts/friends/running group over a predetermined length of time (e.g., the last week), or the like. In some examples, the device can allow a user to select a different attribute of the workout as the goal by displaying a different interface associated with a different attribute of the workout in response to a request from the user. In some examples, the request can be made by a vertical or horizontal swipe gesture across the touch sensitive display of the device, a button press, a movement of a rotatable input mechanism of the device, a user contact having a characteristic intensity above an intensity threshold on a display of the device, or any other desired form of input.

Figure 53:
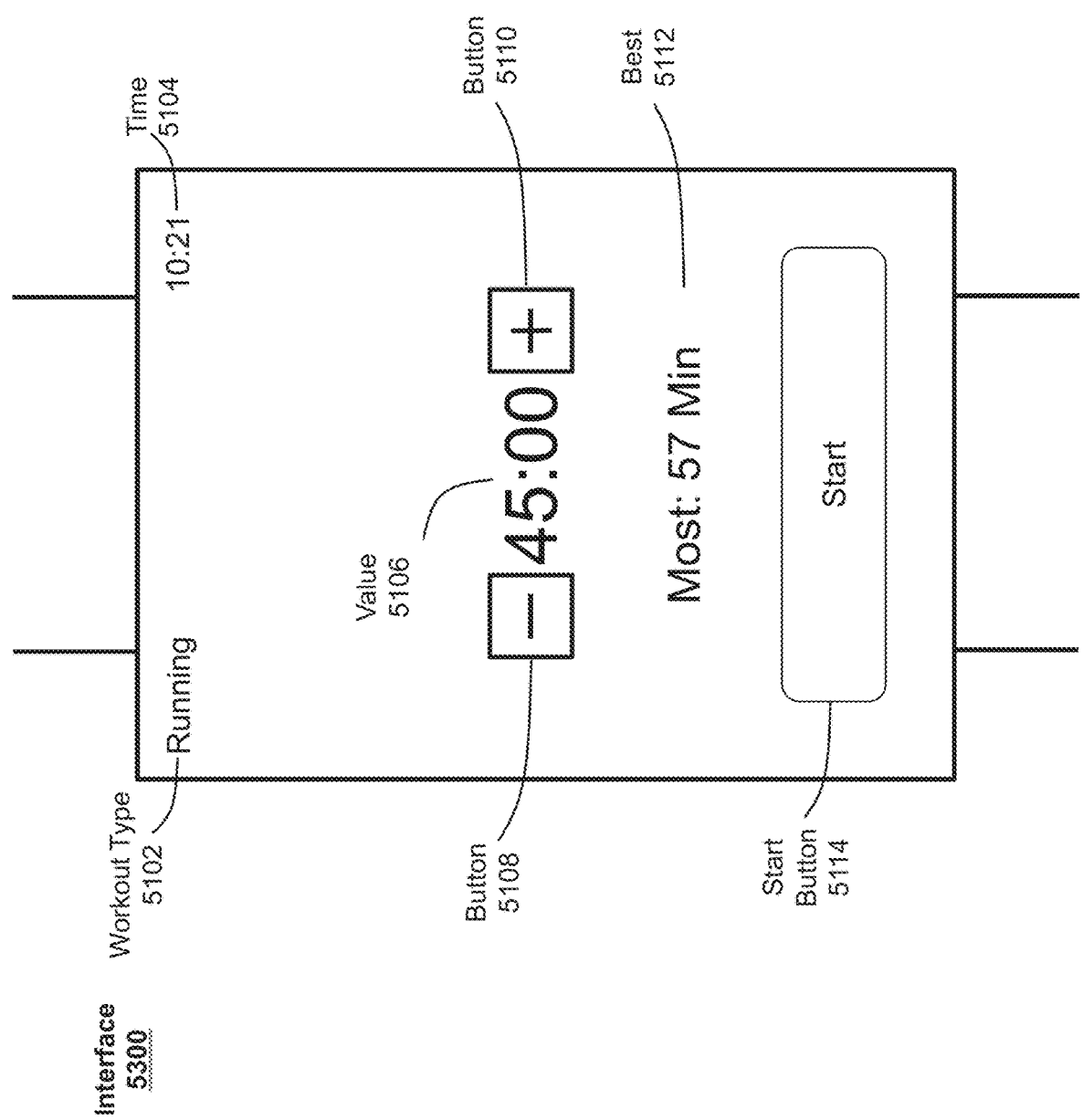

FIG. 53 illustrates another example interface 5300 that can be displayed at block 4804 of process 4800 in response to receiving a selection of a "running" type of workout at block 4802 (e.g., by a user selecting the "Running" option in either interface 4900 or 5000) or in response to a request to select a different workout attribute from interface 5100 or 5200. Similar to interfaces 5100 and 5200, interface 5300 can include a workout type identifier 5102 indicating that the "Running" type of workout was selected, a time indicator 5104 indicating the current time, a value 5106 for the attribute of the workout, buttons 5108 and 5110 for adjusting the value 5106, a best value 5112 of the attribute of the workout, and a start button 5114 for selecting the goal and beginning the workout. In this example, the duration attribute of the workout is being selected and the value for that attribute can be selected by adjusting value 5106 up or down using buttons 5110 or 5108, respectively. In other examples, the value for that attribute can be selected by moving (e.g., rotating) a rotatable input mechanism of the device. The initial value 5106 displayed in interface 5300 can be a default value (e.g., 0), a value used in a previous workout, an average value from two or more previous workouts, or any other desired value. Once the desired value 5106 is displayed, a user can select the start button 5114 to set the workout goal to be a duration goal having the value of value 5106. In some examples, best value 5112 can be selectable and can cause the goal of the workout to be the attribute and value of the displayed best value 5112. For example, in response to a selection of best value 5112 made by a user tapping on the touch-sensitive display at a location corresponding to best value 5112, the goal of the workout can be set to a duration goal of 57 minutes. In other examples, best value 5112 can represent a value determined based on past performance of the user, the user's contacts, the user's friends, a predefined group of users, or the like. For example, best value 5112 can instead represent the greatest length of time run by the user over a predetermined length of time (e.g., the last week), an average length of time run by the user, an average length of time run by the user over a predetermined length of time (e.g., the last week), a greatest length of time run by the user's contacts/friends/running group, a greatest length of time run by the user's contacts/friends/running group over a predetermined length of time (e.g., the last week), an average length of time run by the user's contacts/friends/running group, an average length of time run by the user's contacts/friends/running group over a predetermined length of time (e.g., the last week), or the like. In some examples, the device can allow a user to select a different attribute of the workout as the goal by displaying a different interface associated with a different attribute of the workout in response to a request from the user. In some examples, the request can be made by a vertical or horizontal swipe gesture across the touch sensitive display of the device, a button press, a movement of a rotatable input mechanism of the device, a user contact having a characteristic intensity above an intensity threshold on a display of the device, or any other desired form of input.

Figure 54:
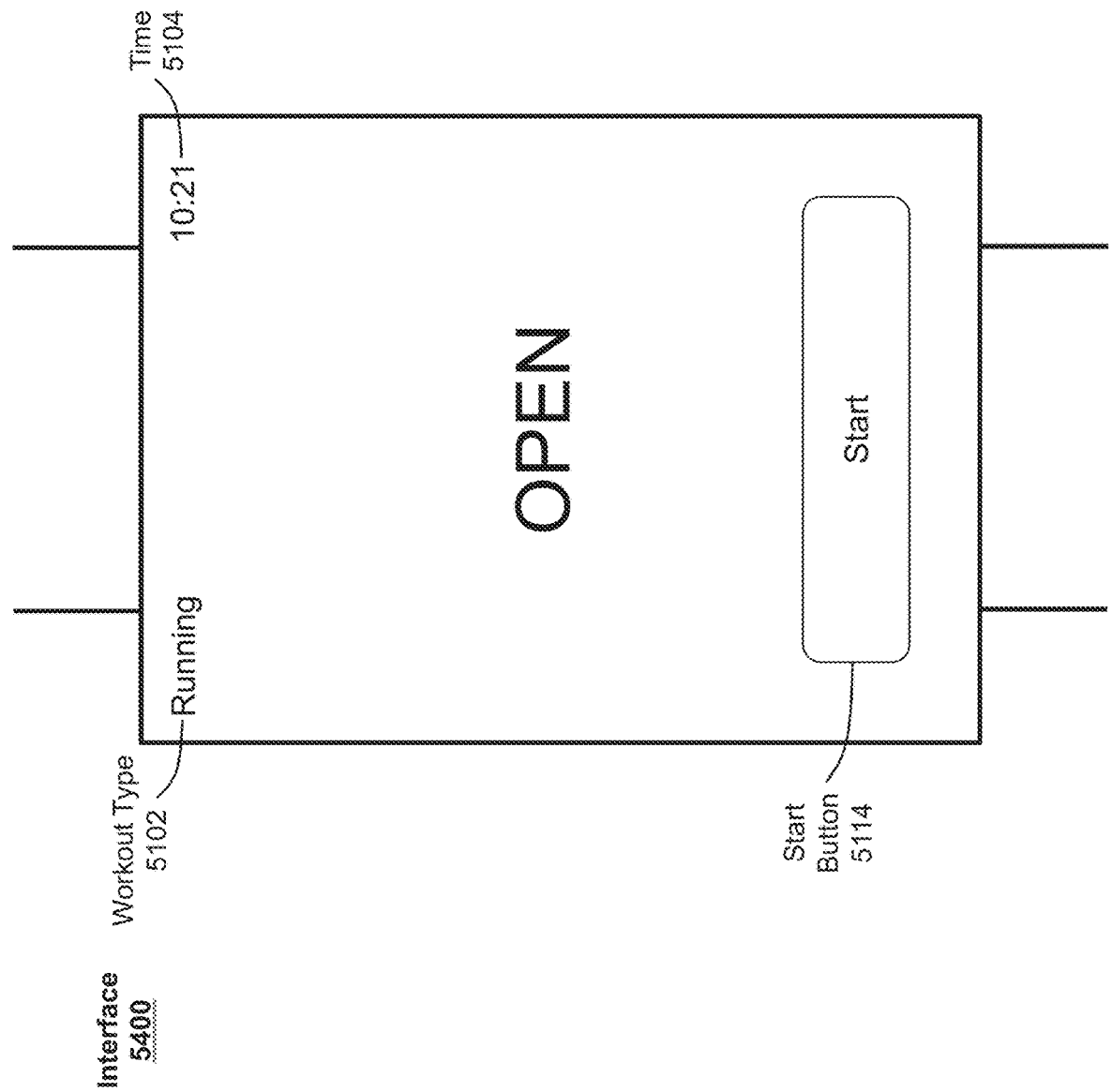

FIG. 54 illustrates another example interface 5400 that can be displayed at block 4804 of process 4800 in response to receiving a selection of a "running" type of workout at block 4802 (e.g., by a user selecting the "Running" option in either interface 4900 or 5000) or in response to a request to select a different workout attribute from interface 5100, 5200, or 5300. Similar to interfaces 5100 5200, and 5300, interface 5400 can include a workout type identifier 5102 indicating that the "Running" type of workout was selected, a time indicator 5104 indicating the current time, and a start button 5114 for selecting the goal and beginning the workout. However, since interface 5400 may be used to perform a workout without a specific goal, interface 5400 may not include a value 5106 for the attribute of the workout, buttons 5108 and 5110 for adjusting the value 5106, and a best value 5112 of the attribute of the workout.

In some examples, the color of the text and/or any other element displayed in interfaces 5100, 5200, 5300, and 5400 can be color-coded based on the associated attribute of the workout. For example, the text and/or elements displayed within interface 5100 can be displayed using a first color (e.g., blue) associated with the distance attribute, the text and/or elements displayed within interface 5200 can be displayed using a second color pink) associated with the Calorie attribute, the text and/or elements displayed within interface 5300 can be displayed using a third color (e.g., yellow) associated with the duration attribute, and the text and/or elements displayed within interface 5400 can be displayed using a fourth color (e.g., green) associated with another attribute or with selecting no attribute.

In some examples, the device can select one of interfaces 5100, 5200, 5300, and 5400 to display at block 4804 based on the workout attribute selected as a goal for the last workout, the frequency that the workout attributes have been selected as a goal for previous workouts, a user-selected preference, or the like.

While example interfaces for selecting specific workout attributes for the "running" type of workout have been provided in FIGS. 51-54, it should be appreciated that interfaces for selecting any workout attribute of any type of workout can be provided based on the types of attributes associated with the workout selected at block 4802. For example, if the type of workout selected at block 4802 was "yoga," an interface for selecting a duration goal or a Calorie goal may be displayed, but an interface for selecting a distance goal may not be displayed.

Figure 55:
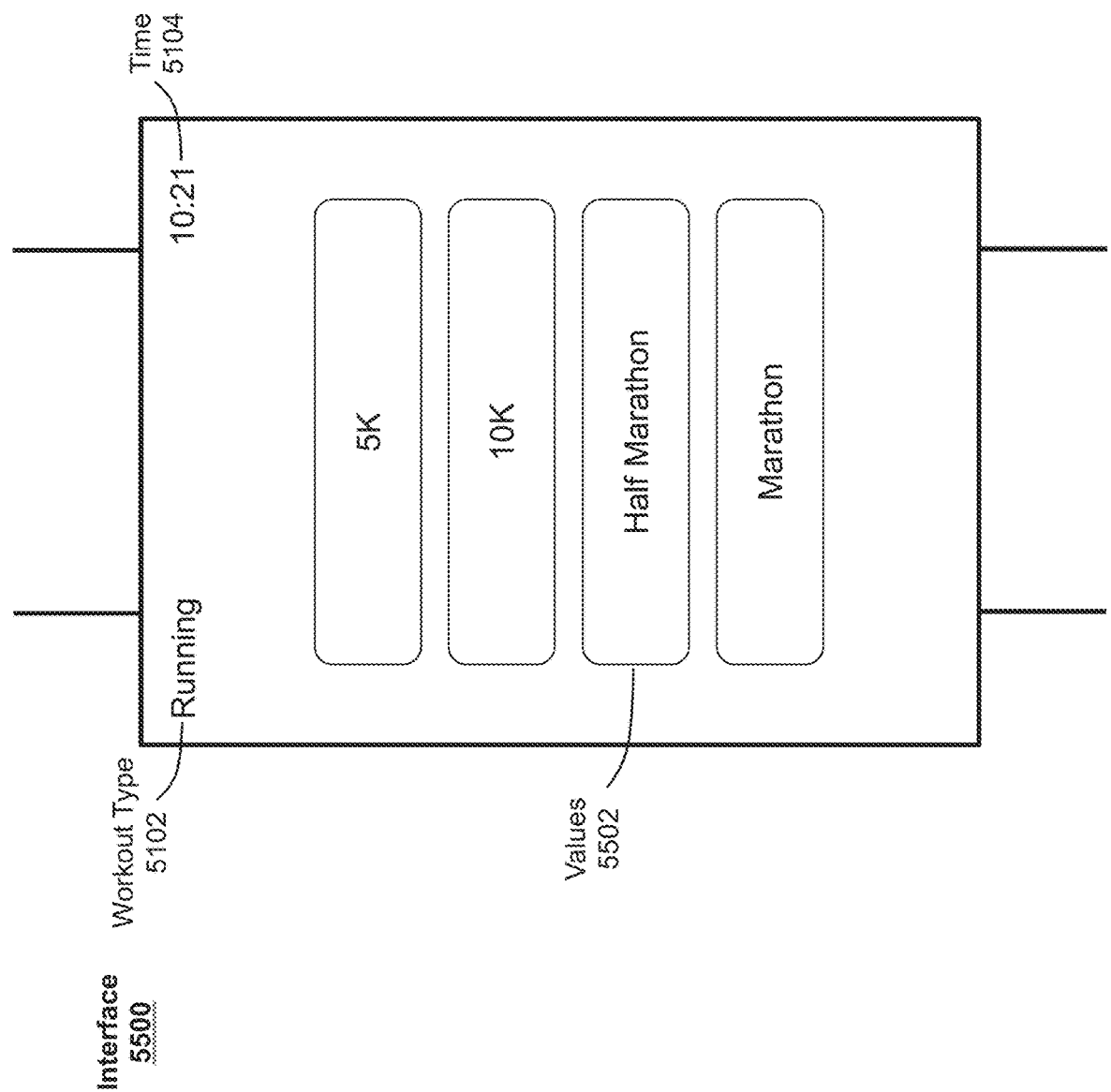
Figure 56:
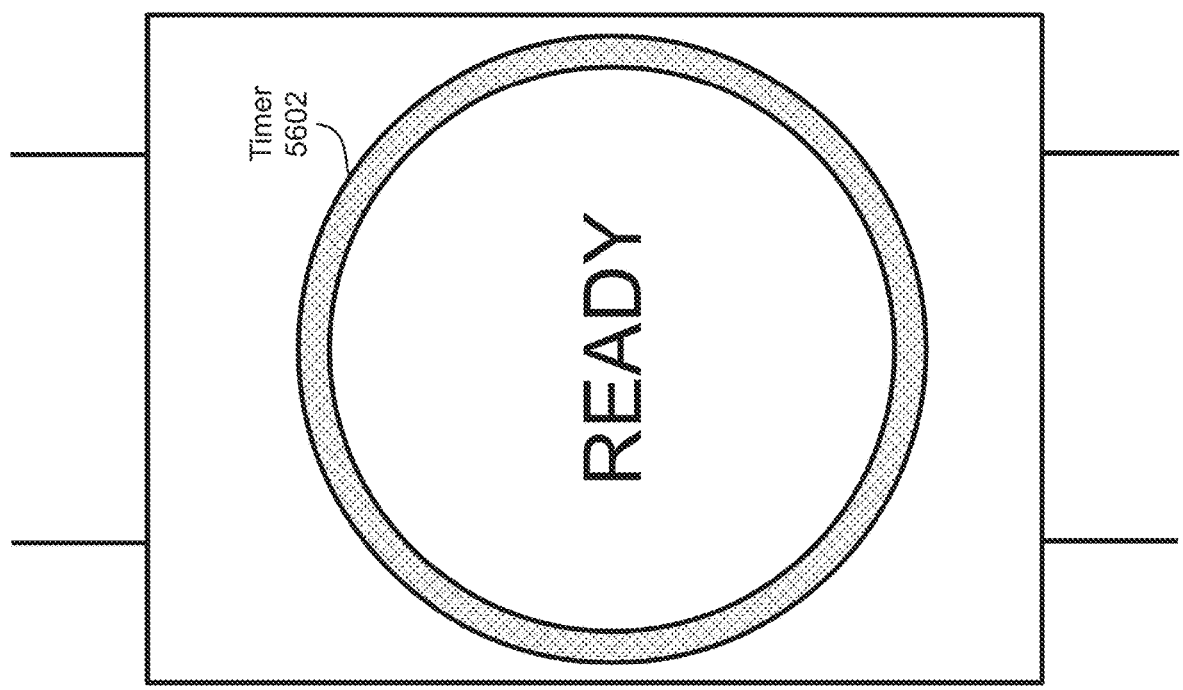
FIGS. 56-59 illustrate exemplary interfaces for notifying a user that a workout is about to begin according to various examples.
Figure 57:
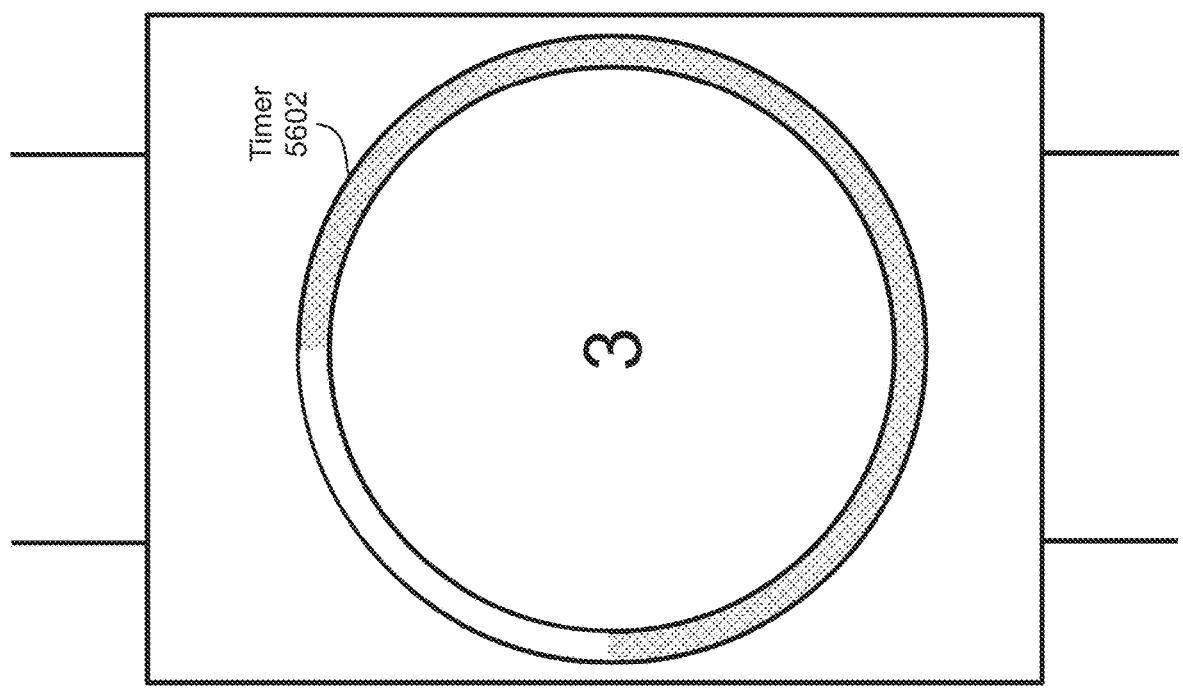
Figure 58:
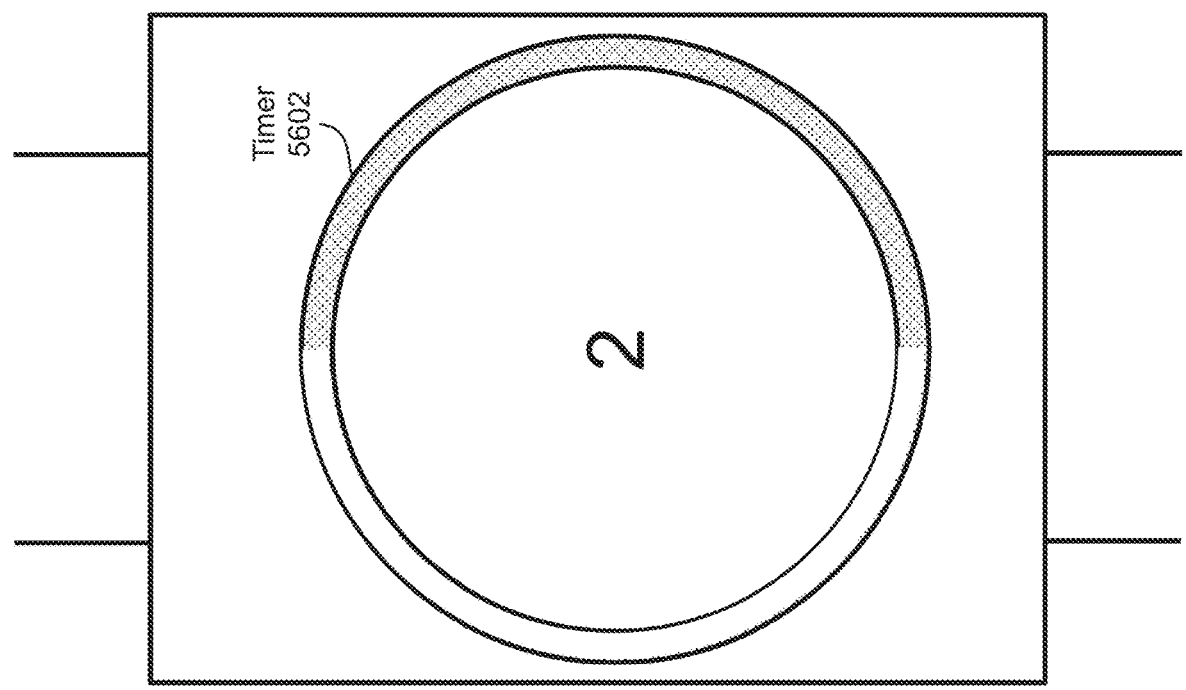
Figure 59:
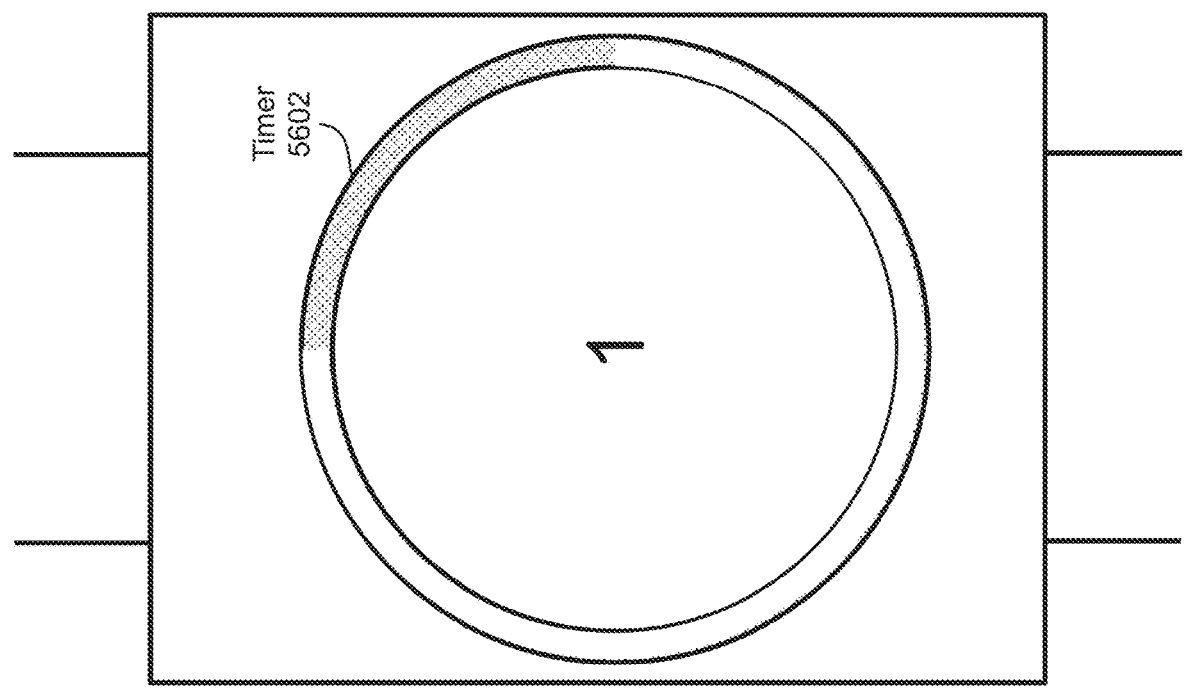

Additionally, it should be appreciated that the interfaces can include other input mechanisms for selecting a goal value, such as a text box, a list, a pull-down menu, or the like. For example, FIG. 55 illustrates another example interface 5500 that can be displayed at block 4804 of process 4800 in response to receiving a selection of a "running" type of workout at block 4802 (e.g., by a user selecting the "Running" option in either interface 4900 or 5000) or in response to a request to select a different workout attribute from interface 5100, 5200, 5300, or 5400. For example, interface 5500 can be displayed in response to detecting a user contact having a characteristic intensity above an intensity threshold on a display of the device or in response to a swipe gesture across a touch-sensitive display while interface 5100 is being displayed. Since interface 5100 is associated with the distance workout attribute, interface 5500 can also be associated with the distance workout attribute. Similar to interfaces 5100, 5200,5300, and 5400, interface 5500 can include a workout type identifier 5102 indicating that the "Running" type of workout was selected and a time indicator 5104 indicating the current time. However, interface 5500 can further include a list of common goal values 5502. The list can include values frequently selected by the user, values frequently selected by multiple users, values associated with a popular or current event (e.g., a distance used by an Olympic event, a distance of a charity run, etc.). In other examples, the list can include values determined based on past performance of the user, the user's contacts, the user's friends, a predefined group of users, or the like. For example, the list can include a longest distance run by the user, a longest distance run by the user over a predetermined length of time (e.g., the last week), an average distance run by the user, an average distance run by the user over a predetermined length of time (e.g., the last week), a longest distance run by the user's contacts/friends/running group, a longest distance run by the user's contacts/friends/running group over a predetermined length of time (e.g., the last week), an average distance run by the user's contacts/friends/running group, an average distance run by the user's contacts/friends/running group over a predetermined length of time (e.g., the last week), or the like. In response to a selection of one of values 5502, the goal of the workout can be selected to be the attribute associated with interface 5500 and the selected value 5502. For example, in response to a selection of the "5K" value 5502, the goal of the workout can be set to a distance goal of 5 kilometers. While interface 5500 shows example values for the distance attribute, it should be appreciated that similar interfaces can be displayed for other workout attributes in response to a user request (e.g., a user contact having a characteristic intensity above an intensity threshold on a display of the device) while other interfaces 5200, 5300, or 5400 (or other interfaces for other workout attributes) are being displayed and can include a list of common values for those other workout attributes.

In some examples, in response to a selection of start button 5114 in any of interfaces 5100, 5200, 5300, or 5400, or in response to a selection of one of the commonly used values 5502 in interface 5500, the device can display a countdown before beginning the workout selected at block 4802 using the goal selected at block 4804. FIGS. 56, 57, 58, and 59 illustrate example interfaces 5600, 5700, 5800, and 5900 having a timer ring 5602 that can be displayed. In these examples, the countdown can be three seconds long. However, other durations (including zero) can be used.

Referring back to FIG. 48, at block 4806 the workout can be initiated and a workout interface can be displayed. Initiating the workout can include activating one or more activity sensors (e.g., sensors 168, 359, and 520) and recording activity data provided by those one or more activity sensors. In some examples, the activity sensors activated at block 4806 can be selected based on the type of workout selected at block 4802. For example, a biometric sensor for measuring heart rate, GPS sensor for measuring position, and accelerometer for measuring motion to determine distance traveled can be activated if a running type of workout was selected at block 4802. However, if a cycling type of workout was selected at block 4802, a biometric sensor for measuring heart rate and a GPS sensor for measuring position may be activated at block 4802, but an accelerometer may not be activated. This may be done because an accelerometer may not provide reliable information in determining distance traveled on a bike and can be left inactive to save power. Other combinations of activity sensors can selectively be activated for other types of workouts.

Figure 60:
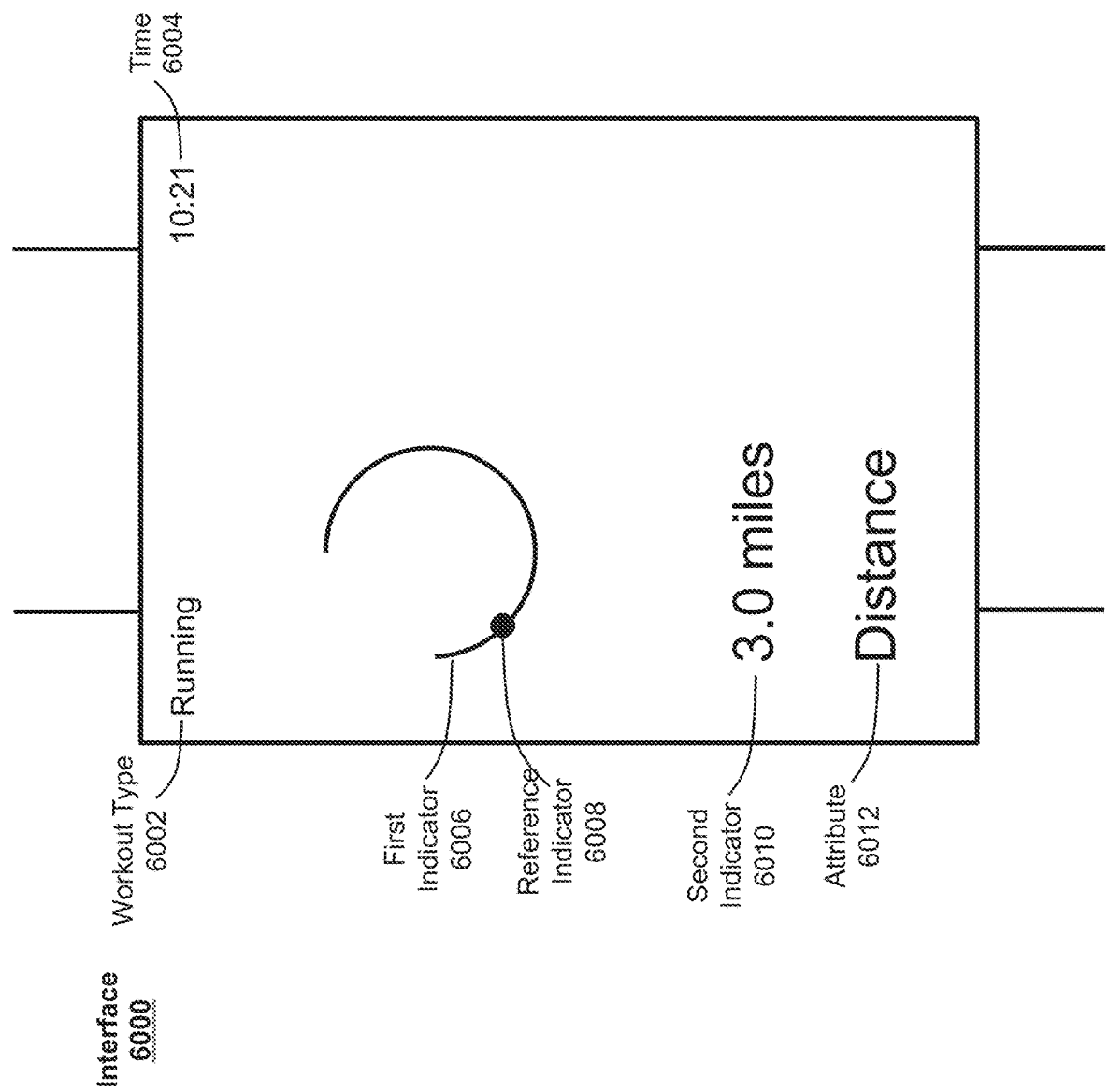
FIGS. 60-65 illustrate exemplary workout interfaces for monitoring a user's workout according to various examples.

In some examples, the workout interface displayed at block 4806 can include information associated with one or more attributes of the workout and the goal selected at block 4804. FIG. 60 illustrates an example workout interface 6000 that can be displayed at block 4806 in response to receiving a selection of a "running" type of workout at block 4802 (e.g., by a user selecting the "Running" option in either interface 4900 or 5000). As shown, interface 6000 can include a workout type identifier 6002 indicating that the "Running" type of workout was selected, a time indicator 6004 indicating the current time, a first indicator 6006 indicating a progress relative to the goal selected at block 4804, a second indicator 6010 providing information associated with a workout attribute, and a workout attribute indicator 6012 identifying the workout attribute represented by second indicator 6010.

First indicator 6006 can include a representation of the current value and goal value of workout attribute selected as the goal at block 4804. In the example shown in FIG. 60, first indicator 6006 can include a ring having two visually distinct parts—a completed portion of the ring and an uncompleted portion of the ring. While not shown, in some examples, the uncompleted portion of the ring can be shaded or colored in a manner that is visually distinct from the completed portion. The two parts of the ring can be scaled to visually indicate relative progressive measures of the current value of the goal attribute compared to the goal value of the attribute. For example, the ring of first indicator 6006 can be scaled such that the entire length of its circumference represents the goal value of the selected workout attribute (e.g., a distance goal of 4 miles). The completed portion of the ring can be configured to represent the current value of the workout attribute (e.g., current distance of 3.0 miles traveled during the workout) and the remaining uncompleted portion of the ring can be configured to represent the amount remaining to be completed by the user to achieve the goal (e.g., 1 mile). In other words, the completed portion of the ring represents what user has achieved, and the uncompleted portion of the ring represents what user needs to achieve to complete goal. Respective sizes of the completed and uncompleted portions of the ring can be updated in real-time to reflect the most current progressive measure of the workout attribute. For example, as additional activity is detected, the completed portion of the ring can increase in size in the clockwise direction and the uncompleted portion of the ring can decrease in size. In this way, the ring can start as being entirely uncompleted, and as the user gets closer to reaching the goal value, the ring can begin to become completed in the clockwise direction.

In some examples, the leading edge of the completed portion of the ring of first indicator 6006 can be displayed having a different appearance or texture than the trailing parts of the completed portion of the ring. For example, the leading edge of the completed portion of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the workout goal. Additionally, in some examples, if the current value of the attribute represented by first indicator 6006 exceeds the goal value, the leading edge of the completed portion of the ring can continue to traverse the ring and overlap a previously completed portion of the ring. By displaying the leading edge using a different shade or texture, the user can distinguish the leading edge from a previously completed portion of the ring.

In some examples, first indicator 6006 can further include a reference indicator 6008 representing supplemental information relevant to the user's workout. Examples of supplemental information that can be additionally provided on the display include, non-exclusively, timed-based goals that are adjusted in accordance with a passage of time (e.g., certain percentage(s) of the goal to be completed by certain time within the workout, such as 10% to be completed by 10 minutes into the workout, 80% to be completed by 80 minutes into the workout, etc. such that the indicator would be moving along the ring throughout the workout to indicate the changing percentage of the goal to be completed depending on the time during the workout), history of user's past workout(s) (e.g., amount of the attribute attained at the same time during a previous workout performed by the user, a best workout performed by the user, or an average workout performed by the user), workout data of other users different from the user of the device (e.g., amount of the attribute attained at the same time during a previous workout performed by one or more other users, a best workout performed by one or more other users, or an average workout performed by one or more other users), or the like.

Second indicator 6010 can include a representation of a current value of a workout attribute of the type of workout selected at block 4802. The workout attribute represented by second indicator 6010 can be the same workout attribute represented by first indicator 6006 or can represent a different workout attribute. In the example shown in FIG. 60, second indicator 6010 can represent the current value of the distance attribute of the workout, which is the same workout attribute represented by first indicator 6006. As shown, the current value of the distance attribute is 3.0 miles, indicating that the user has run a total distance of 3.0 miles during the current workout. Second indicator 6010 can be updated in real-time to reflect the most current progressive measure of the workout attribute. Workout attribute indicator 6012 provides a textual representation of the workout attribute represented by second indicator 6010.

In some examples, first indicator 6006 can be color-coded based on the workout attribute that it represents. The colors can be the same as those used in interfaces 5100, 5200, 5300, and 5400 to allow a user to quickly determine that attribute being represented. For example, since first indicator 6006 represents the distance attribute, it can be displayed in the same color used to display interface 5100 (e.g., blue). Similarly, second indicator 6010 and attribute 6012 can also be color-coded based on the workout attribute that they represent. The colors can be the same as those used in interfaces 5100, 5200, 5300, and 5400. For example, since second indicator 6010 and attribute 6012 represent the distance attribute, they can be displayed in the same color used to display interface 5100 (e.g., blue).

In some examples, the device can display a different attribute of the workout for viewing within the workout interface in response to a request from the user. In some examples, the request can be made by a vertical or horizontal swipe gesture across the touch sensitive display of the device, a touch on the touch sensitive display of the device, a button press, a movement of a rotatable input mechanism of the device, a user contact having a characteristic intensity above an intensity threshold on a display of the device, or any other desired form of input.

Figure 61:
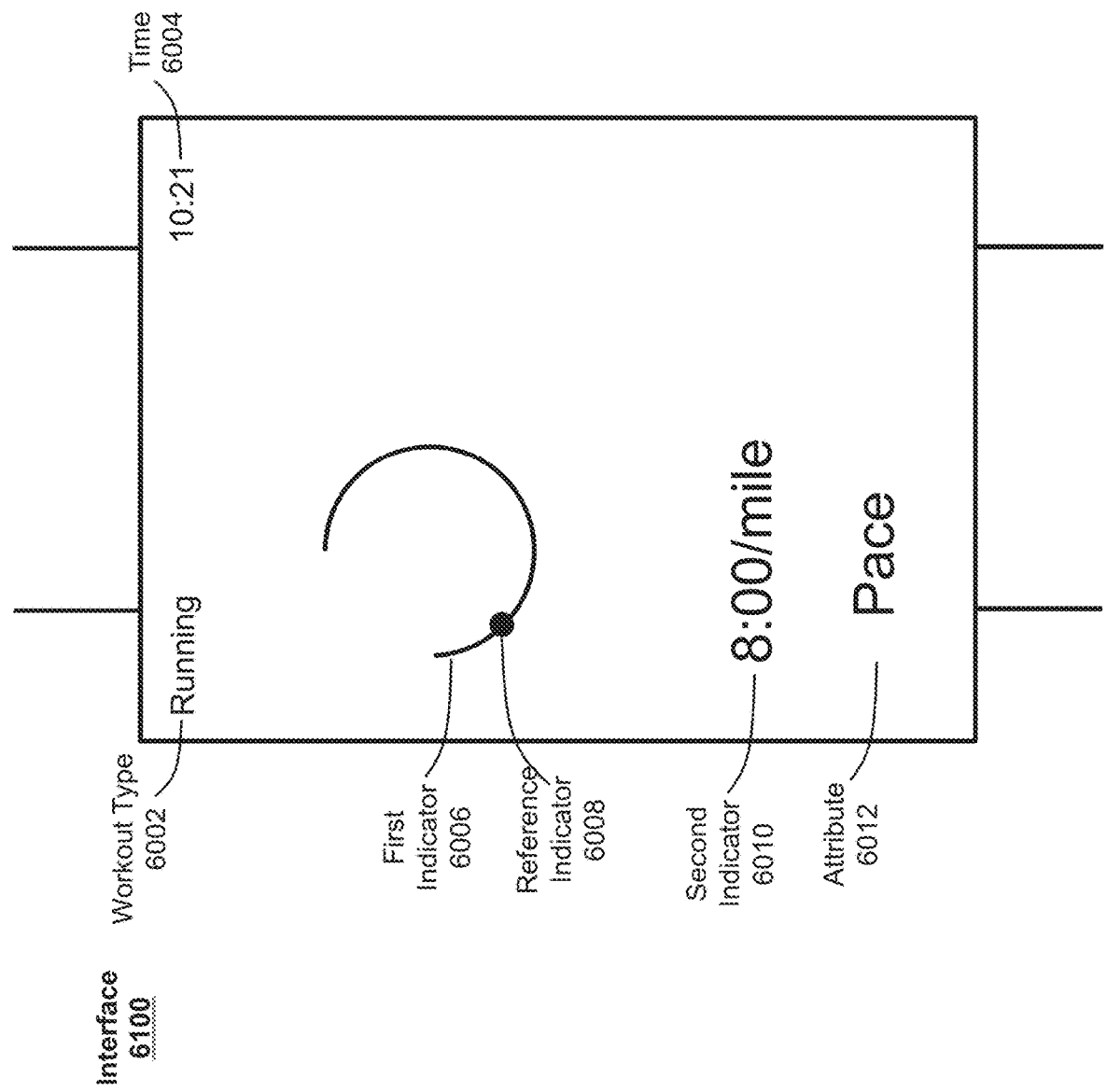

FIG. 61 illustrates another example interface 6100 that can be displayed in response to a request to view a different workout attribute from interface 6000. Similar to interface 6000, interface 6100 can include the workout type identifier 6002, time indicator 6004, first indicator 6006, reference indicator 6008, second indicator 6010, and attribute indicator 6012. As shown, first indicator 6006 can represent the same workout attribute as that of first indicator 6006 in interface 6000 (e.g., the distance attribute) because the goal of the workout has not changed. However, the attribute represented by second indicator 6010 and attribute indicator 6012 in interface 6100 can be different than that in interface 6000. In the illustrated example, second indicator 6010 and attribute indicator 6012 can represent the pace attribute of the workout and can indicate that the user is currently running at an 8 minute per mile pace. By changing the attribute represented by second indicator 6010 and attribute indicator 1612, the device can allow a user to customize the workout interface to display information that is of interest to the user.

Figure 62:
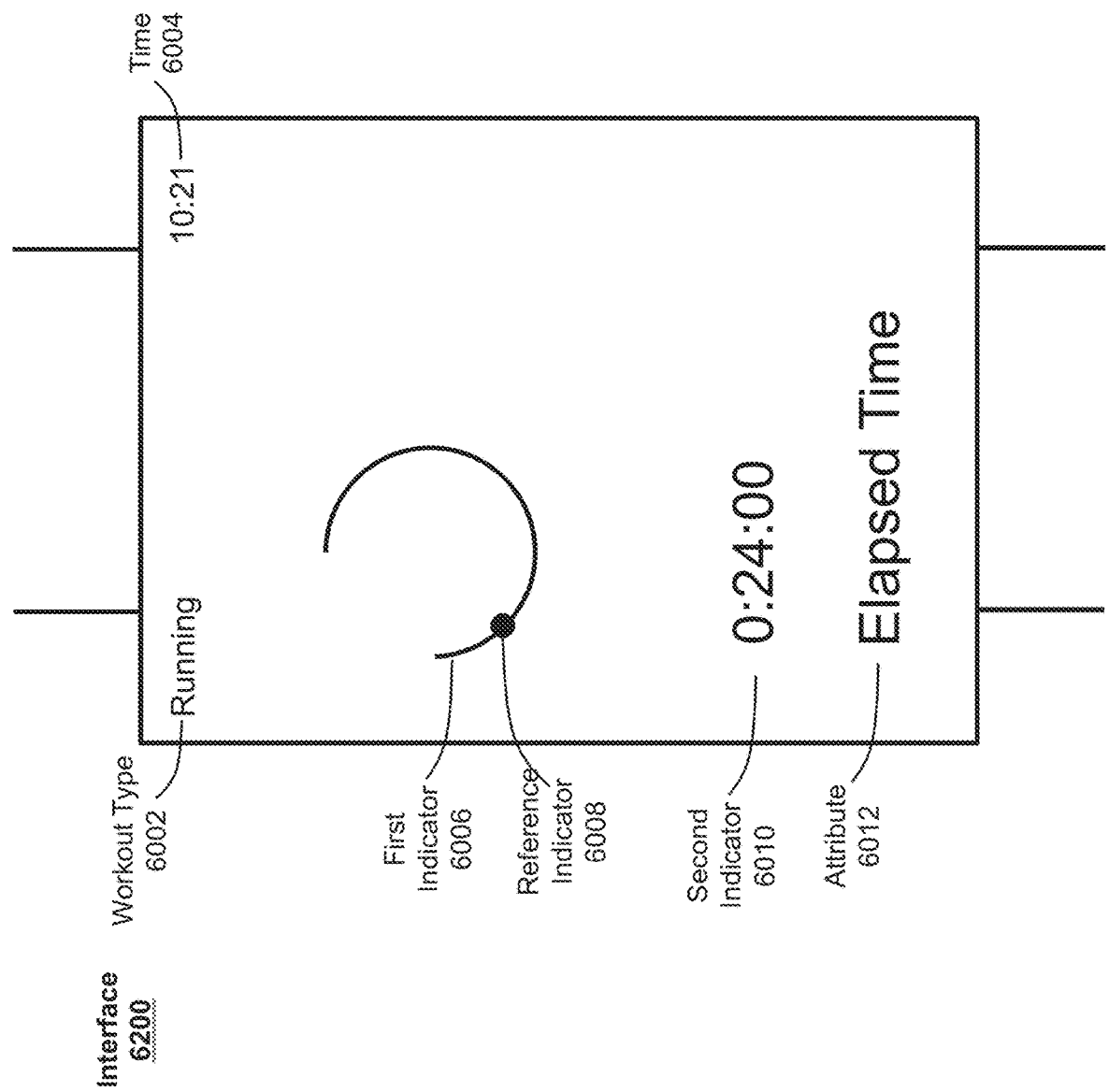
Figure 63:
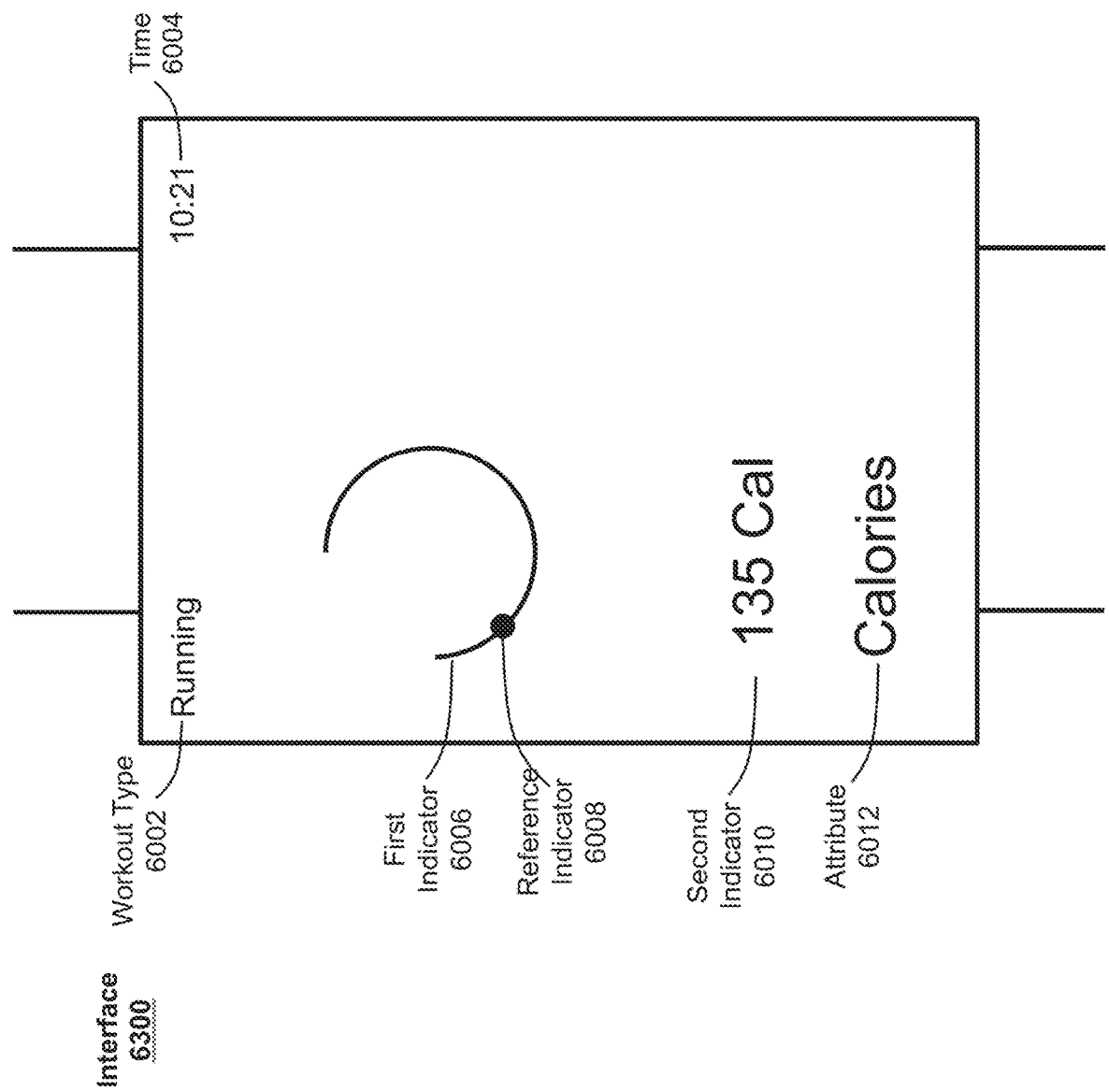

FIGS. 62 and 63 illustrate other example interfaces 6200 and 6300 that can be displayed in response to a request to view a different workout attribute from interface 6000 or 6100. Similar to interfaces 6000 and 6100, these interfaces can include the workout type identifier 6002, time indicator 6004, first indicator 6006, reference indicator 6008, second indicator 6010, and attribute indicator 6012. As shown in both figures, first indicator 6006 can represent the same workout attribute as that of first indicator 6006 in interfaces 6000 and 6100 (e.g., the distance attribute) because the goal of the workout has not changed. However, the attribute represented by second indicator 6010 and attribute indicator 6012 in interfaces 6200 and 6300 can be different than those in interfaces 6000 and 6100. In particular, second indicator 6010 and attribute indicator 6012 can represent a duration attribute of the workout in interface 6200 and a Calorie attribute of the workout in interlace 6300.

In some examples, the device can cause time indicator 6004 to represent a different time value in response to a request from the user. In some examples, the request can be made by a tap on time indicator 6004 on the touch sensitive display of the device, a button press, a user contact having a characteristic intensity above an intensity threshold on a display of the device, or any other desired form of input. In response to the request from the user, the device cause time indicator 6004 to represent a different time value, such as the current duration attribute of the workout or the current pace attribute of the workout.

Figure 64:
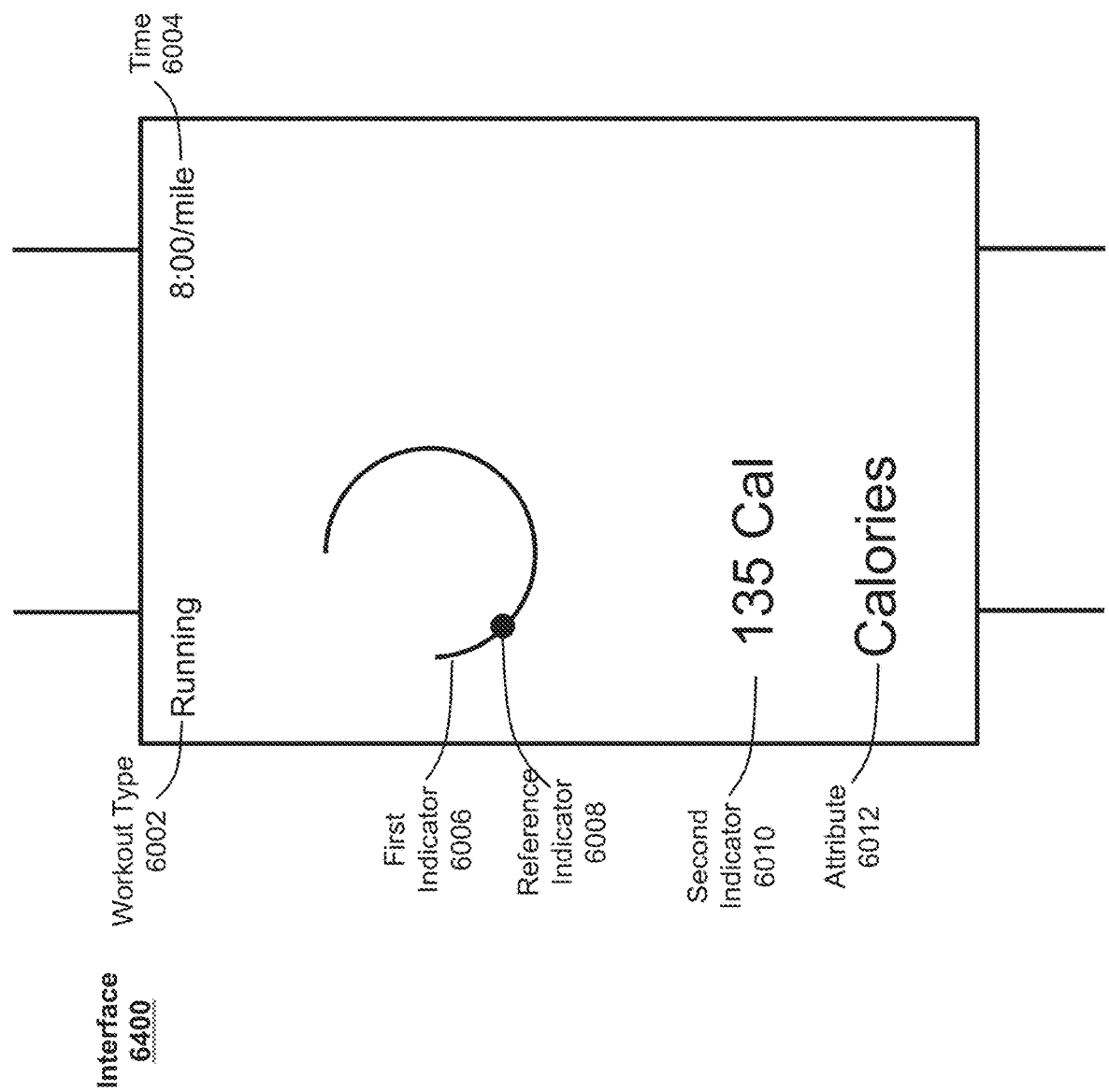
Figure 65:
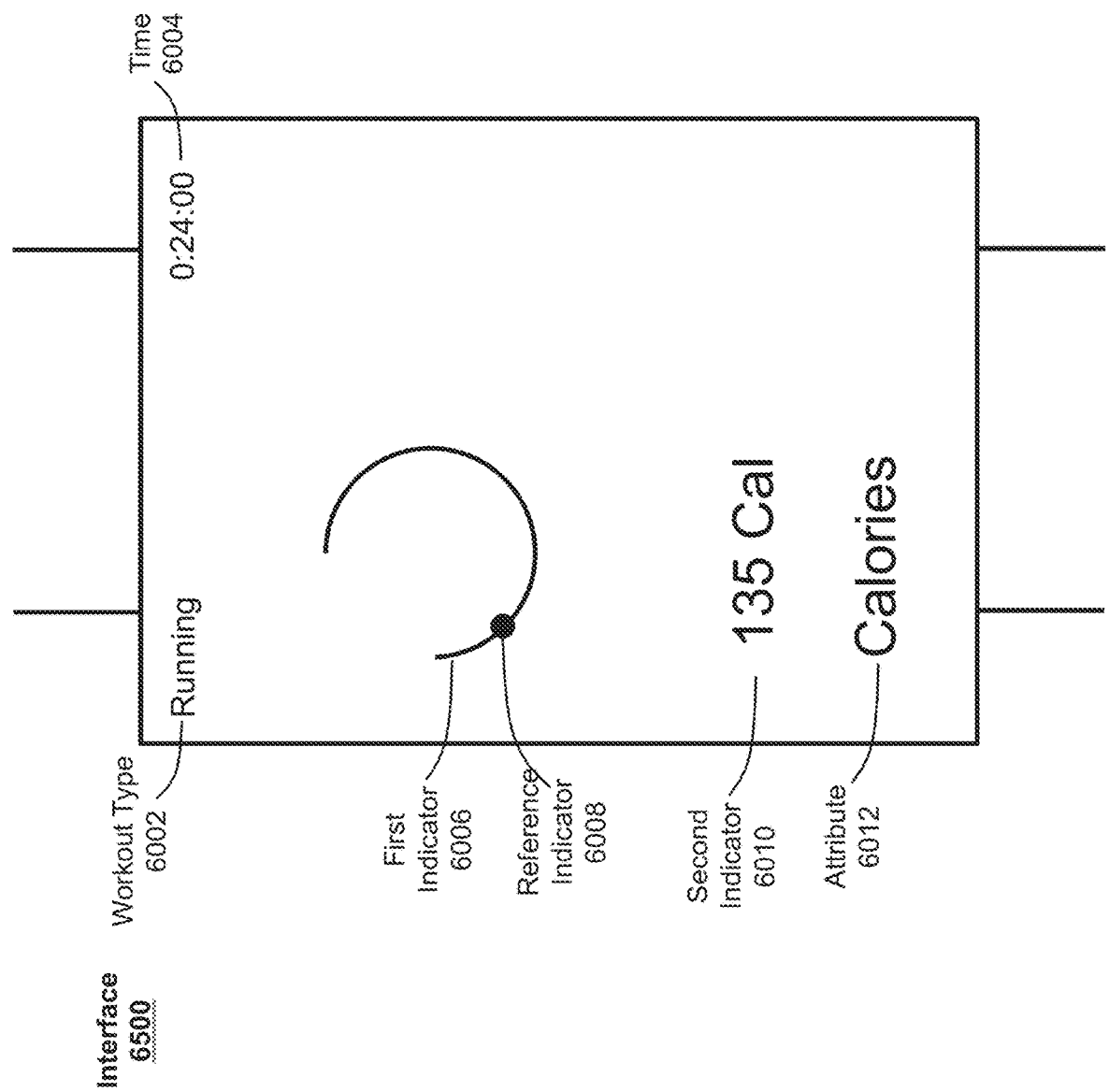

For example, FIG. 64 illustrates an example interface 6400 that can be displayed in response to a request cause time indicator 6004 to represent a different time value from interface 6300. Interface 6400 can be identical to interface 6300, except that time indicator 6004 in interface 6400 can instead represent the current duration of the workout (e.g., 24 minutes). Similarly, FIG. 65 illustrates an example interface 6500 that can be displayed in response to a request cause time indicator 6004 to represent a different time value from interface 6300 or 6400. Interface 6500 can be identical to interfaces 6300 and 6400, except that time indicator 6004 in interface 6500 can instead represent the current pace of the workout (e.g., 8 minutes per mile).

In some examples, if second indicator 6010 and attribute indicator 6012 represent a time attribute associated with the workout (e.g., duration attribute or pace attribute), the device may not cause time indicator 6004 to represent that same time attribute in response to a request from the user to change the time represented by time attribute 6004. For example, if second indicator 6010 and attribute indicator 6012 both represent a duration attribute of the workout, repeated requests to change the time represented by time indicator 6004 may cause the device to cause time indicator 6004 to sequentially change between the current time and the pace of the workout, but may not represent the duration of the workout.

Referring back to FIG. 48, at block 4808 one or more processors of the device can receive activity data that is representative of sensed physical activity of a user from an activity sensor. At block 4810, the one or more processors can process the received activity data to update values of attributes of the workout stored on the device. For example, a timer can be used to update the duration of the workout based on a difference between a current value of the timer and a value of the timer when the workout was initiated at block 4806. Additionally, an accelerometer, motion sensor, gyroscope, biometric sensor, and/or GPS sensor can be used to update a distance traveled during the workout and can additionally or alternatively be used to update a number of Calories burned during the workout (in combination with the user's age, gender, and weight). The timer can be used in combination with the accelerometer, motion sensor, and/or GPS sensor to update a pace of the user during the workout. Other activity sensors can similarly be used to determine and update values of other workout attributes.

At block 4812, one or more processors of the device can update the workout interface (e.g., those shown in FIGS. 60-65) to reflect the updated values of the workout attributes determined at block 4810. For example, the first indicator 6006 can be adjusted to reflect the user's progress toward the goal, reference indicator 6008 can be moved to reflect the updated pace value, and second indicator 6010 can be updated to reflect the updated value of the attribute represented by second indicator 6010.

Blocks 4808, 4810, and 4812 can continue to be repeated to provide the user with up to date information associated with the attributes of the workout via the workout interface. In some examples where the workout application is running in the background of the device or while the display of the device is deactivated, block 4812 can be omitted and blocks 4808 and 4810 can repeatedly be performed to monitor the user's workout and update the monitored attributes such that an accurate display of the attributes can later be provided to the user when the physical activity application is reopened or the display of the device is activated. In some examples, upon activating the display of the device, the workout interface previously displayed (e.g., one of the interfaces displayed in FIGS. 60-65) before deactivating the display can be displayed. This workout interface can be displayed while the device is in a locked state or can be displayed in response to unlocking the device.

Figure 66:
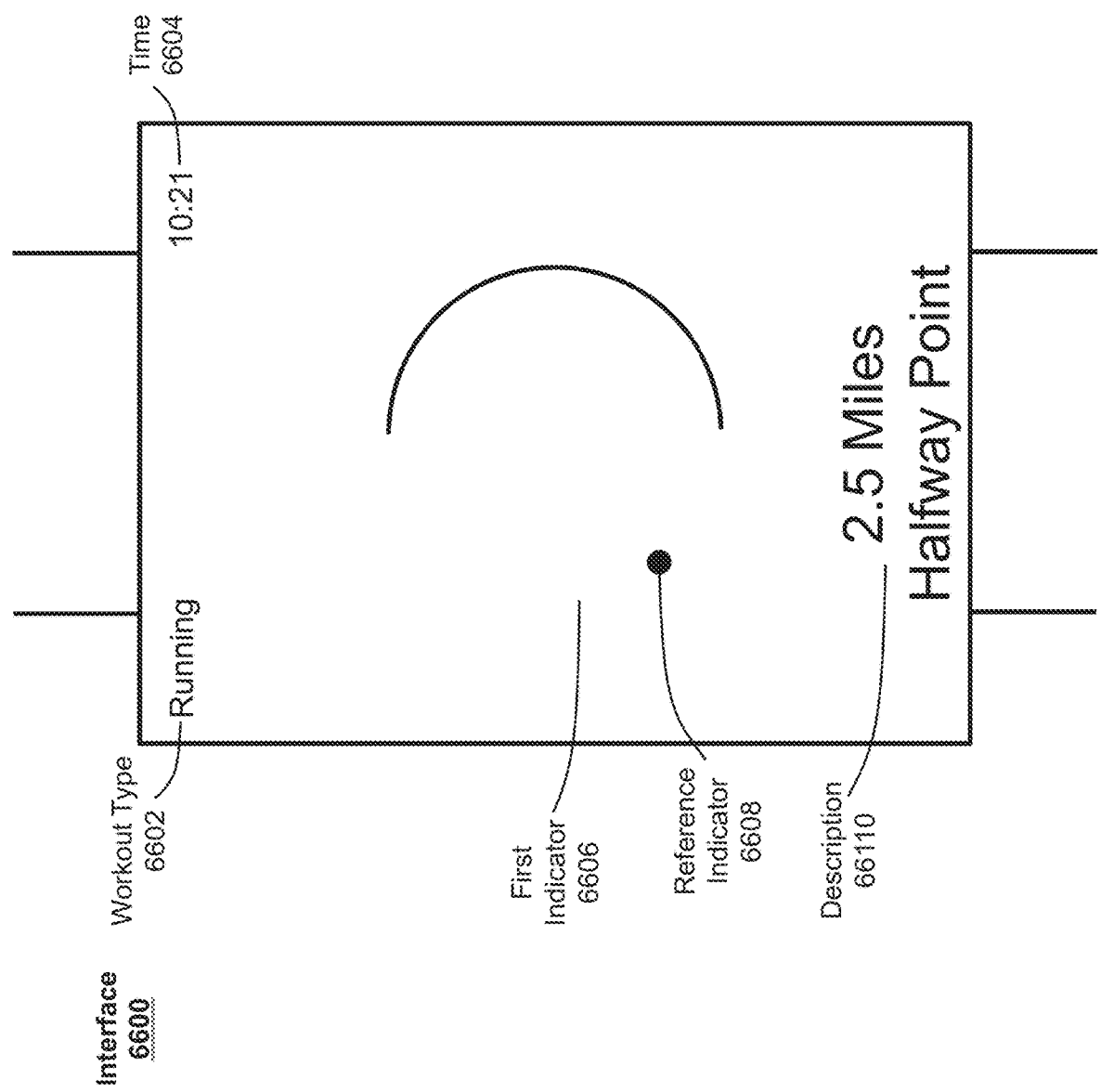
FIGS. 66-69 illustrate exemplary interfaces for presenting notifications to a user according to various examples.

In some examples, process 4800 can further include providing notifications to the user. The notifications can be triggered based on one or more of the attributes meeting one or more notification criteria. For example, FIG. 66 illustrates an example notification interface 6600 that can be displayed by the device in response to the current distance of the workout being equal to half of the goal value of the distance attribute. As shown, interface 6600 can include a workout type identifier 6602 indicating that the "Running" type of workout was selected, a time indicator 6604 indicating the current time, a first indicator 6606, a reference indicator 6608, and a notification description 6610. In some examples, first indicator 6606 and reference indicator 6608 can be enlarged versions of first indicator 6006 and reference indicator 6008 of the workout interface. In some examples, the display of interface 6600 can be accompanied by an audio and/or haptic notification to get the user's attention if the user is not looking at the device when the notification is triggered.

Note that details of the processes described above with respect to processes 4800 (e.g., FIG. 48) are also applicable in an analogous manner to the other processes described herein. For example, processes 1500, 1600, 2200, 2400, 4000, 7900, 8600, and 9200 may include one or more of the characteristics of the various methods described above with reference to processes 4800. For example, the activity data, activity types, displayed values and other elements described above with reference to processes 4800 optionally have one or more of the characteristics of the activity data, activity types, displayed values and other elements described herein (e.g., processes 1500, 1600, 2200, 2400, 4000, 7900, 8600, and 9200). For brevity, these details are not repeated.

Figure 67:
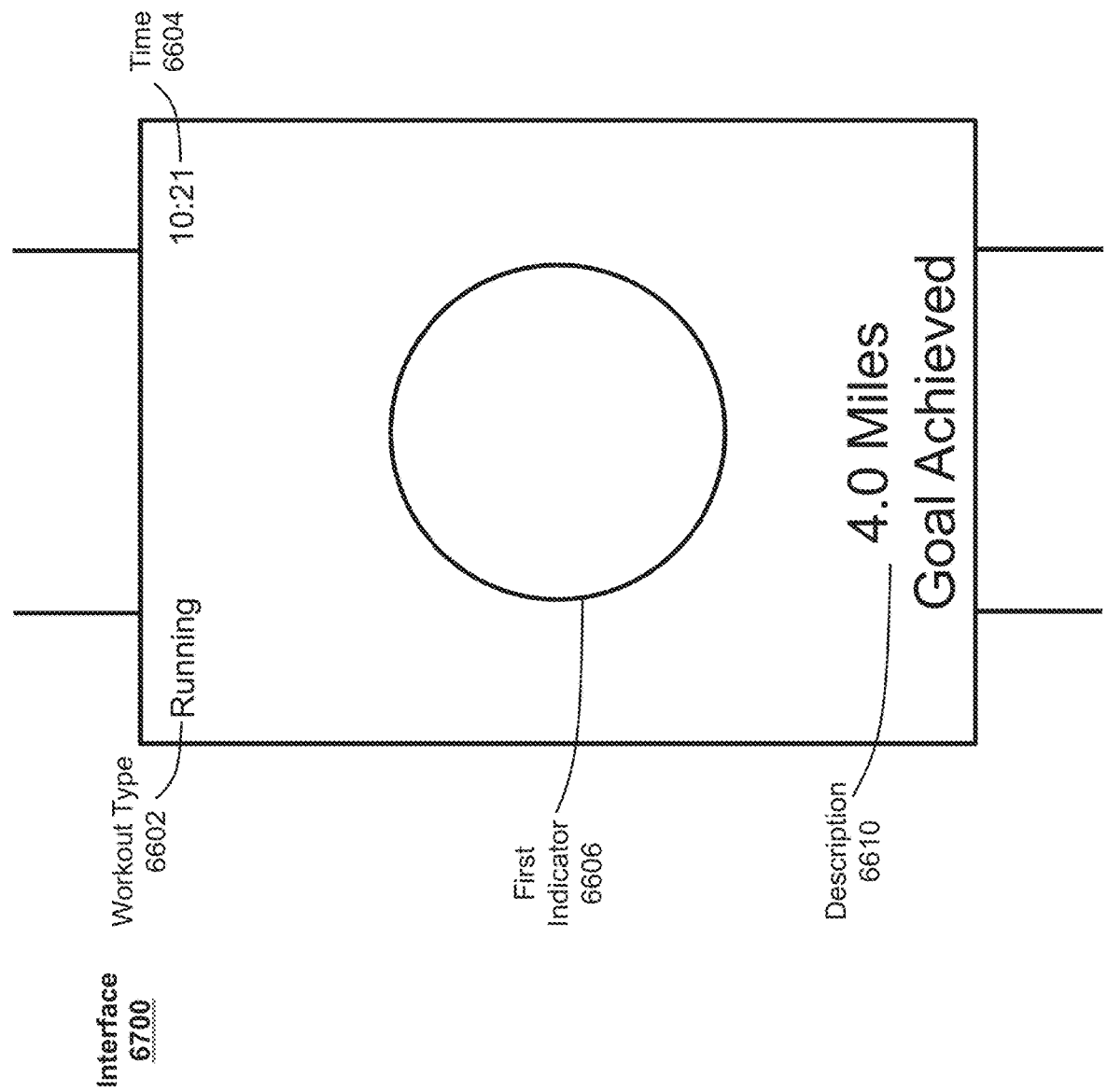

FIG. 67 illustrates another example notification interface 6700 that can be displayed by the device in response to the user reaching the goal of the workout. Similar to interface 6600, interface 6700 can include a workout type identifier 6602 indicating that the "Running" type of workout was selected, a time indicator 6604 indicating the current time, a first indicator 6606, a reference indicator 6608, and a notification description 6610.

Figure 68:
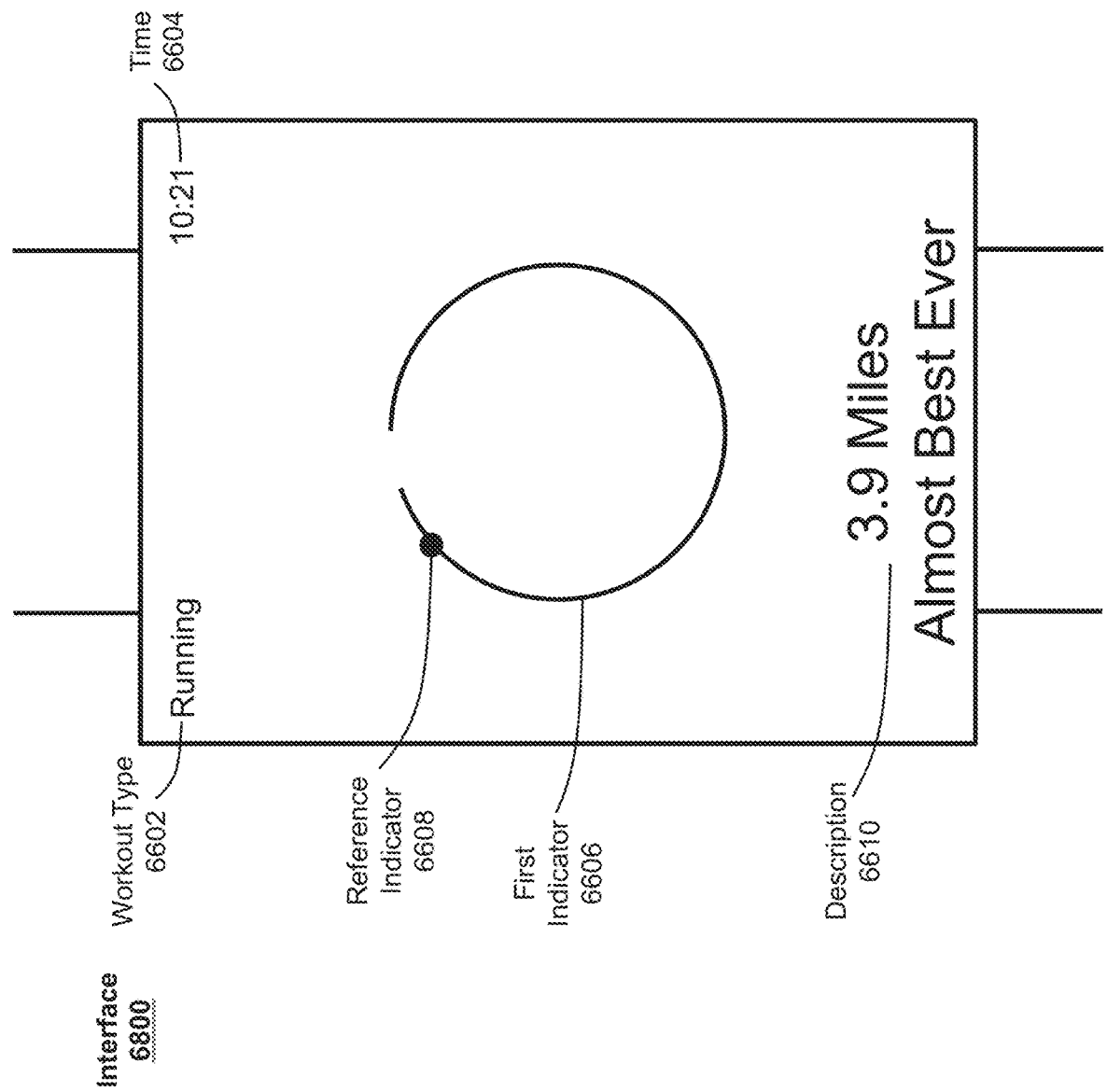

FIG. 68 illustrates another example notification interface 6800 that can be displayed by the device in response to current value of an attribute of the workout being within a threshold value from the goal value and being done at a pace that is better than any previous workouts. For example, as shown in FIG. 68, the current value of the distance traveled is equal to 3.9 miles as indicated by description 6610 and is within a threshold value (e.g., 0.1 miles) from the goal value of 4.0 miles. Additionally, the pace of the user is better than a previous best pace (e.g., represented by reference indicator 6608) since the leading edge of first indicator 6606 is closer to completing the ring than reference indicator 6608. Thus, the device can cause a display of notification interface 6800 to notify the user that he/she is close to completing a workout that breaks one or more workout attribute records. This can advantageously motivate a user to finish their workout with additional effort to beat the previous record.

Figure 69:
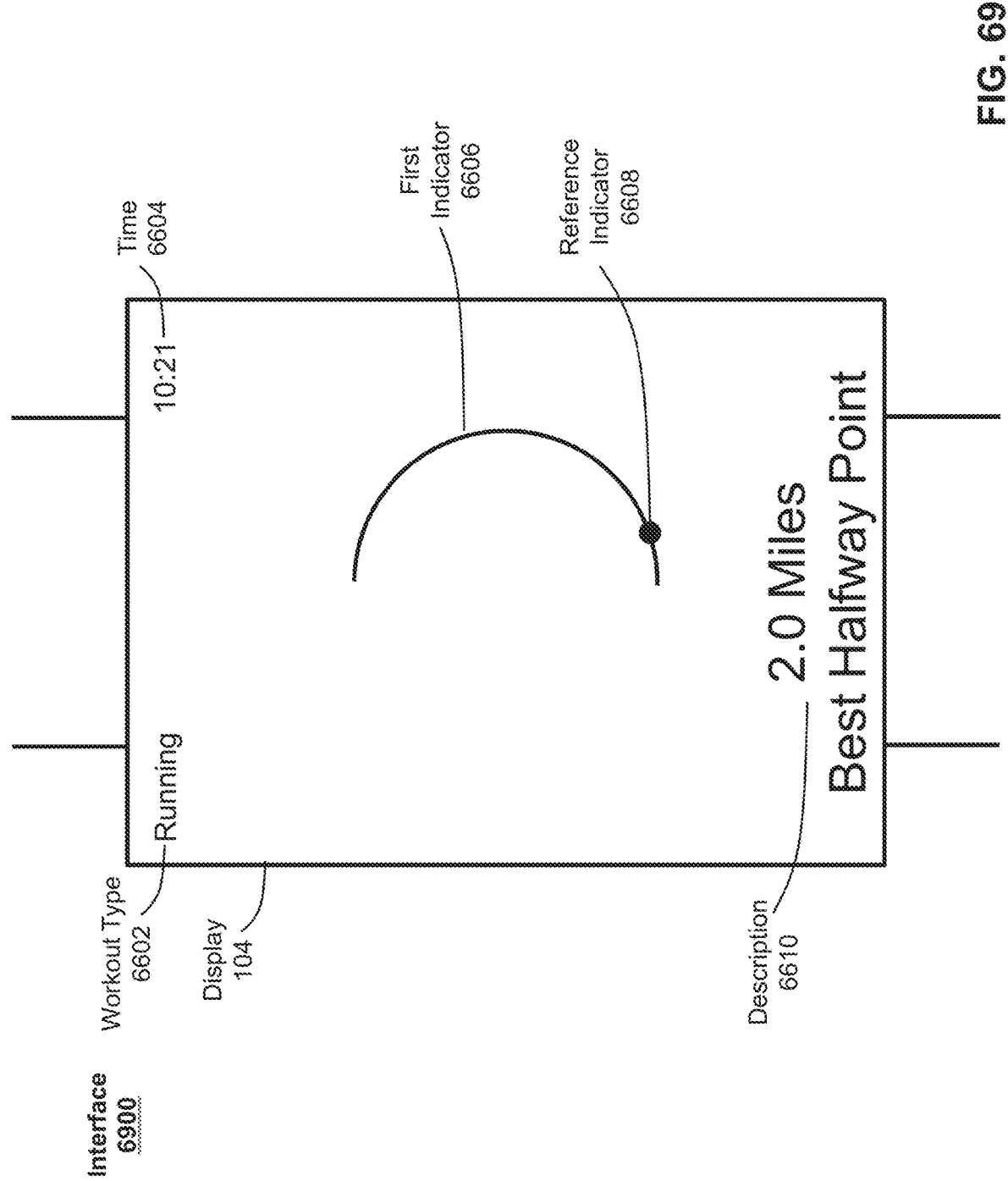

FIG. 69 illustrates another example notification interface 6900 that can be displayed by the device in response to current value of an attribute of the workout being equal to half of the goal value of the workout attribute and being done at a pace that is better than any previous workouts. For example, as shown in FIG. 69, the current value of the distance traveled is equal to 2.0 miles, which is equal to half of the goal value of 4.0 miles. Additionally, the pace of the user is better than a previous best pace (e.g., represented by reference indicator 6608) since the leading edge of first indicator 6606 is closer to completing the ring than reference indicator 6608. Thus, the device caused a display of notification interface 6900 to notify that user that he/she is on the way to completing a workout that breaks one or more workout attribute records. This can advantageously motivate a user to finish their workout with additional effort to beat the previous record.

While example notifications are described above, it should be appreciated that other notifications can be presented to the user in response to other notification criteria.

Figure 70:
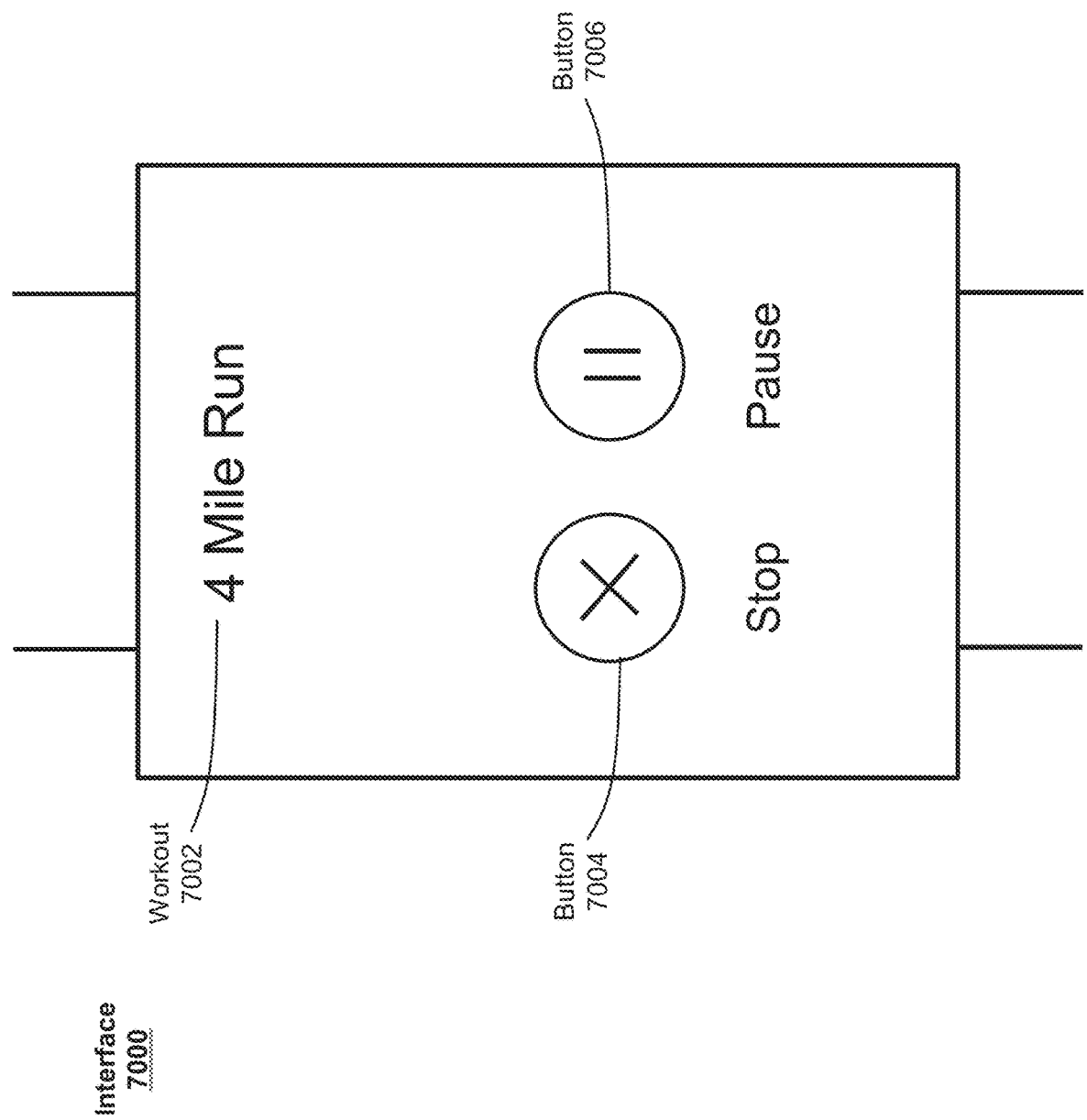
FIGS. 70 and 71 illustrate exemplary interfaces for pausing or stopping a workout according to various examples.
Figure 71:
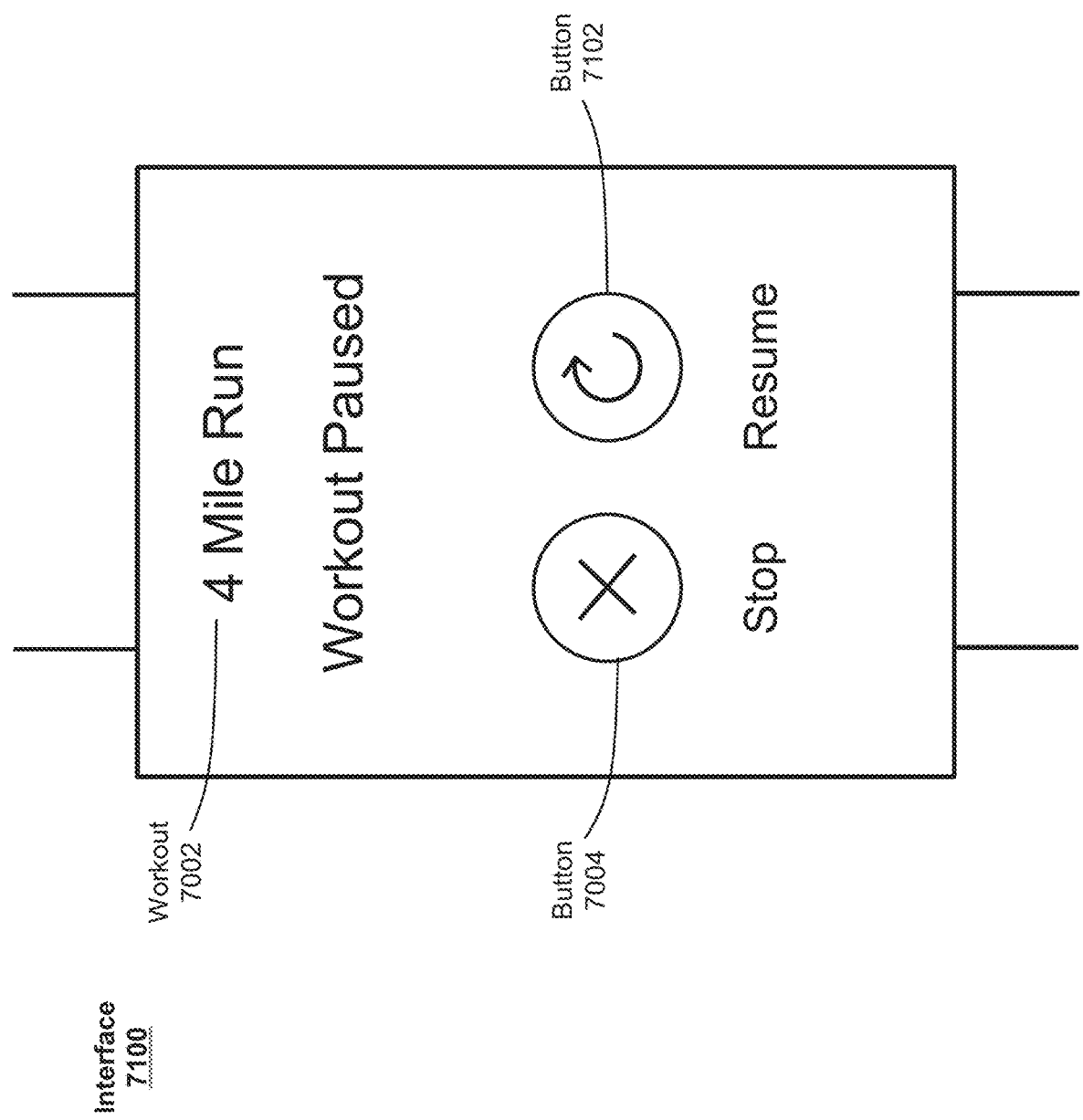

In some examples, the device can pause or end a workout in response to a request from the user. In some examples, the request can be made by a button press, a user contact having a characteristic intensity above an intensity threshold on a display of the device, or any other desired form of input. For example, FIG. 70 illustrates an example interface 7000 that can be displayed in response to a user contact having a characteristic intensity above an intensity threshold on a display of the device while the workout interface is being displayed. As shown, interface 7000 can include a workout description 7002 identifying the type of workout and the goal for the workout, a stop button 7004, and a pause button 7006. In response to a selection of pause button 7006, the workout can be paused, meaning that the one or more processors of the device stop receiving activity data from the activity sensors and/or do not include received activity data as part of the workout. For example, while paused, the duration of the workout may not be incremented with the passage of time, the distance traveled may not be increased in response to movement by the user, and the Calories burned may not be increased in response to movement by the user or passage of time. Additionally, in response to a selection of pause button 7006, the device can display the interface that was previously displayed when the user pressed on the touch sensitive display, causing interface 7000 to be shown. This can allow the user to navigate through the various workout interfaces to view any desired attribute of the workout.

In response to another button press, a user contact having a characteristic intensity above an intensity threshold on a display of the device, or any other desired form of input while the workout is paused, the device can display interface 7100. As shown, interface 7100 can include a workout description 7002 identifying the type of workout and the goal for the workout, a stop button 7004, and a resume button 7102. In response to a selection of resume button 7102, the device can resume the workout and display the workout interface that was previously displayed before interface 7100 was displayed. In other words, the one or more processors of the device can resume receiving activity data from the activity sensors and/or can include received activity data as part of the workout. In response to a selection of stop button 7004 while either interface 7000 or 7100 is displayed, the device can end the workout. In some examples, this can include deactivating some or all of the activity sensors and storing the attributes of the workout in the device as a completed workout. In some examples, the device can transmit the stored workout attributes to be stored on a remote database (e.g., to user server 714 to be stored on user database 716).

Figure 72:
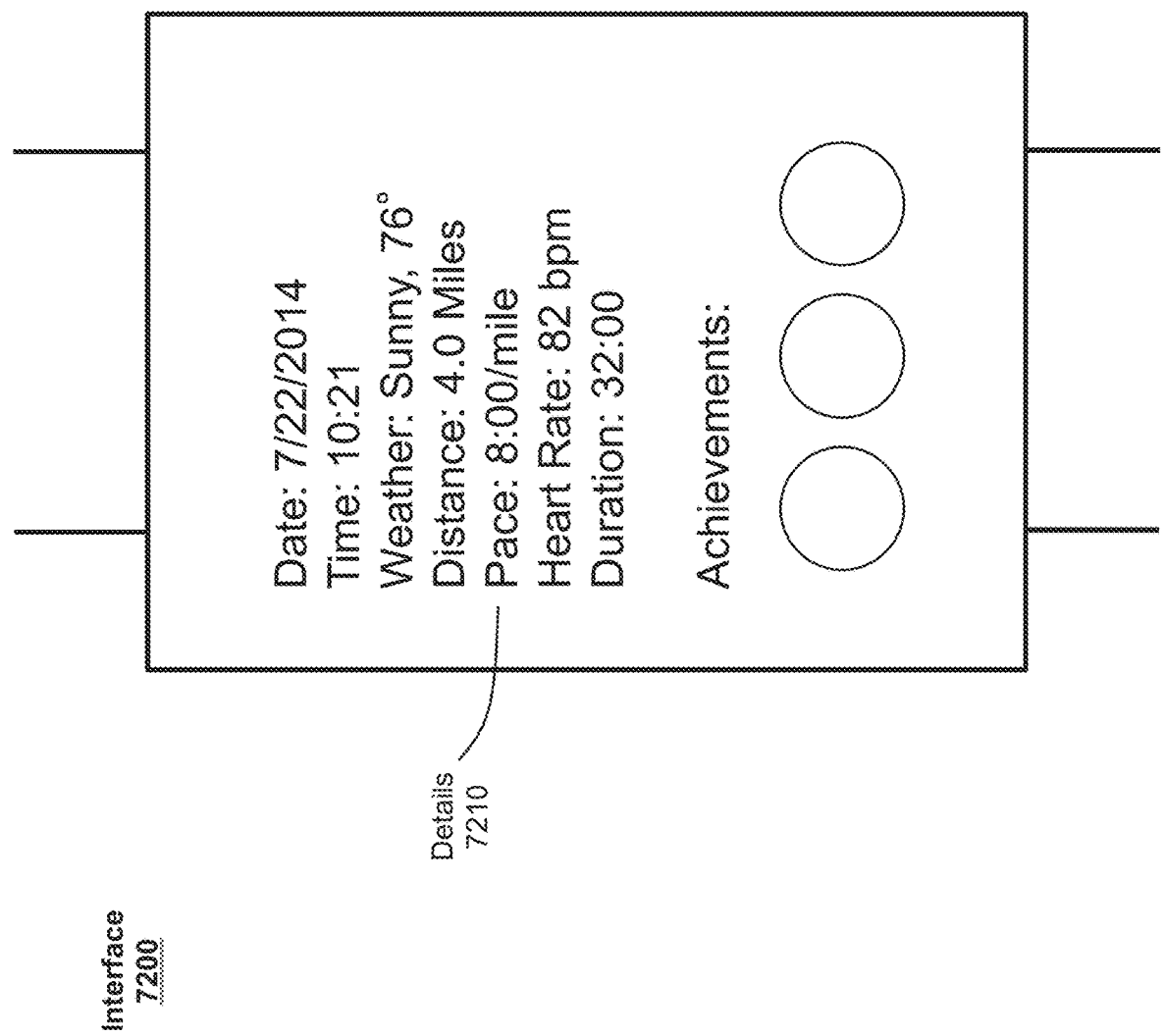
FIG. 72 illustrates an exemplary interface for presenting workout summary information to a user according to various examples.

In some examples, after receiving a request to stop the workout via interface 7000 or 7100, one or more processors of the device can cause a display of a summary of the completed workout. For example, FIG. 72 illustrates example summary interface 7200 that can be displayed. As shown, interface 7200 can include summary details 7210 that can include a date of the workout, a time the workout was performed, the weather when the workout was performed, and information associated with other workout attributes (e.g., distance, pace, heart rate, duration, or the like). In some examples, some or all of details 7210 can be selected to cause the device to display detailed information associated with the selected detail. For example, in response to a user selection of "Pace," the device can display a breakdown of the user's pace over time throughout the workout.

Additionally, interface 7200 can provide the user with rewards, such as a display one or more achievements in the form of badges or other visual representations. The achievements can be awarded to a user in response to the one or more of the attributes of the workout satisfying a predetermined criteria or an achievement criteria, such as breaking a workout attribute record, performing a threshold number of workouts over a length of time (e.g., 5 workouts within 5 days, etc.), or the like. Additional rewards that can be provided to the user can include, but are not limited to, visual rewards, such as animations, glowing or pulsating graphics, 3D images, lighting effects, badges, or the like; sound rewards, such as alerts, ringtones, music, voice, or the like; vibrations; or any combinations of rewards thereof.

Figure 73:
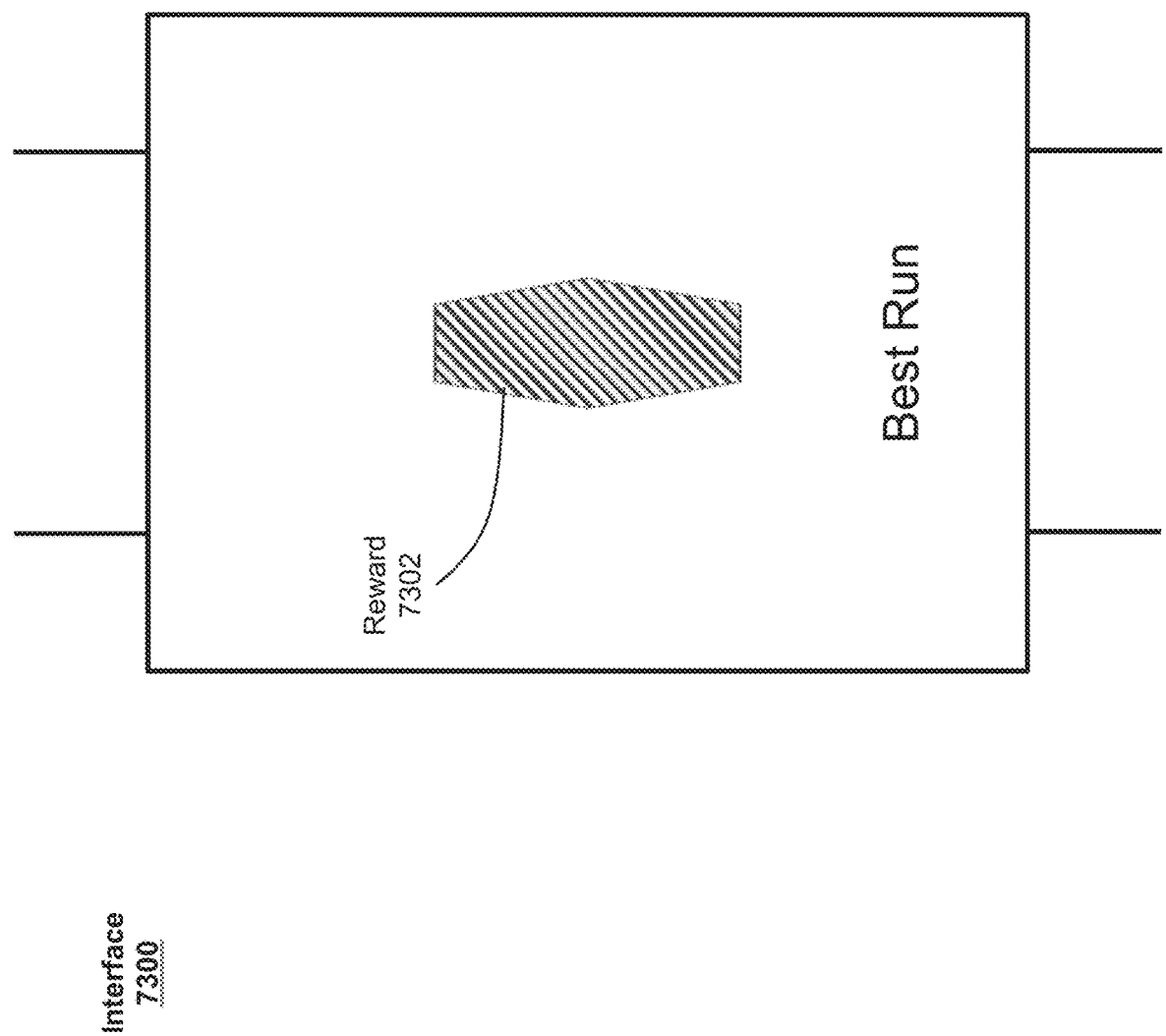
FIGS. 73-75 illustrate exemplary interfaces for presenting rewards to a user according to various examples.
Figure 74:
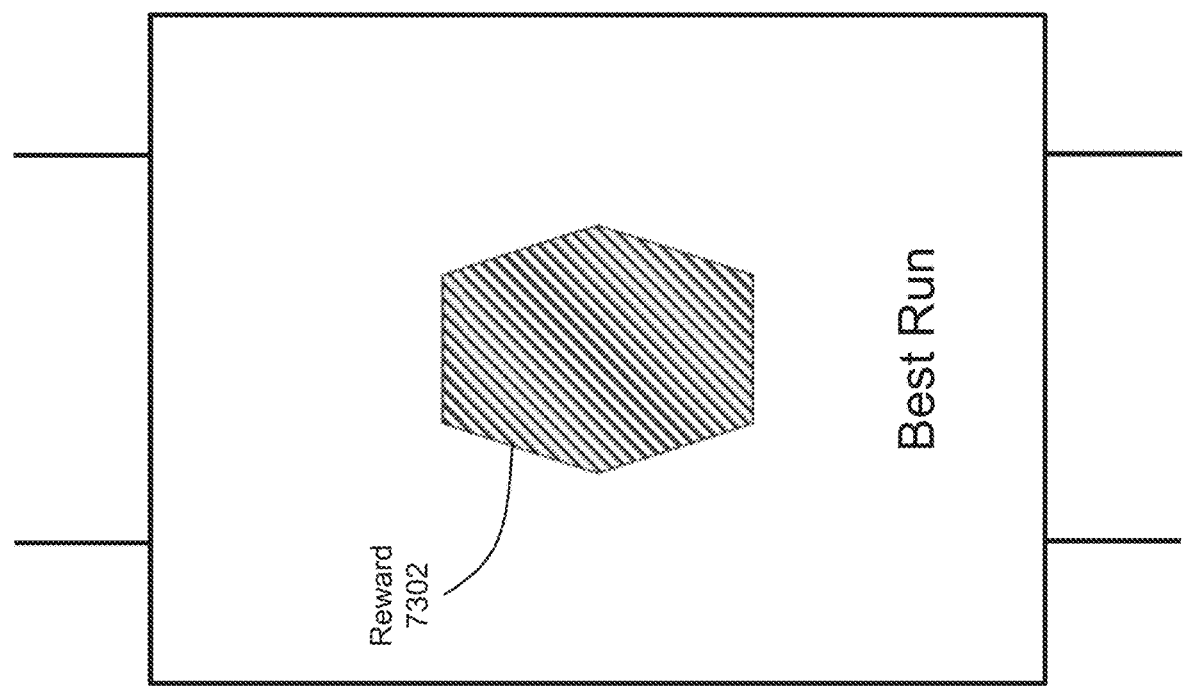
Figure 75:
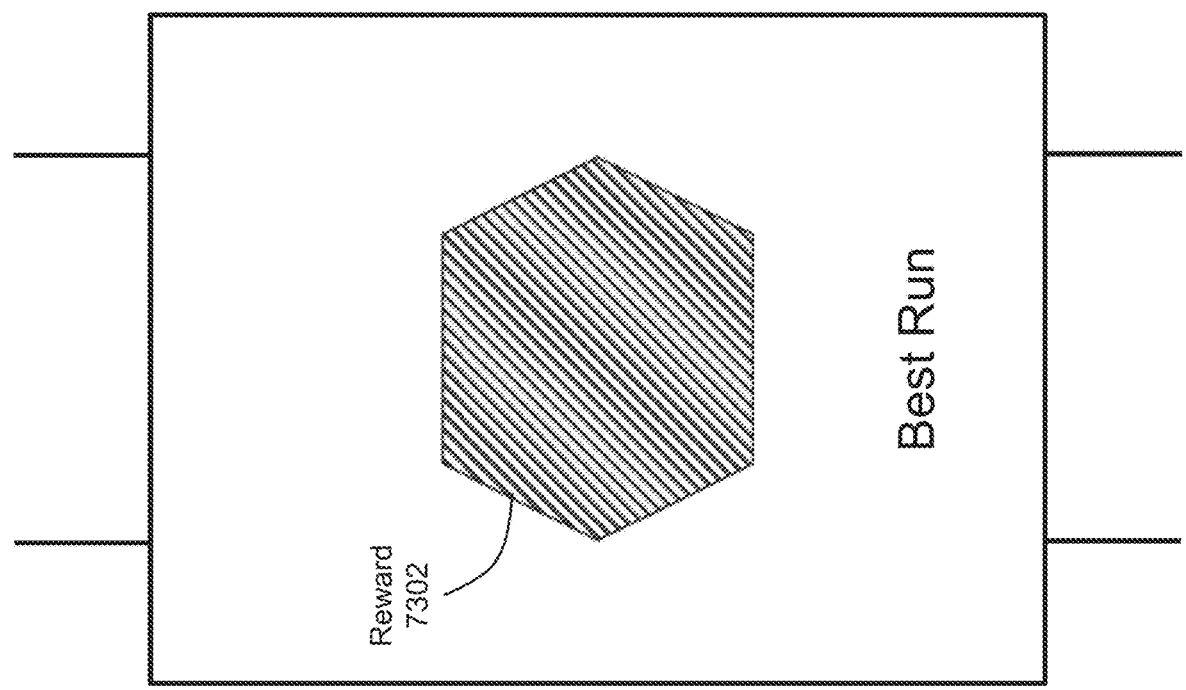

In some examples, additionally or alternatively to displaying the rewards in interface. 7200, the device can individually display one or more of the rewards. For example, FIGS. 73, 74, and 75 illustrate reward 7302 being presented to the user for the user achieving their best run. In the illustrated examples, reward 7302 is being animated on the display as being rotated into view until facing the user, as shown in FIG. 75. It should be appreciated that the rewards can be displayed and animated on the display in any other desired manner.

In some examples, the rewards and/or workout details can be shared with one or more other users or one or more social networks. In these examples, the rewards and/or workout details can be automatically shared or the user can be prompted to share individual achievements or workout details. The device can communicate the achievement or workout information directly to user devices associated with other users and/or servers for sharing on social networking websites using any wired or wireless technology (e.g., via a communication unit)

Achievement Sharing

Figure 76:
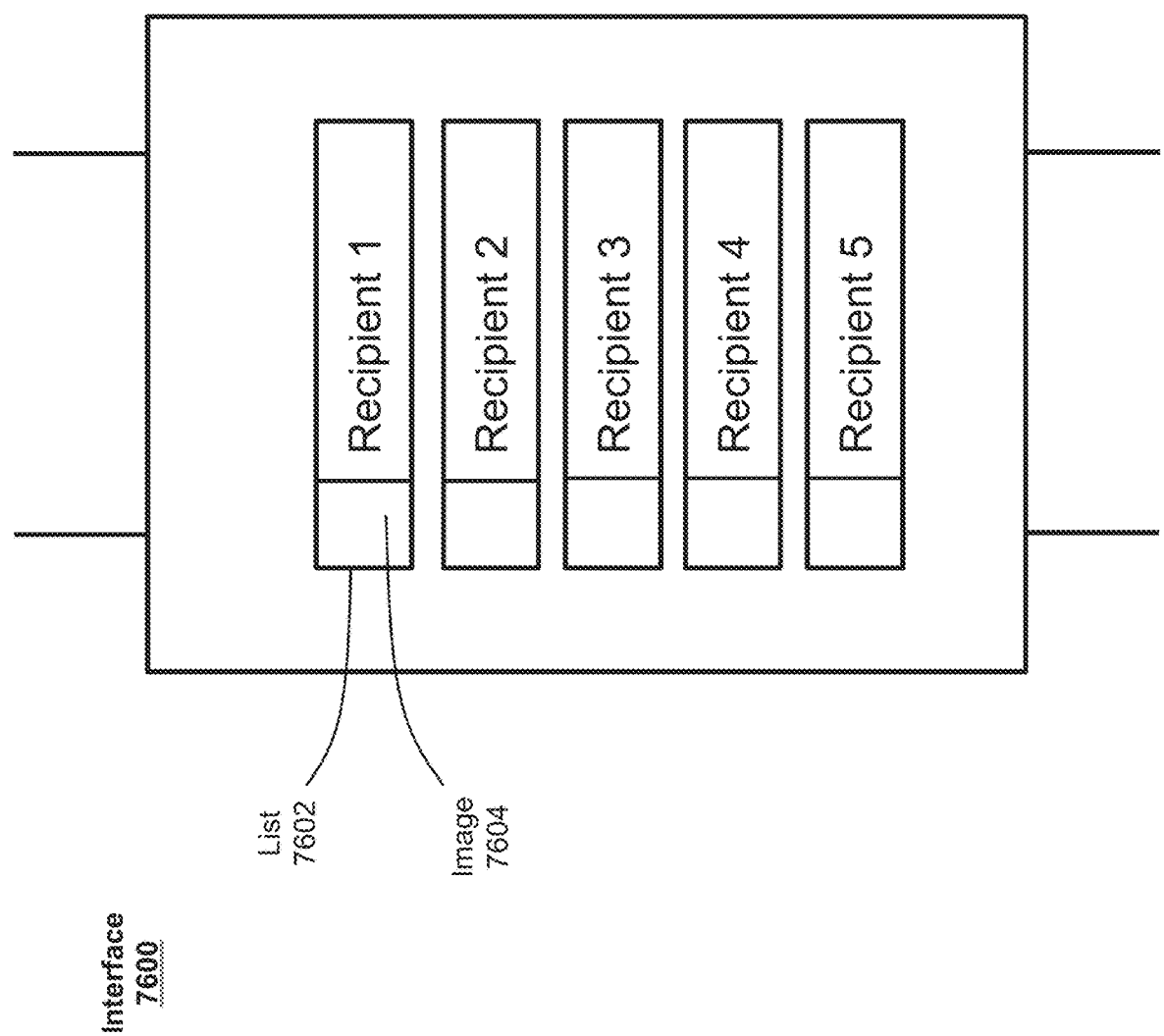
FIG. 76 illustrates an exemplary interface for sharing physical activity and/or workout information according to various examples.

FIG. 76 illustrates an example interface 7600 that can be displayed in response to a user request to share a workout (e.g., received while interface 7200 is displayed) or to share a reward (e.g., while interface 7300 is displayed). The request can include any type of user input, such as a button press, a user contact having a characteristic intensity above an intensity threshold on a display of the device, tap or swipe on a touch-sensitive display, or the like. As shown in FIG. 76, interface 7600 can include a list of potential recipients 7602 with which the user can share the reward or workout information. In some examples, list 7602 can include contacts from the user's contact list, social media services, combinations thereof, or the like. The recipients in the list can be based on a frequency that the user communicates with the recipient, a designation by the user that the recipient is a favorite, or the like. In some examples, one or more of the recipients in list 7602 can include a text description of the recipient (e.g., a name, phone number, email address, etc.) and/or an image representing the recipient (e.g., social media logo, picture of the recipient's face, etc.) In response to a selection of one or more of the recipients in list 7602, the device can communicate the selected reward and/or workout information to the selected recipients. In some examples when a reward is selected, an animated file can be transmitted to the recipient to allow the recipient to view the reward in a manner similar to that shown in FIGS. 73-75.

Figure 77:
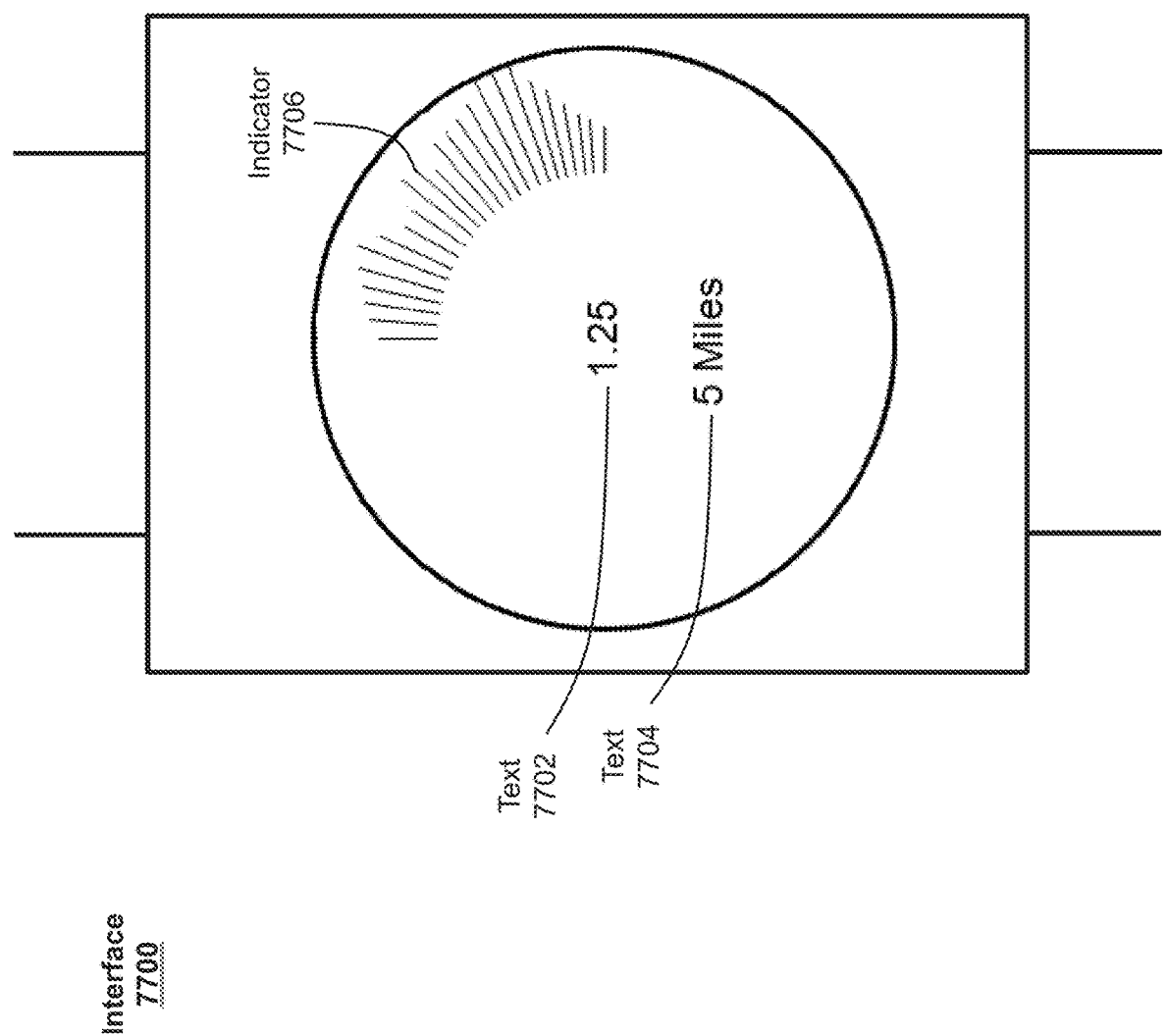
FIG. 77 illustrates an exemplary workout interface for monitoring a user's workout according to various examples.

While the examples described above are associated with tale running type of workout, it should be appreciated that similar interfaces can be displayed for other types of workouts. Additionally, while specific interfaces are shown and described, it should be appreciated that other interfaces can be used to display the recorded attributes of a user's workout. For example, FIG. 77 illustrates another exemplary interface 7700 that can be displayed in place of any of the interfaces shown in FIGS. 60-65. As shown, interface 7700 can include a text description 7702 of a current value of an attribute of the workout, a text description 7704 of the goal of the workout, and an indicator 7706 similar to indicator 6006 showing the user's progress towards the goal. For example, text description 7702 indicates that the user has traveled 1.25 miles and text description 7704 indicates that the user's goal is to travel 5 miles. Indicator 7706 is one-fourth complete, indicating that the user is 25% towards their goal. Additionally, indicator 7706 includes lines of varying length, where the length of each line represents and attribute of the user's physical activity at corresponding distances during the run. For example, the length of each line can indicate the user's running intensity (e.g., speed, number of Calories burned per unit time, etc.) at the various distances of the user's run. As the user continues to run, indicator 7706 can be completed in the clockwise direction using additional lines having varying lengths based on the user's running intensity.

In some examples, activity data received at block 4808 of process 4800 can also be used by the physical activity application to perform any of processes 1500 (e.g., at block 1504), 2200 (e.g., at block 2204), and 4000 (e.g., at block 4004). In this way, a workout monitored using the workout application performing process 4800 can be counted towards the physical activity attributes monitored by the physical activity application. In other words, the activity data corresponding to a workout monitored using process 4800 can also be used to update the values of the physical activity attributes being monitored by the physical activity application. For example, Calories expended during a running workout can be counted towards the Calories expended and represented by first portion 4102a in interface 4100. Similarly, the minutes spent running during the workout can be counted towards the minutes of physical activity over the threshold intensity represented by first portion 4104a in interface 4100.

Third Party Activity Data

In some examples, the electronic device performing process 1500, 2200, 4000, or 4800 can receive activity data from an activity sensor of another electronic device (e.g., another wearable electronic device, sensor 602, 604, 606, or 608, or user device 722 or 724) or from an application running on the electronic device other than the physical activity application or the workout application (e.g., one of sensor applications 613 or applications 617). Activity data from these sources can be referred to as "third party activity data." In some examples, in response to receiving third party activity data, the electronic device can determine whether or not to use the third party activity data to update the values of the physical activity attributes being monitored by the physical activity application. This can include determining whether the third party activity data represents a workout monitored using an application other than the workout application. If it is determined that the third party activity data represents a workout from an application other than the workout application, the electronic device can determine whether a workout monitored using the workout application (e.g., performing process 4800) exists during the same time as the third party activity data workout. If it is determined that the third party activity data represents a workout and that there is no workout monitored using the workout application (e.g., performing process 4800), the electronic device can use the third party physical activity data to update the physical activity attributes being monitored by the physical activity application. This can include performing any of processes 1500, 2200, and 4000 using the third party physical activity data as the physical activity received at blocks 1504, 2204, or 4004.

Figure 78:
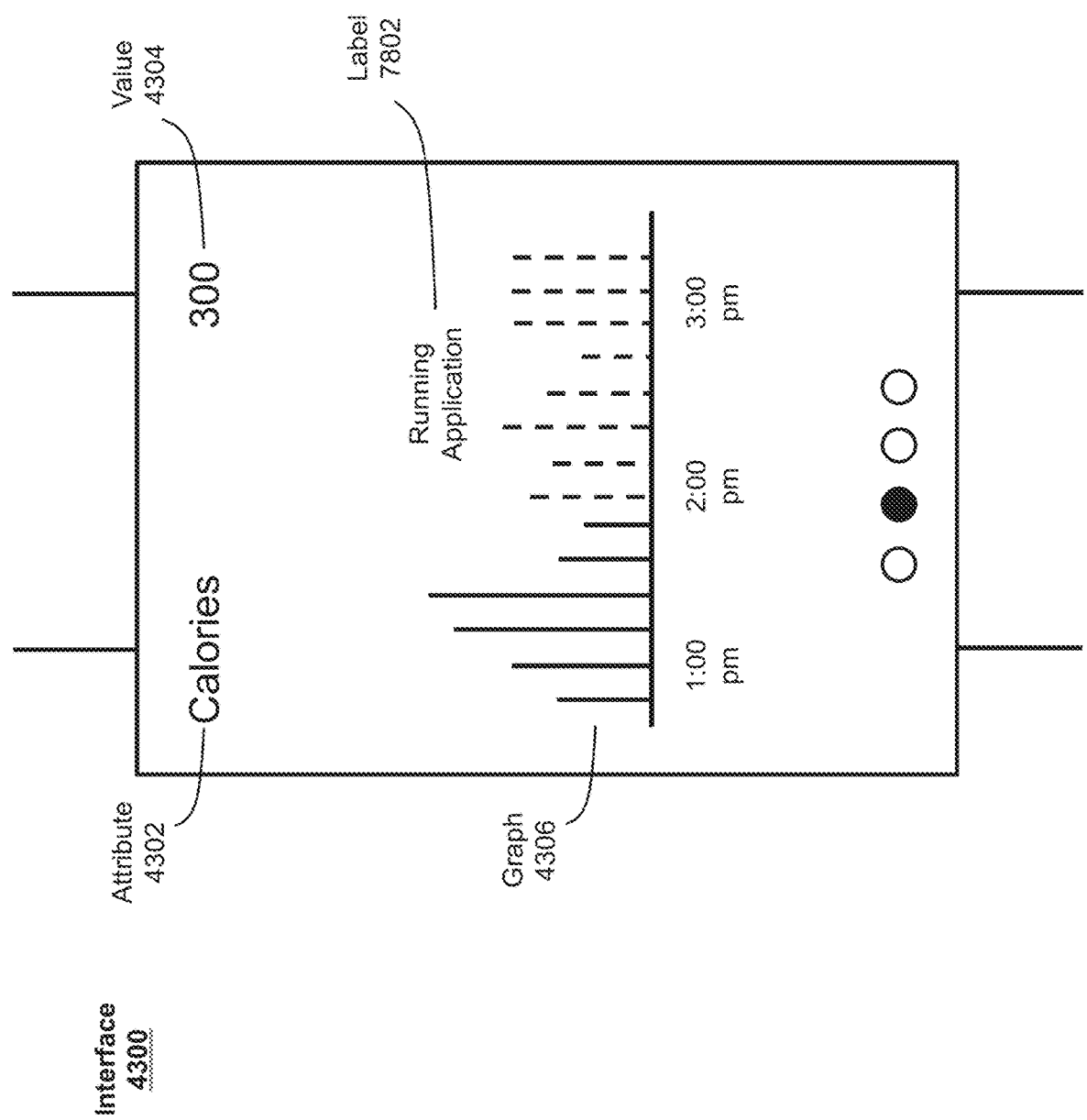
FIG. 78 illustrates an exemplary interface for displaying third party physical activity data according to various examples.

In some examples when third party physical activity data is used to update the physical activity attributes being monitored by the physical activity application, the electronic device can distinguish the third party physical activity data from physical activity data received from the physical activity application or the workout application. In some examples, this can be done by displaying portions (e.g., lines) of graph 4306 or 4506 in the detailed view of interface 4300 or 4500 in a different color if the activity data used to generate the portions includes third party physical activity data. For example, as shown in FIG. 78, if third party physical activity data is received for a running workout monitored using a third party running application that lasted from 2 p.m. to 3 p.m., the lines of graph 4306 in interface 4300 corresponding to 2 p.m. to 3 p.m. can be displayed in a different color. Additionally, a textual label 7802 identifying the source of the third party physical activity data can be displayed. In the illustrated example, label 7802 indicates that the source of the third party physical activity data is the "Running Application."

Aggregated View of Activity and Workout Data

As discussed above, the electronic device (e.g., device 100, 300, 500, or 610) can be configured to monitor attributes of a user's physical activity and/or workouts performed by the user using process 1500, 2200, 4000, or 4800. In some examples, data representing the monitored physical activity or workouts can be transmitted by the electronic device to another user device (e.g., user device 722 or 724) or to a remote database (e.g., database 716) to allow the data to be viewed by the other user device. In some examples, the other user device can present the data representing the monitored physical activity or workouts using the same interfaces as used by the electronic device (e.g., interfaces shown in FIGS. 17-21, 23, 25-39, 41-47, and 50-77), or can present the data using different interfaces.

Figure 79:
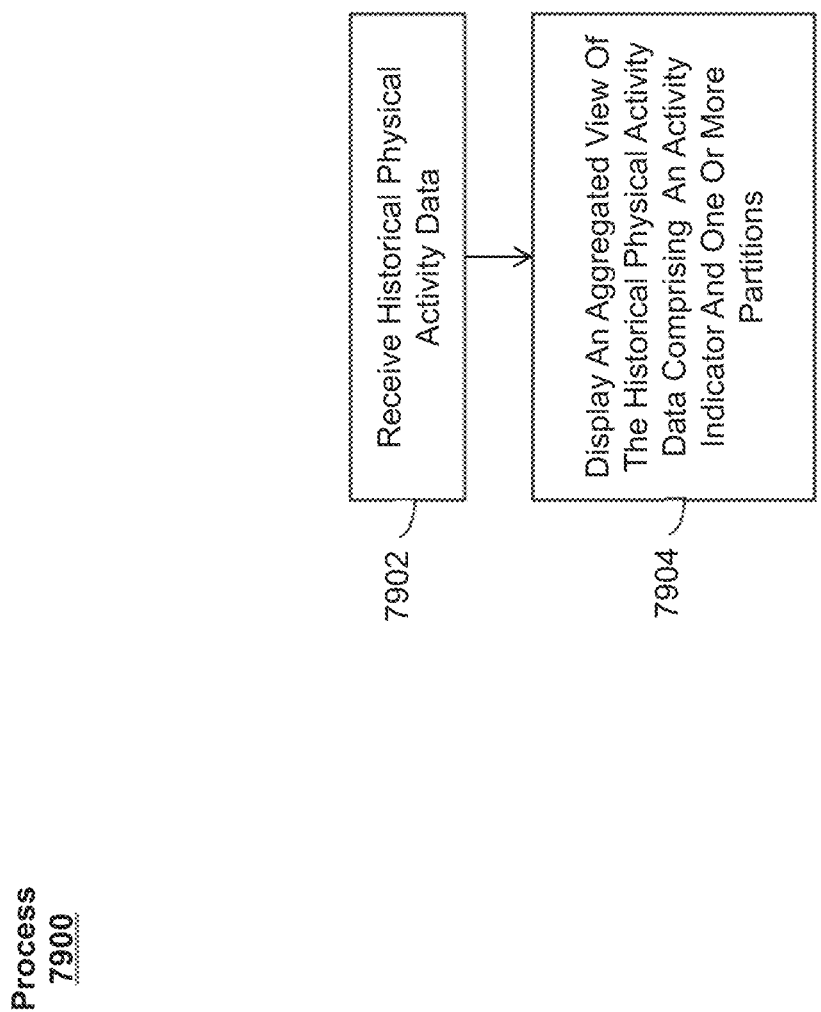
FIG. 79 illustrates an exemplary process for displaying an aggregated view of historical physical activity data according to various examples.

FIG. 79 illustrates an example process 7900 for displaying data representing a user's physical activity and/or workouts according to various examples. In some examples, process 7900 can be performed by an electronic device similar to user device 722 or 724, such as a mobile phone, tablet computer, laptop computer, desktop computer, or the like. At block 7902, the electronic device can receive historical physical activity data from another electronic device (e.g., device 100, 300, 500, or 610) or from a remote database (e.g., user database 716). The historical activity data can include attributes of a user's physical activity from one or more days monitored using a process similar to process 1500, 2200, or 4000 and/or attributes of one or more of the user's workouts monitored using a process similar to process 4800. The historical physical activity data can include any of the physical activity data received from the physical activity sensors, values of the physical activity and workout attributes, summaries of the physical activity and workouts, or the like. Some operations in process 7900 may be combined, the order of some operations may be changed, and some operations may be omitted.

As described below, process 7900 provides intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

Figure 80:
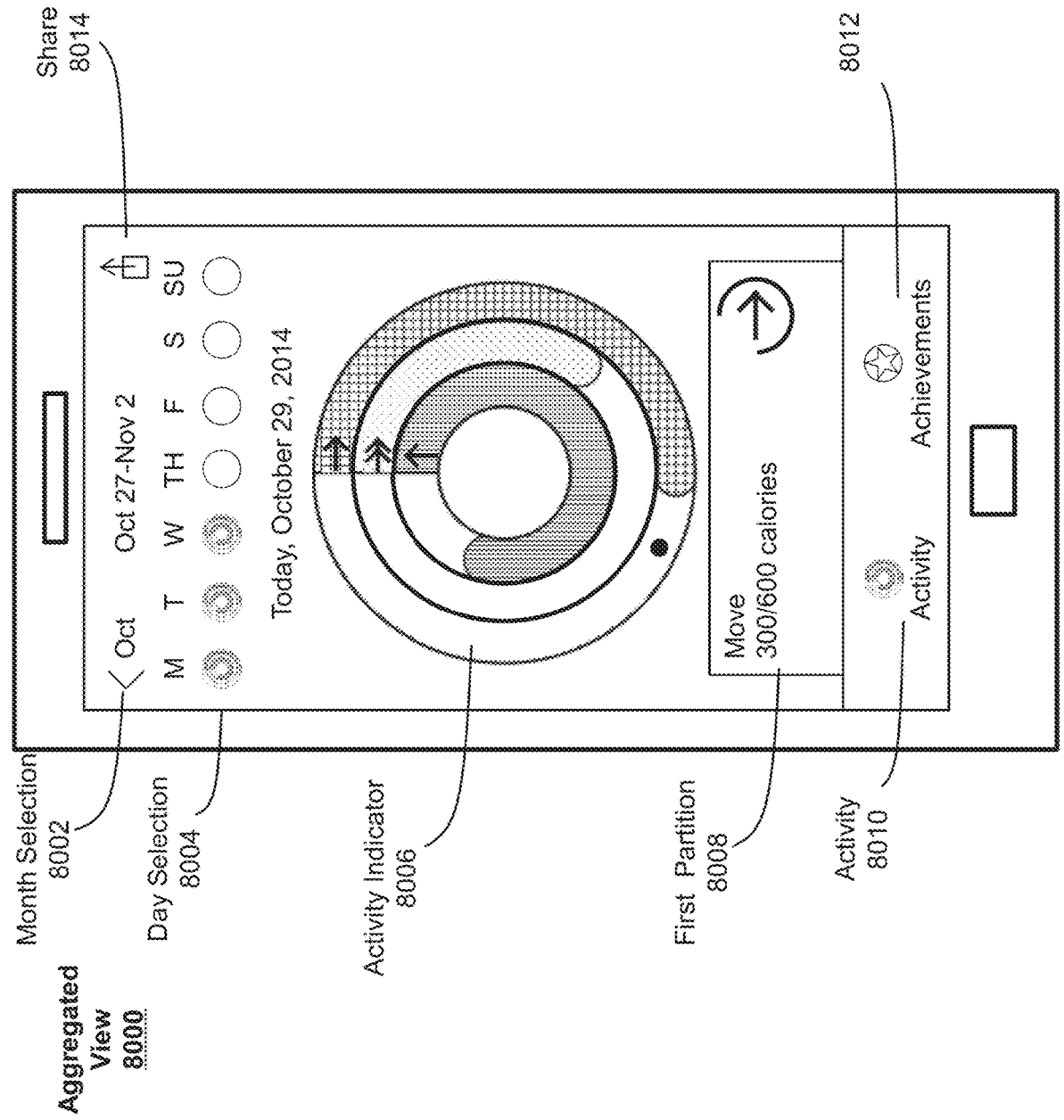
FIGS. 80-85 illustrate exemplary aggregated views of historical physical activity data according to various examples.

At block 79114, the electronic device can display an aggregated view of the historical physical activity data. FIG. 80 illustrates an example daily aggregated view 8000 that can be displayed by the electronic device at block 7904. As shown, aggregated view 8000 can include month selection button 8002, day selection buttons 8004, activity interface button 8010, achievement interface button 8012, and share button 8014. Aggregated view 8000 can further include activity indicator 8006 and first partition 8008 representing physical activity data corresponding to the day selected using day selection buttons 8004 (Oct. 29, 2014). Activity indicator 8006 can be similar to the activity indicator shown in FIG. 41. For example, activity indicator 8006 can include concentric rings, with the outer ring representing a daily number of active Calories expended, the center ring representing a daily number of minutes spent performing physical activity above a physical activity threshold (e.g., an intensity above a brisk walk or 3 METs), and the inner ring can represent a number of hours in the day during which the user stood for at least 60 seconds within a 90 second segment of time. Also shown in aggregated view 8000 is a portion of first partition 8008, which can include additional information associated with the physical activity data represented by the outer ring of activity indicator 8006.

Note that details of the processes described above with respect to process 7900 (e.g., FIG. 79) are also applicable in an analogous manner to the other processes described herein. For example, processes 1500, 1600, 2200, 2400, 4000, 4800, 8600, and 9200 may include one or more of the characteristics of the various methods described above with reference to processes 7900. For example, the activity data, activity types, displayed values and other elements described above with reference to processes 7900 optionally have one or more of the characteristics of the activity data, activity types, displayed values and other elements described herein (e.g., processes 1500, 1600, 4000, 4800, 2200, 2400, 4000, 8600, and 9200). For brevity, these details are not repeated.

Figure 81:
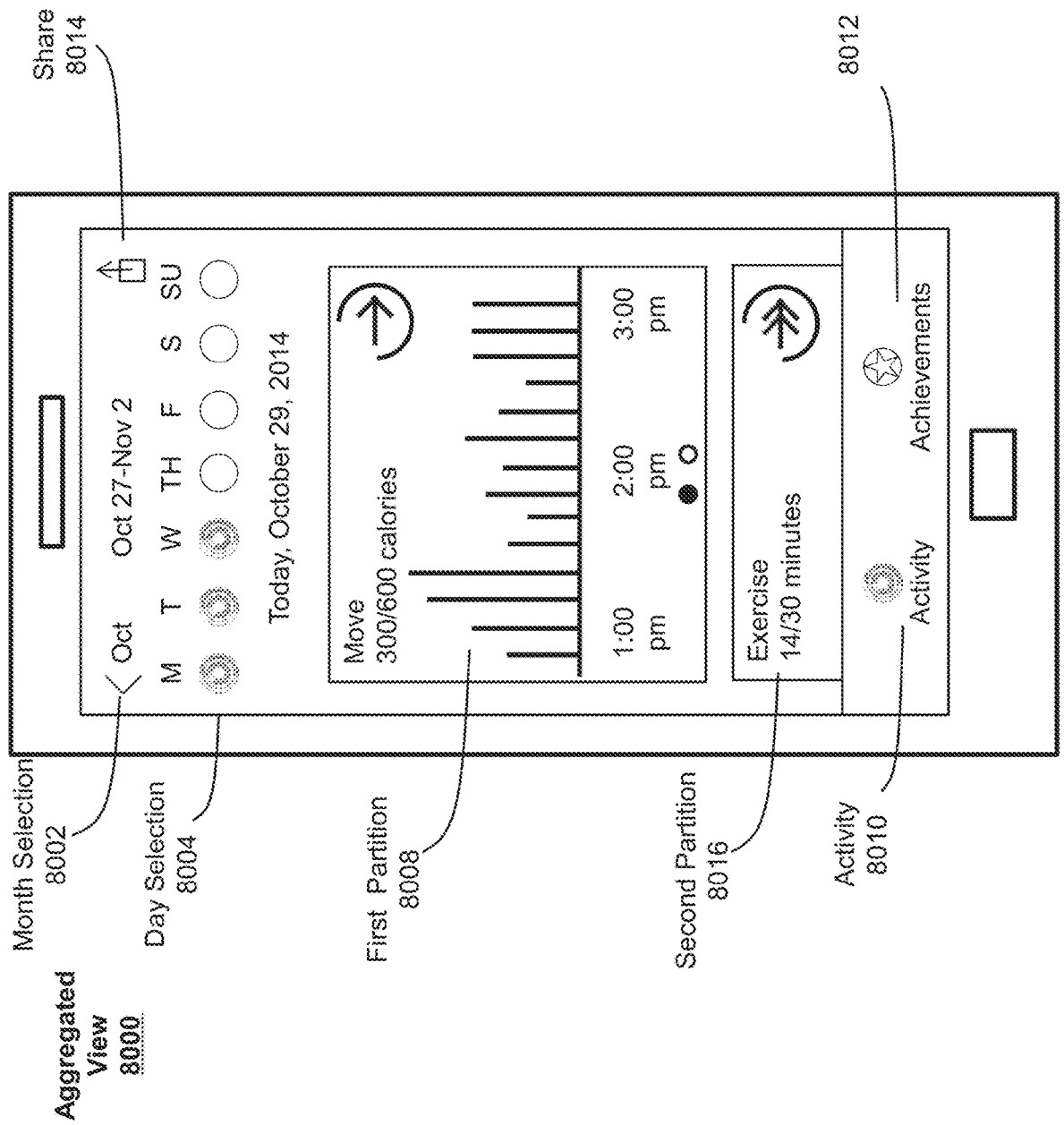

FIG. 81 shows another view of aggregated view 8000 that can be displayed in response to a request by the user to perform a scrolling operation (e.g., by performing a swiping gesture from the bottom to the top of the touch-sensitive display) while the view shown in FIG. 80 is displayed. As shown, the entirety of first partition 8008 can be displayed and, similar to interface 4300, can include a textual description of the contents of the partition ("Move"), a numerical summary of the associated physical activity data ("300/600 Calories"), a visual indicator representative of the type of the associated physical activity data (right-facing arrow that matches the visual indicator on the outer ring of activity indicator 8006), and a graphical representation of the physical activity data. Also shown in aggregated view 8000 is a portion of second partition 8008, which can include additional information associated with the physical activity data represented by the center ring of activity indicator 8006.

Figure 82:
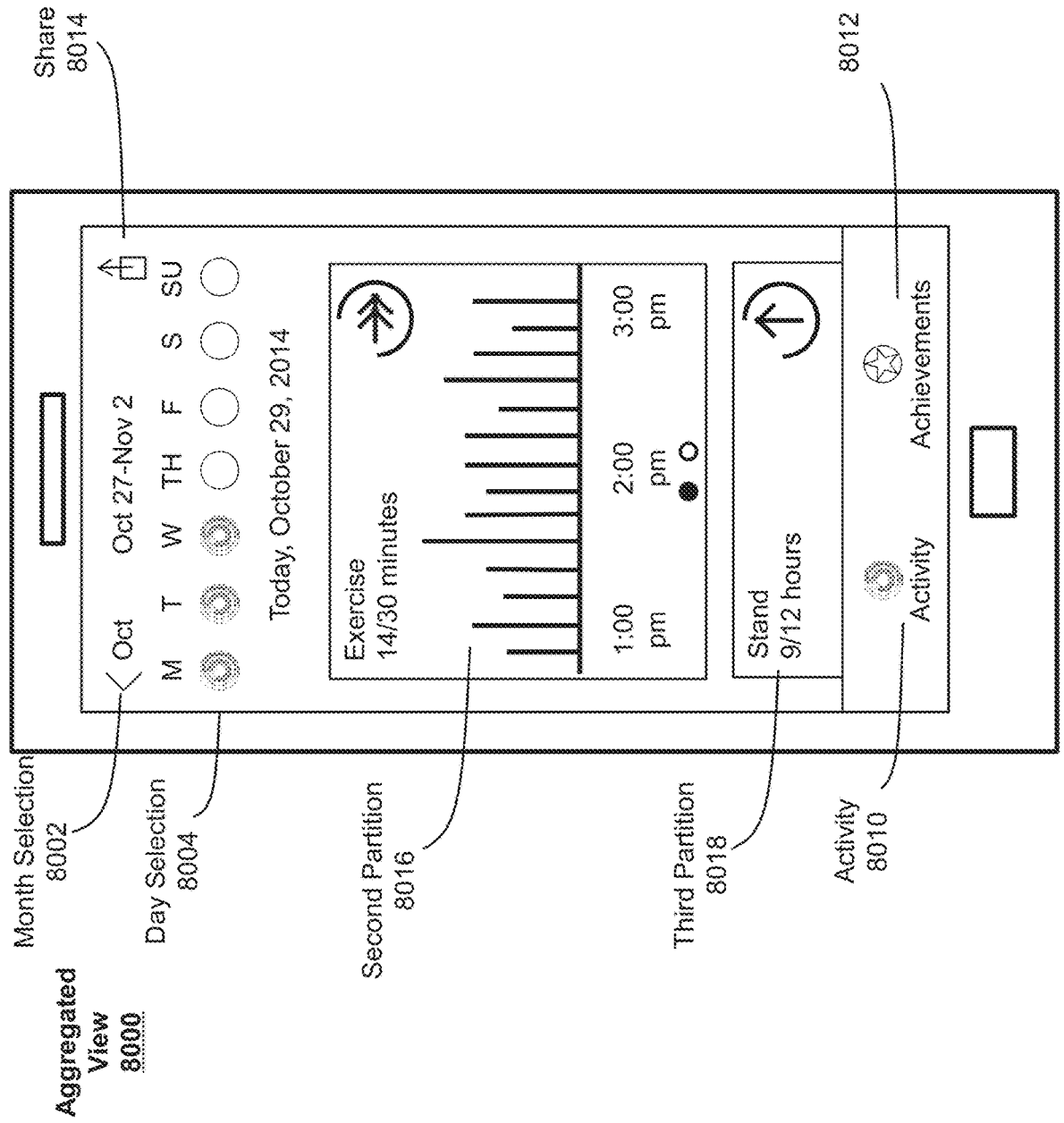

FIG. 82 shows another view of aggregated view 8000 that can be displayed in response to a request by the user to perform a scrolling operation (e.g., by performing a swiping gesture from the bottom to the top of the touch-sensitive display) while the view shown in FIG. 81 is displayed. As shown, the entirety of second partition 8016 can be displayed and, similar to interface 4500, can include a textual description of the contents of the partition ("Exercise"), a numerical summary of the associated physical activity data ("14/30 minutes"), a visual indicator representative of the type of the associated physical activity data (double right-facing arrow that matches the visual indicator on the center ring of activity indicator 8006), and a graphical representation of the physical activity data. Also shown in aggregated view 8000 is a portion of third partition 8018, which can include additional information associated with the physical activity data represented by the inner ring of activity indicator 8006.

Figure 83:
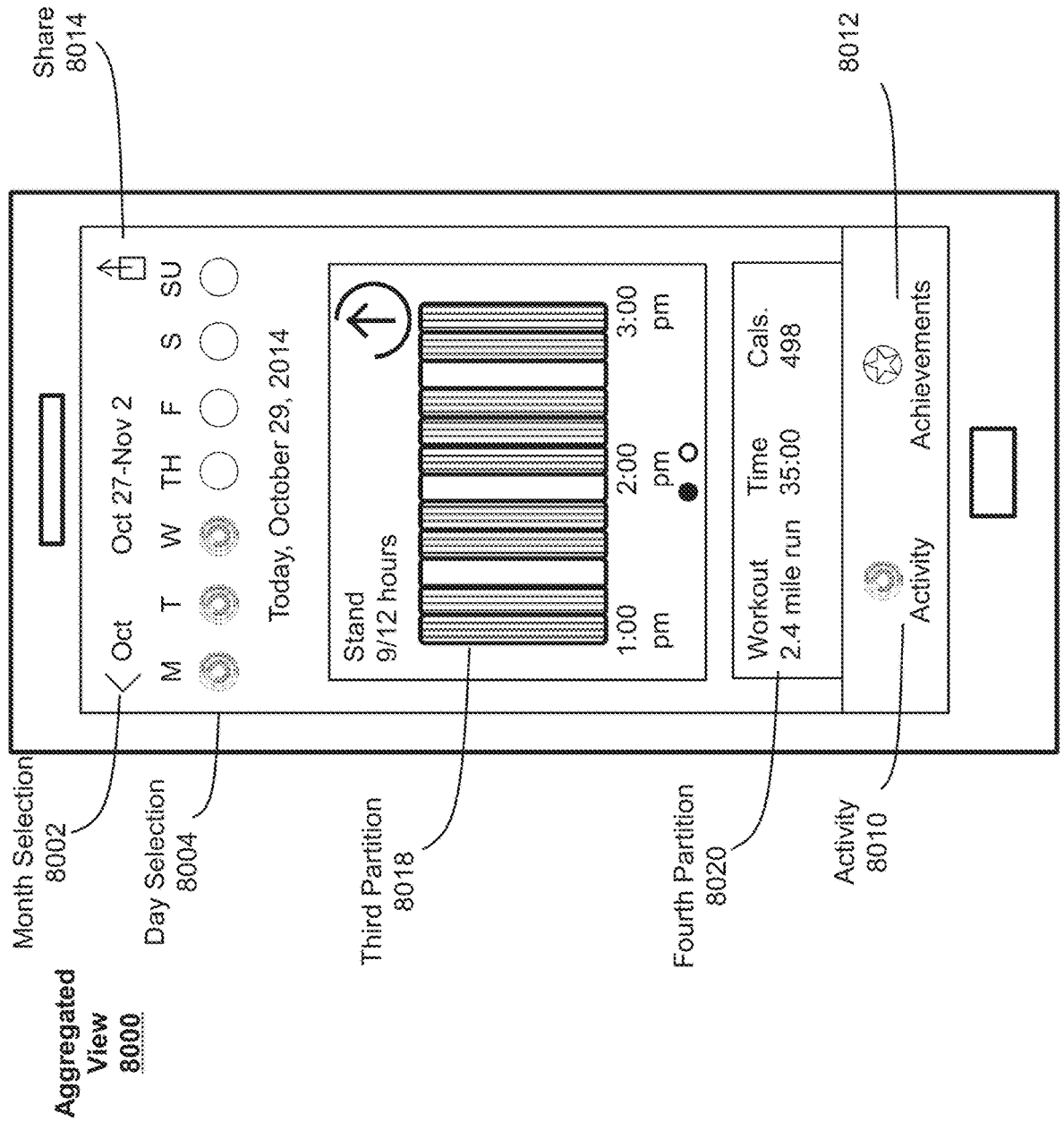

FIG. 83 shows another view of aggregated view 8000 that can be displayed in response to a request by the user to perform a scrolling operation (e.g., by performing a swiping gesture from the bottom to the top of the touch-sensitive display) while the view shown in FIG. 82 is displayed. As shown, the entirety of third partition 8018 can be displayed and, similar to interface 4700, can include a textual description of the contents of the partition ("Stand"), a numerical summary of the associated physical activity data ("9/12 hours"), a visual indicator representative of the type of the associated physical activity data (upward-facing arrow that matches the visual indicator on the inner ring of activity indicator 8006), and a graphical representation of the physical activity data. Also shown in aggregated view 8000 is a portion of fourth partition 8020, which can include information associated with a recorded workout.

Figure 84:
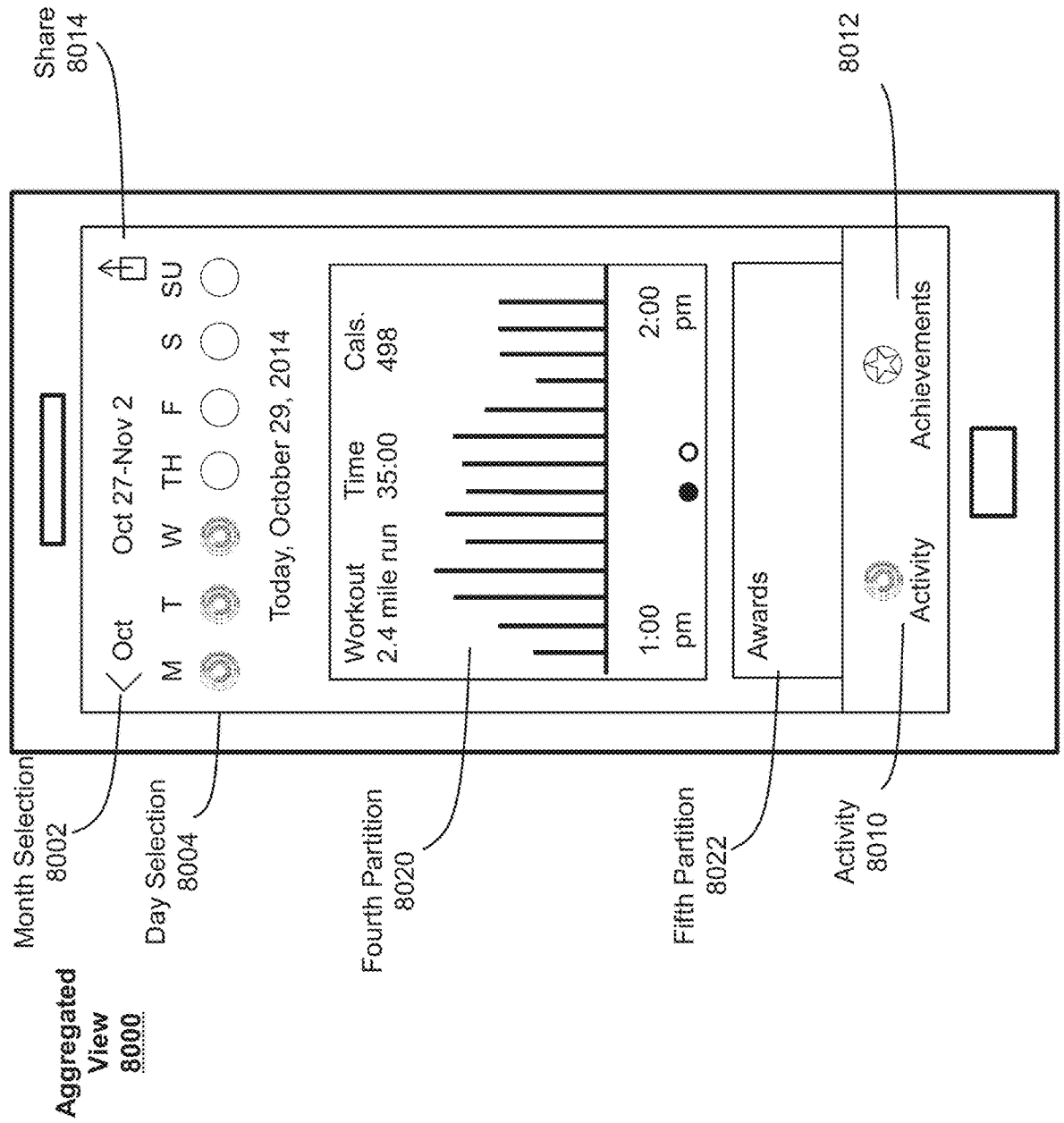

FIG. 84 shows another view of aggregated view 8000 that can be displayed in response to a request by the user to perform a scrolling operation (e.g., by performing a swiping gesture from the bottom to the top of the touch-sensitive display) while the view shown in FIG. 83 is displayed. As shown, the entirety of fourth partition 8020 can be displayed and can include a textual description of the contents of the partition ("Workout"), a numerical summary of the workout ("2.4 mile run," "35:00," 498"), a visual indicator representative of the type of the associated physical activity data (upward-facing arrow that matches the visual indicator on the inner ring of activity indicator 8006), and a graphical representation of an attribute of the workout. Also shown in aggregated view 8000 is a portion of fifth reward partition 8022, which can include information associated with one or more rewards earned by the user.

Figure 85:
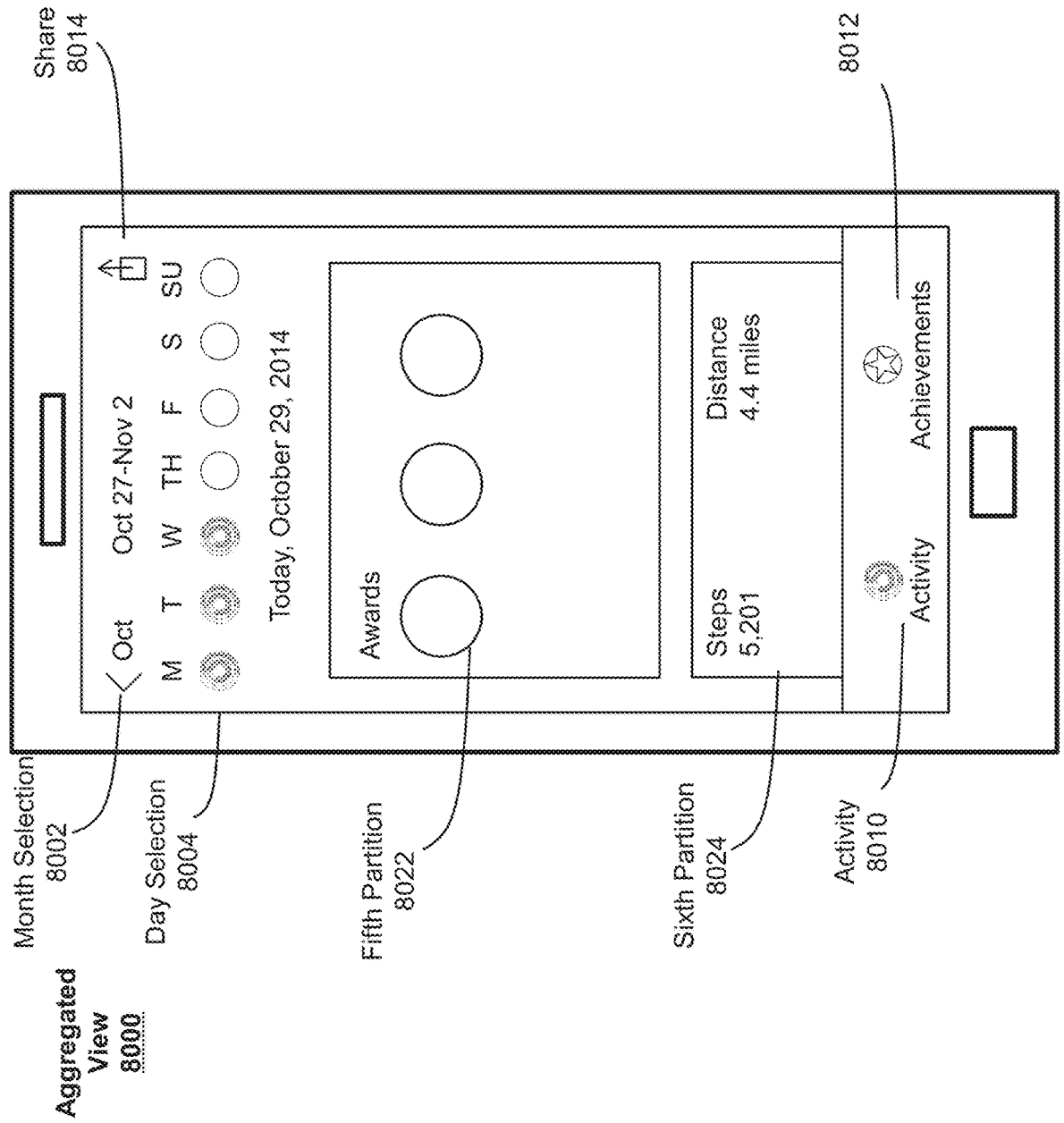

FIG. 85 shows another view of aggregated view 8000 that can be displayed in response to a request by the user to perform a scrolling operation (e.g., by performing a swiping gesture from the bottom to the top of the touch-sensitive display) while the view shown in FIG. 84 is displayed. As shown, the entirety of fifth partition 8022 can be displayed and can include a textual description of the contents of the partition ("Awards") and a visual representation of one or more awards earned by the user. The visual representation of the one or more rewards can match the rewards presented to the user in the interfaces shown in FIGS. 72-75. Also shown in aggregated view 8000 is a portion of sixth summary partition 8024, which can include summary information of the user's daily physical activity.

In some examples, third party physical activity data can be used to generate the historical physical activity data shown in aggregated view 8000. In these examples, the third party physical activity data can be distinguished from physical activity data received, from the physical activity application or the workout application within aggregated view 8000. For example, this can be accomplished by displaying portions (e.g., lines) of the graphs shown in partitions 8008, 8016, 8018, or 8020 in a different color if the activity data used to generate the portions includes third party physical activity data in a manner similar to that shown in FIG. 78, discussed above. Additionally, a textual label identifying the source of the third party physical activity data can be displayed alongside the identified portions of the graphs corresponding to the third party physical activity data.

Figure 86:
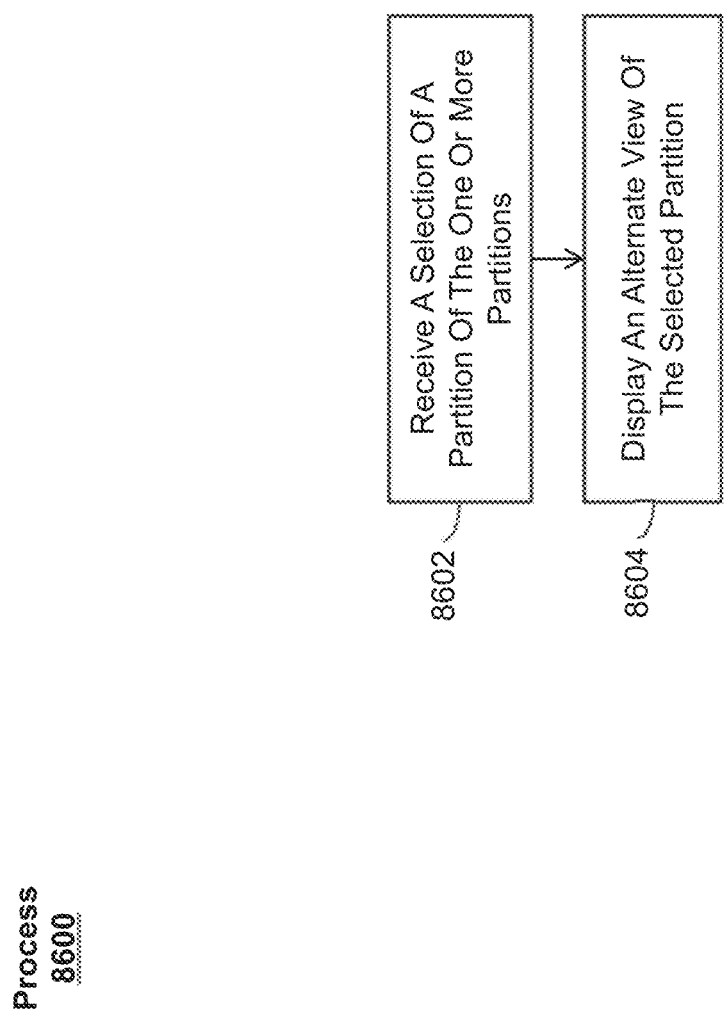
FIG. 86 illustrates an exemplary process for displaying an aggregated view of historical physical activity data according to various examples.
Figure 87:
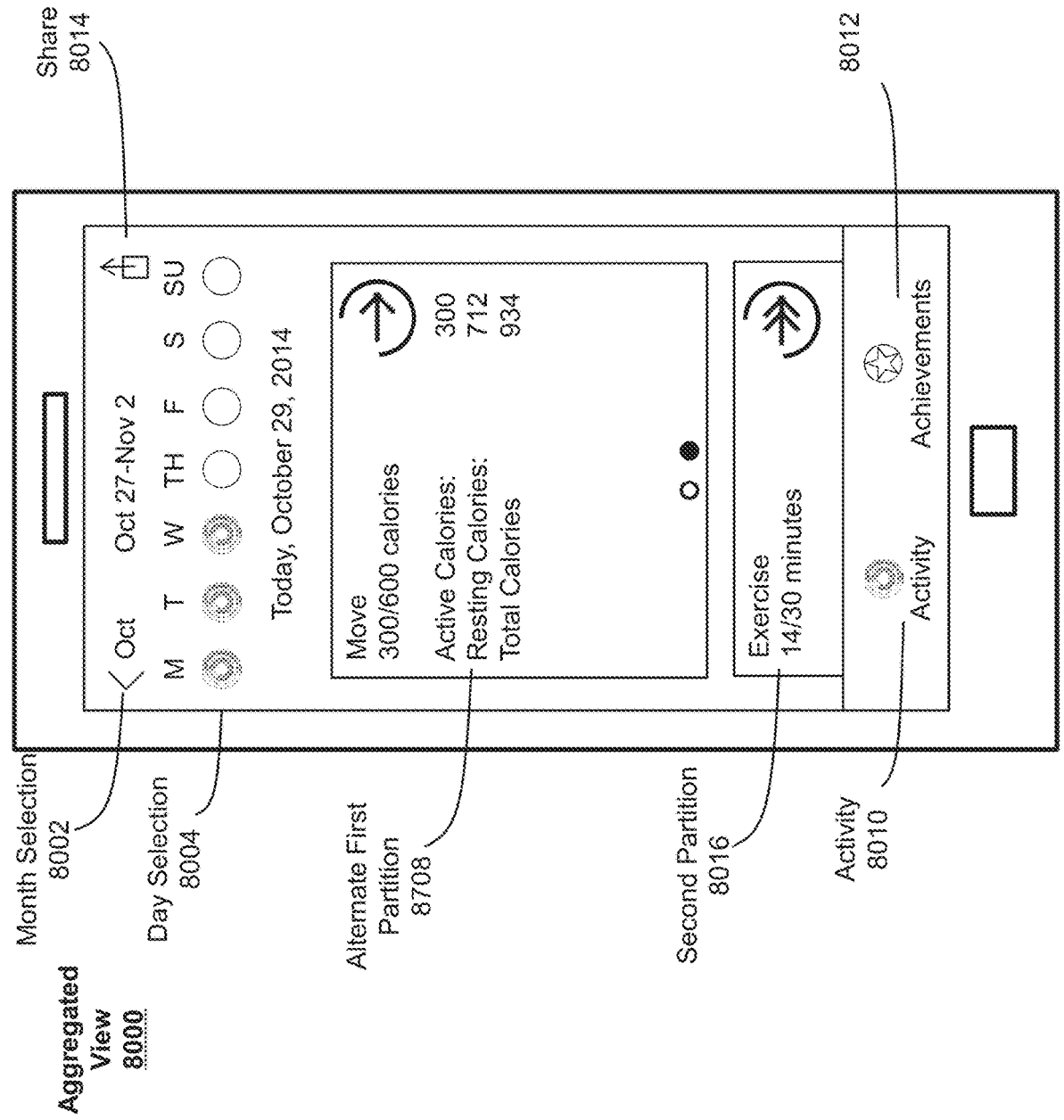
FIGS. 87 and 88 illustrate exemplary aggregated views of historical physical activity data according to various examples.
Figure 88:
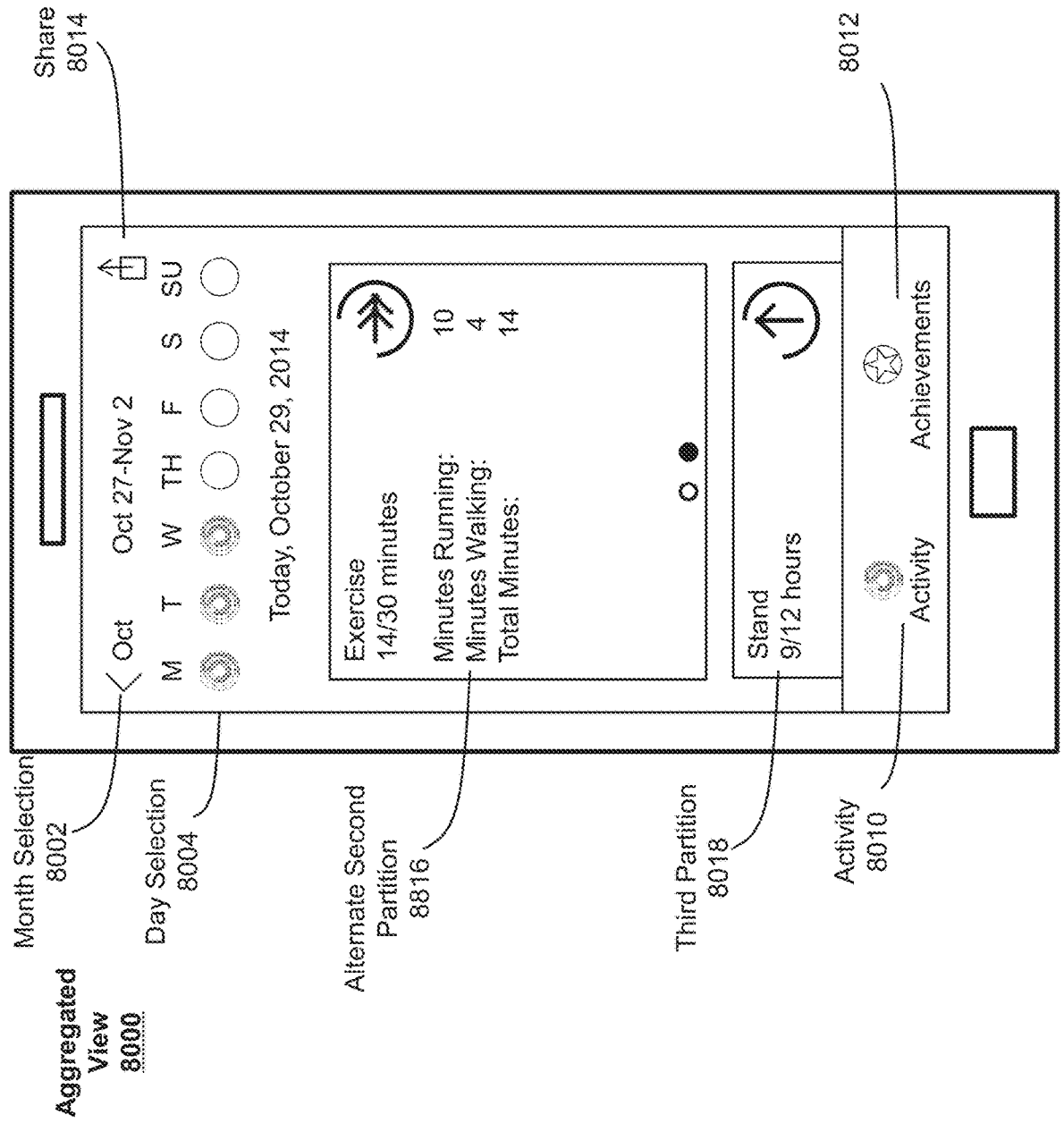

In some examples, some or all of the partitions shown in aggregated view 8000 can be selected by a user, causing the electronic device to display an alternate view of the selected partition that displays the information contained in the selected partition in a different way and/or contains additional or different information associated with the type of physical activity data associated with the selected partition. FIG. 86 illustrates an exemplary process 8600 for displaying an alternate view of a partition that can be performed after process 7900 by an electronic device similar to user device 722 or 724, such as a mobile phone, tablet computer, laptop computer, desktop computer, or the like. At block 8602, a selection of a partition of the aggregated view can be received. The selection can be made by a touch on a touch-sensitive display, a user contact having a characteristic intensity above an intensity threshold on a display of the device, a swipe gesture performed across the touch-sensitive display, or the like. For example, a selection of partition 8008 can be received by detecting a swipe gesture from right to left across first partition 8008 of aggregated view 8000, shown in FIG. 81. Some operations in process 8600 may be combined, the order of some operations may be changed, and some operations may be omitted.

As described below, process 8600 provides intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 8604, an alternate view of the selected partition can be displayed. Continuing with the example above, in response to detecting the swipe gesture from right to left across first partition 8008 of aggregated view 8000, shown in FIG. 81, an alternate first partition 8708, shown in FIG. 87, can be displayed. Similar to first partition 8008, alternate first partition 8708 can include a textual description of the contents of the partition ("Move"), a numerical summary of the associated physical activity data ("300/600 Calories"), and a visual indicator representative of the type of the associated physical activity data (right-facing arrow that matches the visual indicator on the outer ring of activity indicator 8006). Additionally, alternate first partition 8708 can include additional information in the form of a detailed breakdown of the user's daily Calorie expenditure. While specific example information that can be included in alternate first partition 8708 is provided, it should be appreciated that any other type of information can instead by display. First partition 8008 can again be displayed in response to a swipe gesture performed across alternate first partition 8708 from left to right.

Note that details of the processes described above with respect to process 8600 (e.g., FIG. 86) are also applicable in an analogous manner to the other processes described herein. For example, processes 1500, 1600, 2200, 2400, 4000, 4800, 7900, and 9200 may include one or more of the characteristics of the various methods described above with reference to processes 8600. For example, the activity data, activity types, displayed values and other elements described above with reference to processes 8600 optionally have one or more of the characteristics of the activity data, activity types, displayed values and other elements described herein (e.g., processes 1500, 1600, 2200, 2400, 4000, 4800, 7900, and 9200) For brevity, these details are not repeated.

In some examples, alternate views of other partitions of aggregate view 8000 can be displayed in response to a selection similar to that described above for first partition 8008. For example, in response to detecting a swipe gesture from right to left across second partition 8016 of aggregated view 8000, shown in FIG. 82, an alternate second partition 8816, shown in FIG. 88, can be displayed. Similar to second partition 8016, alternate second partition 8816 can include a textual description of the contents of the partition ("Exercise"), a numerical summary of the associated physical activity data ("14/30 minutes"), and a visual indicator representative of the type of the associated physical activity data (double right-facing arrow that matches the visual indicator on the center ring of activity indicator 8006). Additionally, alternate second partition 8816 can include additional information in the form of a detailed breakdown of the user's daily exercise minutes. While specific example information that can be included in alternate second partition 8816 is provided, it should be appreciated that any other type of information can instead by display. Second partition 8016 can again be displayed in response to a swipe gesture performed across alternate second partition 8816 from left to right. Similar alternate views can be displayed for any of the other partitions and can include any desired information formatted in any desired manner.

In some examples, in response to a selection of a different day selection button 8004, activity indicator 8006 and partitions 8008, 8016, 8018, 8020, 8022, and 8024 can be replaced with an activity indicator and partitions that reflect the historical physical activity data corresponding to the selected day. For example, in response to a user selection of "T" from day selection buttons 8004, an activity indicator and partitions representing the historical physical activity data from Oct. 28, 2014 can be displayed.

Figure 89:
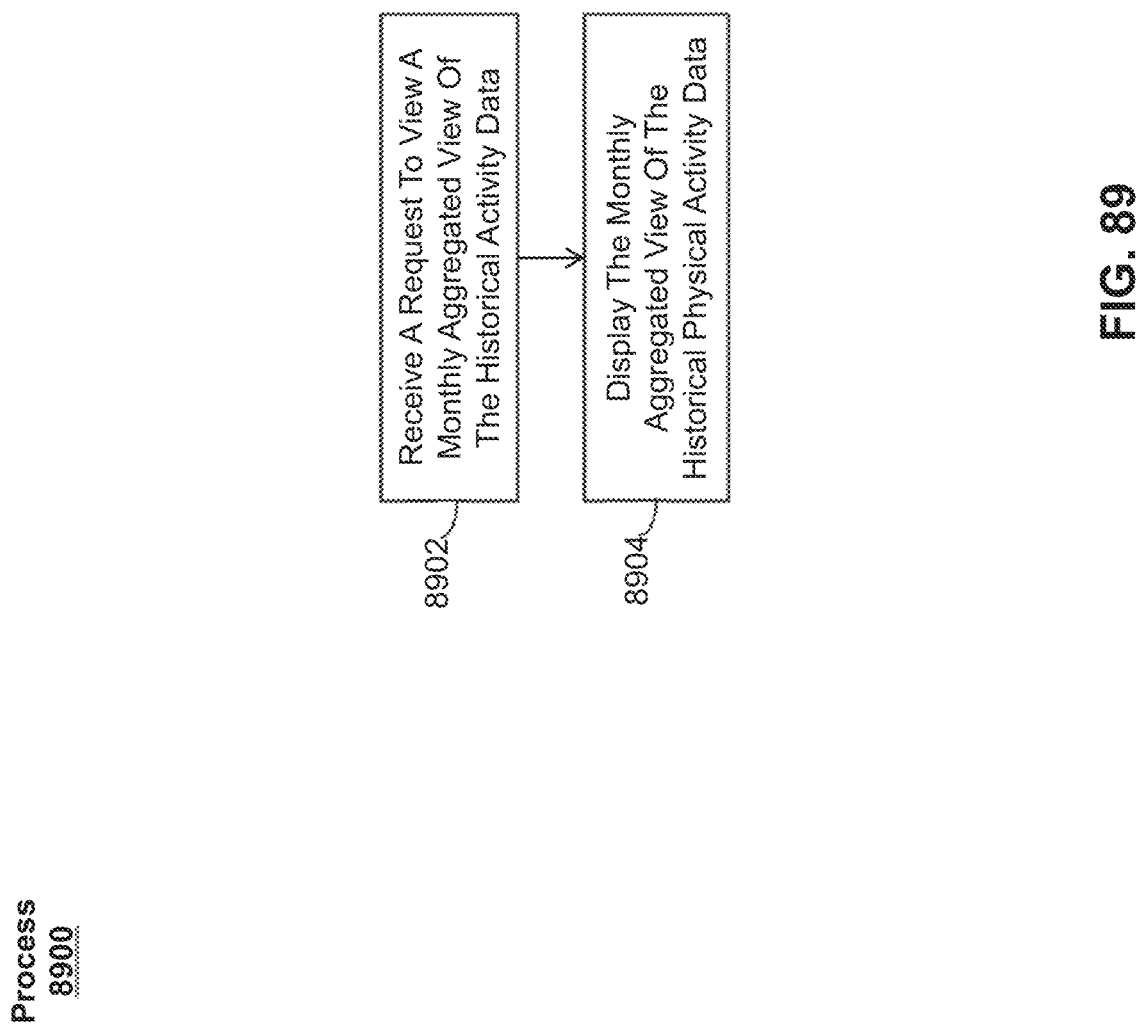
FIG. 89 illustrates an exemplary process for displaying a monthly aggregated view of historical physical activity data according to various examples.
Figure 90:
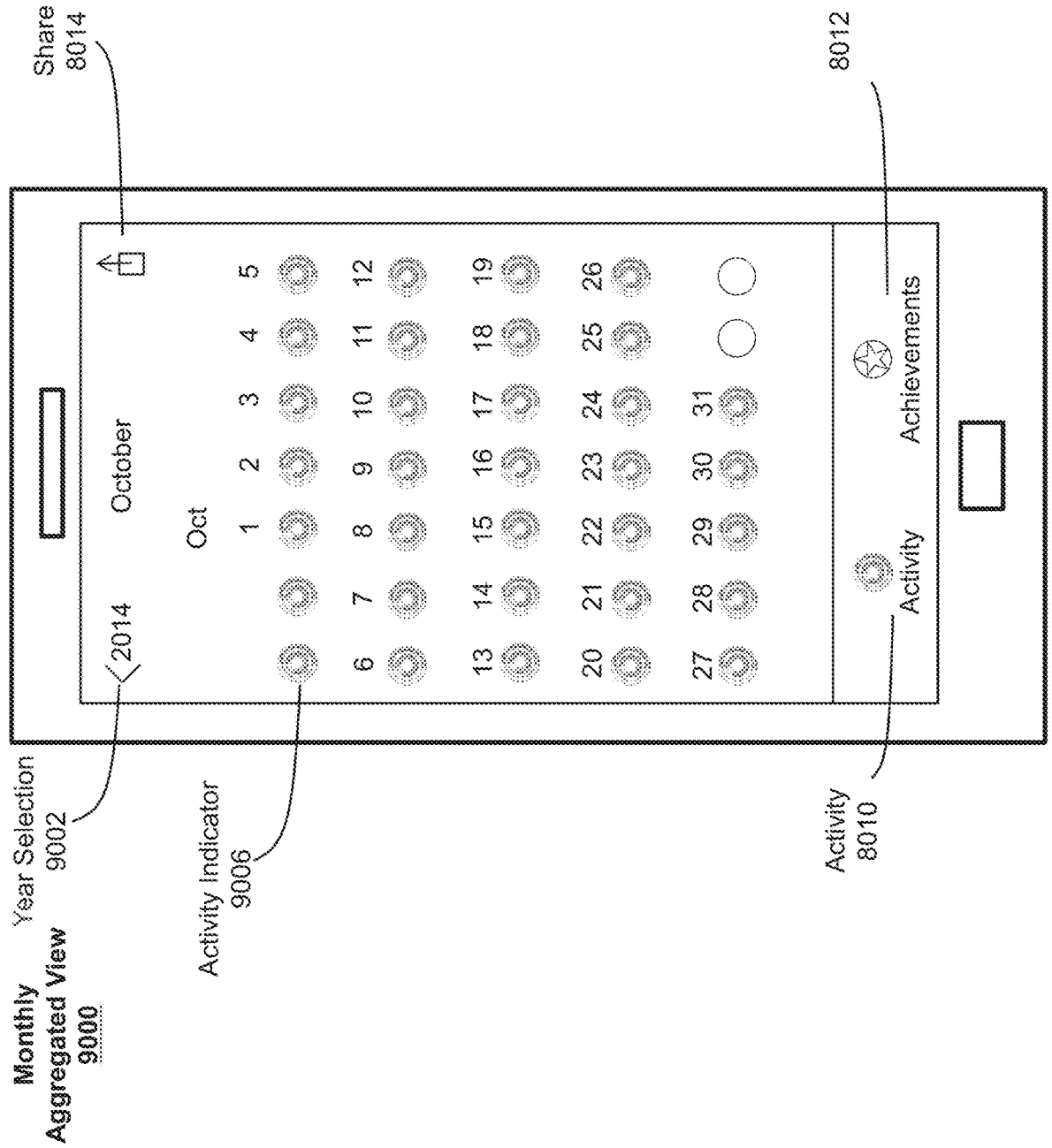
FIGS. 90 and 91 illustrate exemplary monthly aggregated view of historical physical activity data according to various examples.

In some examples, the electronic device can display the historical physical activity data in different ways. For example, FIG. 89 illustrates an exemplary process 8900 that can be performed after process 7900 by an electronic device similar to user device 722 or 724 to display a user's historical physical activity data by month. Some operations in process 8900 may be combined, the order of some operations may be changed, and some operations may be omitted.

As described below, process 8900 provides intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 8902, a request to view a monthly aggregated view of the historical physical activity data can be received. In some examples, the request can be made by a selection of month selection button 8002 in aggregated view 8000. At block 8904, the electronic device can display the monthly aggregated view of the historical physical activity data. In some examples, the electronic device can display a monthly aggregated view similar to monthly aggregated view 9000, shown in FIG. 90. As illustrated, monthly aggregated view 9000 can include year selection button 9002 for selecting a different month to view, activity interface button 8010, achievement interface button 8012, and share button 8014. Monthly aggregated view 9000 can further include an activity indicator 9006 for each of the days of the presently selected month (October). Activity indicator 9006 can be similar to activity indicator 8006 and the activity indicator shown in FIG. 41 and can reflect the values of the represented physical activity attributes. In some examples, each activity indicator 9006 can include concentric rings, with the outer ring representing a daily number of active Calories expended, the center ring representing a daily number of minutes spent performing physical activity above a physical activity threshold (e.g., an intensity above a brisk walk or 3 METs), and the inner ring can represent a number of hours in the day during which the user stood for at least 60 seconds within a 90 second segment of time on the corresponding day. Monthly aggregated view 9000 advantageously allows a user to quickly view the amount of physical activity performed each day during the month.

Note that details of the processes described above with respect to process 8900 (e.g., FIG. 89) are also applicable in an analogous manner to the other processes described herein. For example, processes 1500, 1600, 2200, 2400, 4000, 4800, 7900, and 8600 may include one or more of the characteristics of the various methods described above with reference to processes 8900. For example, the activity data, activity types, displayed values and other elements described above with reference to processes 8900 optionally have one or more of the characteristics of the activity data, activity types, displayed values and other elements described herein (e.g., processes 1500, 1600, 2200, 2400, 4000, 4800, 7900, and 8600). For brevity, these details are not repeated.

Figure 91:
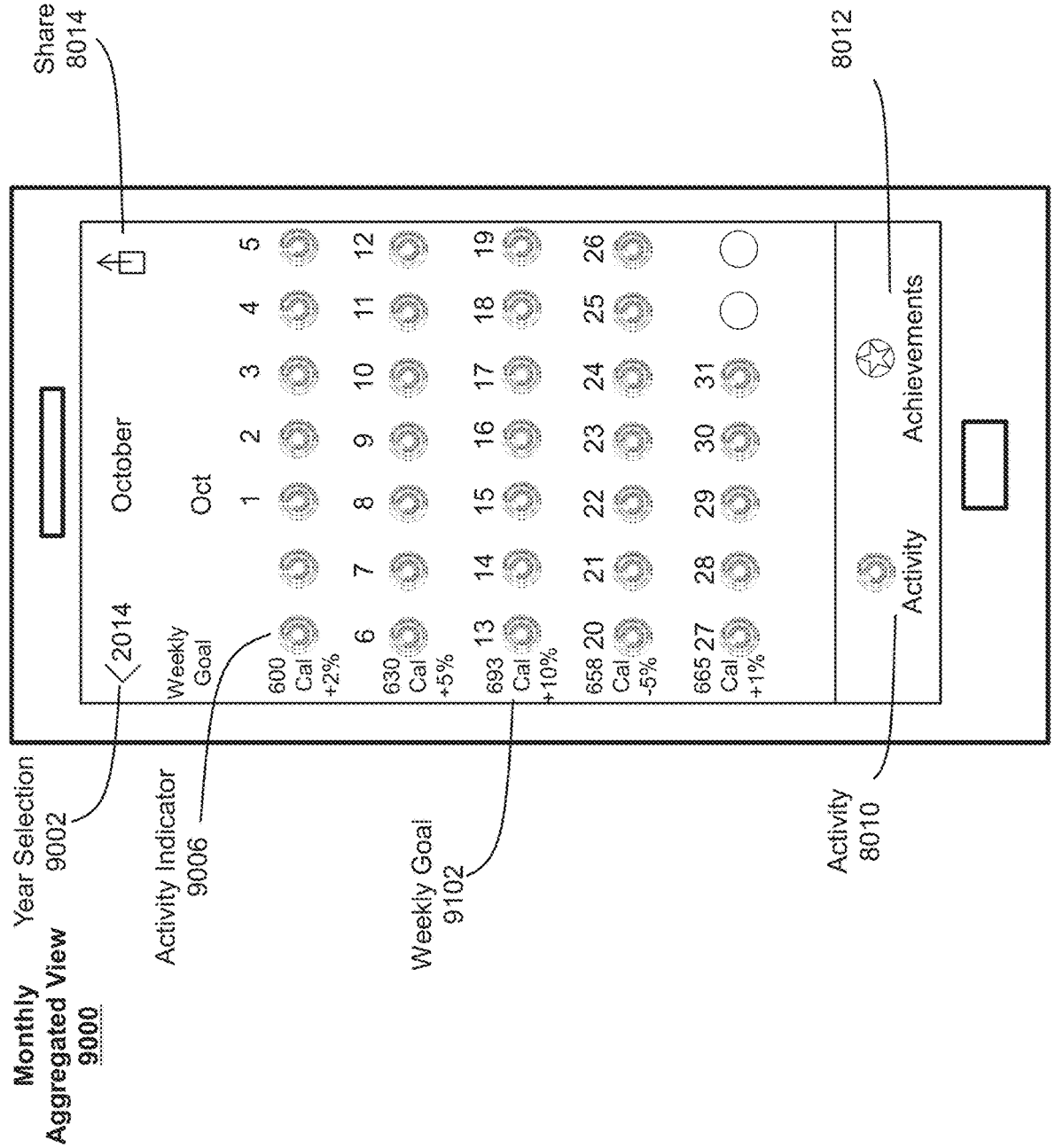

In some examples, as shown in FIG. 91, the electronic device can display weekly goals 9102 for one of the physical activity attributes represented by a ring of activity indicators 9006 within monthly aggregated view 9000. For example, weekly goals 9102 can include the daily Calorie expenditure goal for the week and a percent change from the previous week's goal. In some examples, weekly goals 9102 can be displayed in response to a swipe gesture performed from left to right across monthly aggregated view 9000.

Figure 92:
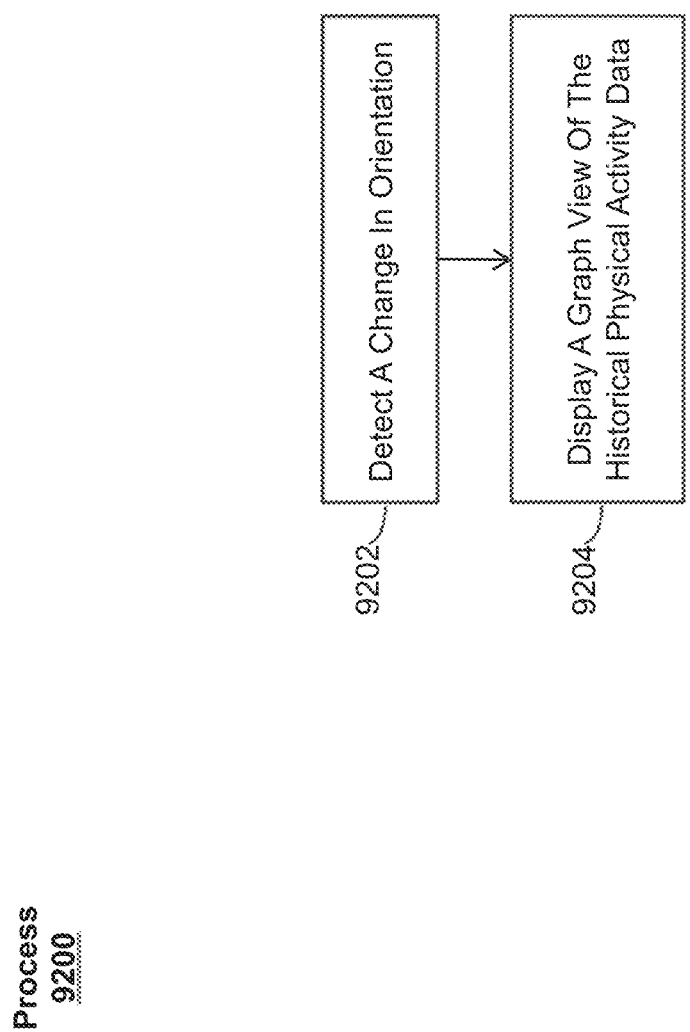
FIG. 92 illustrates an exemplary process for displaying a graph view of historical physical activity data according to various examples.
Figure 93:
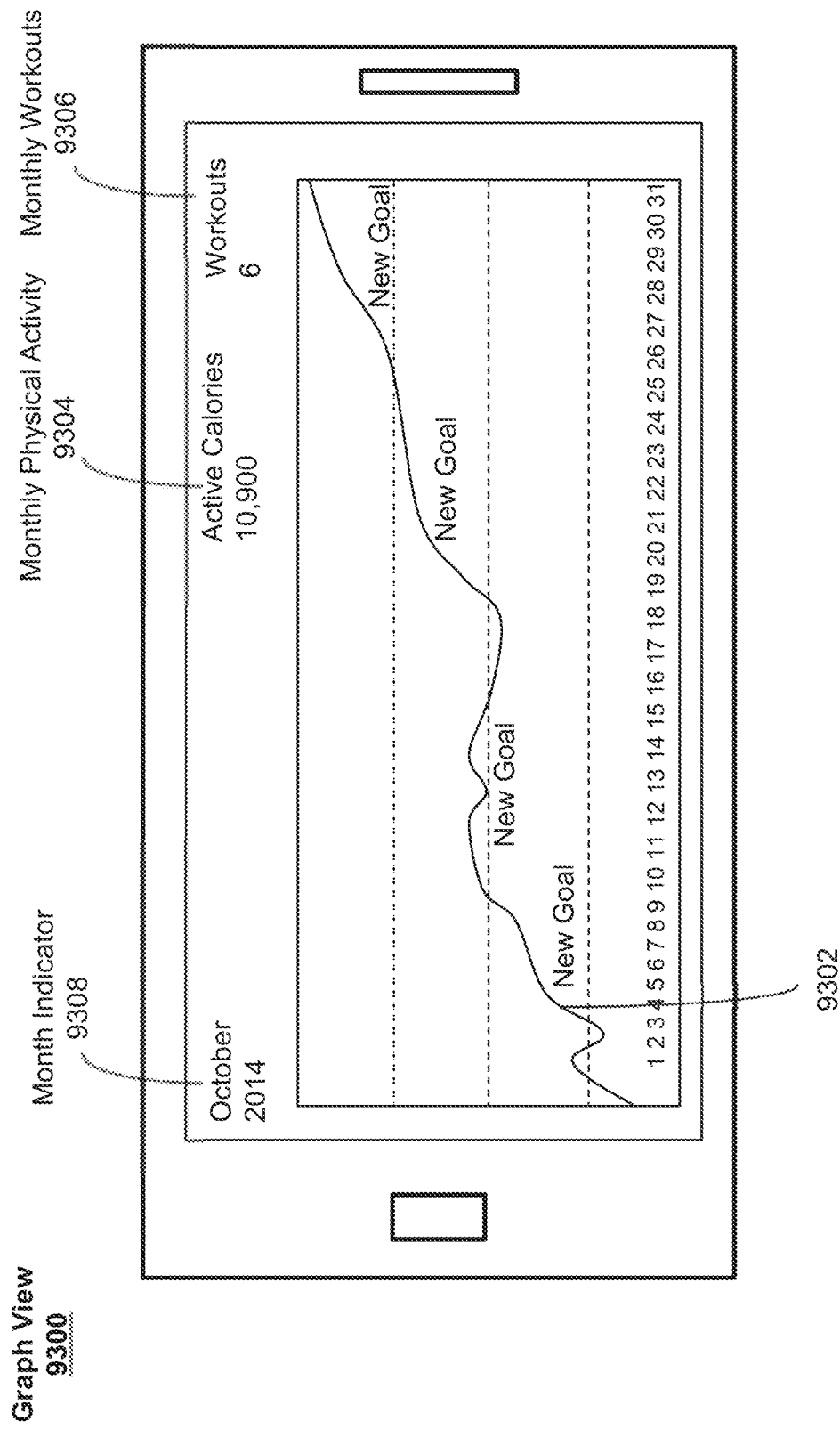
FIGS. 93 and 94 illustrate exemplary graph views of historical physical activity data according to various examples.

FIG. 92 illustrates an example process 9200 for displaying physical activity data based on an orientation of the device according to various examples. Process 9200 can be performed after process 8900 by an electronic device similar to user device 722 or 724. Some operations in process 9200 may be combined, the order of some operations may be changed, and some operations may be omitted.

As described below, process 9200 provides intuitive ways to monitor attributes of a user's physical activity or inactivity and generate user interfaces for displaying the same. The process reduces the cognitive burden on a user when monitoring attributes of the user's physical activity or inactivity, thereby creating a more efficient human-machine interface. For battery-operated computing devices, enabling a user to monitor attributes of the user's physical activity or inactivity and generate user interfaces for displaying the same more quickly and more efficiently conserves power and increases the time between battery charges.

At block 9202, a change in orientation of the device can be detected. For example, a gyroscope and/or an accelerometer within the user device can indicate that the orientation of the device has been changed from portrait to landscape. In response to a detected change in orientation by a threshold amount, the process can proceed to block 9204.

At block 9204, a graph view of the historical physical activity data can be displayed. In some examples, the graph view can be similar to graph view 9300, shown in FIG. 93. Graph view 9300 can include a line graph representation 9302 of one of the attributes represented by a ring of activity indicators 9006. In the illustrated example, the attribute can include the daily number of Calories expended. Interface 9300 can further include "New Goal" labels identifying when the user's daily activity goal changed. Interface 9300 can further include month indicator 9308 identifying the month corresponding to the displayed physical activity data, monthly physical activity summary 9304 indicating the total number of active Calories expended during the month, and monthly workout summary 9306 indicating the total number of workouts recorded during the month.

Note that details of the processes described above with respect to process 9200 (e.g., FIG. 92) are also applicable in an analogous manner to the other processes described herein. For example, processes 1500, 1600, 2200, 2400, 4000, 4800, 7900, and 8600 may include one or more of the characteristics of the various methods described above with reference to processes 9200. For example, the activity data, activity types, displayed values and other elements described above with reference to processes 9200 optionally have one or more of the characteristics of the activity data, activity types, displayed values and other elements described herein (e.g., processes 1500, 1600, 2200, 2400, 4000, 4800, 7900, and 8600). For brevity, these details are not repeated.

Figure 94:
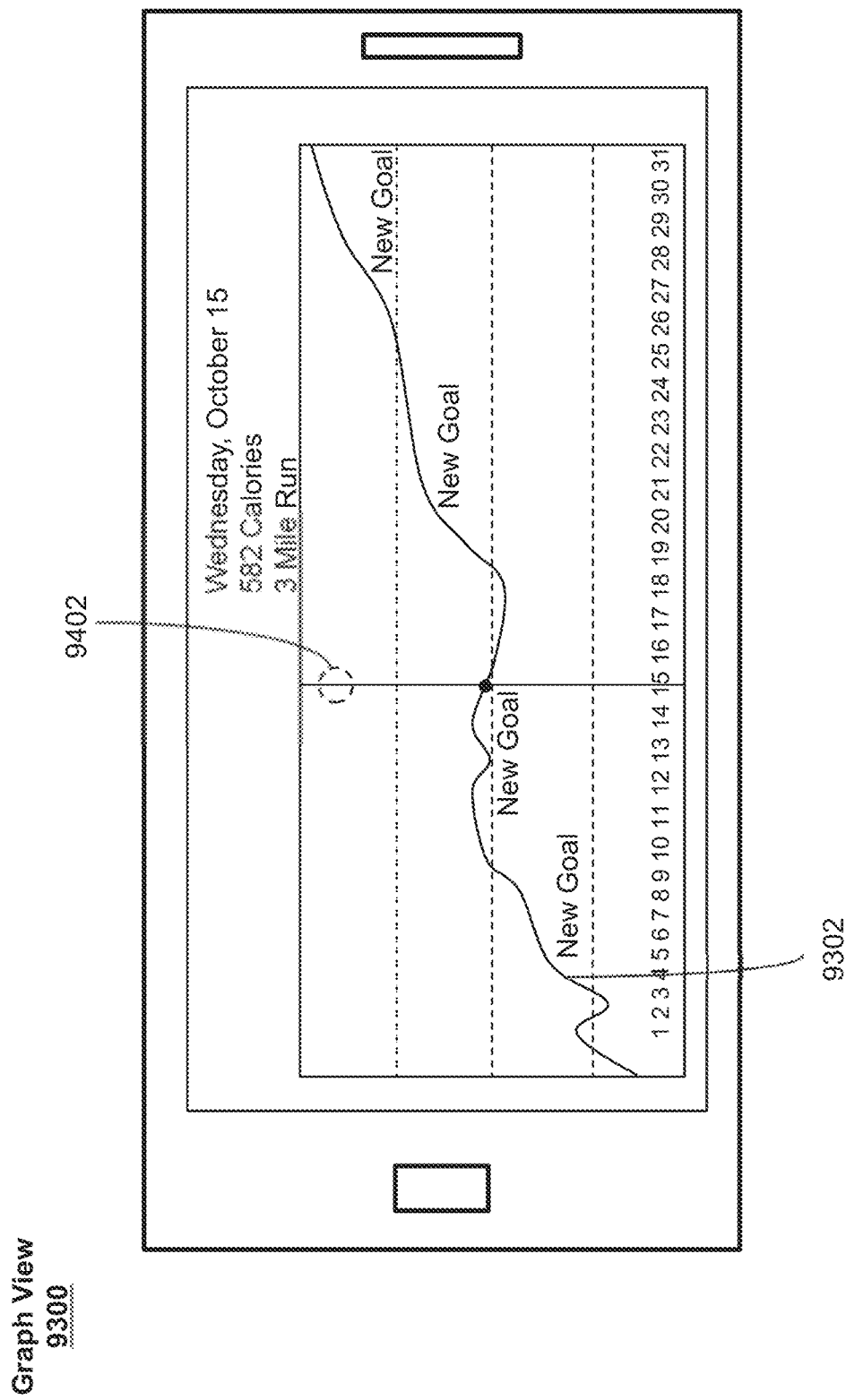

In some examples, a user input can be applied to the displayed graph to cause a display of a value of line graph representation 9302 at a horizontal position (e.g., a day) corresponding to the location of the user input. For example, FIG. 94 shows a user input applied at location 9402. In response to detecting this user input, the electronic device can display the date (Wednesday, October 15) and the associated value (582 Calories) for the selected day. Additionally, in some examples, if a workout was recorded on the selected day, a brief description of the workout can also be displayed (3 mile run). In some examples, a user input can be continuously applied to the displayed graph and moved in a horizontal direction to scrub through values of line graph representation 9302. For example, in response to detecting that the user input received at location 9402 is moved in the left direction, the circle marker displayed over line graph representation 9302 can be animated such that it appears to move along the line graph representation 9302 at horizontal positions corresponding to the current horizontal position of the user input. Similarly, the displayed value can change to reflect the value of the data set represented by line graph representation 9302 at the horizontal position of the user input.

In some examples, in response to a selection of achievement interface button 8012, the device can display an achievement interface 9500 similar to that shown in FIG. 95. As shown, interface 9500 can include reward icons 9502 corresponding to various achievements that can be obtained by the user, such as best workout, fastest run, longest run, exercising for 5 consecutive days, etc. In response to a selection of a reward icon 9502, the device can display additional information associated with the reward, such as the date that the reward was obtained, information about the workout during which the workout was obtained, or the like. In some examples, the rewards obtained by the user can be displayed in color, while rewards not yet obtained by the user can be displayed as being grayed-out. The device can display aggregated view 8000 in response to a selection of activity interface button 8010.

In some examples, some or all of the information displayed in aggregated view 8000 or achievement view 9500 can be shared with one or more other users or one or more social networks in response to a selection of share button 8014. In some examples, the device can display a list of share options in response to a user selecting share button 8014. For example, the list of share options can include the option to share the displayed information via SMS, email, a cloud sharing service, one or more social networks, or the like. In response to a selection of one of the share options, the device can transmit some or all of the information displayed on the device to the selected destination.

Activity Goal Setting Assessment

In some examples, a summary interface can be displayed at the end of each week. The summary interface can include a text description of the user's performance over the week with respect to one or more goals. For example, the summary interface can indicate the number of days during the week that the user met or exceeded their daily expended Calorie goal (e.g., represented by the outer ring of activity indicator 4101 or 8006). In addition, the electronic device can calculate a new goal for the user based on their performance during the week and can present the new goal to the user. The user can accept the new goal as the goal to be used for the next week or can modify the goal up or down based on their preference. In some examples, during the first 3 weeks that the goal is being calculated, the goal can be calculated using the table shown in FIG. 96. For example, if the user achieved their goal during 1 or 2 days during the first or second week, the goal can be lowered to the average of the lowest 4 days. If the user achieved their goal during 1 or 2 days during the third week, the goal can be lowered by 10%. If the user achieved their goal during 3 days during any of the first, second, or third weeks and their daily average for the week was 75% or more of the goal value, the goal can be lowered by 10%. If the user achieved their goal during 3 days during the first or second week and their daily average for the week was less than 75% of the goal value, the goal can be lowered to the average of the lowest 4 days. If the user achieved their goal during 3 days during the third week and their daily average for the week was less than 75% of the goal value, the goal can be lowered by 10%. If the user achieved their goal during 4 days during the first or second week and their daily average for the week was 75% or more of the goal value, the goal can remain the same. If the user achieved their goal during 4 days during the third week and their daily average for the week was 75% or more of the goal value, the goal can be increased by 10%, If the user achieved their goal during 4 days during the first or second week and their daily average for the week was less than 75% of the goal value, the goal can by lowered to the average of the lowest 3 days during the week. If the user achieved their goal during 4 days during the third week and their daily average for the week was less than 75% of the goal value, the goal can be lowered by 10%. If the user achieved their goal during 5-6 days during the first week, the goal can remain the same. If the user achieved their goal during 5-6 days during the second week, the goal can be raised by 10%. If the user achieved their goal during 5-6 days during the third week, the goal can remain the same. If the user achieved their goal during 7 days during the first or second week and their daily average for the week was 125% or more of the goal value, the goal can be increased to the average of the 7 days. If the user achieved their goal during 7 days during the third week and their daily average for the week was 125% or more of the goal value, the goal can be increased by 10%. In some examples, after the first 3 weeks, the goal can be lowered by 10% if the number of goal days achieved over the last 3 weeks is equal to 9 or less, the goal can remain the same if the number of goal days achieved over the last 3 weeks is equal to 10-14, and the goal can be increased by 10% if the number of goal days achieved over the last 3 weeks is equal to 15-21. While a specific algorithm is provided for calculating the new goal value, it should be appreciated that other algorithms can be used to calculate the new goal value based on the historical performance of the user.

Figure 97:
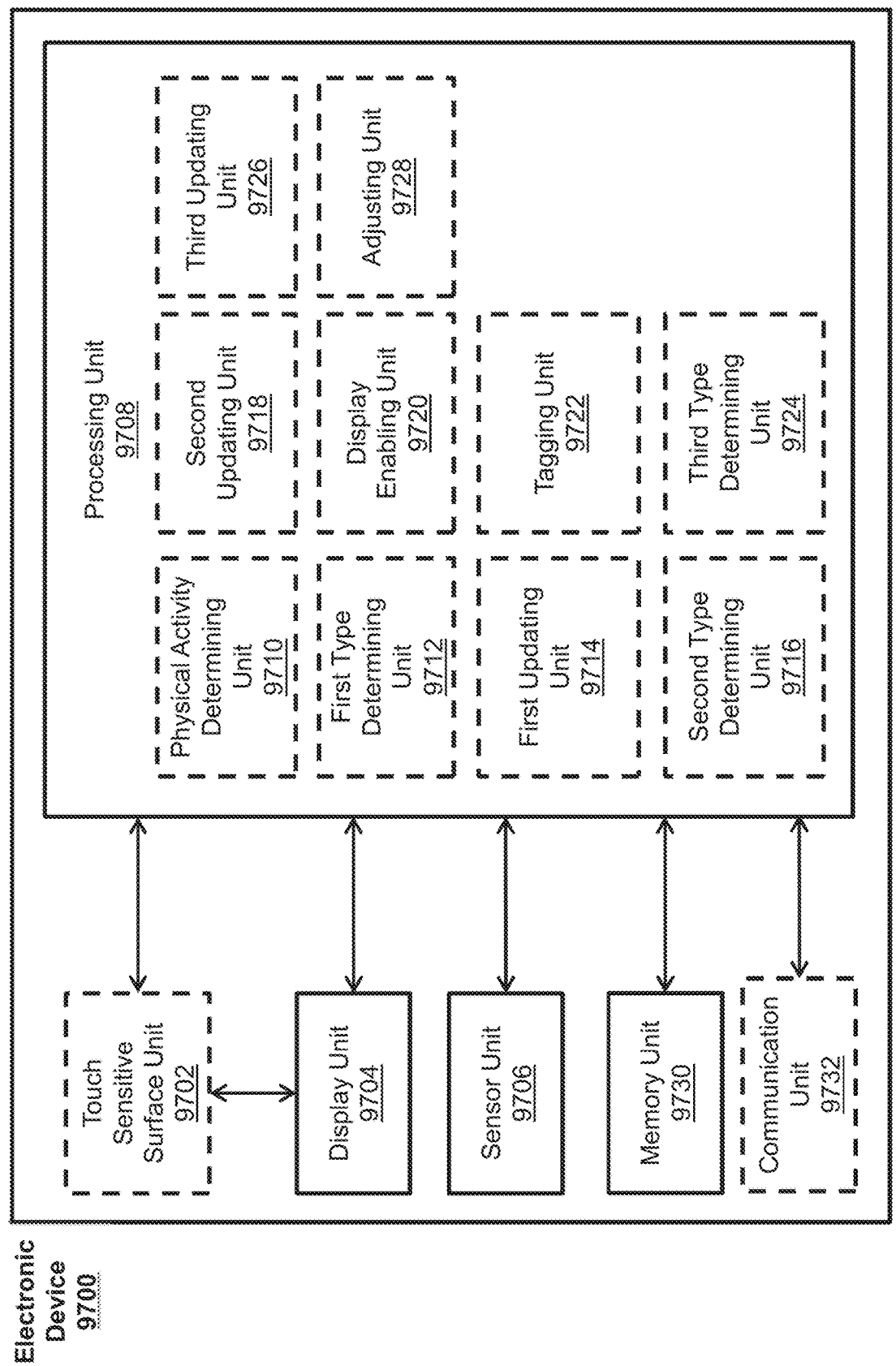
FIGS. 97-102 illustrate functional block diagrams of electronic devices according to various examples.

In accordance with some embodiments, FIG. 97 shows a functional block diagram of an electronic device 9700 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 97 can be combined or separated into sub-blocks to implement the principles of the various described examples. Therefore, the description herein optionally supports any possible combination or separation or further definition of the functional blocks described herein.

As shown in FIG. 97, electronic device 9700 can include a display unit 9704 configured to display graphical objects, a sensor unit 9706 configured to detect movement associated with the electronic device 9700 and generate activity data based on the detected movement, a memory unit 9730 configured to store values, and a processing unit 9708 coupled to sensor unit 9706, memory unit 9730, and display unit 9704. In some examples, electronic device 9700 can include a touch-sensitive surface unit 9702 configured to receive user gestures and a communication unit 9732 configured to receive communication; the processing unit 9708 may be coupled to the touch-sensitive surface unit 9702. In some examples, processing unit 9708 can include a physical activity determining unit 9710, a first type determining unit 9712, a first updating unit 9714, a second type determining unit 9716, a second updating unit 9718, a display enabling unit 9720, tagging unit 9722, third type determining unit 9724, third updating unit 9726, and adjusting unit 9728.

Processing unit 9708 can be configured to determine (e.g., with physical activity determining unit 9710), that a physical activity has been performed by a user wearing an electronic device based on activity data generated by a sensor unit 9706, determine (e.g., with first type determining unit 9712) whether the physical activity corresponds to a first type based on a first set of criteria and determine (e.g., with second type determining unit 9716) whether the physical activity corresponds to a second type based on a second set of criteria. Processing unit 9708 can be further configured to update (e.g., with first updating unit 9714), in response to determining that the physical activity corresponds to the first type, a first value stored in the memory unit 9730 based on the activity data, and update (e.g., with second updating unit 9718), in response to determining that the physical activity corresponds to the second type, a second value stored in the memory device. Processing unit 9708 can be further configured to enable display (e.g., with display enabling unit 9720), on the display unit 9704, of the first value representing an aggregate amount of the first type of physical activity detected from the sensor over a period of time, and enable display (e.g., with display enabling unit 9720), on the display unit 9704, of the second value representing an aggregate amount of the second type of physical activity detected from the sensor over the period of time.

In some embodiments, the sensor unit 9706 comprises two or more sensors,

In some embodiments, the sensor unit 9706 comprises a GPS sensor, an accelerometer, a directional sensor, a gyroscope, a timer sensor, a biometric sensor, or a motion sensor.

In some embodiments, the activity data is generated by the sensor based on detection of one or more types of physical activity, the one or more types of physical activity comprising walking, running, going up stairs, or jumping.

In some embodiments, the second set of criteria comprises a number of steps taken per unit time.

In some embodiments, the second set of criteria comprises an amount of Calories burned per unit time.

In some embodiments, the second set of criteria comprises a speed. In some examples, the second set of criteria comprises the first set of criteria.

In some embodiments, the second type of activity is a subset of the first type of activity.

In some embodiments, processing unit 9708 can be further configured to determine (e.g., with third type determining unit 9724) whether the physical activity associated with the activity data corresponds to a third type based on a third set of criteria and, in response to determining that the physical activity corresponds to the third type, update (e.g., with third updating unit 9726) a third value stored in the memory device based on the received activity data. Processing unit 9708 can be further configured to display (e.g., with displaying unit 9720) the third value representing an aggregate amount of the third type of physical activity detected from the sensor over the period of time.

In some examples, the third set of criteria includes the second set of criteria and the first set of criteria.

In some examples, the third type of activity is a subset of the second type of activity and a subset of the first type of activity.

In some examples, the first value represents an aggregate amount of Calories burned by the user from performing the first type of physical activity over the period of time.

In some examples, the display of the second value is indicative of an aggregate amount of time spent by the user for performing the second type of physical activity over the period of time.

In some examples, the first indicator and the second indicator each comprise an image and a text.

In some examples, the first indicator comprises a first portion representing the first value and a second portion representing a difference between the first value and a first goal value stored in the memory, and the second indicator comprises a third portion representing the second value and a fourth portion representing a difference between the second value and a second goal value stored in the memory.

In some examples, the first indicator and the second indicator are concentric rings.

In other examples, the first indicator and the second indicator are adjacent bars.

In some examples, processing unit 9708 can be further configured to automatically adjust (e.g., using adjusting unit 9728) the first goal value based on a passage of time.

In some examples, the period of time is one day.

In some examples, processing unit 9708 can be further configured to receive (e.g., using receiving unit 9730), via the communication unit 9732, from an external device remotely located from the electronic device, activity data associated with devices different from the electronic device.

In some example, the display unit 9704 is a touch-sensitive display unit.

In some example, the electronic device 9700 is a watch.

The operations described above with reference to FIGS. 15 and 16 are, optionally, implemented by components depicted in FIGS. 1A-1B, and 97. For example, the operations described with reference to blocks 1504, 1506, 1508, and/or 1510 may be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B, and 97.

Figure 98:
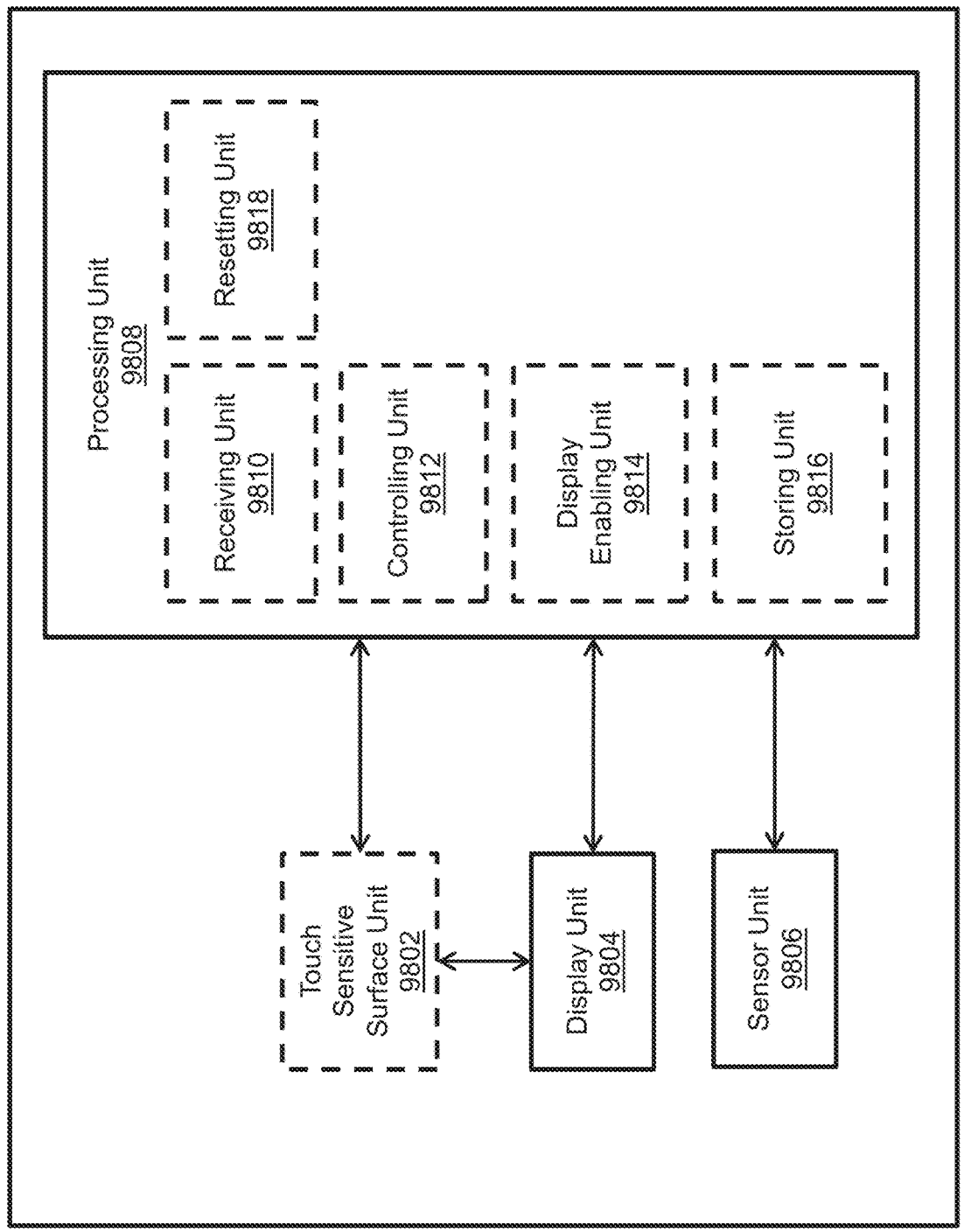

In accordance with some embodiments, FIG. 98 shows a functional block diagram of an electronic device 9800 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 98 can be combined or separated into sub-blocks to implement the principles of the various described examples. Therefore, the description herein optionally supports any possible combination or separation or further definition of the functional blocks described herein.

As shown in FIG. 98, electronic device 9800 can include a sensor unit 9806 configured to detect movement associated with the electronic device and generate activity data based on the detected movement, a display unit 9804 configured to display graphical objects, and a processing unit 9808 coupled to the sensor unit 9806, and the display unit 9804. In some example, electronic device 9800 can include a touch-sensitive surface unit 9802 configured to receive user gestures and coupled to processing unit 9808. In some examples, processing unit 9808 can include a receiving unit 9810, a controlling unit 9812, a display enabling unit 9814, a storing unit 9816, and a resetting unit 9818.

Processing unit 9808 can be configured to receive (e.g., using receiving unit 9810), from the sensor unit 9806, activity data that is representative of physical activity performed by a user detected by the sensor, control (e.g., with controlling unit 9812) an inactivity timer that measures a length of time that the user is inactive based on the activity data, wherein controlling the inactivity timer comprises resetting a value of the inactivity timer in response to determining, based on the activity data, that the user has performed a threshold amount of activity, and enable display (e.g., with display enabling unit 9814), on the display unit 9804 of an inactivity tracking interface, wherein the inactivity tracking interface comprises a visual representation of the value of the inactivity timer.

In some examples, controlling the inactivity timer further comprises, after pausing the inactivity timer, updating an amount of detected activity to include the physical activity performed by the user.

In some examples, determining, based on the activity data, that the user has performed the threshold amount of activity comprises determining that the amount of detected activity has reached the threshold amount of activity.

In some examples, controlling the inactivity timer further comprises resetting the amount of detected activity in response to determining that the amount of the detected activity has reached the threshold amount of activity.

In some examples, the threshold amount of activity is equal to 100 steps.

In some examples, controlling the inactivity timer further comprises, after pausing the inactivity timer: resetting the amount of detected activity in response to determining that the user is inactive for more than a threshold length of time; and starting the inactivity timer in response to determining that the user is inactive for more than the threshold length of time.

In some examples, the inactivity tracking interface further comprises a visual representation of the amount of detected activity.

In some examples, the visual representation of the amount of detected activity comprises a first graphic image or a first text.

In some examples, the visual representation of the amount of detected activity comprises a first ring.

In some examples, the visual representation of the value of the inactivity timer comprises a second ring that is concentric to the first ring.

In some examples, the visual representation of the amount of detected activity comprises a first portion that is representative of the amount of detected activity and a second portion that is representative of a difference between the amount of detected activity and the threshold amount of activity. In some examples, a ratio between a size of the first portion and a size of the second portion is equal to a ratio between the amount of detected activity and the difference between the amount of detected activity and the threshold amount of activity.

In some examples, the visual representation of the value of the inactivity timer comprises a second image or a second text.

In some examples, the inactivity tracking interface further comprises a visual representation of a value of an inactivity counter. In some examples, controlling unit 9812 can be configured to control the inactivity timer further by, in response to the value of the inactivity timer reaching an inactivity threshold: incrementing the value of the inactivity counter; and resetting the value of the inactivity timer.

In some examples, the inactivity threshold is equal to one hour.

In some examples, the inactivity threshold is a user-defined value.

In some examples, wherein the visual representation of the value of the inactivity timer comprises a third portion that is representative of the value of the inactivity timer and a fourth portion that is representative of a difference between the value of the inactivity timer and the inactivity threshold. In some examples, a ratio between a size of the third portion and a size of the fourth portion is equal to a ratio between the value of the inactivity timer and the difference between the value of the inactivity tinier and the inactivity threshold.

In some examples, controlling unit 9812 can be configured to control the inactivity timer by: starting the inactivity timer in response to determining that the user is inactive based on the activity data; and pausing the inactivity timer in response to determining that the user is active based on the activity data.

In some examples, determining that the user is active comprises determining that the user is walking, running, going up stairs, or jumping based on the activity data.

In some examples, determining that the user is inactive comprises determining that the user is not active based on the activity data.

In some examples, processing unit 9808 can be further configured to periodically: store (e.g., using storing unit 9816) the value of the inactivity counter; and reset (e.g., using resetting unit 9818), after storing the value of the inactivity counter, the value of the inactivity counter.

In some examples, periodically comprises once a day.

In some examples, the activity sensor comprises a global positioning system (GPS) sensor, pedometer, accelerometer, biometric sensor, gyroscope, or motion sensor.

The operations described above with reference to FIGS. 22 and/or 24 are, optionally, implemented by components depicted in FIGS. 1A-1B, and 98. For example, the operations described with reference to blocks 2204, 2206, 2404, and/or 2416 may be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B, and 98.

Figure 99:
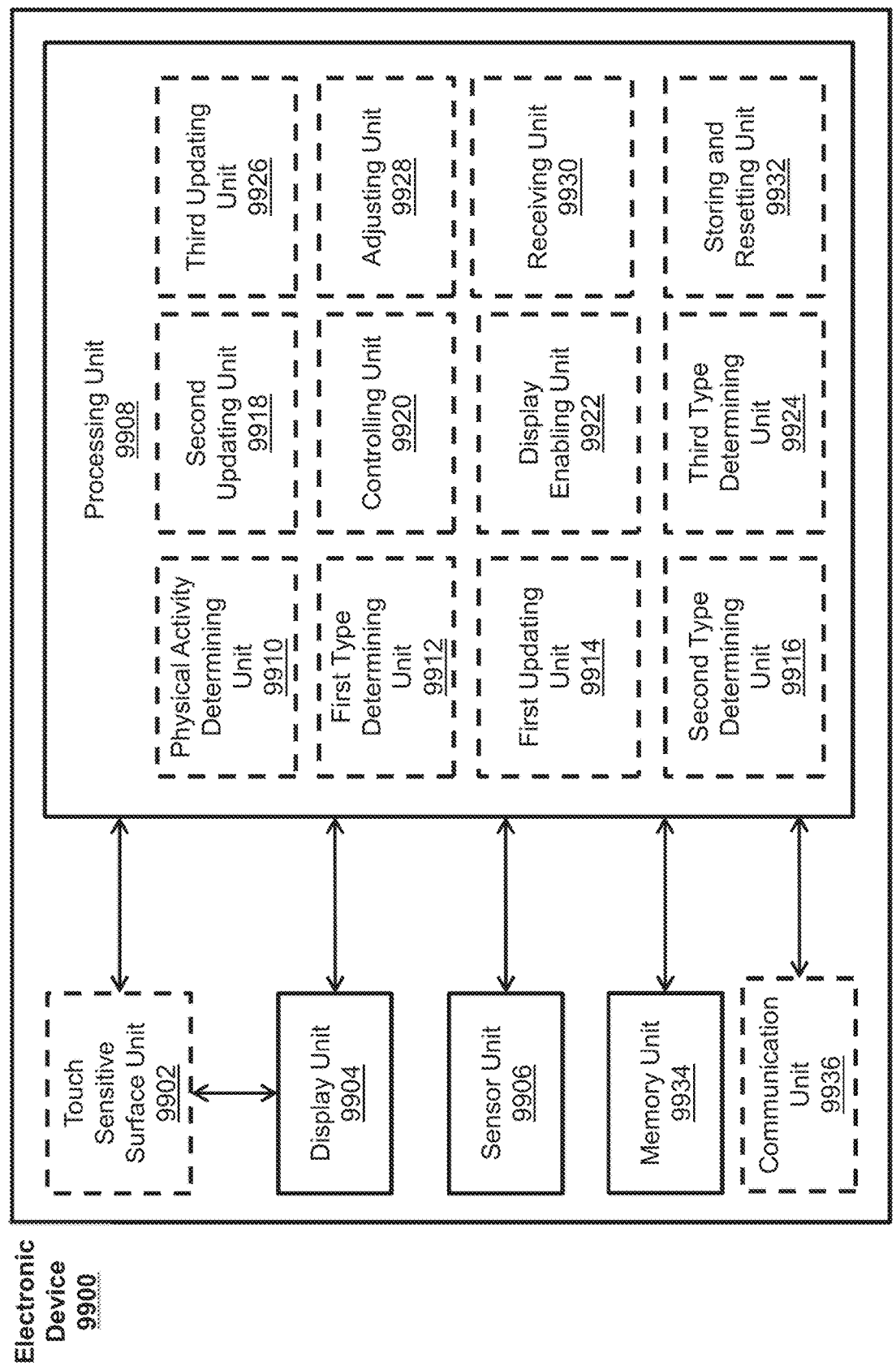

In accordance with some embodiments, FIG. 99 shows a functional block diagram of an electronic device 9900 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 99 can be combined or separated into sub-blocks to implement the principles of the various described examples. Therefore, the description herein optionally supports any possible combination or separation or further definition of the functional blocks described herein.

As shown in FIG. 99, electronic device 9900 can include a display unit 9904 configured to display graphical objects, sensor unit 9906 configured to detect movement associated with the electronic device and generate activity data based on the detected movement, memory unit 9934 configured to store values, and a processing unit 9908 coupled to display unit 9904, sensor unit 9906, and memory unit 9934. In some examples, electronic device 9900 includes a touch-sensitive surface unit 9902 configured to receive user gestures and a communication unit 9936 configured to receive communications, both of which may be coupled to processing unit 9908. In some examples, processing unit 9908 can include a physical activity determining unit 9910, a first type determining unit 9912, a first updating unit 9914, a second type determining unit 9916, a second updating unit 9918, a controlling unit 9920, a display enabling unit 9922, a third type determining unit 9924, a third updating unit 9926, an adjusting unit 9928, a receiving unit 9930, and a storing and resetting unit 9932.

Processing unit 9908 can be configured to determine (e.g., with physical activity determining unit 9910), that a physical activity has been performed by a user wearing an electronic device, based on activity data generated by the sensor unit 9906 and determine (e.g., with first type determining unit 9912) whether the physical activity corresponds to a first type based on a first set of criteria and determine (e.g., with first type determining unit 9912) whether the physical activity corresponds to a second type based on a second set of criteria. Processing unit 9908 can be further configured to update (e.g., with first updating unit 9914), in response to determining that the physical activity corresponds to the first type, a first value stored in the memory unit 9934 based on the activity data and update (e.g., with second updating unit 9918), in response to determining that the physical activity corresponds to the second type, a second value stored in the memory device based on the activity data. Processing unit 9908 can be further configured to control (e.g., with controlling unit 9920) an inactivity timer that measures a length of time that the user is inactive based on the activity data, wherein controlling the inactivity timer comprises: resetting a value of the inactivity timer in response to determining, based on the activity data, that the user has performed a threshold amount of activity; incrementing the value of an inactivity counter in response to the value of the inactivity timer reaching an inactivity threshold; and resetting the value of the inactivity timer in response to the value of the inactivity timer reaching an inactivity threshold. Processing unit 9908 can be further configured to enable display (e.g., with display enabling unit 9922) of a first indicator representative of the first value, the first value representing an aggregate amount of the first type of physical activity detected from the sensor over a period of time; a second indicator representative of the second value, the second value representing an aggregate amount of the second type of physical activity detected from the sensor over the period of time; and a third indicator representative of the value of the inactivity counter.

In some examples, the activity data is generated by the sensor based on detection of one or more types of physical activity, the one or more types of physical activity comprising walking, running, going up stairs, or jumping.

In some examples, the second set of criteria comprises a number of steps taken per unit time.

In some examples, the second set of criteria comprises an amount of Calories burned per unit time.

In some examples, the second set of criteria comprises a speed.

In some examples, the second set of criteria comprises the first set of criteria.

In some examples, the second type of activity is a subset of the first type of activity.

In some examples, processing unit 9908 can be further configured to determine (e.g., using third type determining unit 9924), whether the physical activity associated with the activity data corresponds to a third type based on a third set of criteria. Processing unit 9908 can be further configured to update (e.g., with third updating unit 9926), in response to determining that the physical activity corresponds to the third type, a third value, stored in the memory device, based on the received activity data. Processing unit 9908 can be further configured to enable display (e.g., with display enabling unit 9922) of a third indicator representing the third value, the third value representing an aggregate amount of the third type of physical activity detected from the sensor over the period of time.

In some examples, the third set of criteria includes the second set of criteria and the first set of criteria.

In some examples, the third type of activity is a subset of the second type of activity and a subset of the first type of activity.

In some examples, the first value represents an aggregate amount of Calories burned by the user from performing the first type of physical activity over the period of time.

In some examples, the display of the second value is indicative of an aggregate amount of time spent by the user for performing the second type of physical activity over the period of time.

In some examples, the first indicator and the second indicator each comprise an image and a text.

In some examples, the first indicator comprises a first portion representing the first value and a second portion representing a difference between the first value and a first goal value stored in the memory. In some examples, the second indicator comprises a third portion representing the second value and a fourth portion representing a difference between the second value and a second goal value stored in the memory.

In some examples, the first indicator and the second indicator are concentric rings.

In some examples, the first indicator and the second indicator are adjacent bars.

In some examples, processing unit 9908 can be further configured to automatically adjust (e.g., using adjusting unit 9928), the first goal value based on a passage of time.

In some examples, the period of time is one day.

In some examples, processing unit 9908 can be further configured to receive (e.g., using receiving unit 9930), from an external device remotely located from the electronic device, activity data associated with devices different from the electronic device.

In some examples, processing unit 9908 can be further configured to control (e.g., with controlling unit 9920) the inactivity timer by, after pausing the inactivity timer, updating an amount of detected activity to include the physical activity performed by the user.

In some examples, determining, based on the activity data, that the user has performed the threshold amount of activity comprises determining that the amount of detected activity has reached the threshold amount of activity.

In some examples, processing unit 9908 can be further configured to control (e.g., with controlling unit 9920) the inactivity timer by resetting the amount of detected activity in response to determining that the amount of the detected activity has reached the threshold amount of activity.

In some examples, the threshold amount of activity is equal to 100 steps.

In some examples, processing unit 9908 can be further configured to control (e.g., with controlling unit 9920) the inactivity timer by, after pausing the inactivity timer resetting the amount of detected activity in response to determining that the user is inactive for more than a threshold length of time; and starting the inactivity tinier in response to determining that the user is inactive for more than the threshold length of time.

In some examples, the inactivity tracking interface further comprises a visual representation of the amount of detected activity.

In some examples, the visual representation of the amount of detected activity comprises a first graphic image or a first text.

In some examples, the visual representation of the amount of detected activity comprises a first ring.

In some examples, the visual representation of the value of the inactivity timer comprises a second ring that is concentric to the first ring.

In some examples, the visual representation of the amount of detected activity comprises a first portion that is representative of the amount of detected activity and a second portion that is representative of a difference between the amount of detected activity and the threshold amount of activity. In some examples, a ratio between a size of the first portion and a size of the second portion is equal to a ratio between the amount of detected activity and the difference between the amount of detected activity and the threshold amount of activity.

In some examples, the visual representation of the value of the inactivity counter comprises a second image or a second text.

In some examples, the inactivity threshold is equal to one hour.

In some examples, the inactivity threshold is a user-defined value.

In some examples, the visual representation of the value of the inactivity counter comprises a third portion that is representative of the value of the inactivity counter and a fourth portion that is representative of a difference between the value of the inactivity counter and a length of a predetermine period of time. In some examples, a ratio between a size of the third portion and a size of the fourth portion is equal to a ratio between the value of the inactivity counter and the difference between the value of the inactivity counter and the length of the predetermined period of time.

In some examples, processing unit 9908 can be configured to control with controlling unit 9920) the inactivity timer by starting the inactivity timer in response to determining that the user is inactive based on the activity data; and pausing the inactivity timer in response to determining that the user is active based on the activity data.

In some examples, determining that the user is active comprises determining that the user is standing, walking, running, going up stairs, or jumping based on the activity data.

In some examples, determining that the user is inactive comprises determining that the user is not active based on the activity data.

In some examples, processing unit 9908 can be further configured to store (e.g., using storing and resetting unit 9932) the value of the inactivity counter and reset the value of the inactivity counter after storing the value of the inactivity counter.

In some examples, periodically comprises once a day.

In some examples, the activity sensor comprises a global positioning system (GPS) sensor, pedometer, accelerometer, biometric sensor, gyroscope, or motion sensor.

The operations described above with reference to FIG. 40 are, optionally, implemented by components depicted in FIGS. 1A-1B, and 99. For example, the operations described with reference to blocks 4004, 4012, and/or 4014 may be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B, and 9.

Figure 100:
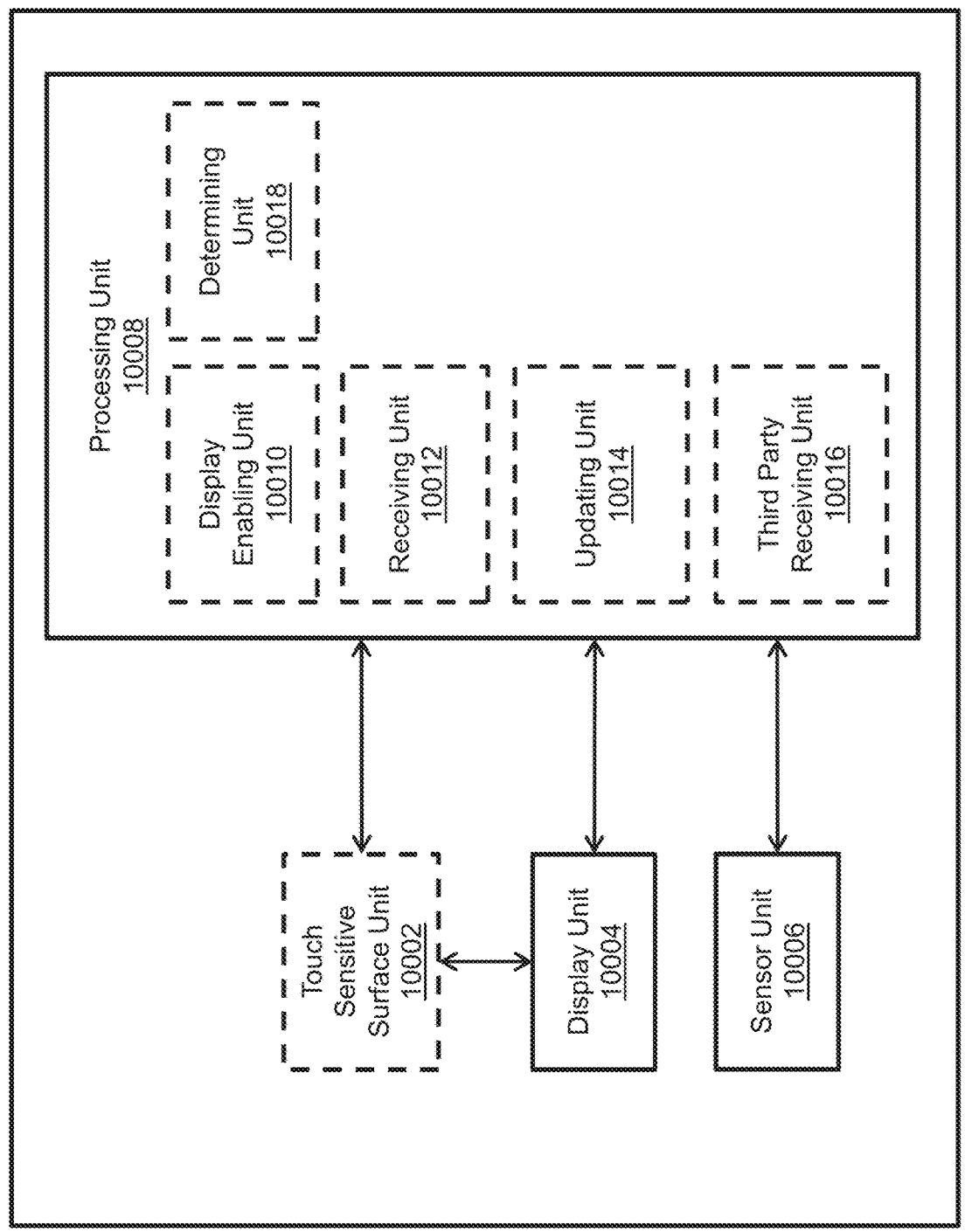

FIG. 100 shows a functional block diagram of an electronic device 10000 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 100 can be combined or separated into sub-blocks to implement the principles of the various described examples. Therefore, the description herein optionally supports any possible combination or separation or further definition of the functional blocks described herein.

As shown in FIG. 100, electronic device 10000 can include a sensor unit 10006 configured to detect movement associated with the electronic device and generate activity data based on the detected movement, a display unit 10004 configured to display graphical objects, and a processing unit 10008 coupled to the sensor unit 10006, and the display unit 10004. In some example, electronic device 10000 can include a touch-sensitive surface unit 10002 configured to receive user gestures coupled to processing unit 10008. In some examples, processing unit 10008 can include a displaying unit 10010, a receiving unit 10012, an updating unit 10014, a third party receiving unit 10016, and a determining unit 10018.

Processing unit 10008 can be configured to enable display (e.g., with display enabling unit 10010), on the display unit 10004, of an activity indicator, wherein the activity indicator comprises: a first indicator representative of an aggregate amount of a first type of physical activity performed by a user over a period of time; a second indicator representative of an aggregate amount of a second type of physical activity performed by the user over a period of time; and a third indicator representative of an aggregate amount of a third type of physical activity performed by the user over a period of time. Processing unit 10008 can be further configured to receive (e.g., with receiving unit 10012), from the sensor unit 10006, activity data representing movement associated with the electronic device 10000 and update (e.g., with updating unit 10014) the aggregate amount of the first type of physical activity, the aggregate amount of the second type of physical activity, and the aggregate amount of the third type of physical activity based on the activity data.

In some examples, the aggregate amount of the first type of physical activity comprises an amount of Calories expended by the user in performing the first type of physical activity over the period of time.

In some examples, the aggregate amount of the second type of physical activity comprises a number of minutes spent by the user in performing the second type of physical activity over the period of time.

In some examples, the aggregate amount of the third type of physical activity comprises a number of segments of time during which the user performed the third type of physical activity over the period of time.

In some examples, the segments of time comprise hour-long segments of time.

In some examples, the period of time comprises a day.

In some examples, processing unit 10008 can be further configured to update (e.g., with updating unit 10014) the aggregate amount of the first type of physical activity, the aggregate amount of the second type of physical activity, and the aggregate amount of the third type of physical activity based on the activity data by: determining whether the activity data represents the first type of physical activity based on a first set of criteria; in response to determining that the activity data represents the first type of physical activity, updating the aggregate amount of the first type of physical activity based on the activity data; determining whether the activity data represents the second type of physical activity based on a second set of criteria; in response to determining that the activity data represents the second type of physical activity, updating the aggregate amount of the second type of physical activity based on the activity data; determining whether the activity data represents the third type of physical activity based on a third set of criteria; and in response to determining that the activity data represents the third type of physical activity, updating the aggregate amount of the third type of physical activity based on the activity data.

In some examples, the first set of criteria comprises physical activities detected by the electronic device.

In some examples, the second set of criteria comprises an amount of Calories burned per unit time.

In some examples, the second set of criteria comprises a speed.

In some examples, the third set of criteria comprises a predetermined amount of a predetermined type of physical activity.

In some examples, the predetermined amount of the predetermined type of physical activity comprises 60 seconds of standing within a 90 second segment of time.

In some examples, the first indicator comprises a first portion representing the aggregate amount of the first type of physical activity and a second portion representing a difference between the aggregate amount of the first type of physical activity and a first goal value; the second indicator comprises a third portion representing the aggregate amount of the second type of physical activity and a fourth portion representing a difference between the aggregate amount of the second type of physical activity and a second goal value; and the third indicator comprises a fifth portion representing the aggregate amount of the third type of physical activity and a sixth portion representing a difference between the aggregate amount of the third type of physical activity and a third goal value.

In some examples, the first indicator, the second indicator, and the third indicator are concentric rings.

In some examples, processing unit 10008 can be further configured to update the display, on the display unit 10004 of the first indicator, the second indicator, and the third indicator based on the updated values of the aggregate amount of the first type of physical activity, the aggregate amount of the second type of physical activity, and the aggregate amount of the third type of physical activity based on the activity data.

In some examples, processing unit 10008 can be further configured to receive (e.g., with third party receiving unit 10016) activity data generated by an application running on the electronic device.

In some examples, processing unit 10008 can be further configured to determine (e.g., with determining unit 10018) whether to update the aggregate amount of the first type of physical activity, the aggregate amount of the second type of physical activity, and the aggregate amount of the third type of physical activity using the activity data generated by the application running on the electronic device. In some examples, processing unit 10008 can be further configured to update (e.g., with updating unit 10014), in response to determining to update the aggregate amount of the first type of physical activity, the aggregate amount of the second type of physical activity, and the aggregate amount of the third type of physical activity using the activity data generated by the application running on the electronic device 10000, the aggregate amount of the first type of physical activity, the aggregate amount of the second type of physical activity, and the aggregate amount of the third type of physical activity using the activity data generated by the application running on the electronic device 10000.

The operations described above with reference to FIGS. 40 and/or 22 are, optionally, implemented by components depicted in FIGS. 1A-1B, and 100. For example, the operations described with reference to blocks 2204, 2206, 2404, 2416, 4004, 4012, and/or 4014 may be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or subevent is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B, and 100.

Figure 101:
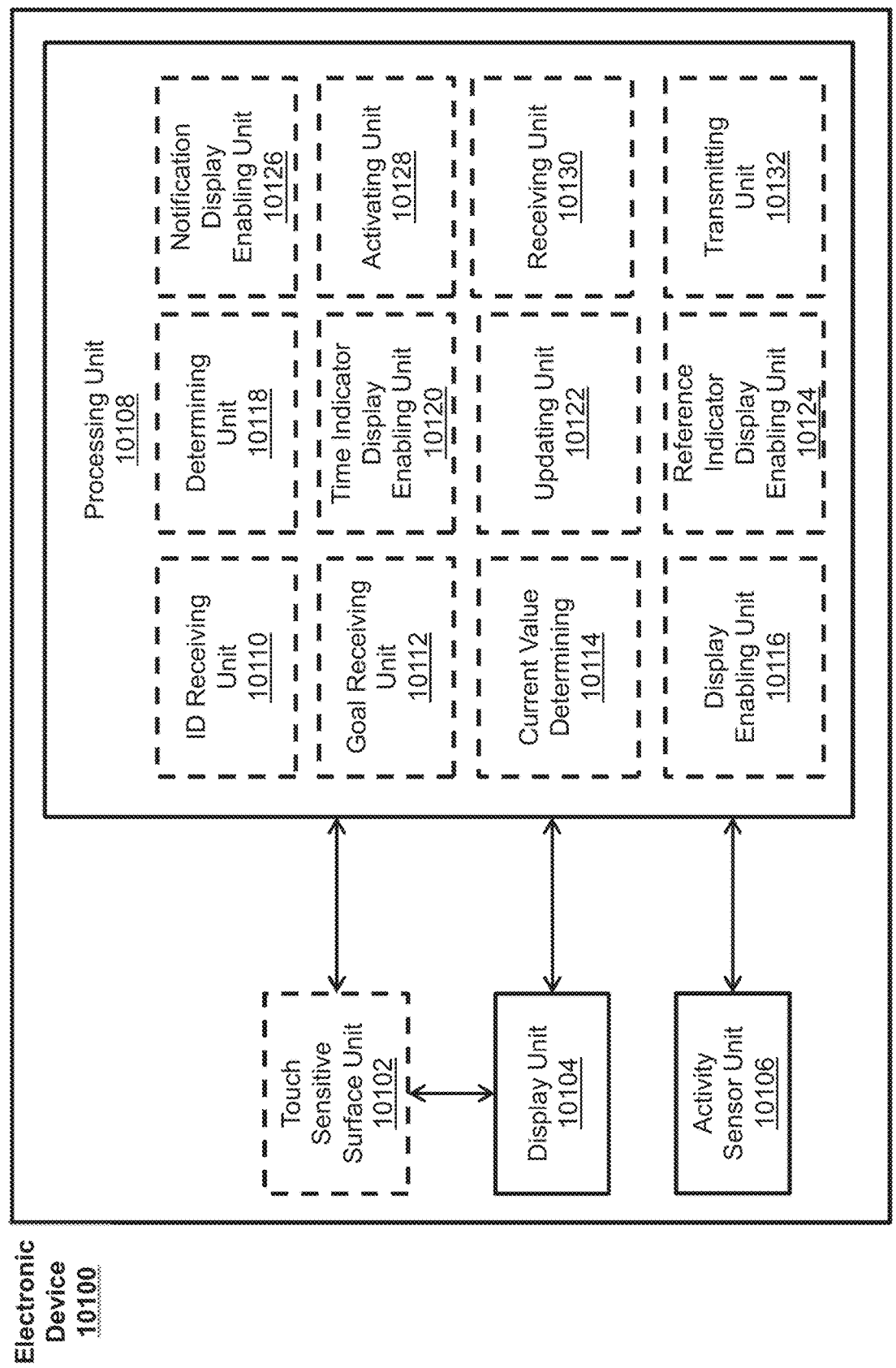

According to some embodiments, FIG. 101 shows a functional block diagram of an electronic device 10100 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 101 can be combined or separated into sub-blocks to implement the principles of the various described examples. Therefore, the description herein optionally supports any possible combination or separation or further definition of the functional blocks described herein.

As shown in FIG. 101, electronic device 10100 can include one or more activity sensor units 10106 configured to detect activity and generate activity data based on the detected activity, a display unit 10104 configured to display graphical objects, and a processing unit 10108 coupled to the one or more activity sensor units 10106, and the display unit 10104. In some example, electronic device 10100 can include a touch-sensitive surface unit 10102 configured to receive user gestures coupled to processing unit 10108. In some examples, processing unit 10108 can include an ID receiving unit 10110, a goal receiving unit 10112, a current value determining unit 10114, a displaying unit 10116, a determining unit 10118, a time indicator display enabling unit 10120, an updating unit 10122, a reference indicator display enabling unit 10124, a notification display enabling unit 10126, an activating unit 10128, a receiving unit 10130, and a transmitting unit 10132.

Processing unit 10108 can be configured to receive (e.g., using ID receiving unit 10110) an identification of a type of workout to be performed, wherein the type of workout is associated with a plurality of workout attributes, receive (e.g., with goal receiving unit 10112) a goal for the type of workout, wherein the goal comprises an identification of a first workout attribute of the plurality of workout attributes and a goal value for the first workout attribute, determine (e.g., with current value determining unit 10114) a current value of the first workout attribute and a current value of a second workout attribute of the plurality of workout attributes based on activity data from one or more activity sensor units 10106, enable display (e.g., with display enabling unit 10116), on display unit 10104, of a first indicator representative of the current value of the first workout attribute relative to the goal value for the first workout attribute, and enable display (e.g., with display enabling unit 10116), on display unit 10104, of a second indicator representative of the current value of the second workout attribute.

In some examples, processing unit 10108 can be further configured to receive (e.g., with ID receiving unit 10110) the identification of the type of workout to be performed by: displaying a list of a plurality of types of workouts; and receiving a selection of the type of workout to be performed from the displayed list of the plurality of types of workouts.

In some examples, the list of the plurality of types of workouts is ordered based on a frequency of performance of the plurality of workouts.

In some examples, the list of the plurality of types of workouts is ordered based on a time since a performance of the plurality of workouts.

In some examples, the list of the plurality of types of workouts comprises a selectable object associated with each type of workout.

In some examples, a size of each of the selectable objects is the same.

In some examples, a size of a selectable object associated with a most recently performed type of workout is larger than a size of selectable objects associated with other types of workouts of the plurality of types of workouts.

In some examples, a size of a selectable object associated with a most frequently performed type of workout is larger than a size of selectable objects associated with other types of workouts of the plurality of types of workouts.

In some examples, the one or more activity sensor units 10106 comprises one or more of a GPS sensor, an accelerometer, a directional sensor, a gyroscope, a timer, a biometric sensor, and a motion sensor.

In some examples, processing unit 10108 can be further configured to receive (e.g., with goal receiving unit 10112) the goal for the type of workout by: displaying an adjustable value associated with the first workout attribute; receiving a selection of the adjustable value; and setting the goal value for the first workout attribute to be equal to the adjustable value.

In some examples, processing unit 10108 can be further configured to receive (e.g., with goal receiving unit 10112) the goal for the type of workout by: displaying a list of a plurality of values associated with the first workout attribute; receiving a selection of a value of the plurality of values; and setting the goal value for the first workout attribute to be equal to the selected value of the plurality of values.

In some examples, the type of workout comprises running, walking, cycling, rowing, yoga, dancing, climbing, swimming, or cross-training.

In some examples, the plurality of workout attributes comprises a duration, a pace, a distance, or a number of Calories expended.

In some examples, the first indicator comprises a first portion representing the current value of the first workout attribute and a second portion representing a difference between the current value of the first workout attribute and the first goal value for the first workout attribute.

In some examples, the first workout attribute is different than the second workout attribute.

In some examples, the first workout attribute is the same as the second workout attribute.

In some examples, processing unit 10108 can be further configured to enable display (e.g., using time indicator display enabling unit 10120) of a time indicator.

In some examples, the time indicator represents a current time.

In some examples, the time indicator represents a duration or a pace associated with the type of workout.

In some examples, processing unit 10108 can be further configured to update (e.g., using updating unit 10122) the display of the time indicator to represent a time other than the current time in response to receiving a selection of the time indicator.

In some examples, the first indicator is displayed in a first color associated with the first workout attribute, and wherein the second indicator is displayed in a second color associated with the second workout attribute.

In some examples, processing unit 10108 can be further configured to update (e.g., with second indicator updating unit 10124) the display of the second indicator to represent a third workout attribute of the plurality of workout attributes in response to receiving a request to change the second indicator.

In some examples, processing unit 10108 can be further configured to enable display (e.g., with reference indicator display enabling unit 10124) of a reference indicator representing a pace associated with a previous workout.

In some examples, processing unit 10108 can be further configured to enable display (e.g., with notification display enabling unit 10126) of a notification in response to a current value of one or more of the plurality of attributes meeting a predetermined criteria.

In some examples, processing unit 10108 can be further configured to activate (e.g., with activating unit 10128) the at least a portion of the one or more activity sensor units 10106 based on the received identification of the type of workout to be performed.

In some examples, processing unit 10108 can be further configured to receive (e.g., with receiving unit 10130) updated activity data from the at least a portion of the one or more activity sensor units 10106. In some examples, processing unit 10108 can be further configured to update (e.g., with updating unit 10122) the current value of the first workout attribute and the current value of the second workout attribute based on the updated activity data.

In some examples, processing unit 10108 can be further configured to update (e.g., with updating unit 10122) the display of the first indicator and the second indicator based on the updated current value of the first workout attribute and the updated current value of the second workout attribute.

In some examples, processing unit 10108 can be further configured to enable display (e.g., with display enabling unit 10116) of a summary interface comprising information associated with the plurality of workout attributes.

In some examples, processing unit 10108 can be further configured to determine (e.g., with determining unit 10118) whether one or more of the plurality of workout attributes satisfies a predetermined criteria. In some examples, processing unit 10108 can be further configured to enable display (e.g., with displaying unit 10116) of a reward in response to determining that the one or more of the plurality of workout attributes satisfies the predetermined criteria.

In some examples, processing unit 10108 can be further configured to receive (e.g., with receiving unit 10130) a request to share the reward. In some examples, processing unit 10108 can be further configured to enable display (e.g., with display enabling unit 10116) of a list of potential rewards. In some examples, processing unit 10108 can be further configured to receive (e.g., with receiving unit 10130) a selection of a recipient from the list of potential recipients. In some examples, processing unit 10108 can be further configured to transmit (e.g., with transmitting unit 10132) the reward to the selected recipient.

In some examples, the display of the list of potential recipients comprises an image of each of the potential recipients.

The operations described above with reference to FIG. 48 are, optionally, implemented by components depicted in FIGS. 1A-1B, and 101. For example, the operations described with reference to blocks 4804, 4808, 4810, and/or 4812 may be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B, and 101.

Figure 102:
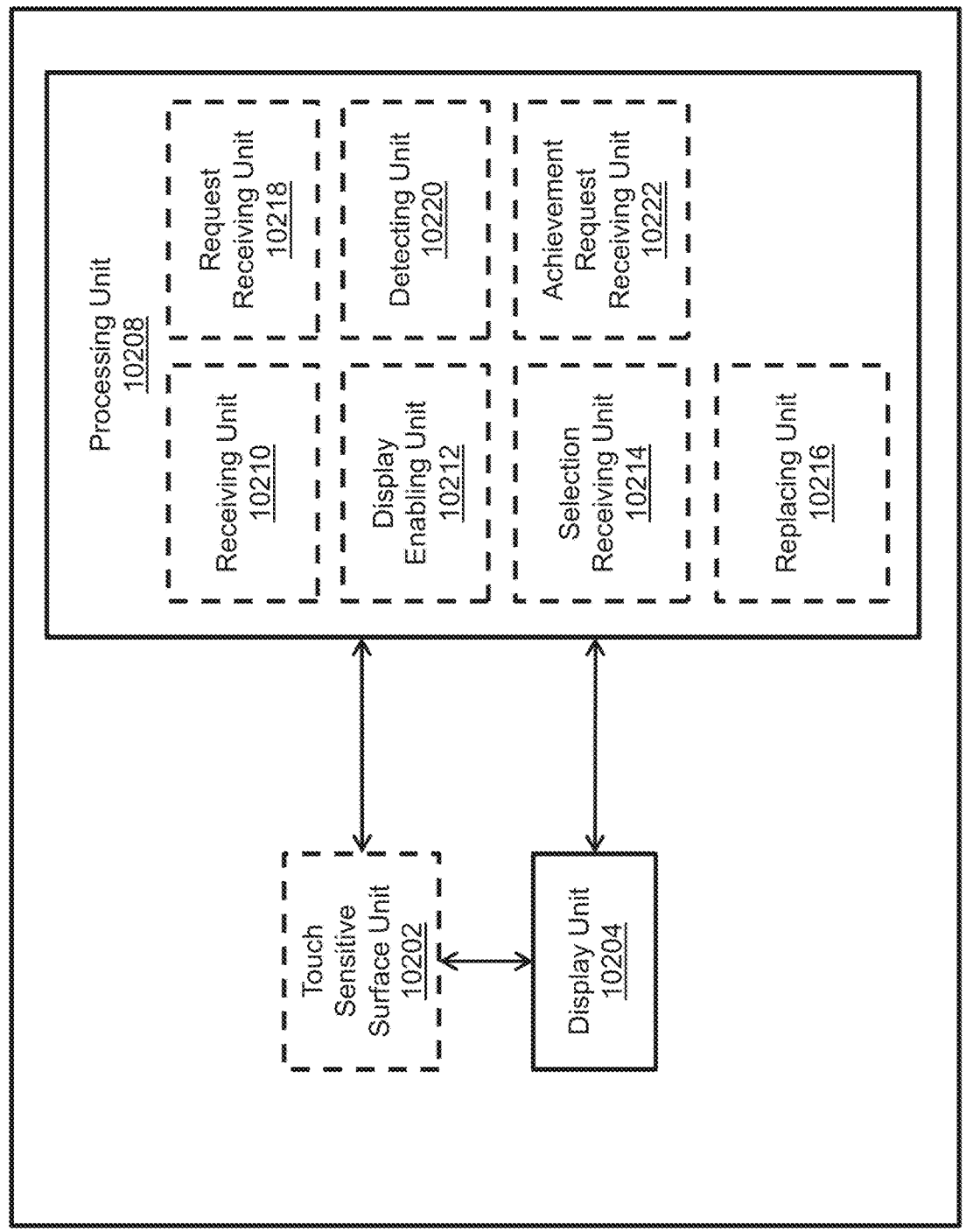

FIG. 102 shows a functional block diagram of an electronic device 10200 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 102 can be combined or separated into sub-blocks to implement the principles of the various described examples. Therefore, the description herein optionally supports any possible combination or separation or further definition of the functional blocks described herein.

As shown in FIG. 102, electronic device 10200 can include a display unit 10204 configured to display graphical objects, a touch-sensitive surface unit 10202 configured to receive user gestures, and a processing unit 10208 coupled to the display unit 10204 and optional touch-sensitive surface unit 10202. In some examples, processing unit 10208 can include a receiving unit 10210, a display enabling unit 10212, a selection receiving unit 10214, a replacing unit 10216, a request receiving unit 10218, a detecting unit 10220, and an achievement request receiving unit 1022.

Processing unit 10208 can be configured to receive (e.g., using receiving unit 10210) historical activity data representing physical activity performed by a user and enable display (e.g., with display enabling unit 10212) of an aggregated view of the historical activity data, wherein the aggregate view comprises: an activity indicator comprising: a first indicator representative of an aggregate amount of a first type of physical activity performed by a user during a period of time; a second indicator representative of an aggregate amount of a second type of physical activity performed by the user during the period of time; and a third indicator representative of an aggregate amount of a third type of physical activity performed by the user during the period of time; and one or more partitions associated with the first, second, or third type of physical activity.

In some examples, the aggregate amount of the first type of physical activity comprises an amount of Calories expended by the user in performing the first type of physical activity over a period of time.

In some examples, the aggregate amount of the second type of physical activity comprises a number of minutes spent by the user in performing the second type of physical activity over the period of time.

In some examples, the aggregate amount of the third type of physical activity comprises a number of segments of time during which the user performed the third type of physical activity over the period of time.

In some examples, the segments of time comprise hour-long segments of time. In some examples, the period of time comprises a day.

In some examples, the one or more partitions comprises: a first partition associated with the first type of physical activity, the first partition comprising a textual representation of the aggregate amount of the first type of physical activity performed by the user during the period of time and a graph representation of the first type of physical activity performed by the user during the period of time; a second partition associated with the second type of physical activity, the second partition comprising a textual representation of the aggregate amount of the second type of physical activity performed by the user during the period of time and a graph representation of the second type of physical activity performed by the user during the period of time; and a third partition associated with the third type of physical activity, the third partition comprising a textual representation of the aggregate amount of the third type of physical activity performed by the user during the period of time and a graph representation of the third type of physical activity performed by the user during the period of time.

Processing unit 10208 can be further configured to receive (e.g., with selection receiving unit 10214) a selection of the first, second, or third partition. In some examples, replacing unit 10216 can be configured to replace the selected partition with an alternate view of the selected partition in response to receiving the selection of the first, second, or third partition.

In some examples, the alternate view of the selected partition comprises additional information from that displayed within the selected partition.

In some examples, the aggregated view of the historical activity data further comprises a workout partition associated with a workout performed by the user.

In some examples, the workout partition comprises: a textual description of the workout; a textual representation of a time spent performing the workout; a textual representation of a number of Calories expended performing the workout; and a graph representation of an attribute of the workout.

In some examples, the aggregated view of the historical activity data further comprises a reward partition comprising one or more rewards obtained by the user during the period of time.

In some examples, the aggregated view of the historical activity data further comprises a summary partition comprising a textual representation of a number of steps taken by the user and a distance traveled by the user during the period of time.

In some examples, re first indicator, the second indicator, and the third indicator are concentric rings.

In some examples, processing unit 10208 can be further configured to receive (e.g., with request receiving unit 10218) a request to view a monthly aggregated view of the historical activity data for a month. In some examples, processing unit 10208 can be further configured to enable display (e.g., with display enabling unit 10212) of the monthly aggregated view of the historical activity data for the month in response to receiving the request to view the monthly aggregated view of the historical activity data for the month.

In some examples, the monthly aggregated view of the historical activity data for the month comprises: one or more daily activity indicators, wherein each of the one or more daily activity indicators is associated with a day of the month, and wherein each of the one or more daily activity indicators comprises: a first indicator representative of an aggregate amount of a first type of physical activity performed by the user during the associated day; a second indicator representative of an aggregate amount of a second type of physical activity performed by the user during the associated day; and a third indicator representative of an aggregate amount of a third type of physical activity performed by the user during the associated day.

In some examples, processing unit 10208 can be further configured to detect (e.g., with detecting unit 10220) a change in orientation of the electronic device while the monthly aggregated view of the historical activity data for the month is being displayed. In some examples, processing unit 10208 can be further configured to enable display (e.g., with display enabling unit 10212) of a graph view of the historical activity data for the month in response to detecting the change in orientation of the electronic device while the monthly aggregated view of the historical activity data for the month is being displayed.

In some examples, the graph view comprises a line graph of the aggregate amount of the first type of physical activity performed by the user for two or more days during the month.

In some examples, the graph view comprises a textual description of a number of Calories burned during the month and a textual description of a number of workouts performed during the month.

In some examples, the graph view comprises a textual description of a workout performed during the month.

In some examples, processing unit 10208 can be further configured to receive (e.g., with achievement request receiving unit 10222) an achievement interface comprising one or more rewards obtained by the user. In some examples, processing unit 10208 can be further configured to enable display (e.g., with display enabling unit 10212) of the achievement interface comprising one or more rewards obtained by the user in response to receiving the request to view the achievement interface comprising one or more rewards obtained by the user.

The operations described above with reference to FIGS. 79, 86, and/or 92 are, optionally, implemented by components depicted in FIGS. 1A-1B, and 101. For example, the operations described with reference to blocks 7902, 8602, and/or 8902 may be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B, and 101.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:

1. An electronic device, comprising:
   one or more processors;
   a display;
   memory storing one or more programs configured to be executed by the one or more processors, the one or more programs including instructions for:
   determining, using the one or more processors, that a physical activity has been performed by a user wearing the electronic device, based on activity data generated by a sensor of the electronic device;
   determining whether the physical activity corresponds to a first type based on a first set of criteria and determining whether the physical activity corresponds to a second type based on a second set of criteria;
   in response to determining that the physical activity corresponds to the first type, updating a first value, stored in the memory, based on the activity data;
   in response to determining that the physical activity corresponds to the second type, updating a second value, stored in the memory, based on the activity data;

for each predetermined segment of time of a plurality of predetermined segments of time:
  resetting the amount of detected activity
  determining whether a threshold amount of a predetermined activity of a predetermined type was performed within a predetermined sub-segment of time for each predetermined segments of time; and
  in accordance with a determination that the threshold amount of the predetermined activity of the predetermined type was performed, incrementing a value of an activity counter, wherein the value of the activity counter is a cumulative number of the plurality of predetermined segments of time during which the threshold amount of the predetermined activity of the predetermined type was performed, wherein each predetermined segment of time of the plurality of predetermined segments of time is a continuous and fixed-length segment of time, and wherein each predetermined segment of time of the plurality of predetermined segments of time is adjacent to another predetermined segment of time of the plurality of predetermined segments; and
concurrently displaying:
  a first indicator representative of the first value, the first value representing an aggregate amount of the first type of physical activity detected from the sensor over a period of time;
  a second indicator representative of the second value, the second value representing an aggregate amount of the second type of physical activity detected from the sensor over the period of time; and
  a third indicator representative of the value of the activity counter relative to the plurality of predetermined segments of time.

2. The electronic device of claim 1, wherein the threshold amount of a predetermined activity of a predetermined type comprises one or more of: a duration of standing, a duration of movement, a number of steps taken, or a length of time.

3. The electronic device of claim 1, the one or more programs further including instructions for:
  updating an amount of detected activity to include e physical activity performed by the user.

4. The electronic device of claim 3, the one or more programs further including instructions for:
  resetting the amount of detected activity in response to determining that the amount of the detected activity has reached the threshold amount of a predetermined activity of a predetermined type.

5. The electronic device of claim 3, the one or more programs further including instructions for:
  resetting the amount of detected activity in response to determining that a predetermined segment of time, of the plurality of predetermined segments of time, has ended.

6. The electronic device of claim 3, the one or more programs further including instructions for:
  after updating the amount of detected activity to include the physical activity performed by the user:
    in response to determining that the user is inactive for more than a threshold length of time, reset the amount of detected activity.

7. The electronic device of claim 1, the one or more programs further comprising instructions for: determining that the user is actively performing, based on the activity data, an activity selected from the group consisting of standing, walking, running, going up stairs, and jumping.

8. The electronic device of claim 1, wherein the activity data is generated by the sensor based on detection of one or more types of physical activity, the one or more types of physical activity selected from the group consisting of walking, running, going up stairs, and jumping.

9. The electronic device of claim 1, wherein the second set of criteria comprises a number of steps taken per unit time, an amount of Calories burned per unit time, a speed, or the first set of criteria.

10. The electronic device of claim 1, wherein the second type of activity is a subset of the first type of activity.

11. The electronic device of claim 1, wherein the first value represents an aggregate amount of Calories burned by the user from performing the first type of physical activity over the period of time, and wherein the second value represents an aggregate amount of time spent by the user performing the second type of physical activity over the period of time.

12. The electronic device of claim 1, wherein:
  the first indicator comprises a first portion representing the first value and a second portion representing a difference between the first value and a first goal value stored in the memory;
  the second indicator comprises a third portion representing the second value and a fourth portion representing a difference between the second value and a second goal value stored in the memory; and
  the third indicator comprises a fifth portion representing the value of the activity counter and a sixth portion representing a difference between the value of the activity counter and a third goal value stored in the memory.

13. The electronic device of claim 1, wherein the first indicator and the second indicator are concentric rings.

14. The electronic device of claim 1, the one or more programs further including instructions for:
  receiving from an external device remotely located from the electronic device, activity data associated with devices different from the electronic device.

15. The electronic device of claim 1, the one or more programs further including instructions for:
  periodically:
    storing the value of the activity counter; and
    after storing the value of the activity counter, resetting the value of the activity counter.

16. The electronic device of claim 1, wherein the activity sensor is one or more sensors selected from the group consisting of a global positioning system (GPS) sensor, a pedometer, an accelerometer, a biometric sensor, a gyroscope, and a motion sensor.

17. A non-transitory computer-readable storage medium storing one or more programs configured to be executed by one or more processors of an electronic device with a display, the one or more programs including instructions for:
  determining that a physical activity has been performed by a user wearing the electronic device, based on activity data generated by a sensor of the electronic device;
  determining whether the physical activity corresponds to a first type based on a first set of criteria and determining whether the physical activity corresponds to a second type based on a second set of criteria;
  in response to determining that the physical activity corresponds to the first type, updating a first value, stored in the memory, based on the activity data;

in response to determining that the physical activity corresponds to the second type, updating a second value; stored in the memory, based on the activity data;

for each predetermined segment of time of a plurality of predetermined segments of time:
  resetting the amount of detected activity;
  determining whether a threshold amount of a predetermined activity of a predetermined type was performed within a predetermined sub-segment of time for each predetermined segments of time; and
  in accordance with a determination that the threshold amount of the predetermined activity of the predetermined type was performed, incrementing a value of an activity counter, wherein the value of the activity counter is a cumulative number of the plurality of predetermined segments of time during which the threshold amount of the predetermined activity of the predetermined type was performed, wherein each predetermined segment of time of the plurality of predetermined segments of time is a continuous and fixed-length segment of time, and wherein each predetermined segment of time of the plurality of predetermined segments of time is adjacent to another predetermined segment of time of the plurality of predetermined segments; and concurrently displaying:
  a first indicator representative of the first value, the first value representing an aggregate amount of the first type of physical activity detected from the sensor over a period of time;
  a second indicator representative of the second value, the second value representing an aggregate amount of the second type of physical activity detected from the sensor over the period of time; and
  a third indicator representative of the value of the activity counter relative to the plurality of predetermined segments of time.

18. The non-transitory computer-readable storage medium of claim 17, wherein the threshold amount of a predetermined activity of a predetermined type comprises one or more of: a duration of standing, a duration of movement, a number of steps taken, or a length of time.

19. The non-transitory computer-readable storage medium of claim 17, the one or more programs further including instructions for:
  updating an amount of detected activity to include the physical activity performed by the user.

20. The non-transitory computer-readable storage medium of claim 19, the one or more programs further including instructions for:
  resetting the amount of detected activity in response to determining that the amount of the detected activity has reached the threshold amount of a predetermined activity of a predetermined type.

21. The non-transitory computer-readable storage medium of claim 19, the one or more programs further including instructions for:
  resetting the amount of detected activity in response to determining that a predetermined segment of time, of the plurality of predetermined segments of time, has ended.

22. The non-transitory computer-readable storage medium of claim 19, the one or more programs further including instructions for:
  after updating the amount of detected activity to include the physical activity performed by the user:
    in response to determining that the user is inactive for more than a threshold length of time, reset the amount of detected activity.

23. The non-transitory computer-readable storage medium of claim 17, the one or more programs further comprising instructions for: determining that the user is actively performing, based on the activity data, an activity selected from the group consisting of standing, walking, running, going up stairs, and jumping.

24. The non-transitory computer-readable storage medium of claim 17, wherein the activity data is generated by the sensor based on detection of one or more types of physical activity, the one or more types of physical activity selected from the group consisting of walking, running, going up stairs, and jumping.

25. The non-transitory computer-readable storage medium of claim 17, wherein the second set of criteria comprises a number of steps taken per unit time, an amount of Calories burned per unit time, a speed, or the first set of criteria.

26. The non-transitory computer-readable storage medium of claim 17, wherein the second type of activity is a subset of the first type of activity.

27. The non-transitory computer-readable storage medium of claim 17, wherein the first value represents an aggregate amount of Calories burned by the user from performing the first type of physical activity over the period of time, and wherein the second value represents an aggregate amount of time spent by the user performing the second type of physical activity over the period of time.

28. The non-transitory computer-readable storage medium of claim 17, wherein:
  the first indicator comprises a first portion representing the first value and a second portion representing a difference between the first value and a first goal value stored in the memory;
  the second indicator comprises a third portion representing the second value and a fourth portion representing a difference between the second value and a second goal value stored in the memory; and
  the third indicator comprises a fifth portion representing the value of the activity counter and a sixth portion representing a difference between the value of the activity counter and a third goal value stored in the memory.

29. The non-transitory computer-readable storage medium of claim 17, wherein the first indicator and the second indicator are concentric rings.

30. The non-transitory computer-readable storage medium of claim 17, the one or more programs further including instructions for:
  receiving from an external device remotely located from the electronic device, activity data associated with devices different from the electronic device.

31. The non-transitory computer-readable storage medium of claim 17, the one or more programs further including instructions for:
  periodically:
    storing the value of the activity counter; and
    after storing the value of the activity counter, resetting the value of the activity counter.

32. The non-transitory computer-readable storage medium of claim 17, wherein the activity sensor is one or more sensors selected from the group consisting of a global positioning system (GPS) sensor, a pedometer, an accelerometer, a biometric sensor, a gyroscope, and a motion sensor.

33. A computer-implemented method comprising:
- determining, using one or more processors, that a physical activity has been performed by a user wearing an electronic device, based on activity data generated by a sensor of the electronic device;
- determining whether the physical activity corresponds to a first type based on a first set of criteria and determining whether the physical activity corresponds to a second type based on a second set of criteria;
- in response to determining that the physical activity corresponds to the first type, updating a first value, stored in the memory, based on the activity data;
- in response to determining that the physical activity corresponds to the second type, updating a second value, stored in the memory, based on the activity data;
- for each predetermined segment of time of a plurality of predetermined segments of time:
  - resetting the amount of detected activity;
  - determining whether a threshold amount of a predetermined activity of a predetermined type was performed within a predetermined sub-segment of time for each predetermined segments of time; and
  - in accordance with a determination that the threshold amount of the predetermined activity of the predetermined type was performed, incrementing a value of an activity counter, wherein the value of the activity counter is a cumulative number of the plurality of predetermined segments of time during which the threshold amount of the predetermined activity of the predetermined type was performed, wherein each predetermined segment of time of the plurality of predetermined segments of time is a continuous and fixed-length segment of time, and wherein each predetermined segment of time of the plurality of predetermined segments of time is adjacent to another predetermined segment of time of the plurality of predetermined segments; and
- concurrently displaying:
  - a first indicator representative of the first value, the first value representing an aggregate amount of the first type of physical activity detected from the sensor over a period of time;
  - a second indicator representative of the second value, the second value representing an aggregate amount of the second type of physical activity detected from the sensor over the period of time; and
  - a third indicator representative of the value of the activity counter relative to the plurality of predetermined segments of time.

34. The computer-implemented method of claim 33, wherein the threshold amount of a predetermined activity of a predetermined type comprises one or more of: a duration of standing, a duration of movement, a number of steps taken, or a length of time.

35. The computer-implemented method of claim 33, further comprising:
- updating an amount of detected activity to include the physical activity performed by the user.

36. The computer-implemented method of claim 35, further comprising:
- resetting the amount of detected activity in response to determining that the amount of the detected activity has reached the threshold amount of a predetermined activity of a predetermined type.

37. The computer-implemented method of claim 35, further comprising:
- resetting the amount of detected activity in response to determining that a predetermined segment of time, of the plurality of predetermined segments of time, has ended.

38. The computer-implemented method of claim 35, further comprising:
- after updating the amount of detected activity to include the physical activity performed by the user:
  - in response to determining that the user is inactive for more than a threshold length of time, reset the amount of detected activity.

39. The computer-implemented method of claim 33, further comprising: determining that the user is actively performing, based on the activity data, an activity selected from the group consisting of standing, walking, running, going up stairs, and jumping.

40. The computer-implemented method of claim 33, wherein the activity data is generated by the sensor based on detection of one or more types of physical activity, the one or more types of physical activity selected from the group consisting of walking, running, going up stairs, and jumping.

41. The computer-implemented method of claim 33, wherein the second set of criteria comprises a number of steps taken per unit time, an amount of Calories burned per unit time, a speed, or the first set of criteria.

42. The computer-implemented method of claim 33, wherein the second type of activity is a subset of the first type of activity.

43. The computer-implemented method of claim 33, wherein the first value represents an aggregate amount of Calories burned by the user from performing the first type of physical activity over the period of time, and wherein the second value represents an aggregate amount of time spent by the user performing the second type of physical activity over the period of time.

44. The computer-implemented method of claim 33, wherein:
- the first indicator comprises a first portion representing the first value and a second portion representing a difference between the first value and a first goal value stored in the memory;
- the second indicator comprises a third portion representing the second value and a fourth portion representing a difference between the second value and a second goal value stored in the memory; and
- the third indicator comprises a fifth portion representing the value of the activity counter and a sixth portion representing a difference between the value of the activity counter and a third goal value stored in the memory.

45. The computer-implemented method of claim 33, wherein the first indicator and the second indicator are concentric rings.

46. The computer-implemented method of claim 33, further comprising:
- receiving from an external device remotely located from the electronic device, activity data associated with devices different from the electronic device.

47. The computer-implemented method of claim 33, further comprising:
- periodically:
  - storing the value of the activity counter; and
  - after storing the value of the activity counter, resetting the value of the activity counter.

48. The computer-implemented method of claim 33, wherein the activity sensor is one or more sensors selected from the group consisting of a global positioning system (GPS) sensor, a pedometer, an accelerometer, a biometric sensor, a gyroscope, and a motion sensor.

* * * * *

UNITED STATES PATENT AND TRADEMARK OFFICE
CERTIFICATE OF CORRECTION

PATENT NO. : 10,978,195 B2
APPLICATION NO. : 15/925652
DATED : April 13, 2021
INVENTOR(S) : Jay Blahnik et al.

It is certified that error appears in the above-identified patent and that said Letters Patent is hereby corrected as shown below:

In the Claims

In Column 125, Line 44, Claim 3, delete "include e" and insert -- include the --, therefor.

In Column 127, Line 3, Claim 17, delete "value;" and insert -- value, --, therefor.

Signed and Sealed this
Twentieth Day of September, 2022

*Katherine Kelly Vidal*
Katherine Kelly Vidal
*Director of the United States Patent and Trademark Office*